United States Patent
Park et al.

(10) Patent No.: US 9,373,806 B2
(45) Date of Patent: Jun. 21, 2016

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicants: DUK SAN NEOLUX CO., LTD., Cheonan-si, Chungcheongnam-do (KR); SAMSUNG DISPLAY CO., LTD., Gyeonggi-do (KR)

(72) Inventors: Junghwan Park, Seoul (KR); Sunhee Lee, Chungcheongnam-do (KR); Soungyun Mun, Gyeonggi-do (KR); Daesung Kim, Gyeonggi-do (KR); Hwasoon Jung, Gyeonggi-do (KR); Wonsam Kim, Chungcheongnam-do (KR); Jihun Byun, Chungcheongnam-do (KR); Bumsung Lee, Chungcheongnam-do (KR); Mi Kyung Kim, Gyeonggi-do (KR); Kwan Hee Lee, Gyeonggi-do (KR); Dae Yup Shin, Gyeonggi-do (KR)

(73) Assignee: DUK SAN NEOLUX CO., LTD., Chungcheongnam-do (KR)

(*) Notice: Subject to any disclaimer, the term of this patent is extended or adjusted under 35 U.S.C. 154(b) by 0 days.

(21) Appl. No.: 14/362,406

(22) PCT Filed: Dec. 21, 2012

(86) PCT No.: PCT/KR2012/011234
§ 371 (c)(1),
(2) Date: Jun. 3, 2014

(87) PCT Pub. No.: WO2013/108997
PCT Pub. Date: Jul. 25, 2013

(65) Prior Publication Data
US 2014/0332793 A1    Nov. 13, 2014

(30) Foreign Application Priority Data

Jan. 18, 2012 (KR) .................. 10-2012-0005545
Oct. 24, 2012 (KR) .................. 10-2012-0118629

(51) Int. Cl.
*H01L 51/54* (2006.01)
*C09K 11/06* (2006.01)
*H01L 51/50* (2006.01)
*H01L 51/00* (2006.01)
*C07D 495/04* (2006.01)

(52) U.S. Cl.
CPC ............. *H01L 51/50* (2013.01); *C07D 495/04* (2013.01); *H01L 51/006* (2013.01); *H01L 51/0061* (2013.01); *H01L 51/0071* (2013.01); *H01L 51/0052* (2013.01); *H01L 51/0067* (2013.01); *H01L 51/0072* (2013.01); *H01L 51/0081* (2013.01); *H01L 51/5016* (2013.01); *H01L 2251/308* (2013.01); *Y02E 10/549* (2013.01)

(58) Field of Classification Search
None
See application file for complete search history.

(56) References Cited

U.S. PATENT DOCUMENTS

| 2009/0309488 A1 | 12/2009 | Kato et al. | |
| 2011/0279020 A1* | 11/2011 | Inoue | C07D 209/82 313/504 |

FOREIGN PATENT DOCUMENTS

| JP | 11-176578 A1 | 7/1999 |
| KR | 10-2008-0085001 A | 9/2008 |
| KR | 10-2010-0130197 A | 12/2010 |
| KR | 10-2011-0058243 A | 6/2011 |
| KR | 10-2011-0066766 A | 6/2011 |
| KR | 10-2011-0116177 A | 10/2011 |
| KR | 10-2011-0133009 A | 12/2011 |
| KR | 10-2011-0133010 A | 12/2011 |
| KR | 10-2012-0030941 A | 3/2012 |
| WO | WO2010-126234 A1 | 11/2010 |
| WO | WO2010-136109 A1 | 12/2010 |
| WO | WO2011-000455 A1 | 1/2011 |

OTHER PUBLICATIONS

Machine translation of KR2011-066766. Date of publication: Jun. 17, 2011.*
International Search Report for PCT/KR2012/011234.

* cited by examiner

*Primary Examiner* — Andrew K Bohaty
(74) *Attorney, Agent, or Firm* — Vorys, Sater, Seymour & Pease LLP; Mih Suhn Koh

(57) ABSTRACT

A compound represented by Formula 1. An organic electric element includes a first electrode, a second electrode, and an organic material layer between the first electrode and the second electrode. The organic material layer includes the compound. When the organic electric element includes the compound in an organic material layer, luminous efficiency, stability, and life span can be improved.

14 Claims, 1 Drawing Sheet

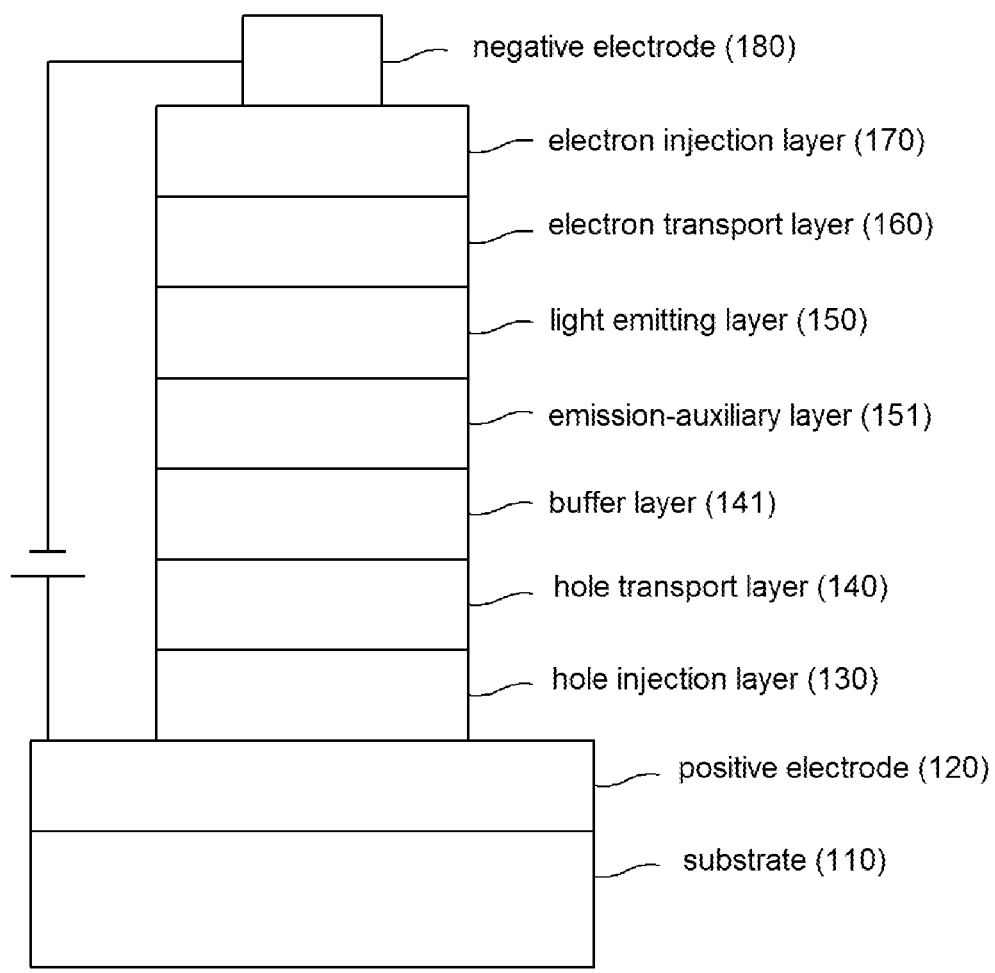

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION AND CLAIM OR PRIORITY

This patent application claims benefit under 35 U.S.C. 119(e), 120, 121, or 365(c), and is a National Stage entry from International Application No. PCT/KR2012/011234, filed Dec. 21, 2012, which claims priority from and the benefit under 35 U.S.C. §119(a) of Korean Patent Application No. 10-2012-0005545, filed on Jan. 18, 2012, and Korean Patent Application No. 10-2012-0118629, filed on Oct. 24, 2012, the contents of which are incorporated herein by reference.

BACKGROUND

1. Technical Field

The present invention relates to a compound for an organic electric element, an organic electric element using the same, and an electronic device thereof.

2. Background Art

In general, an organic light emitting phenomenon refers to a phenomenon in which electric energy is converted into light energy by means of an organic material. An organic electric element utilizing the organic light emitting phenomenon usually has a structure including an anode, a cathode, and an organic material layer interposed therebetween. Here, in many cases, the organic material layer may have a multilayered structure including multiple layers made of different materials in order to improve the efficiency and stability of an organic electric element, and for example, may include a hole injection layer, a hole transport layer, a light emitting layer, an electron transport layer, an electron injection layer, and the like.

A material used as an organic material layer in an organic electric element may be classified into a light emitting material and a charge transport material, for example, a hole injection material, a hole transport material, an electron transport material, an electron injection material, and the like according to its function.

The most problematic issues in an organic electric element are life span and efficiency, and the situation is such that this life span or efficiency issue must be solved as displays become larger and larger. Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase.

However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Further, in order to solve the emission problem with a hole transport layer in a recent organic electric element, an emission-auxiliary layer is present between the hole transport layer and a light emitting layer, and it is time to develop different emission-auxiliary layers according to respective light emitting layers (R, G, B). In general, an electron transferred from an electron transport layer to a light emitting layer and a hole transferred from a hole transport layer to the light emitting layer are recombined to form an exciton. However, since materials to be used in the hole transport layer must have low HOMO values, they mostly have low T1 values, and on account of this, the exciton formed in the light emitting layer is transferred into the hole transport layer, which causes charge unbalance in the light emitting layer and thus light emission at the light emitting layer-hole transport layer interface.

The light emission at the light emitting layer-hole transport layer interface has a problem in that color purity and efficiency are lowered and life span is shortened. Therefore, there is an urgent need to develop an emission-auxiliary layer which has a high T1 value and the HOMO level of which is between the HOMO energy level of a hole transport layer and the HOMO energy level of a light emitting layer.

In addition, it is required to develop a hole injection layer material that retards penetration/diffusion of metal oxides from an anode electrode (ITO) into an organic layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In general, deposition is a main method of forming an OLED, and thus there is an actual need to develop a material that is durable to such a deposition method, that is, a highly heat-resistant material.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a continuous need to develop new materials for an organic material layer.

SUMMARY

In order to solve the above-mentioned problems occurring in the prior art, an object of the present invention is to provide a compound including a five-membered hetero ring, which allows an organic electric element to have high luminous efficiency and low driving voltage and to be improved in color purity and life span, an organic electric element using the same, and an electronic device including the organic electric element.

In accordance with an aspect of the present invention, there is provided a compound represented by Formula below.

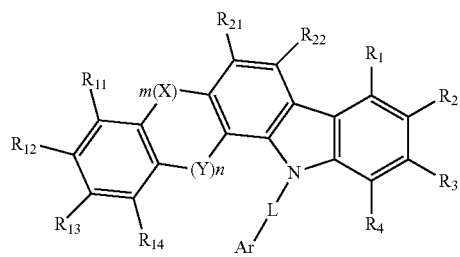

In another aspect of the present invention, there are provided an organic electric element using the compound represented by Formula above and an electronic device including the organic electric element.

By using the compound according to embodiments of the present invention, an organic electric element not only has low driving voltage, but can also be significantly improved in color purity, luminous efficiency, and life span.

BRIEF DESCRIPTION OF THE DRAWINGS

FIG. 1 illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

Unless otherwise stated, the term "halo" or "halogen" as used herein includes fluorine, chlorine, bromine, and iodine.

Unless otherwise stated, the term "alkyl" or "alkyl group" as used herein has, but not limited to, 1 to 60 carbon atoms.

Unless otherwise stated, the term "alkenyl" or "alkynyl" as used herein has, but not limited to, double or triple bonds of 2 to 60 carbon atoms.

Unless otherwise stated, the term "cycloalkyl" as used herein means, but not limited to, alkyl forming a ring having 3 to 60 carbon atoms.

Unless otherwise stated, the term "alkoxy group" as used herein has, but not limited to, 1 to 60 carbon atoms.

Unless otherwise stated, the term "aryl group" or "arylene group" as used herein has, but not limited to, 6 to 60 carbon atoms.

Herein, the aryl group or arylene group means a monocyclic or polycyclic aromatic group, and examples of the aryl group may include a phenyl group, a biphenyl group, a fluorine group, and a spirofluorene group, but are not limited thereto.

Unless otherwise stated, the term "heteroalkyl" as used herein means alkyl containing one or more heteroatoms. Unless otherwise stated, the term "heteroaryl group" or "heteroarylene group" as used herein means, but not limited to, a $C_3$ to $C_{60}$ aryl or arylene group containing one or more heteroatoms, includes both monocyclic and polycyclic rings, and may also be formed in conjunction with an adjacent group.

Unless otherwise stated, the term "heterocyclic alkyl" or "heterocyclic group" as used herein contains one or more heteroatoms, has 2 to 60 carbon atoms, includes both monocyclic and polycyclic rings, and may also be formed in conjunction with an adjacent group. Also, the heterocyclic group may mean an alicyclic and/or aromatic group containing heteroatoms.

Unless otherwise stated, the term "heteroatom" as used herein represents at least one of N, O, S, P, and Si.

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "saturated or unsaturated ring" means a saturated or unsaturated aliphatic ring, an aromatic ring having 6 to 60 carbon atoms, or a hetero ring.

Hetero compounds or hetero radicals other than the above-mentioned hetero compounds each contain, but not limited to, one or more heteroatoms.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_5$-$C_{20}$ heterocyclic group.

FIG. 1 illustrates an organic electric element according to an embodiment of the present invention.

Referring to FIG. 1, an organic electric element 100 according to an embodiment of the present invention includes a first electrode 120 formed on a substrate 100, a second electrode 180, and an organic material layer between the first electrode 120 and the second electrode 180, which contains the compound represented by Formula 1. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer formed on at least one of the sides the first and second electrodes, which is opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150. For example, the inventive compound may be used as the light emitting layer 150, the hole transport layer 140, and/or the emission-auxiliary layer 151.

Since depending on the type and position of a substituent to be attached, a band gap, electrical properties, interfacial properties, and the like may vary even in the same core, long life span and high efficiency can be simultaneously achieved when an optimal combination of energy levels and T1 values, inherent material properties (mobility, interfacial properties, etc.), and the like among the respective layers included in the organic material layer is given.

As already described above, in order to solve the emission problem with a hole transport layer in a conventional organic electric element, an emission-auxiliary layer is preferably formed between the hole transport layer and a light emitting layer, and it is time to develop different emission-auxiliary layers according to respective light emitting layers (R, G, B). However, even when a similar core is used, it is very difficult to infer the characteristics of an emission-auxiliary layer if a used organic material layer varies because the correlation between the emission-auxiliary layer and a hole transport layer and the correlation between the emission-auxiliary layer and a light emitting layer (host) mused be discovered.

Accordingly, in the present invention, a combination of energy levels and T1 values, inherent material properties (mobility, interfacial properties, etc.), and the like among the respective layers included in the organic material layer is optimized by forming the light emitting layer by using the compound represented by Formula 1, and thus the life span and efficiency of the organic electric element can be improved at the same time.

The organic electric element according to an embodiment of the present invention may be manufactured using a PVD (physical vapor deposition) method. For example, the organic electric element may be manufactured by depositing a metal, a conductive metal oxide, or a mixture thereof on the substrate 110 to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a PDA, an electronic dictionary, a PMP, a remote controller, a navigation unit, a game player, various kinds of TVs, and various kinds of computers.

Hereinafter, a compound according to an aspect of the present invention will be described.

The compound according to an aspect of the present invention is represented by Formula 1 below.

[Formula 1]

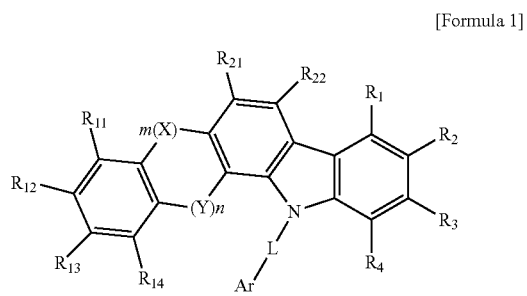

In Formula 1 above, $R_1$ to $R_4$ and $R_{11}$ to $R_{14}$ are each independently selected from the group consisting of hydrogen, deuterium, halogen, a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group containing at least one heteroatom selected from O, N, S, Si, and P, -L-N(R')(R''), a $C_1$-$C_{50}$ alkyl group, a $C_2$-$C_{20}$ alkenyl group, a $C_1$-$C_{30}$ alkoxy group, and a $C_6$-$C_{30}$ aryloxy group.

$R_{21}$ and $R_{22}$ i) are each independently selected from the group consisting of hydrogen, a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group containing at least one heteroatom selected from O, N, S, Si, and P, and -L-N(R')(R''), or ii) are linked together to form a monocyclic or polycyclic ring.

However, only when $R_{21}$ and $R_{22}$ are linked together to form a ring, $R_1$ to $R_4$ and $R_{11}$ to $R_{14}$ all may be hydrogen at the same time. In cases other than the case where $R_{21}$ and $R_{22}$ are linked together to form a ring, at least one of $R_1$ to $R_4$ is not hydrogen, and at the same time, at least one of $R_{11}$ to $R_{14}$ is not hydrogen.

A ring formed by linkage of $R_{21}$ and $R_{22}$ not only may be an aromatic ring or a hetero ring containing at least one heteroatom, but may also take a form in which an aromatic ring and an aliphatic ring are fused. By way of example, $R_{21}$ and $R_{22}$ may be linked together to form an aromatic ring such as benzene, naphthalene, or phenanthrene, wherein the formed aromatic ring may have 6 to 60 nuclear carbon atoms. Also, $R_{21}$ and $R_{22}$ may be linked together to form a hetero ring such as thiophene, furan, pyridine, indole, or quinoline, wherein the formed hetero ring may have 2 to 60 nuclear carbon atoms. Further, in the case of a polycyclic ring, it may be a fused polycyclic ring, a non-fused polycyclic ring in which a plurality of cycles are not fused, or a mixed polycyclic ring in which a fused polycyclic ring and a non-fused polycyclic ring are mixed.

In Formula 1 above, X and Y are each independently S, O, or $SiR_{31}R_{32}$. Here, $R_{31}$ and $R_{32}$ may be each independently hydrogen, a $C_6$-$C_{60}$ aryl group, a $C_2$-$C_{60}$ heterocyclic group containing at least one heteroatom selected from O, N, S, Si, and P, or a $C_1$-$C_{50}$ alkyl group. In the above Formula, m and n are each 0 or 1, with the proviso that the case where both m and n are 0 is excluded. Since m+n is an integer equal to or greater than 1, at least one of X and Y has to exist.

L is selected from the group consisting of a single bond; a $C_6$-$C_{60}$ arylene group; a fluorenyl group; a $C_2$-$C_{60}$ heterocyclic group containing at least one heteroatom selected from O, N, S, Si, and P; and a bivalent aliphatic hydrocarbon group. Here, the arylene group, the fluorenyl group, the heterocyclic group, and the aliphatic hydrocarbon group may be substituted by one or more substituents selected from the group consisting of a nitro group, a cyano group, a halogen group, a $C_1$-$C_{20}$ alkyl group, a $C_6$-$C_{20}$ aryl group, a $C_2$-$C_{20}$ heterocyclic group, a $C_1$-$C_{20}$ alkoxy group, and an amino group.

Ar is a $C_2$-$C_{60}$ heterocyclic group containing at least one heteroatom selected from O, N, S, Si, and P, a $C_6$-$C_{60}$ aryl group, or —N(R')(R'').

R' and R'' defined in the description of $R_1$ to $R_4$ and $R_{11}$ to $R_{14}$, $R_{21}$, Ar, and the like may be each independently a $C_2$-$C_{60}$ heterocyclic group containing at least one heteroatom selected from O, N, S, Si, and P, a $C_6$-$C_{20}$ aryl group, or a fluorenyl group.

When $R_1$ to $R_4$, $R_{11}$ to $R_{14}$, $R_{21}$, $R_{22}$, $R_{31}$, $R_{32}$, Ar, R', and R'' are an aryl group, the aryl group may be substituted by one or more substituents selected from the group consisting of deuterium, halogen, a silane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

When $R_1$ to $R_4$, $R_{11}$ to $R_{14}$, $R_{21}$, $R_{22}$, $R_{31}$, $R_{32}$, Ar, R', and R'' are a heterocyclic group, the heterocyclic group may be substituted by one or more substituents selected from the group consisting of deuterium, halogen, a silane group, a cyano group, a nitro group, a $C_1$-$C_{20}$ alkoxy group, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

When $R_1$ to $R_4$, $R_{11}$ to $R_{14}$, $R_{21}$, $R_{22}$, R', and R'' are a fluorenyl group, the fluorenyl group may be substituted by one or more substituents selected from the group consisting of deuterium, halogen, a silane group, a cyano group, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, a $C_2$-$C_{20}$ heterocyclic group, and a $C_3$-$C_{20}$ cycloalkyl group.

When $R_1$ to $R_4$, $R_{11}$ to $R_{14}$, $R_{21}$, and $R_{22}$ are a fused ring group, the fused ring group may be substituted by one or more substituents selected from the group consisting of deuterium, halogen, a silane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

When $R_1$ to $R_4$, $R_{11}$ to $R_{14}$, $R_{31}$, and $R_{32}$ are an alkyl group, the alkyl group may be substituted by one or more substituents selected from the group consisting of halogen, a silane group, a boron group, a cyano group, a $C_1$-$C_{20}$ alkoxy group, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, a $C_2$-$C_{20}$ heterocyclic group, a $C_7$-$C_{20}$ arylalkyl group, and a $C_8$-$C_{20}$ arylalkenyl group.

When $R_1$ to $R_4$ and $R_{11}$ to $R_{14}$ are an alkenyl group, the alkenyl group may be substituted by one or more substituents selected from the group consisting of deuterium, halogen, a silane group, a cyano group, a $C_1$-$C_{20}$ alkoxy group, a $C_1$-$C_{20}$ alkyl group, a $C_2$-$C_{20}$ alkenyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

When $R_1$ to $R_4$ and $R_{11}$ to $R_{14}$ are an alkoxy group, the alkoxy group may be substituted by one or more substituents selected from the group consisting of deuterium, halogen, a silane group, a $C_1$-$C_{20}$ alkyl group, a $C_6$-$C_{20}$ aryl group, a $C_6$-$C_{20}$ aryl group substituted by deuterium, a $C_2$-$C_{20}$ heterocyclic group, and a $C_3$-$C_{20}$ cycloalkyl group.

When $R_1$ to $R_4$ and $R_{11}$ to $R_{14}$ are an aryloxy group, the aryloxy group may be substituted by one or more substituents selected from the group consisting of deuterium, a silane group, a cyano group, a $C_1$-$C_{20}$ alkyl group, a $C_6$-$C_{20}$ aryl group, a $C_6$-$C_{20}$ aryl group substituted by deuterium, a $C_2$-$C_{20}$ heterocyclic group, and a $C_3$-$C_{20}$ cycloalkyl group.

The compound represented by Formula 1 above may be represented by one of Formulas below.

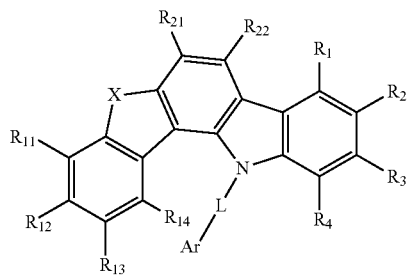

[Formula 2]

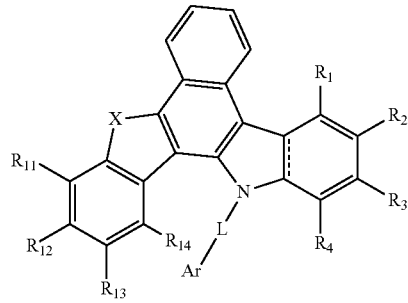

[Formula 3]

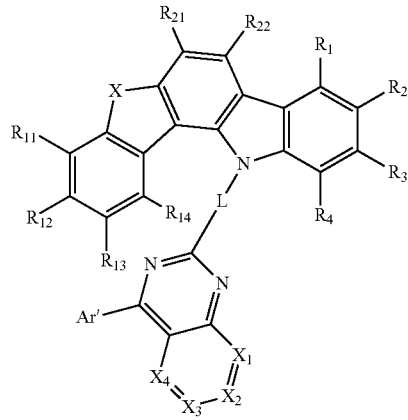

[Formula 4]

[Formula 5]

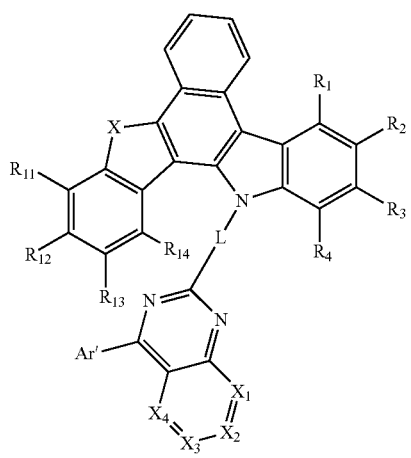

[Formula 6]

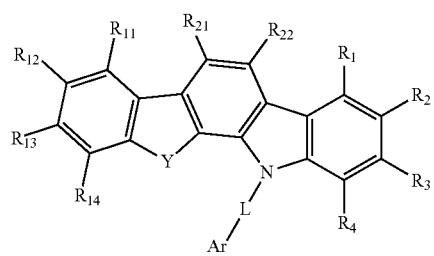

[Formula 7]

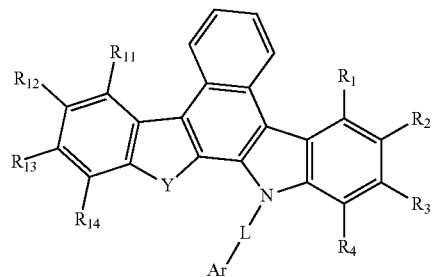

[Formula 8]

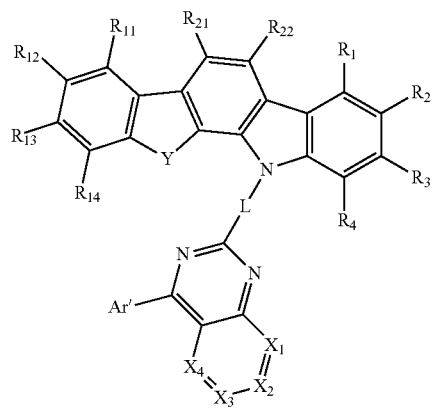

[Formula 9]

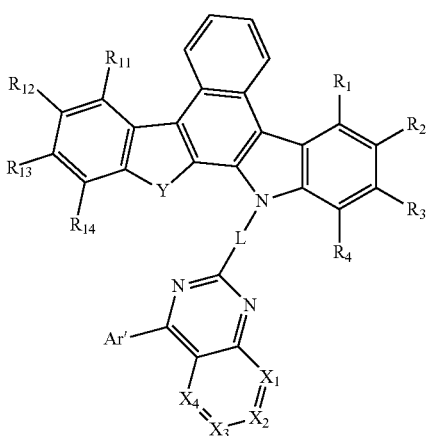

In Formulas 2 to 9 above, Ar' is selected from the group consisting of hydrogen, deuterium, a halogen group, a $C_1$-$C_{20}$ alkyl group, a $C_2$-$C_{20}$ alkenyl group, a $C_1$-$C_{20}$ alkoxy group, -L-N(R')(R''), a $C_6$-$C_{20}$ aryl group, a $C_6$-$C_{20}$ aryl group substituted by deuterium, a $C_7$-$C_{20}$ arylalkyl group, a $C_8$-$C_{20}$ arylalkenyl group, a $C_2$-$C_{20}$ heterocyclic group, a nitrile group, and an acetylene group.

$X_1$-$X_4$ are $CR_{41}$ or N, wherein $R_{41}$ may be hydrogen, deuterium, a $C_6$-$C_{20}$ aryl group, or a $C_2$-$C_{20}$ heterocyclic group, and $R_1$ to $R_4$, $R_{11}$ to $R_{14}$, $R_{21}$, $R_{22}$, R', R'', X, Y, L, and Ar are as defined in Formula 1 above.

More specially, the compound represented by Formula 1 above may be one of compounds below.

1-1

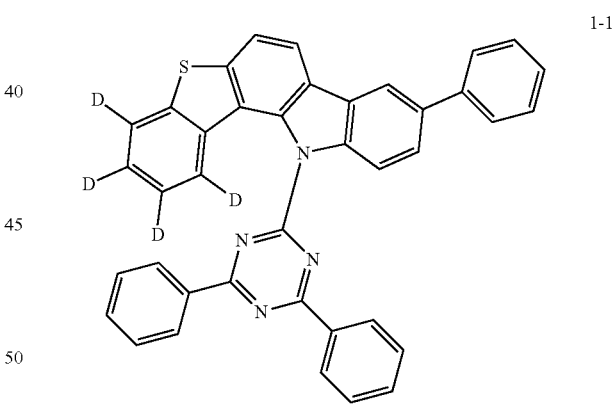

1-2

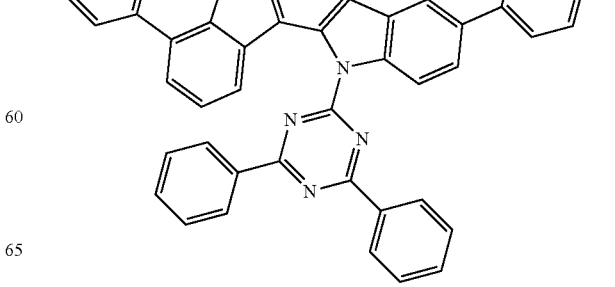

-continued
1-3
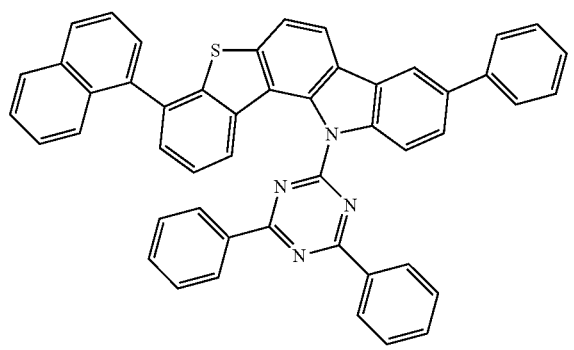
1-4
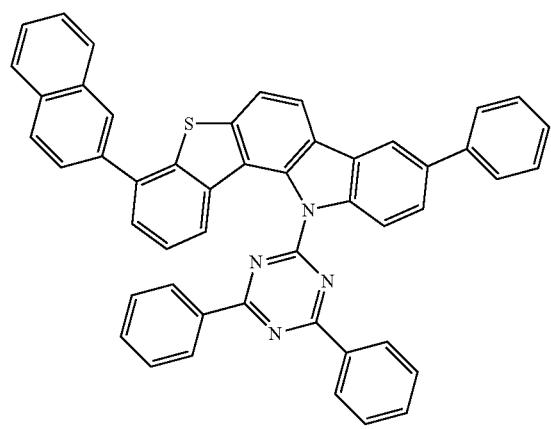
1-5
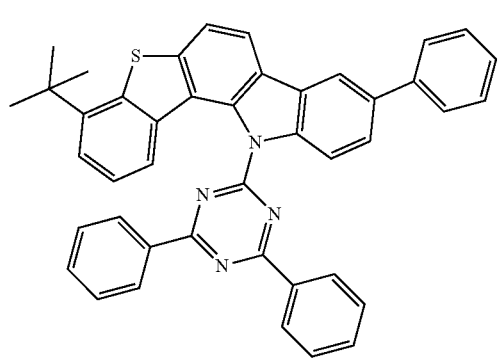
1-6
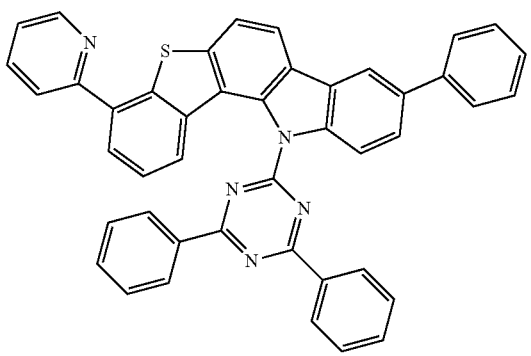
-continued
1-7
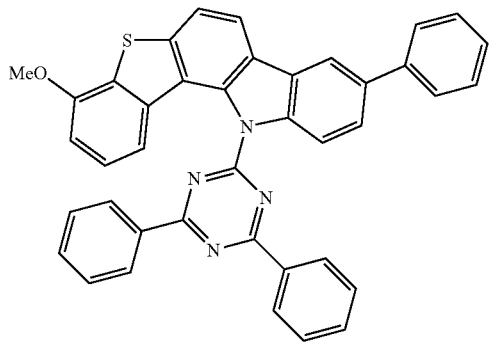
1-8
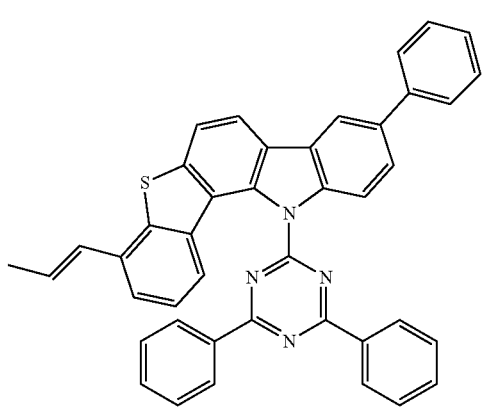
1-9
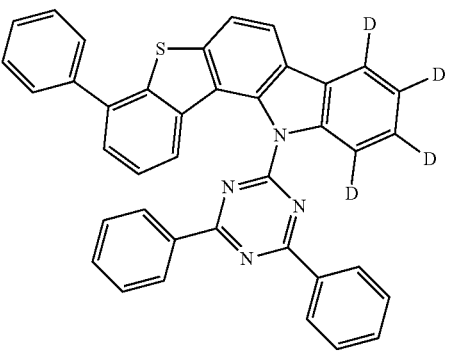
1-10
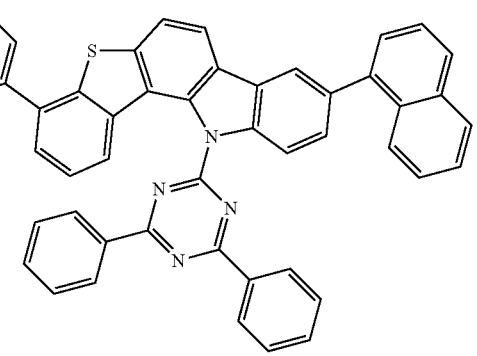

-continued
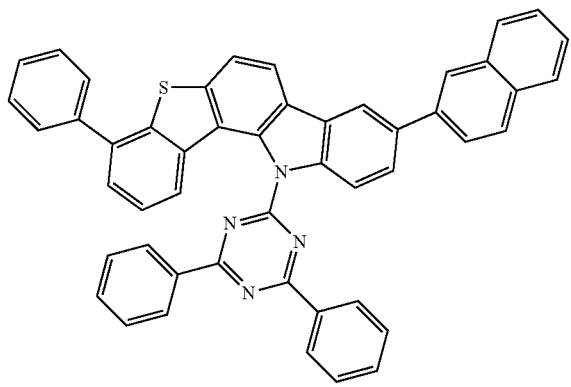
1-11
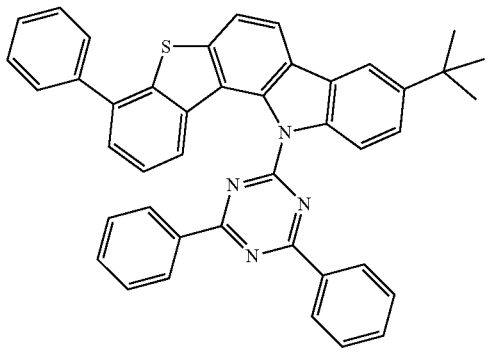
1-12
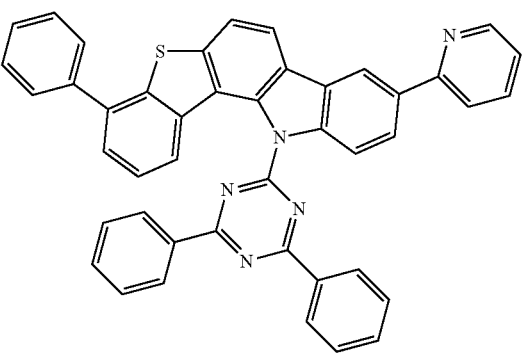
1-13
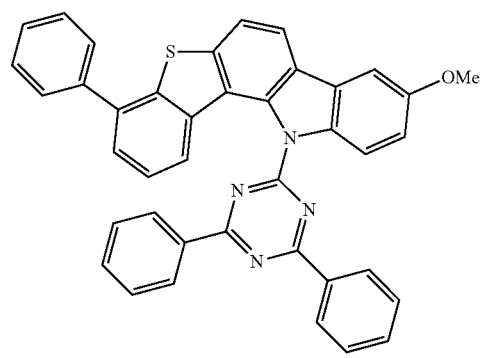
1-14
-continued
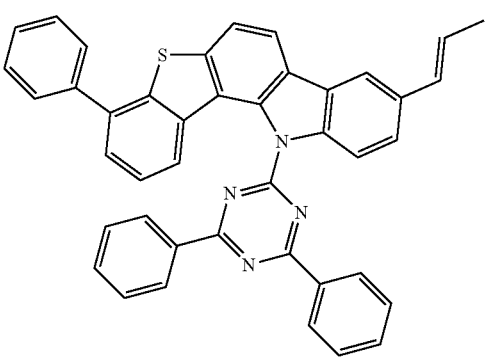
1-15
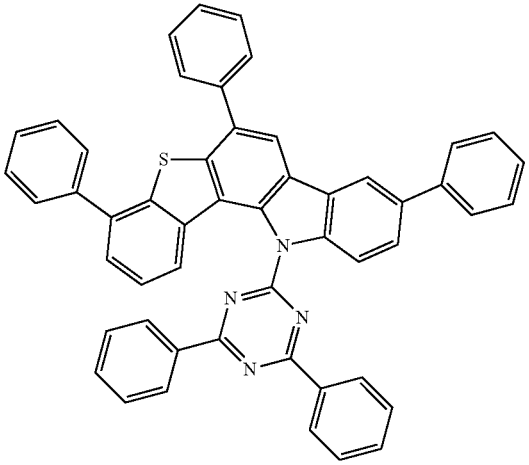
1-16
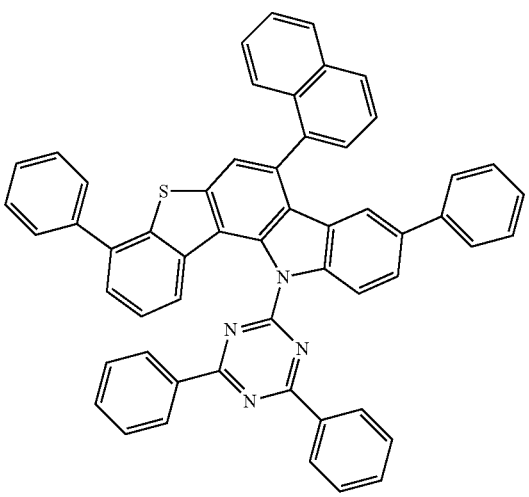
1-17

1-18
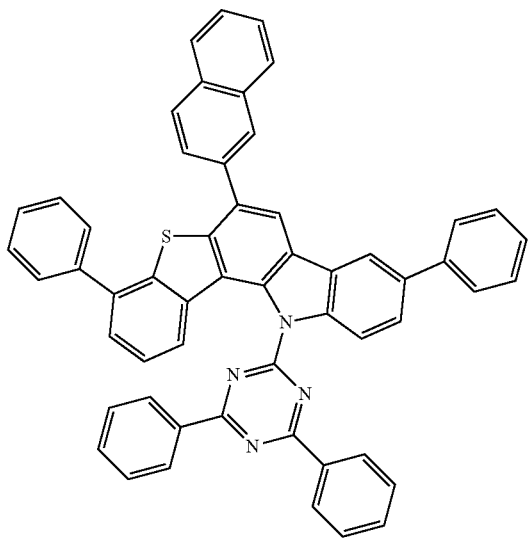
1-19
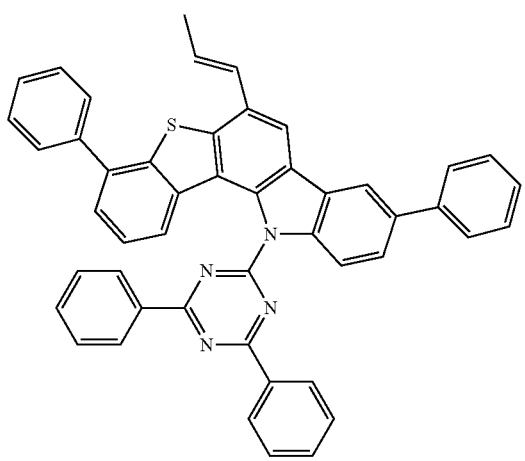
1-20
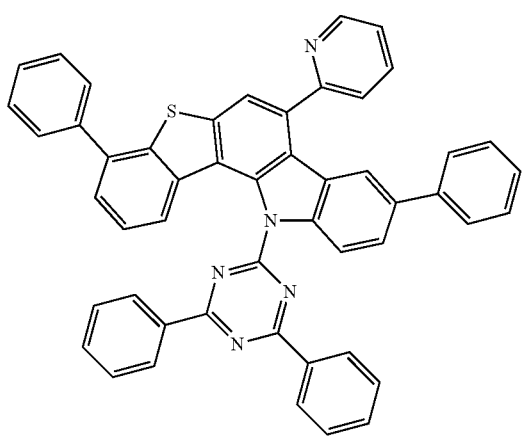
1-21
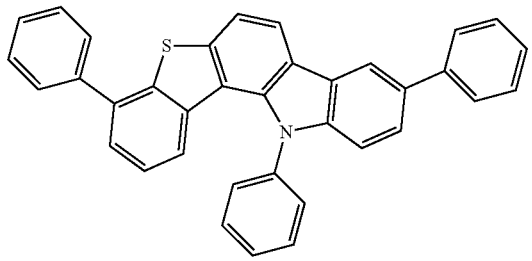
1-22
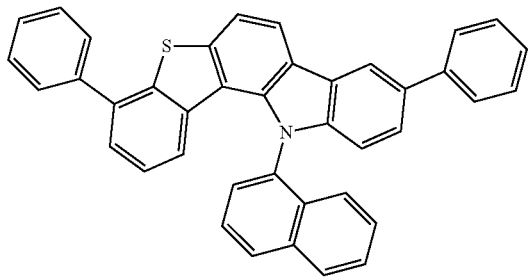
1-23
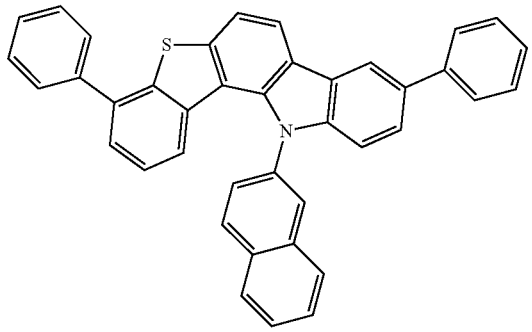
1-24
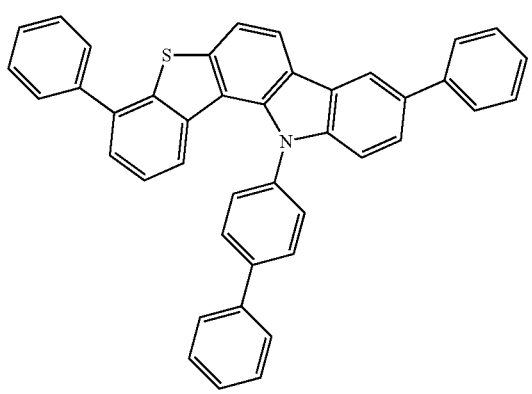

17
-continued
1-25
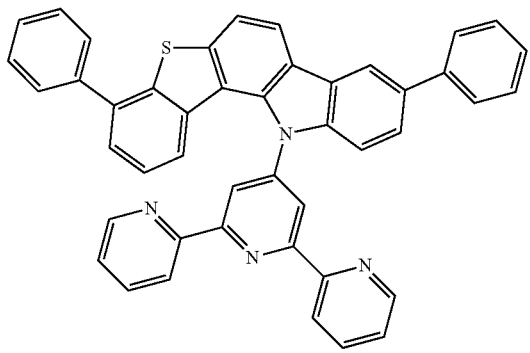
1-26
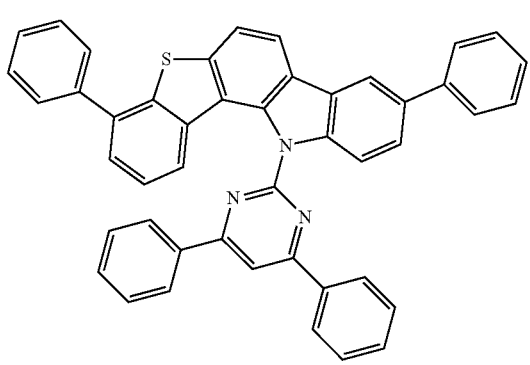
1-27
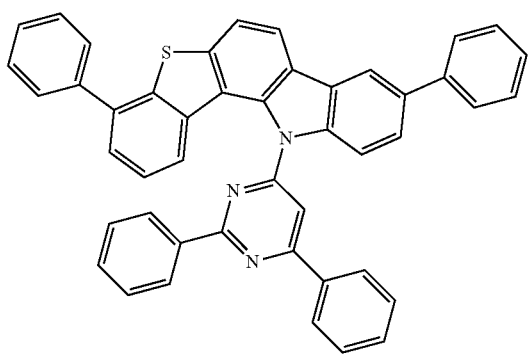
1-28
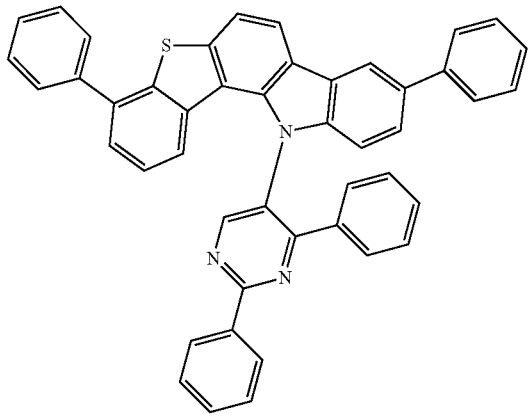
18
-continued
1-29
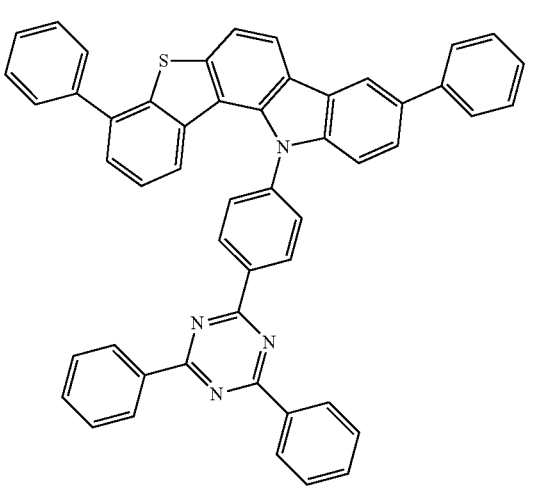
1-30
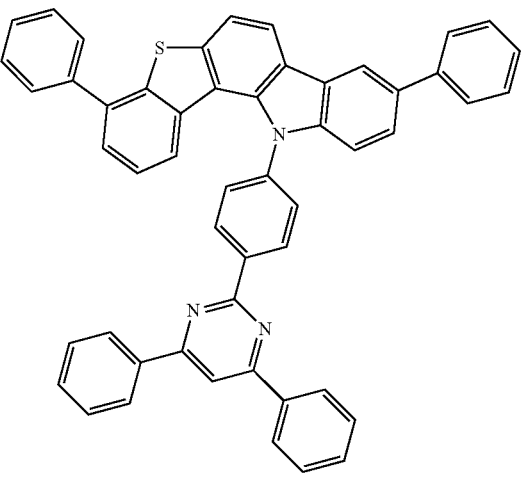
1-31
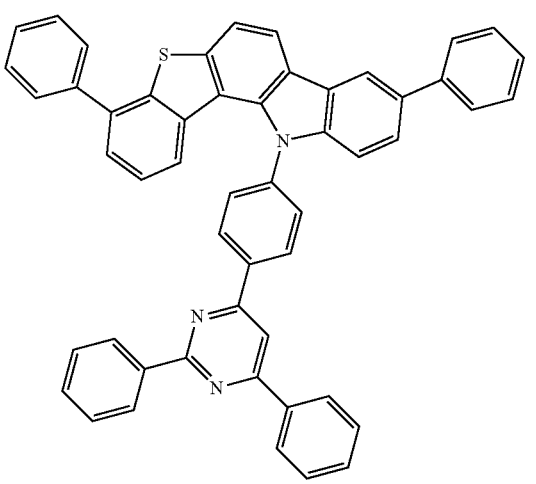

1-32
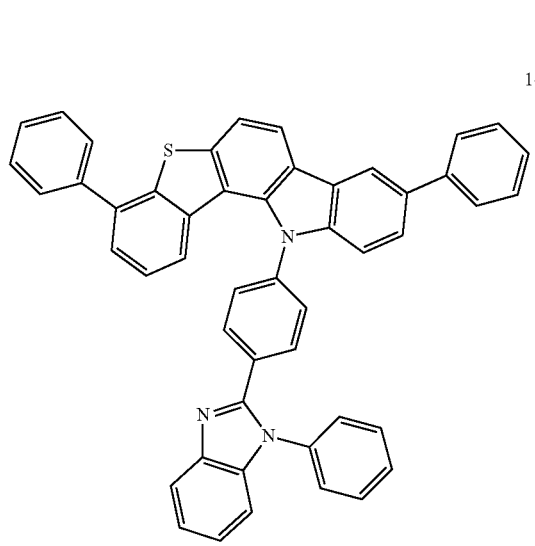
2-1
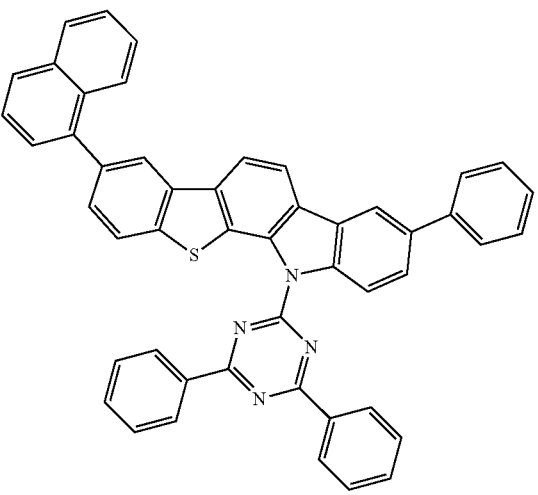
2-2
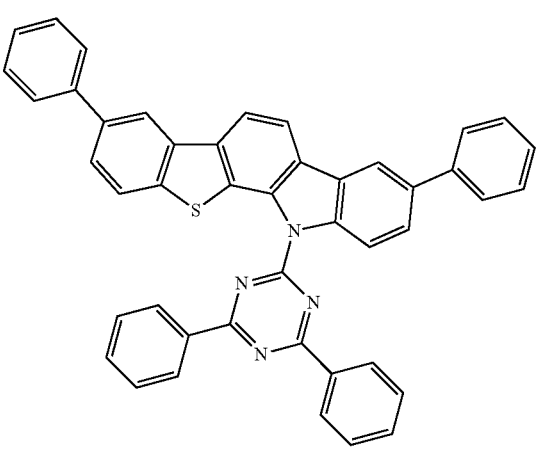
2-3
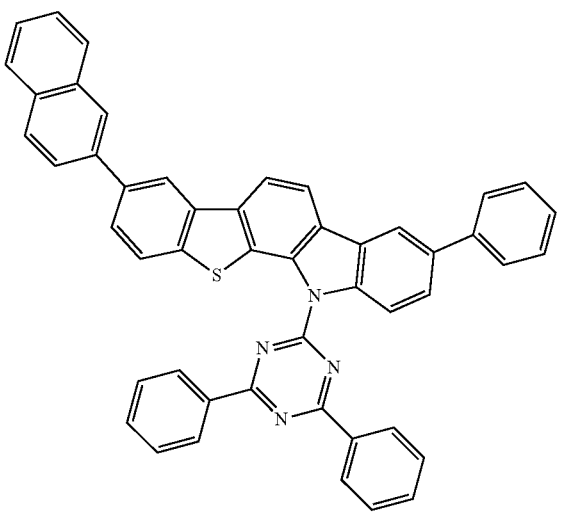
2-4
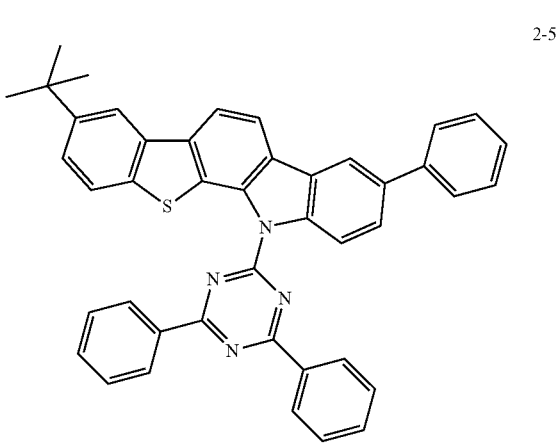
2-5

2-6
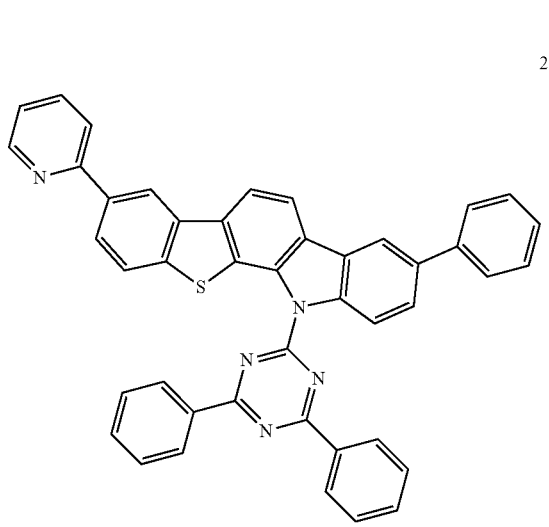
2-9
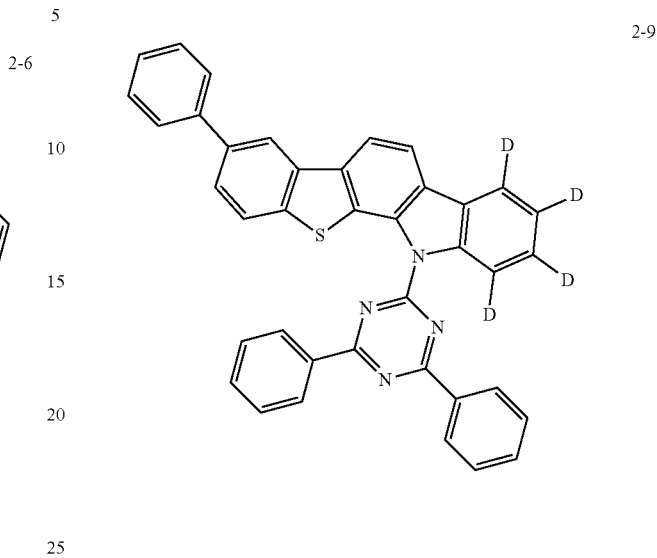
2-7
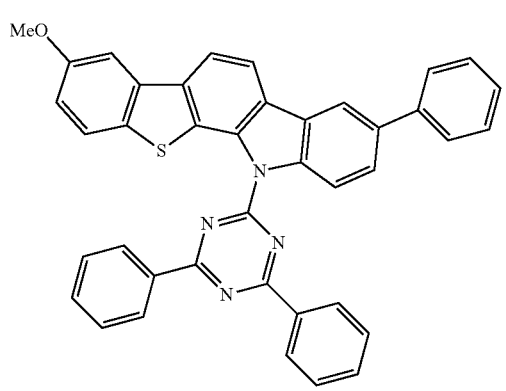
2-10
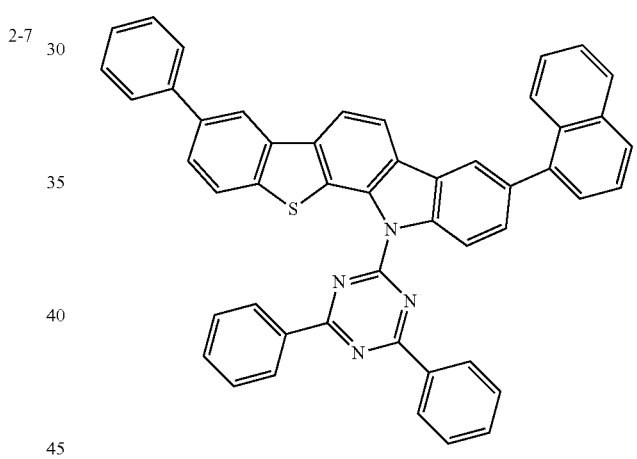
2-8
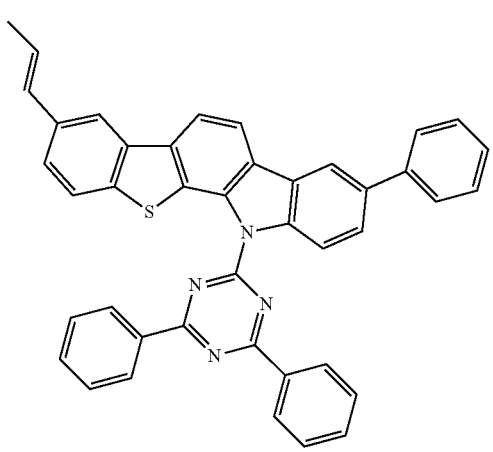
2-11
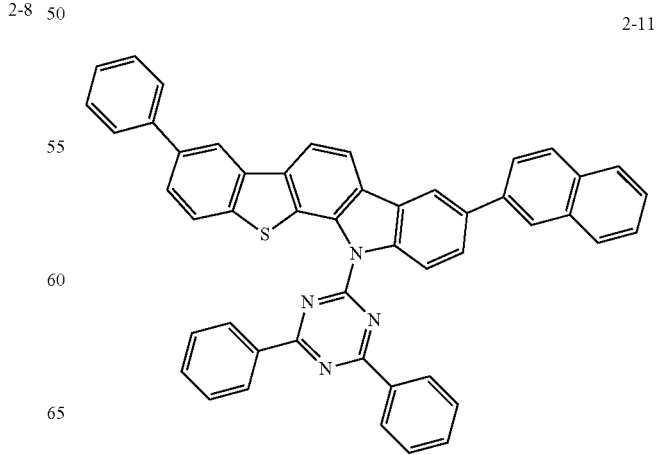

2-12
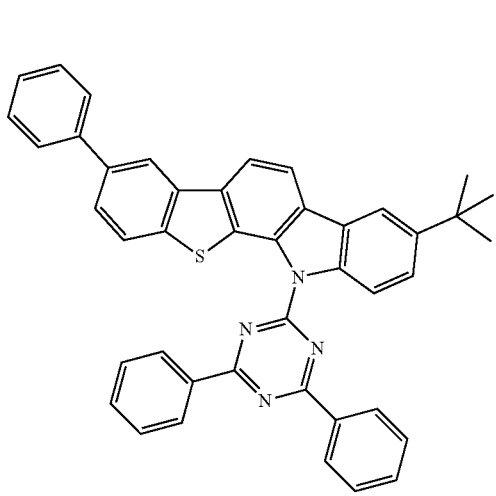
2-13
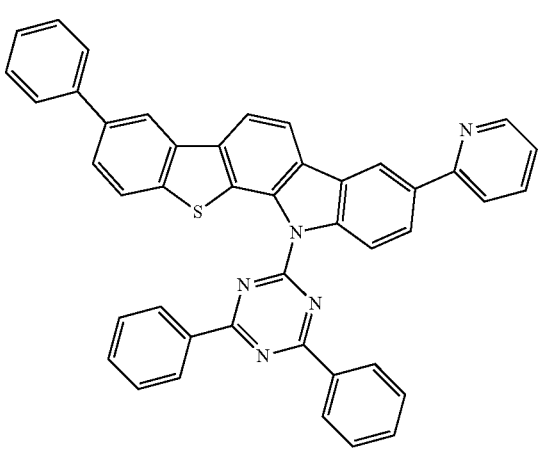
2-14
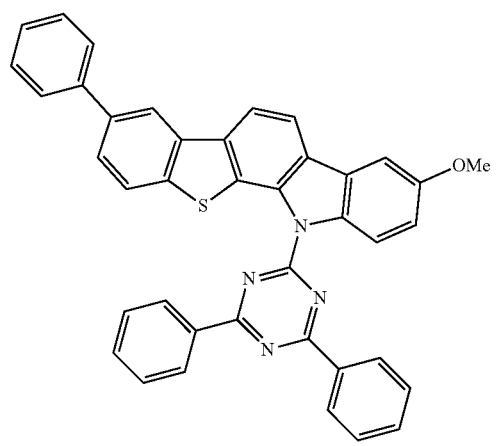
2-15
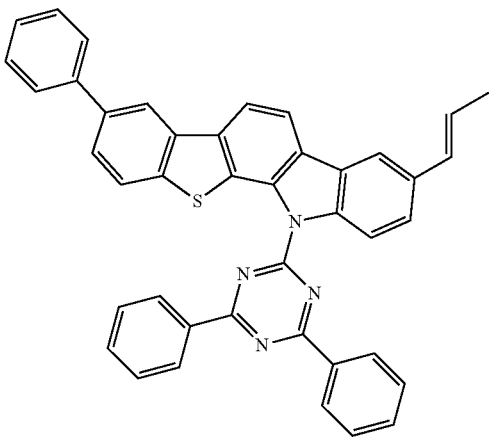
2-16
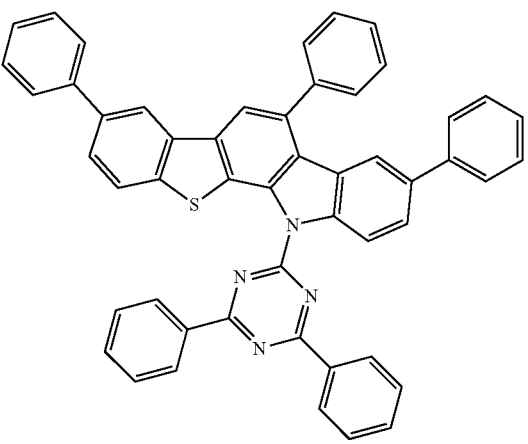
2-17
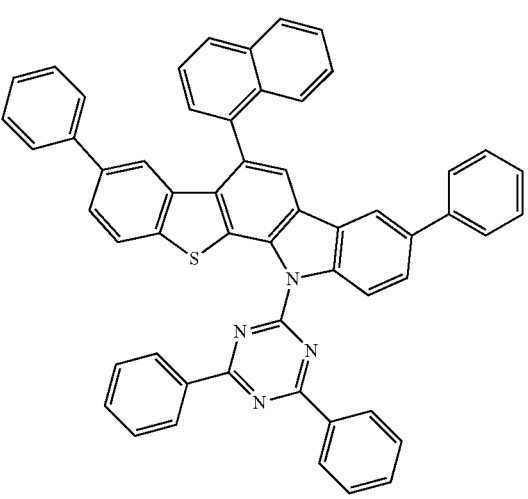

2-18
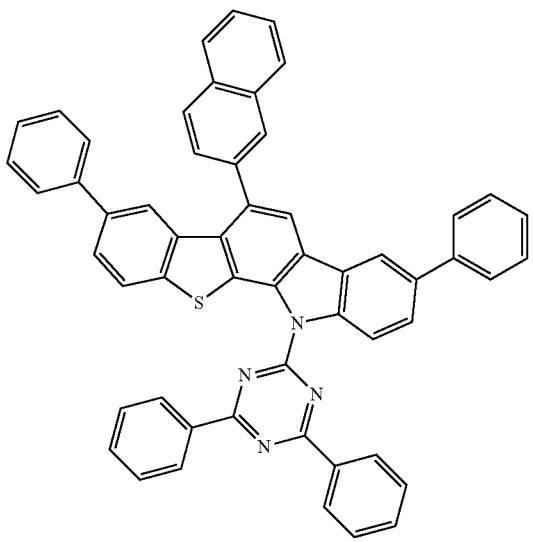
2-19
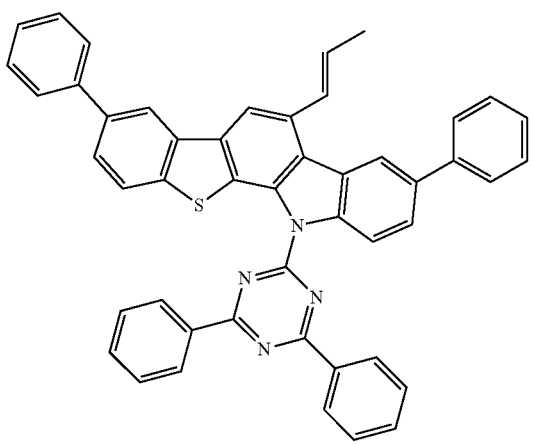
2-20
2-21
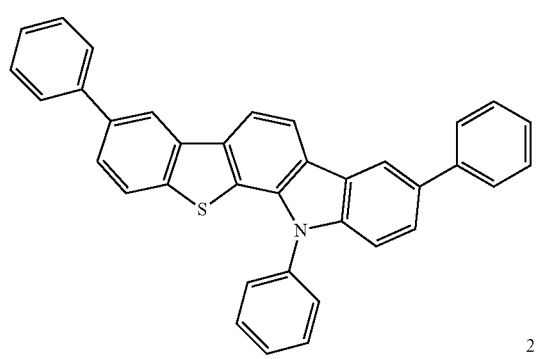
2-22
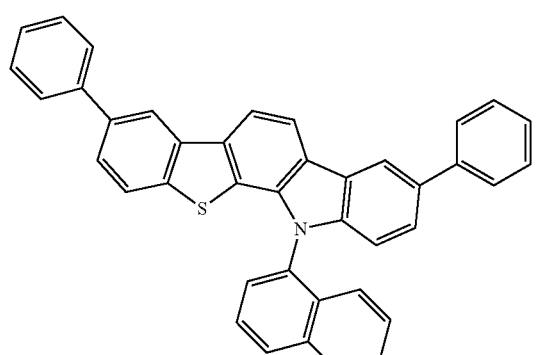
2-23
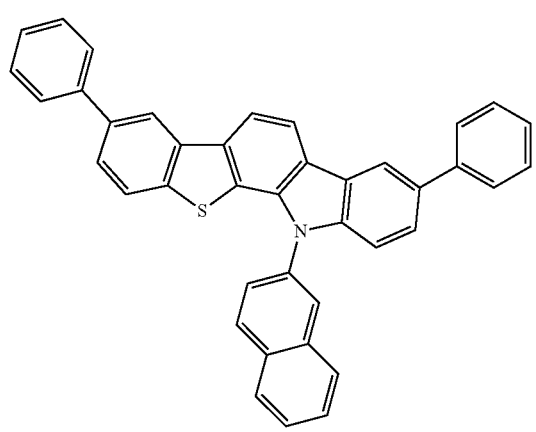
2-24
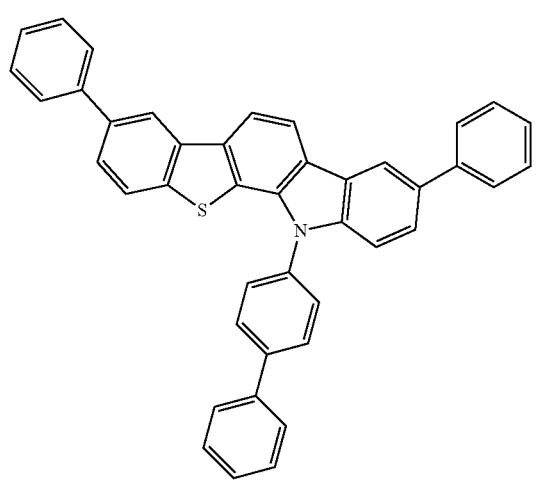

2-25
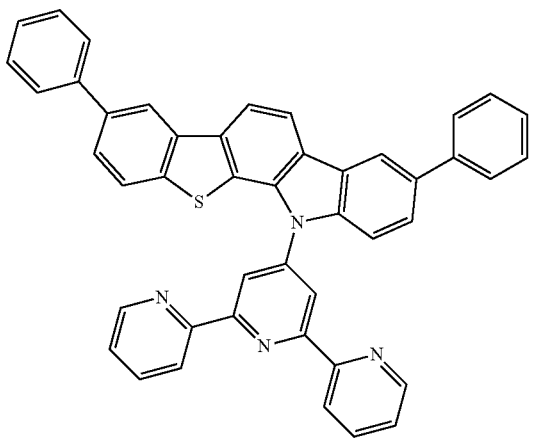
2-26
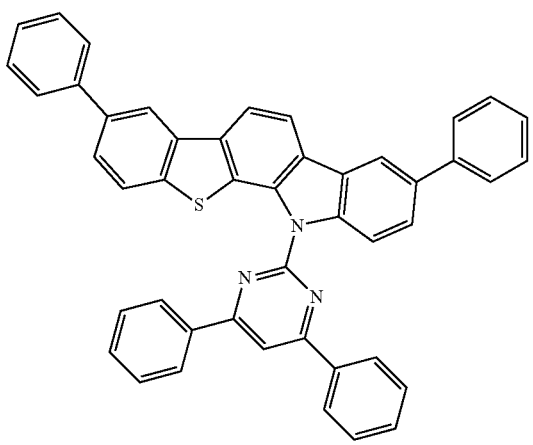
2-27
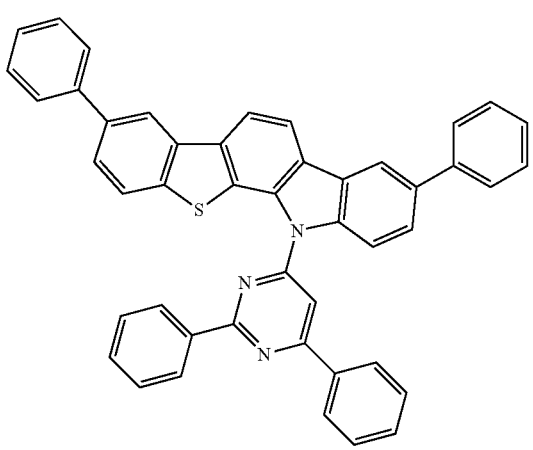
2-28
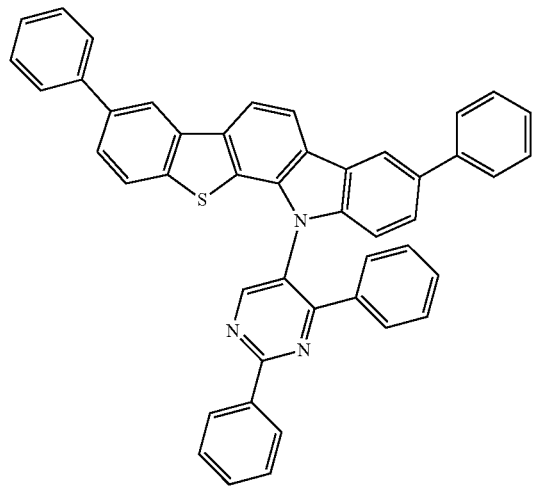
2-29
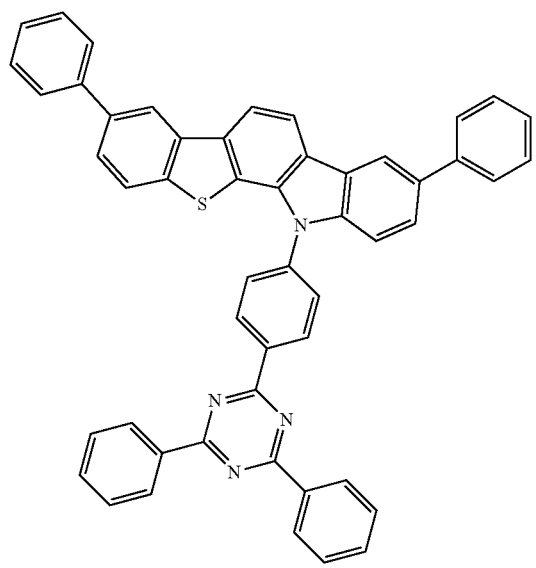
2-30
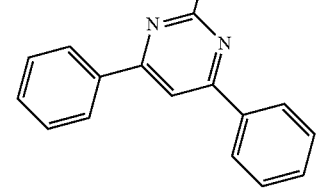

-continued
2-31
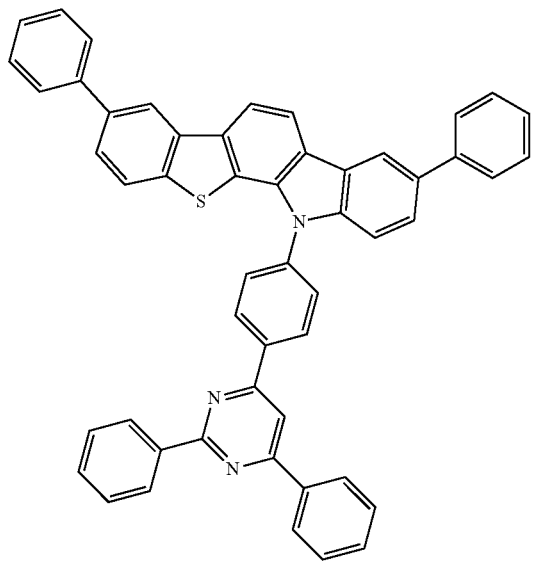
2-32
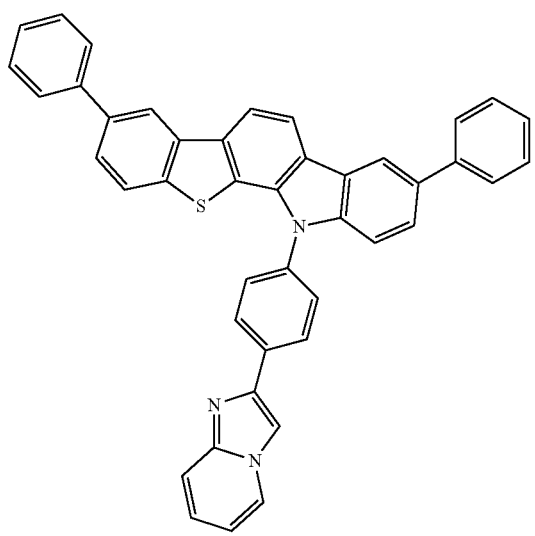
3-1
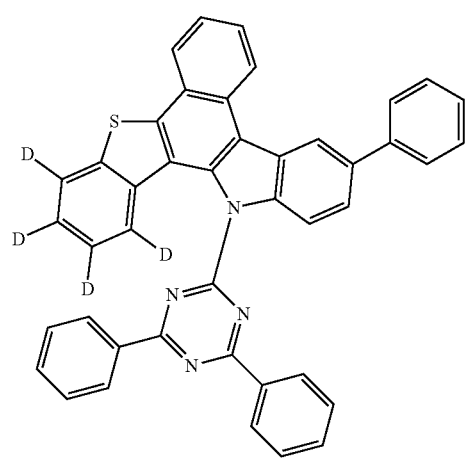
-continued
3-2
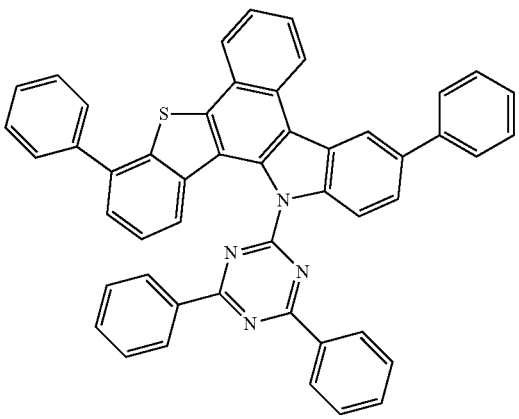
3-3
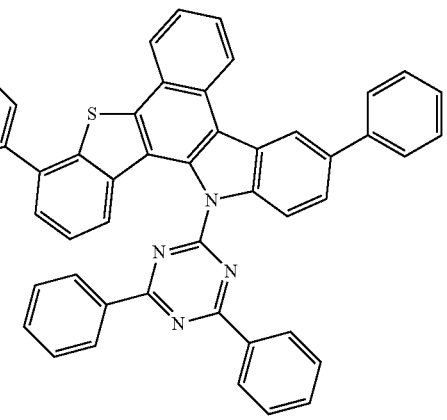
3-4
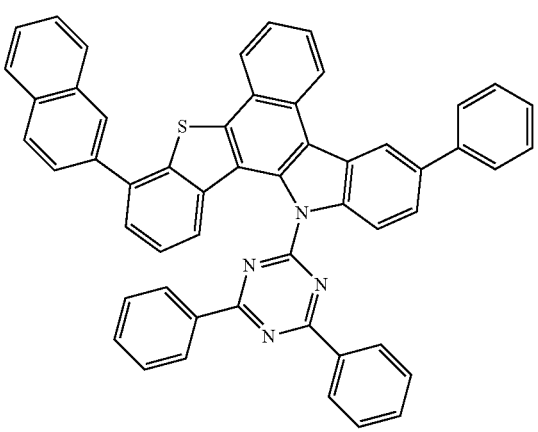

31
-continued
3-5
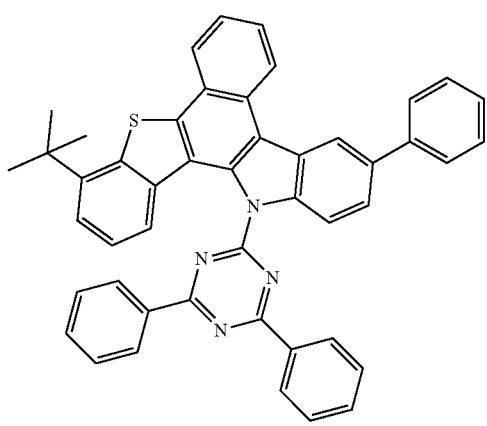
3-6
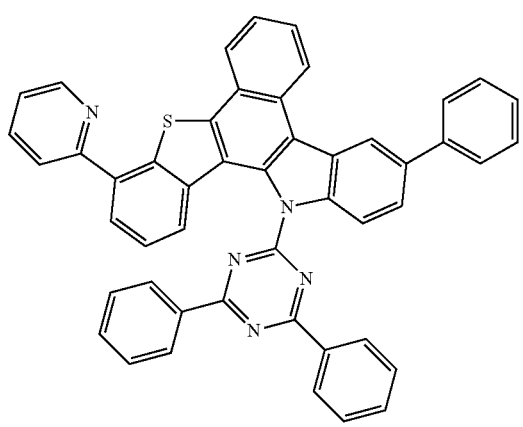
3-7
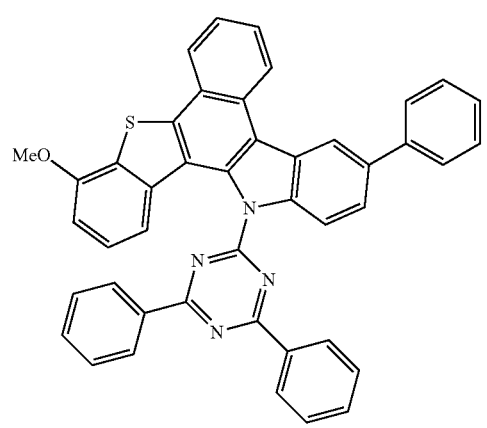
32
-continued
3-8
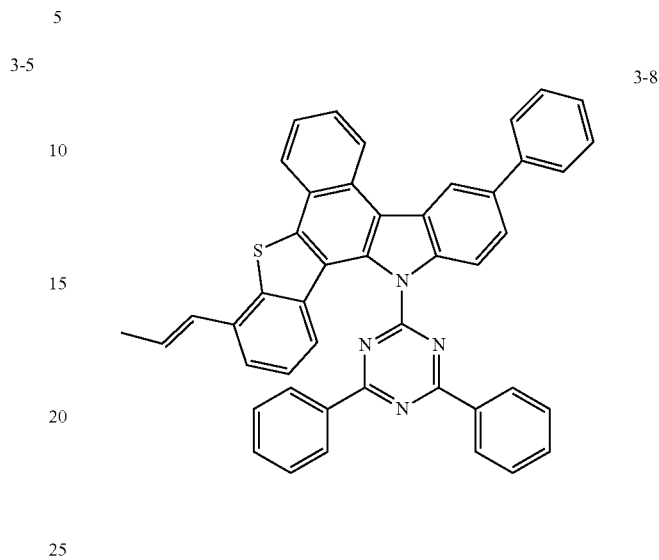
3-9
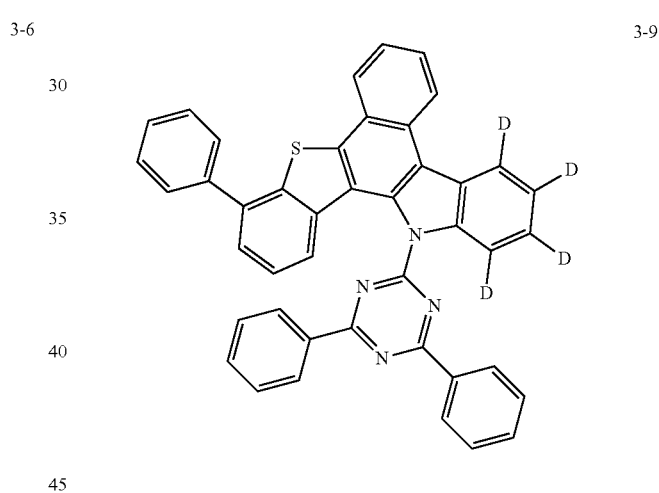
3-10
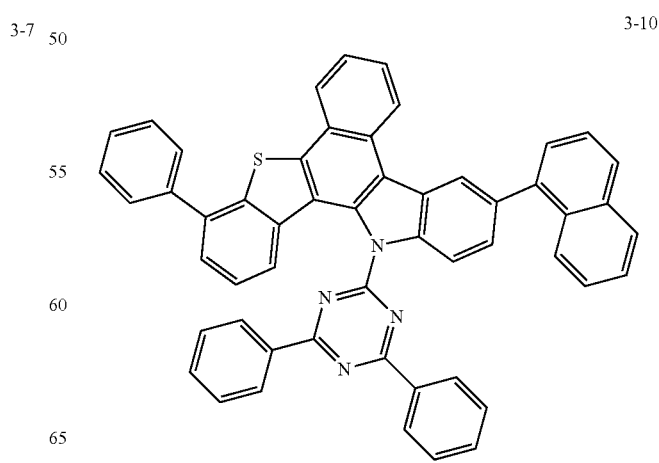

-continued
3-11
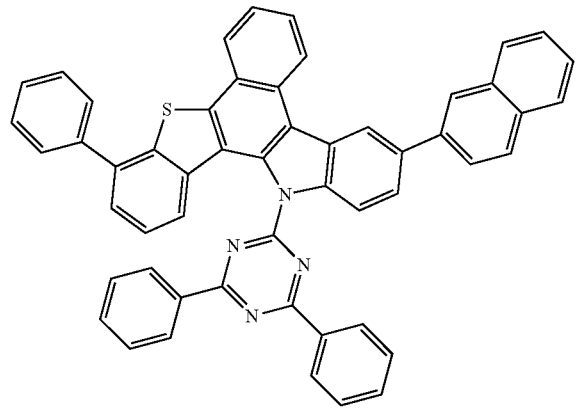
3-12
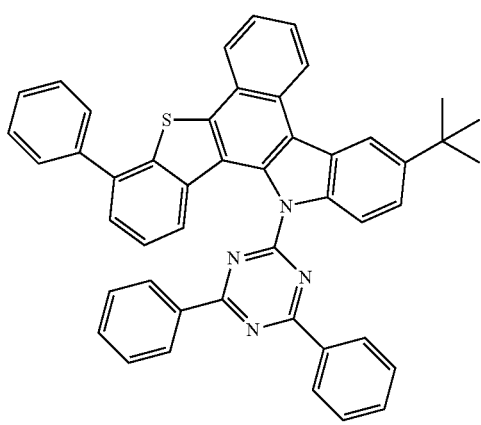
3-13
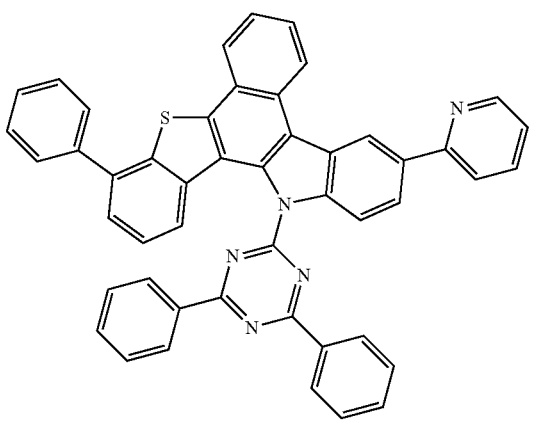
-continued
3-14
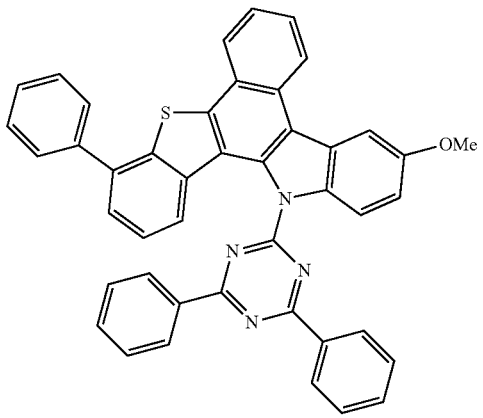
3-15
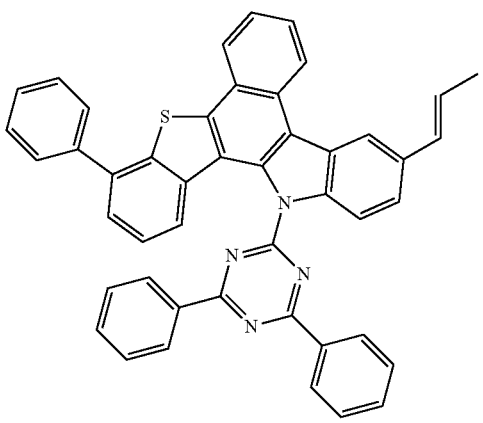
3-16
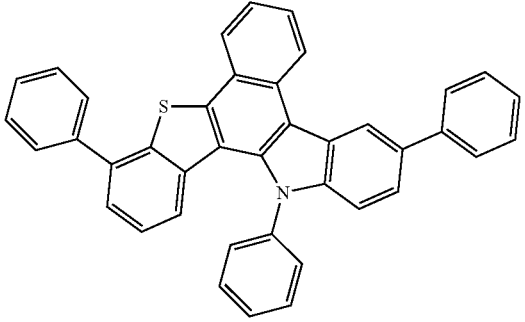
3-17
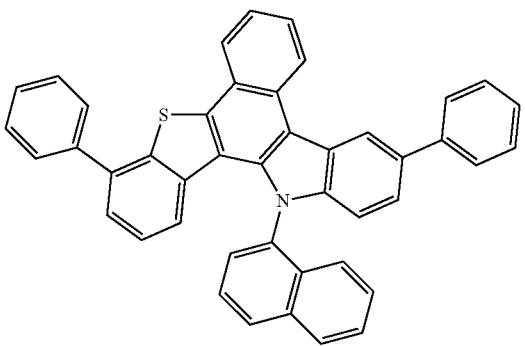

3-18
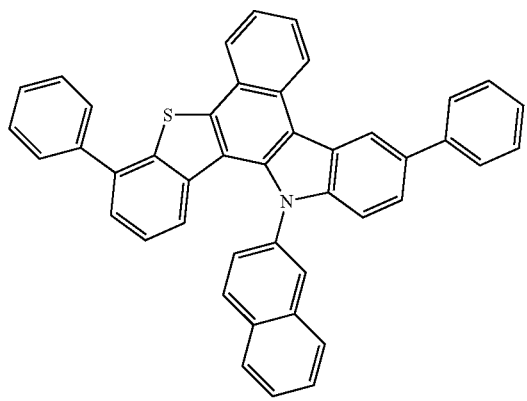
3-21
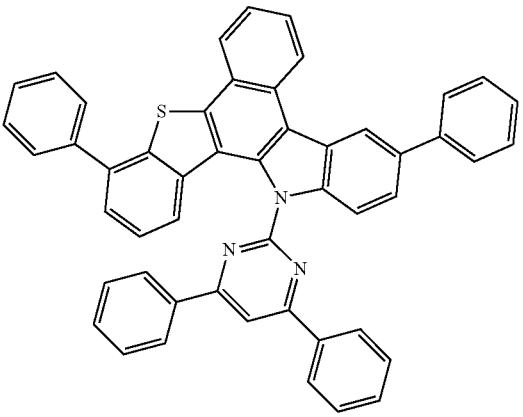
3-19
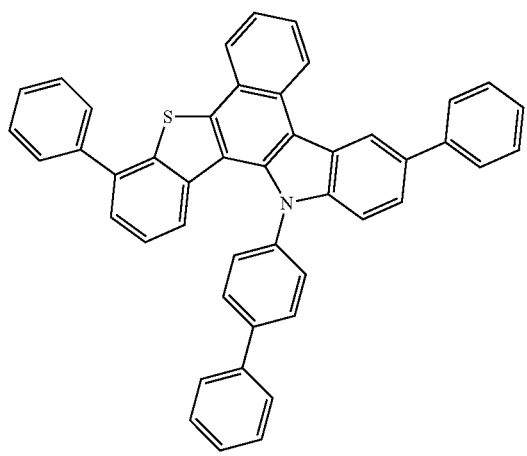
3-22
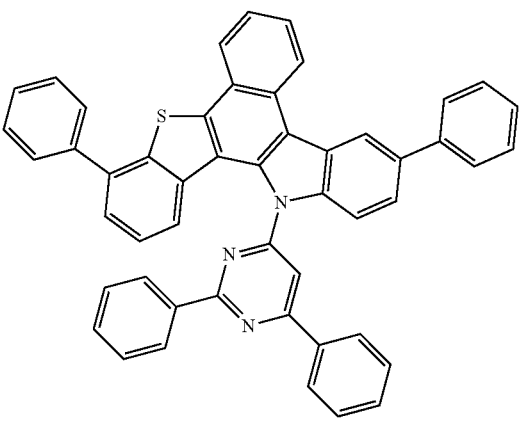
3-20
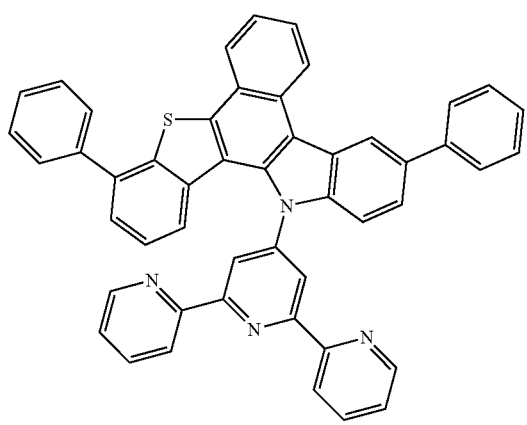
3-23
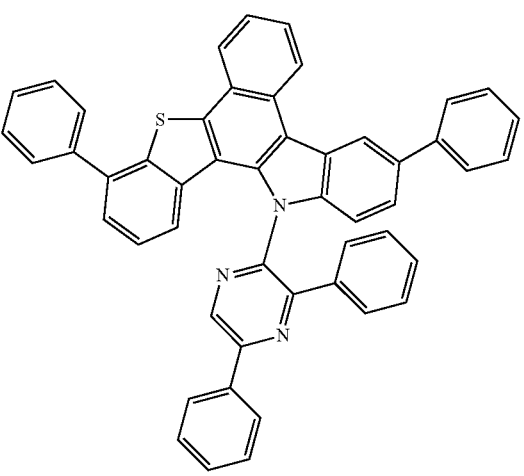

3-24
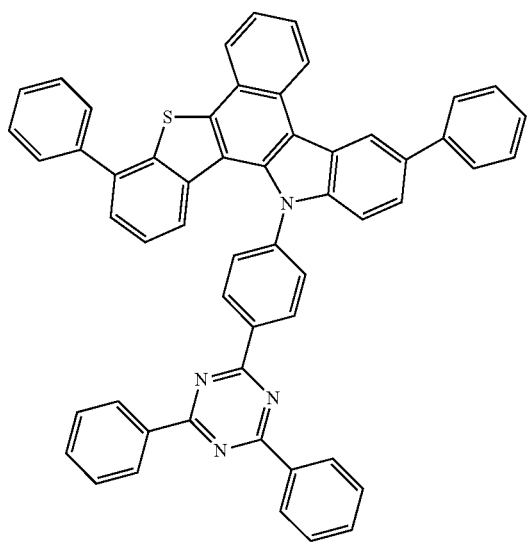
3-25
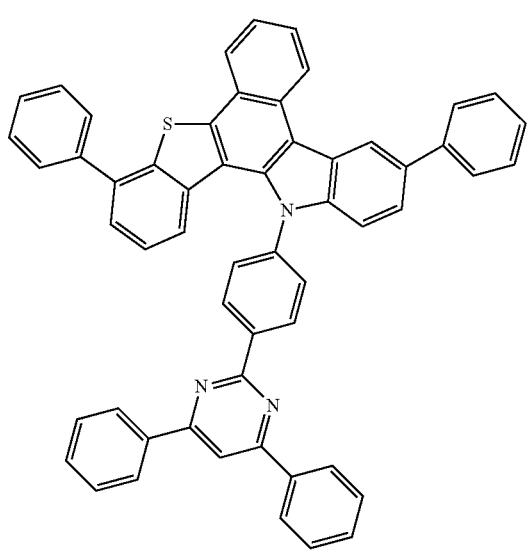
3-26
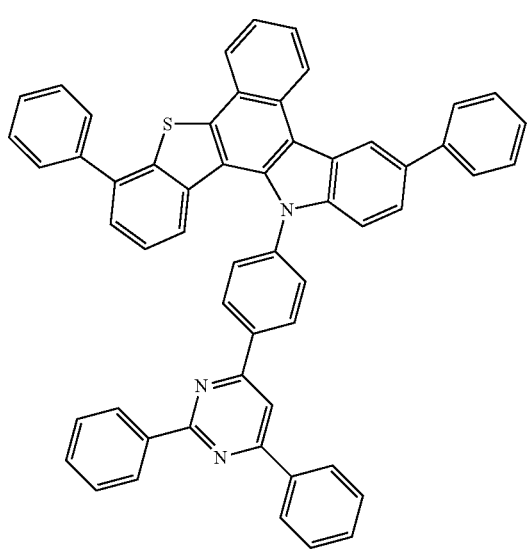
3-27
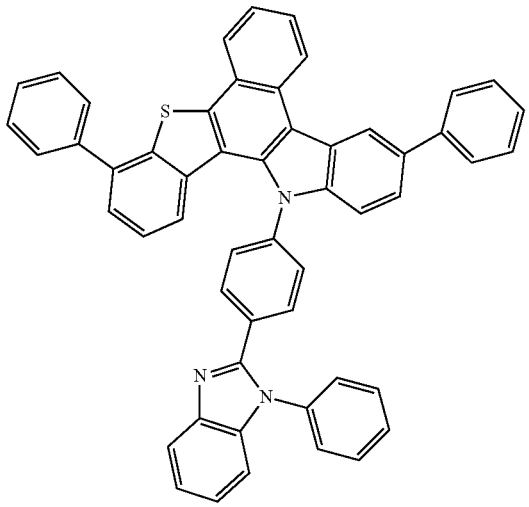
3-28
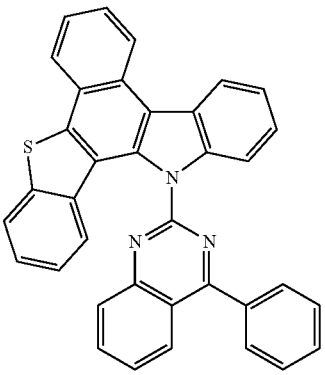
3-29
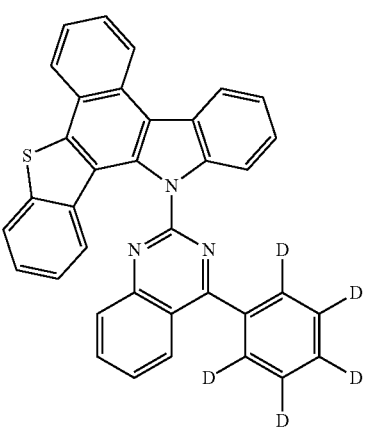

3-30
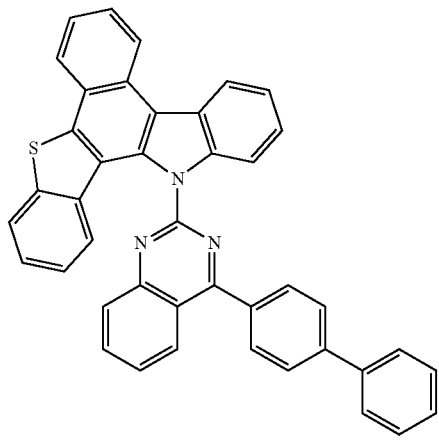
3-31
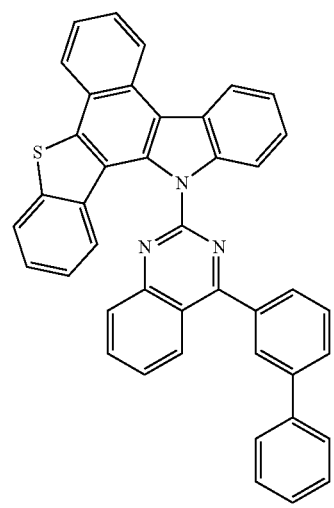
3-32
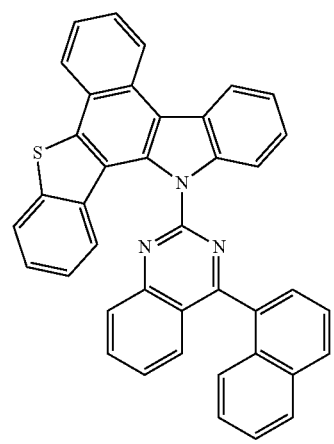
3-33
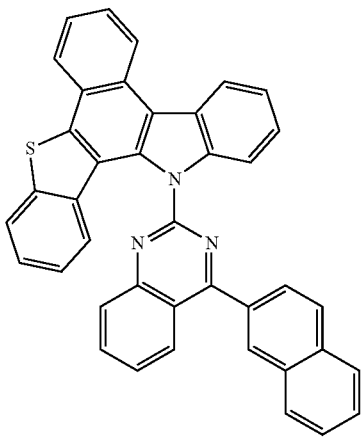
3-34
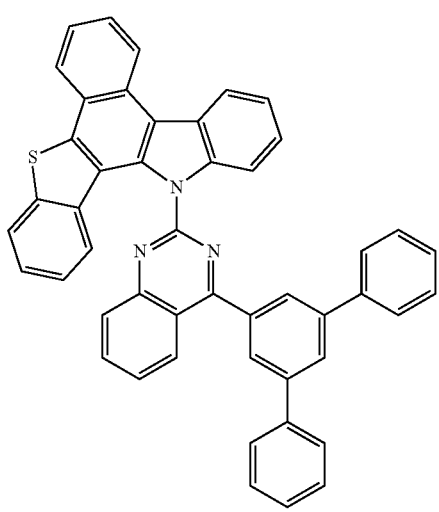
3-35
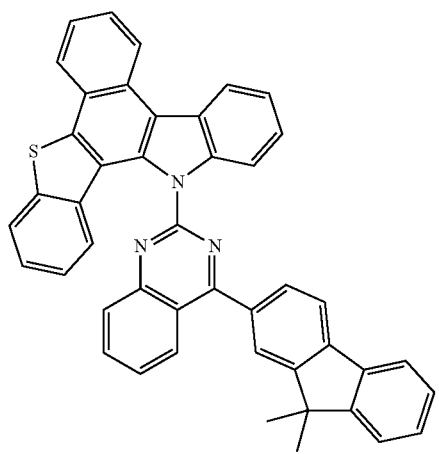

3-36
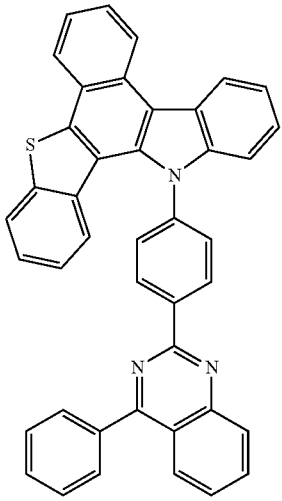
3-37
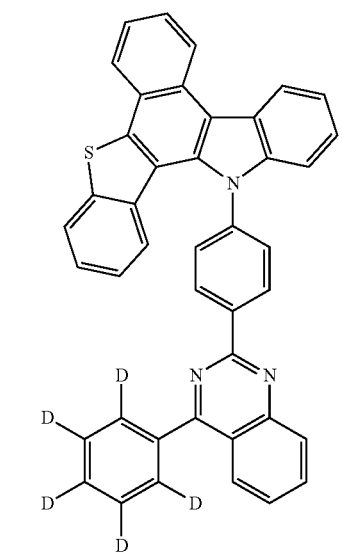
3-38
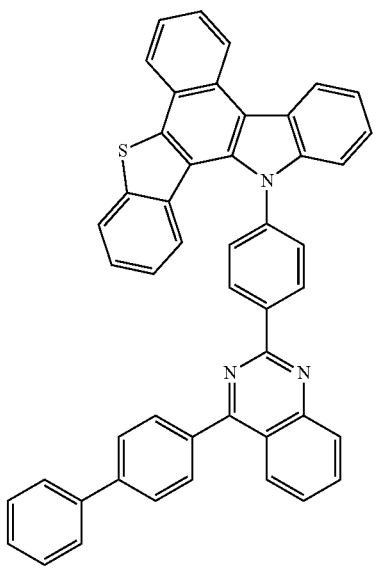
3-39
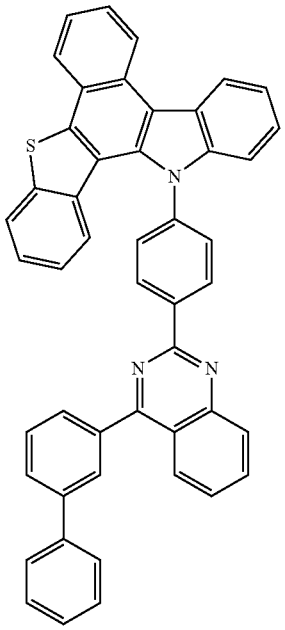
3-40
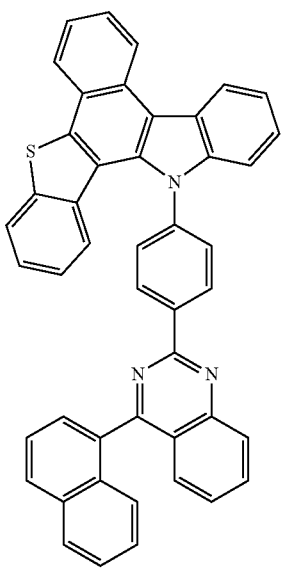

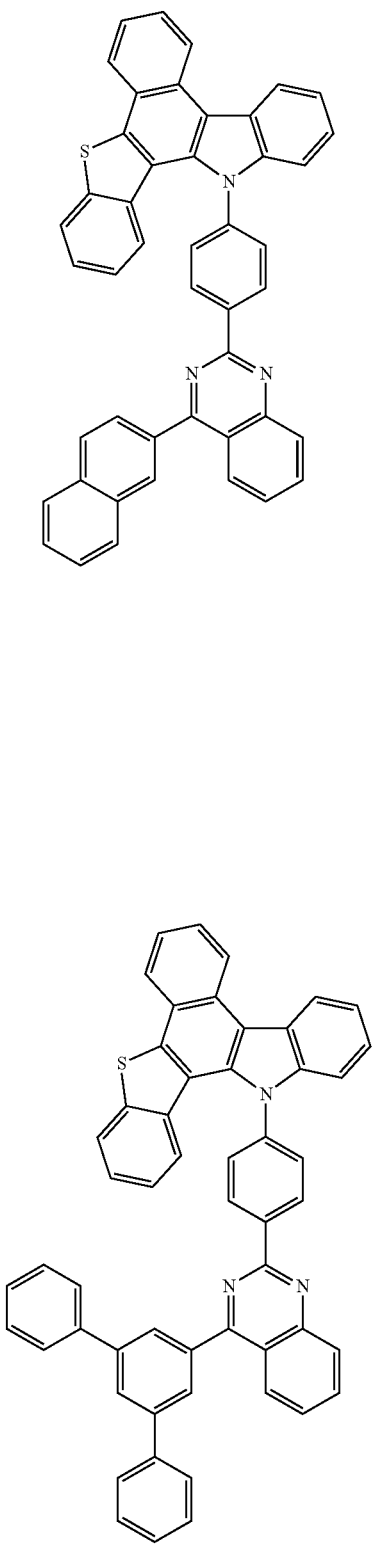
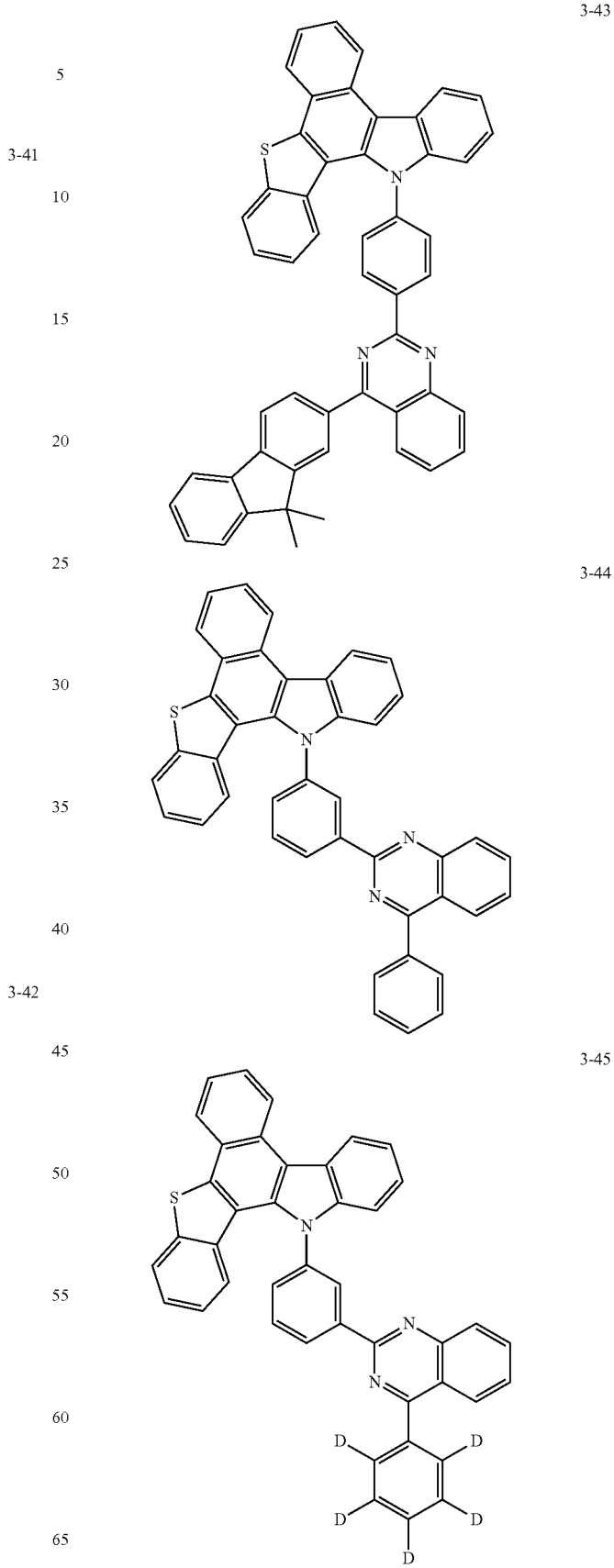

3-46
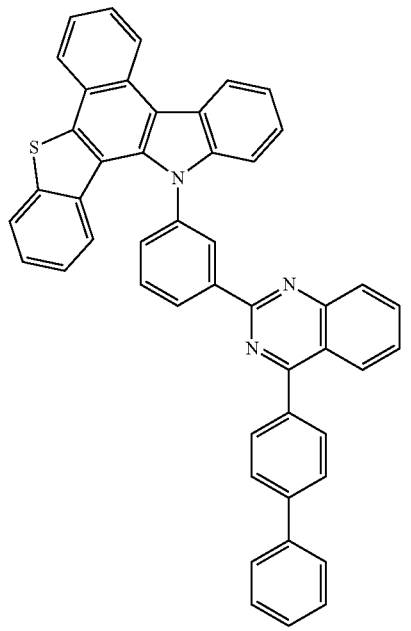
3-47
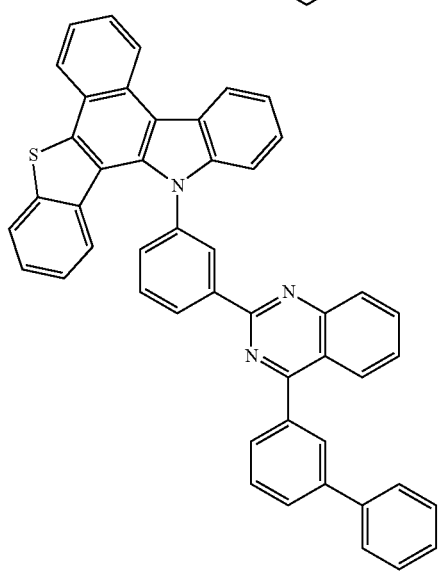
3-48
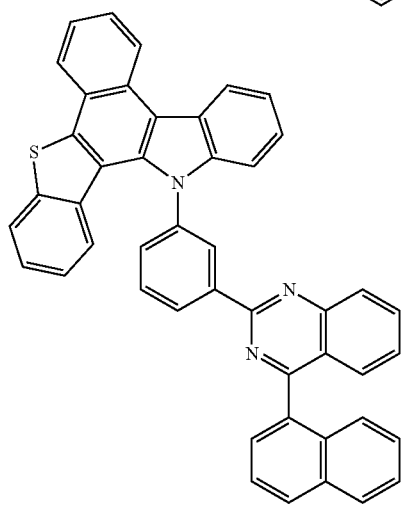
3-49
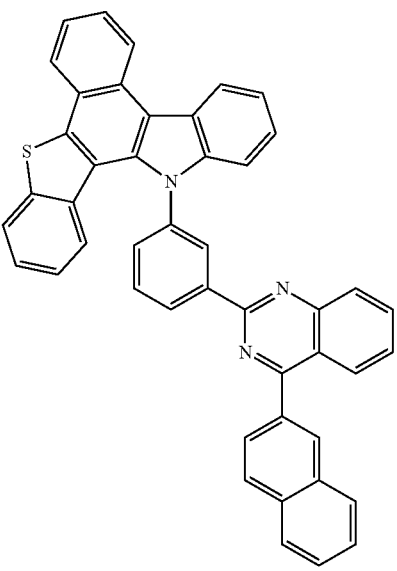
3-50
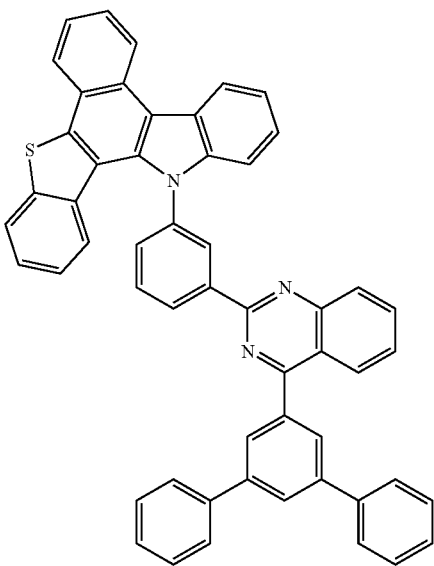

3-51
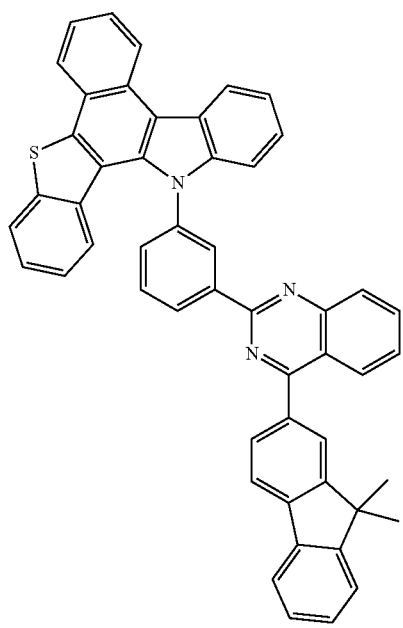
4-3
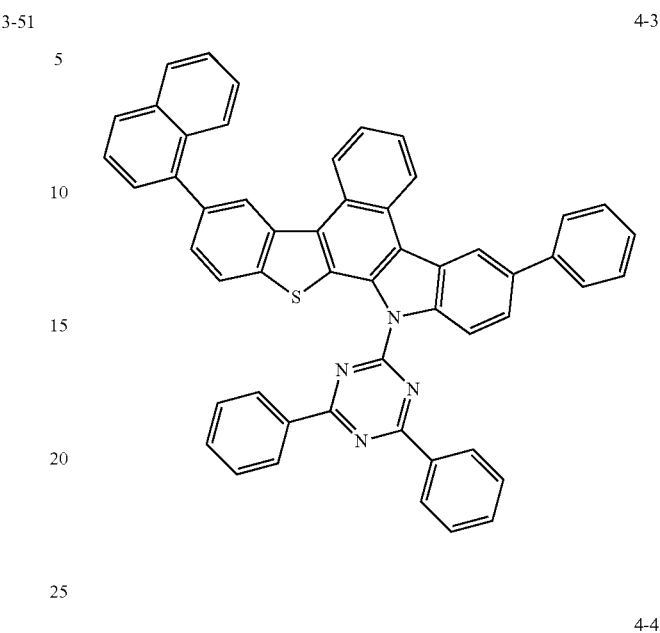
4-1
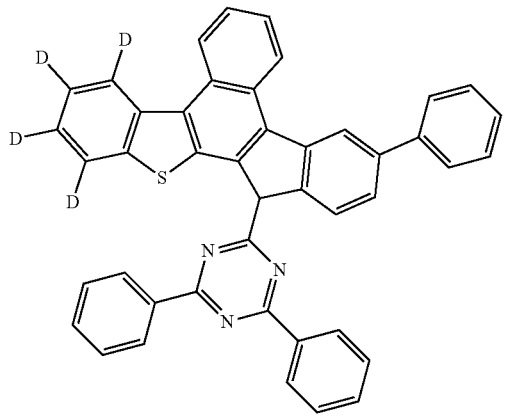
4-4
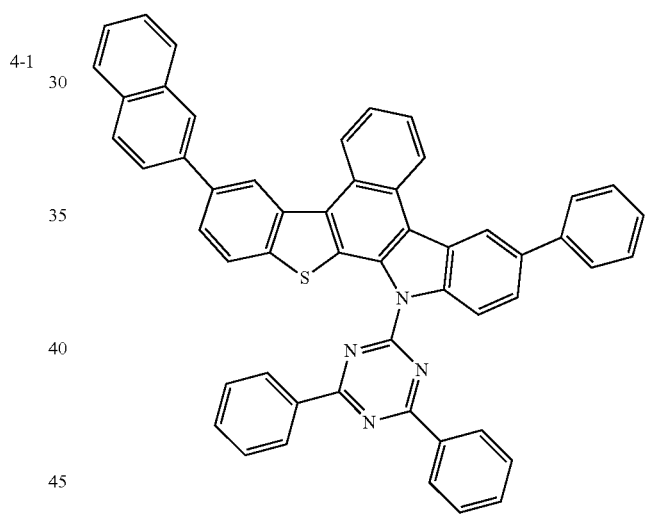
4-2
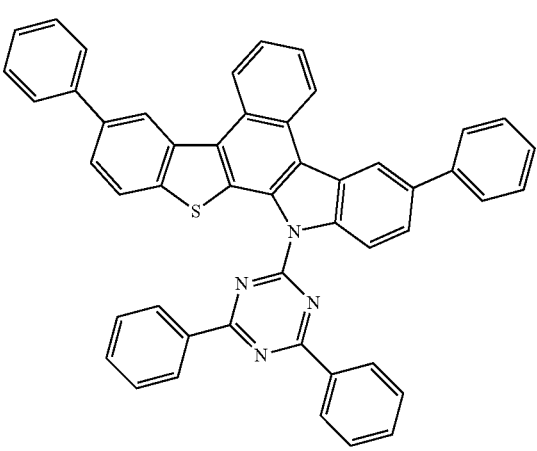
4-5
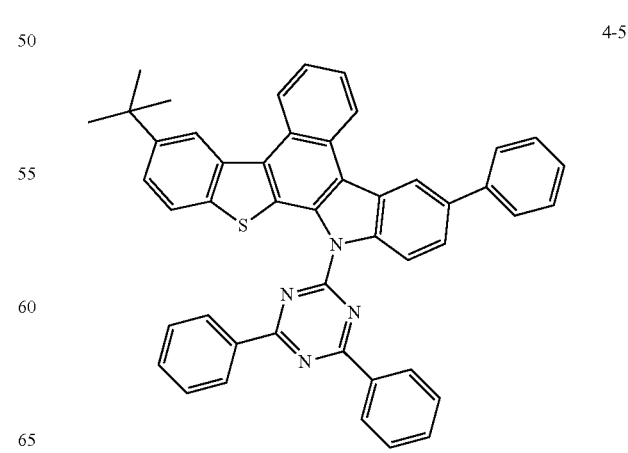

4-6
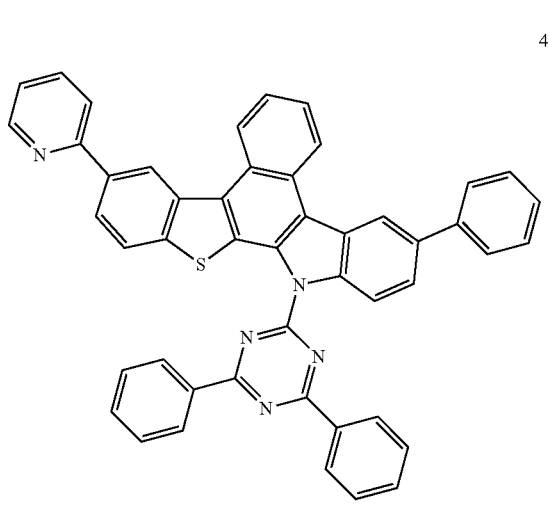
4-7
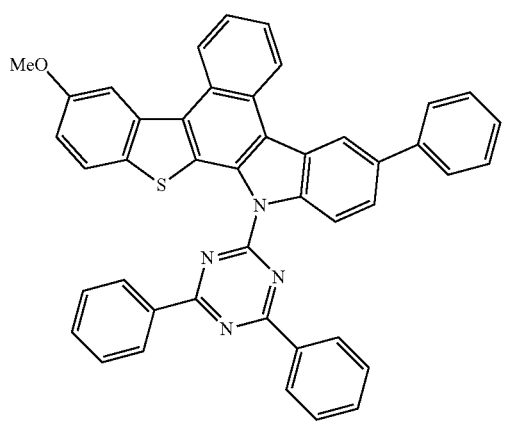
4-8
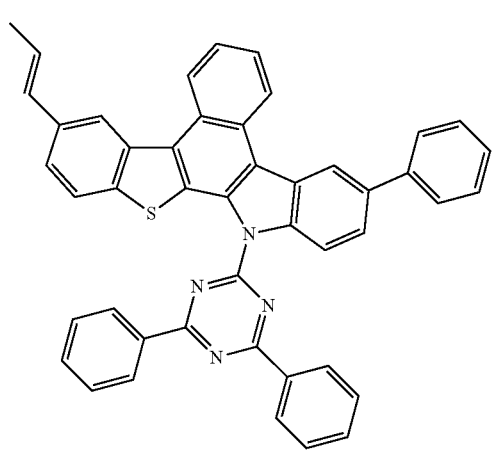
4-9
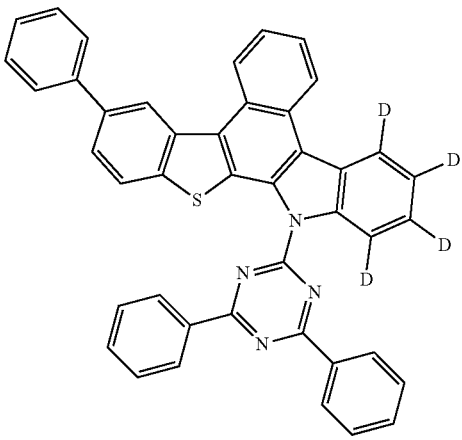
4-10
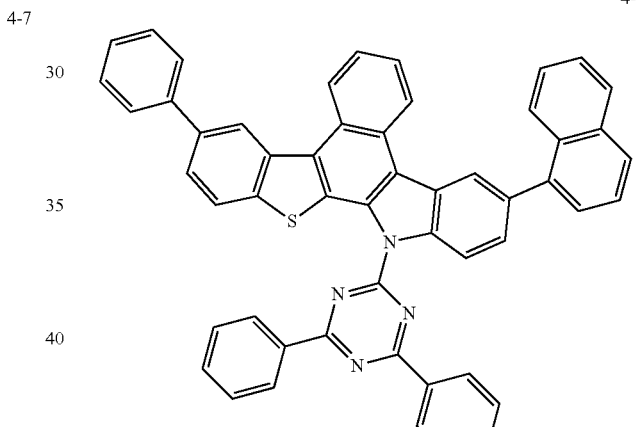
4-11
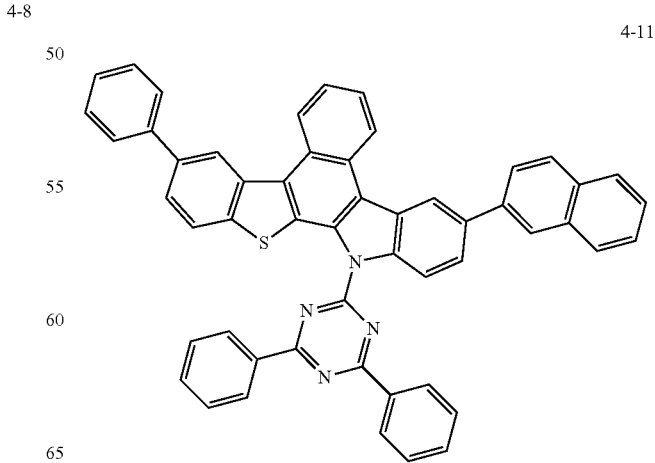

4-12
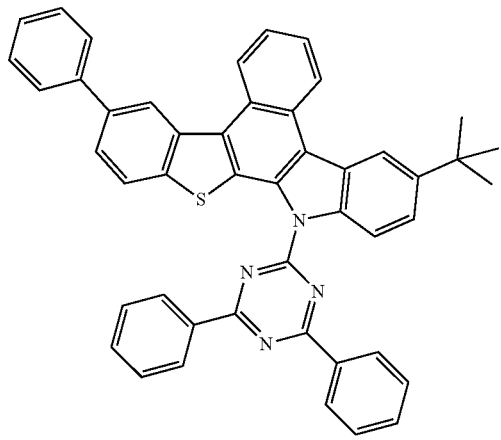
4-13
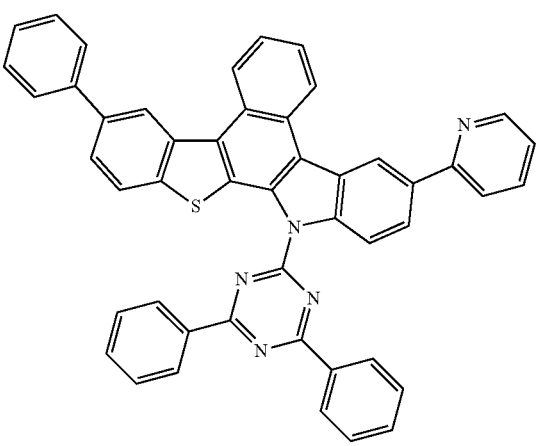
4-14
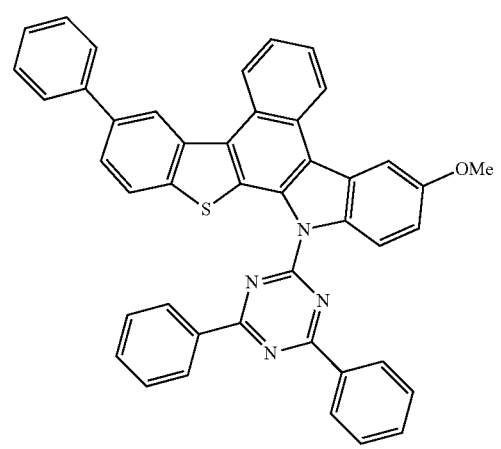
4-15
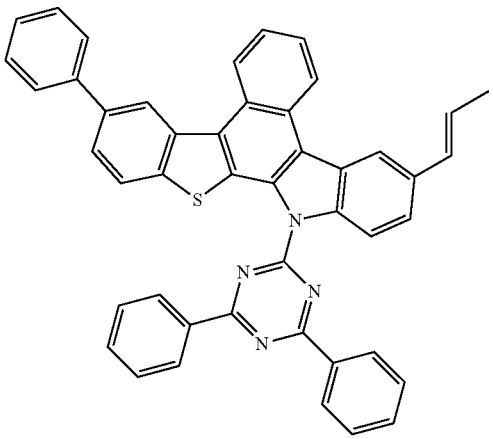
4-16
4-17
4-18

4-19
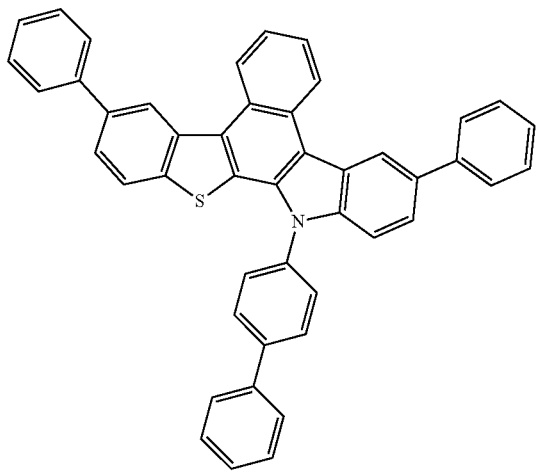
4-20
4-21
4-22
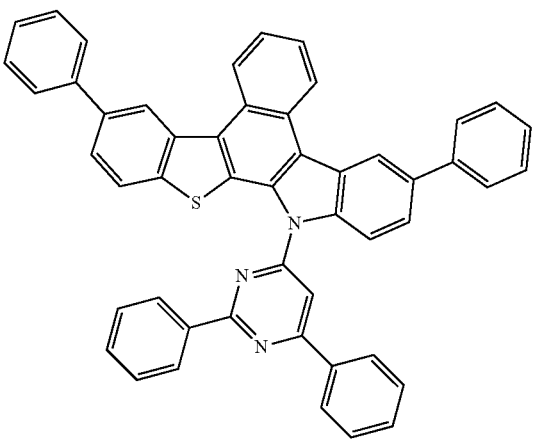
4-23
4-24

US 9,373,806 B2
4-25
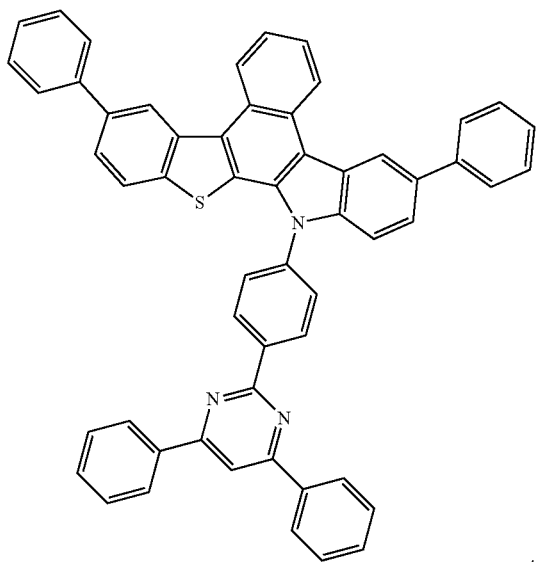
4-26
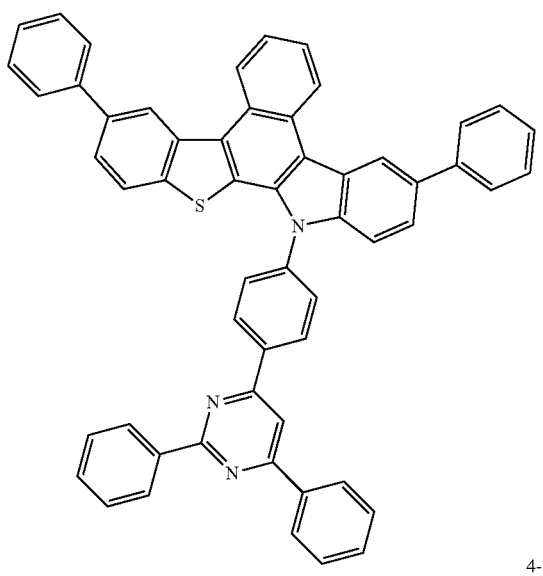
4-27
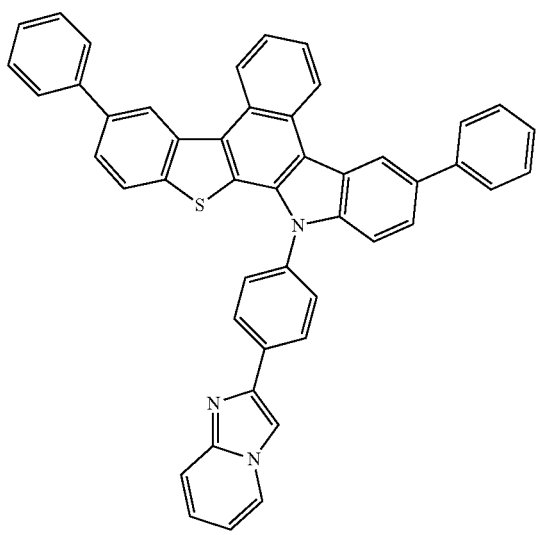
4-28
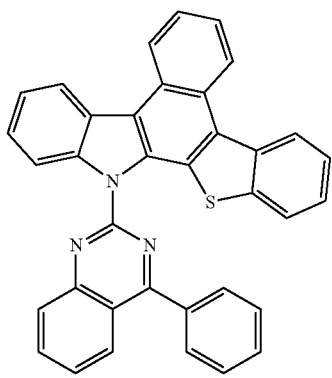
4-29
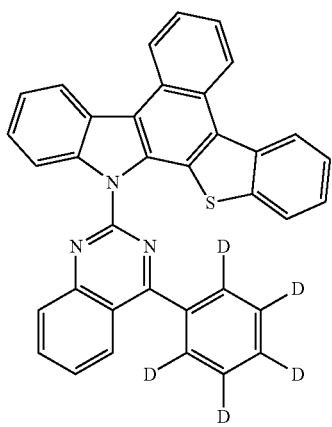
4-30
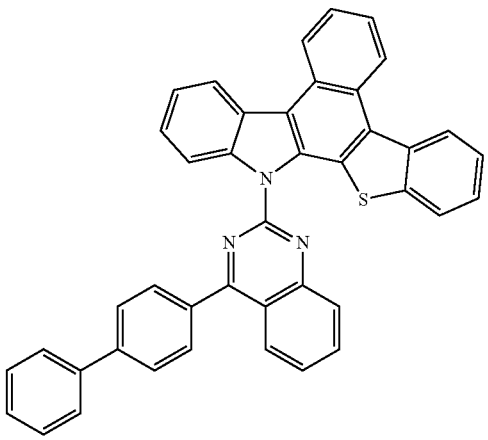

4-31
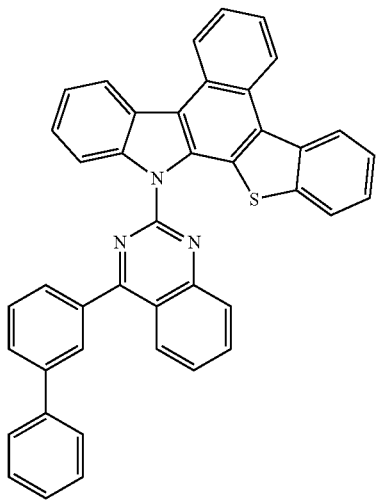
4-32
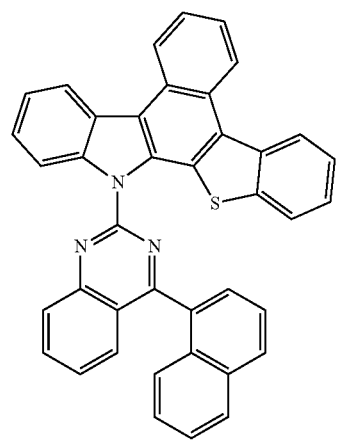
4-33
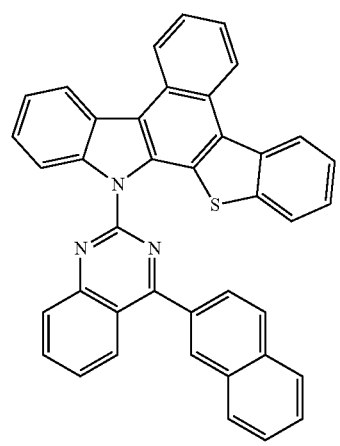
4-34
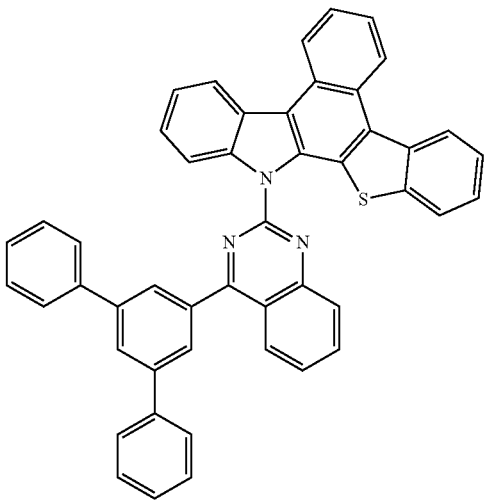
4-35
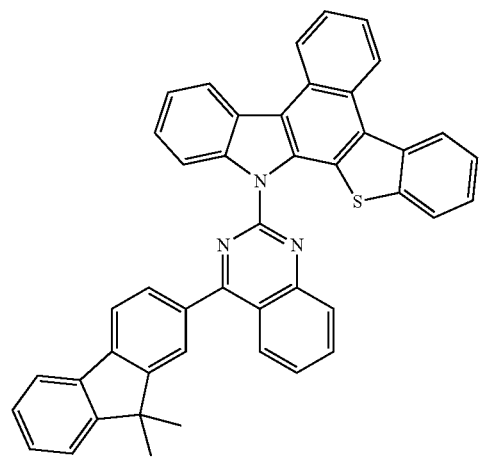
4-36
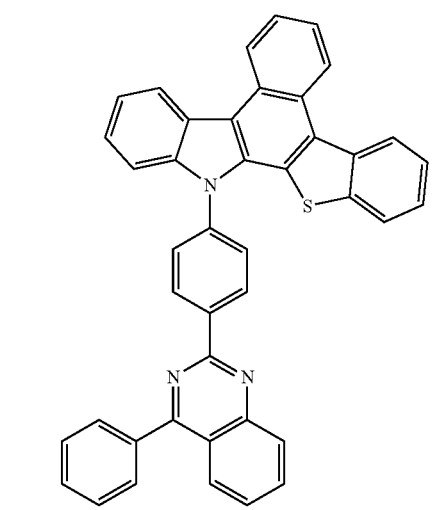

4-37
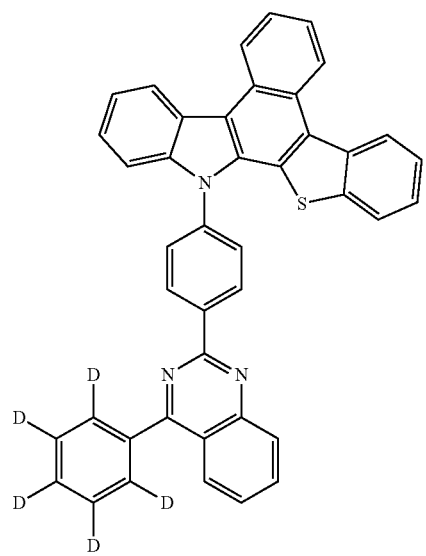
4-39
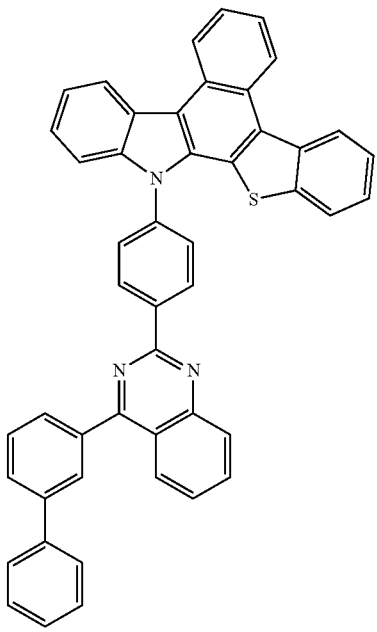
4-38
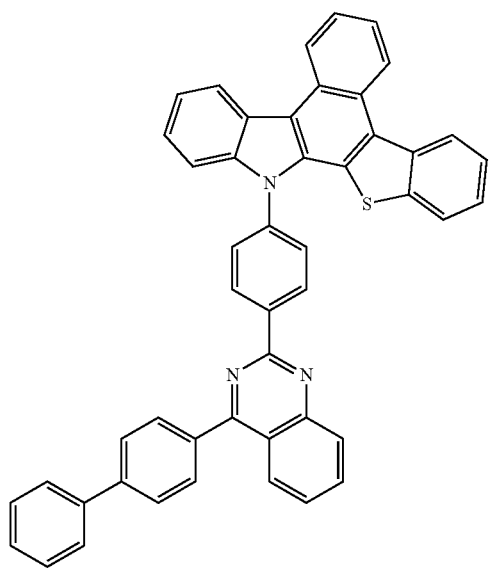
4-40
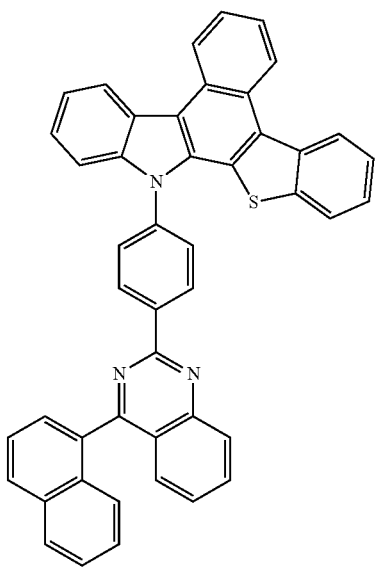

4-41
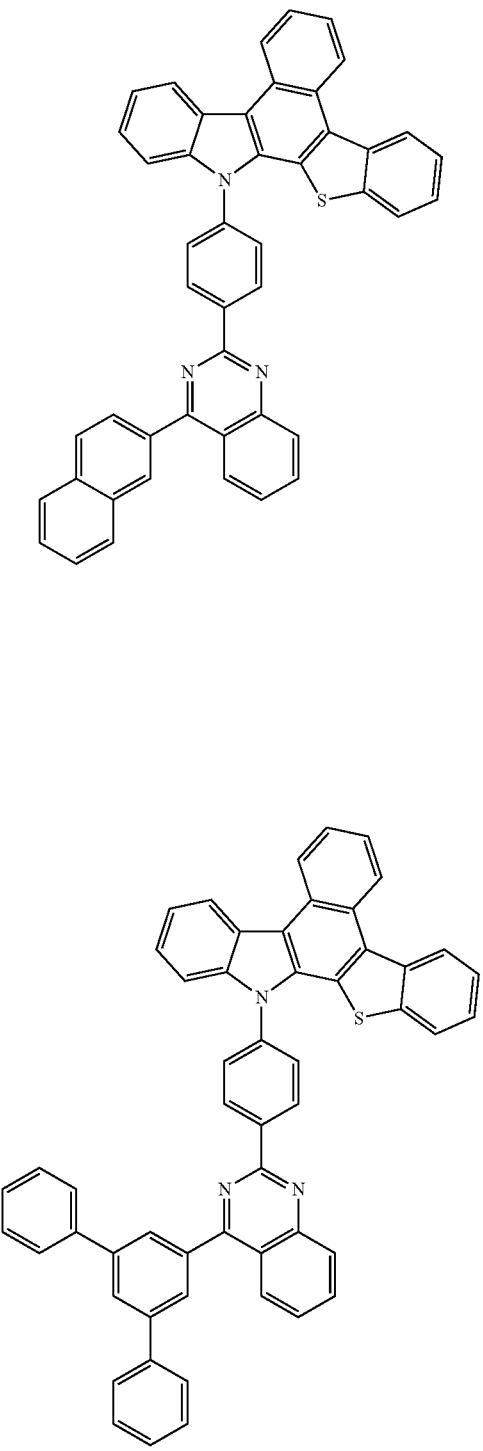
4-42
4-43
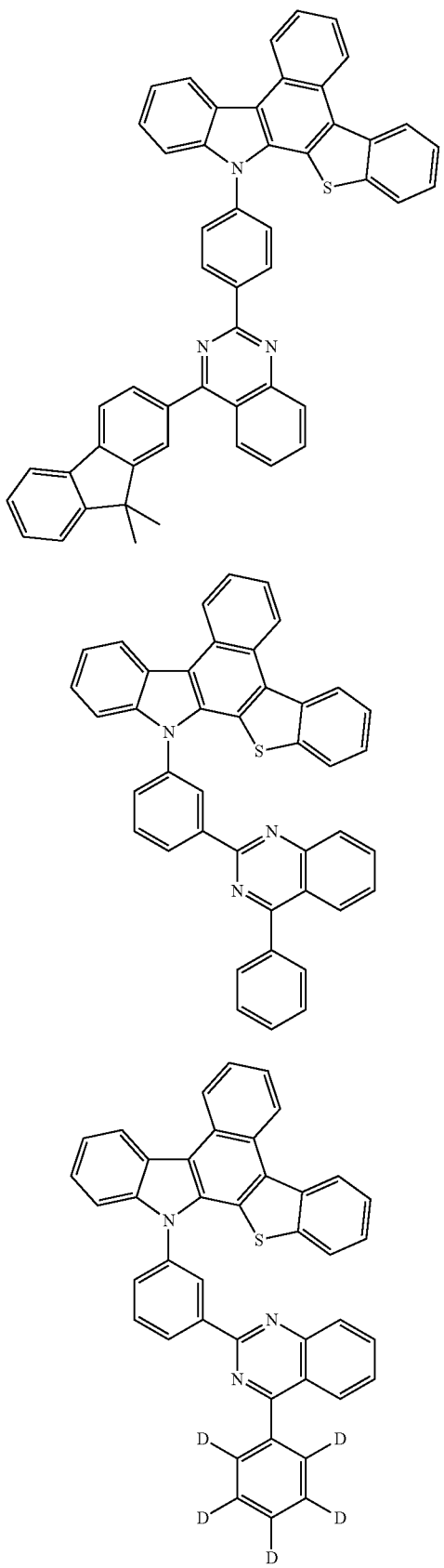
4-44
4-45

4-46
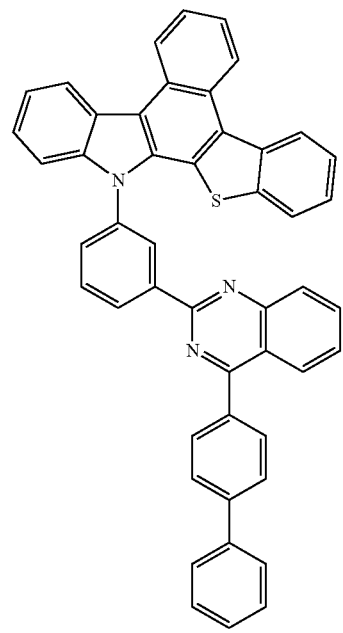
4-47
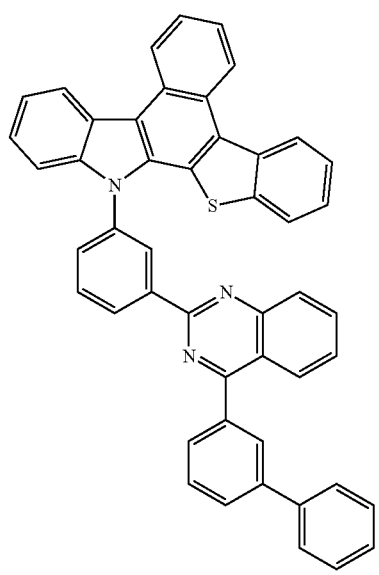
4-48
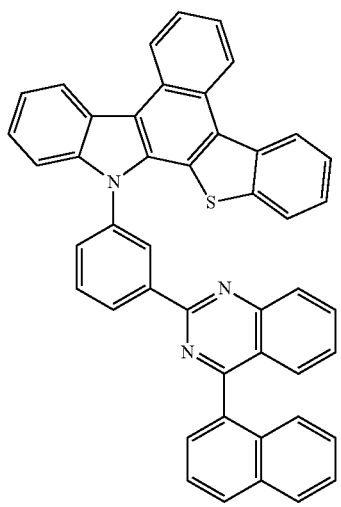
4-49
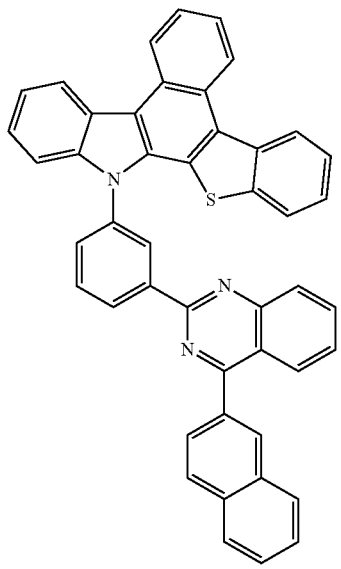
4-50
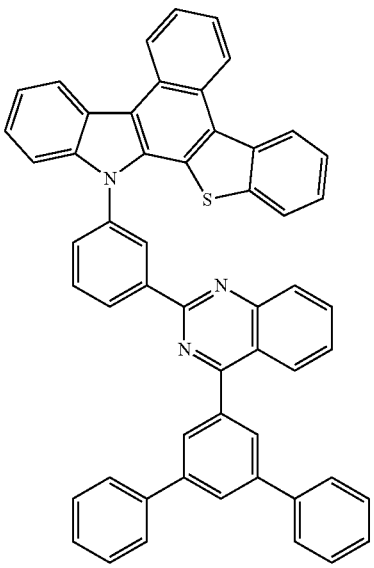

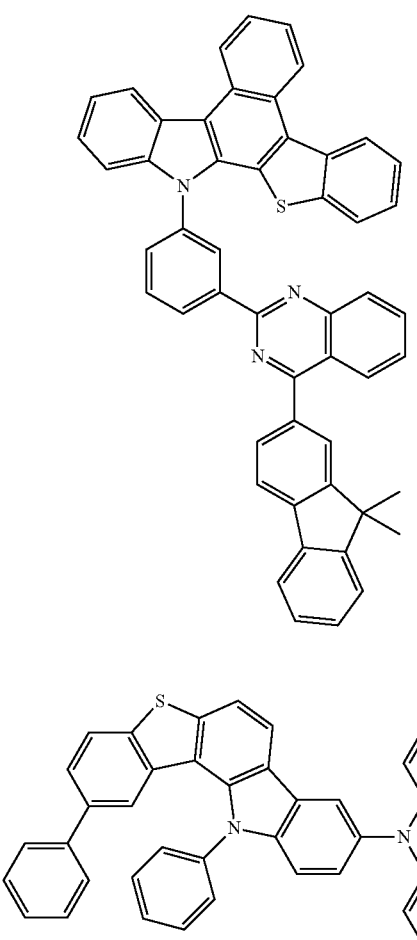
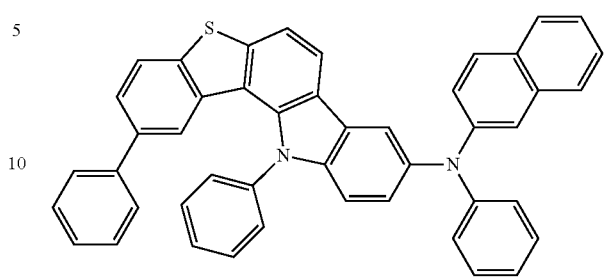
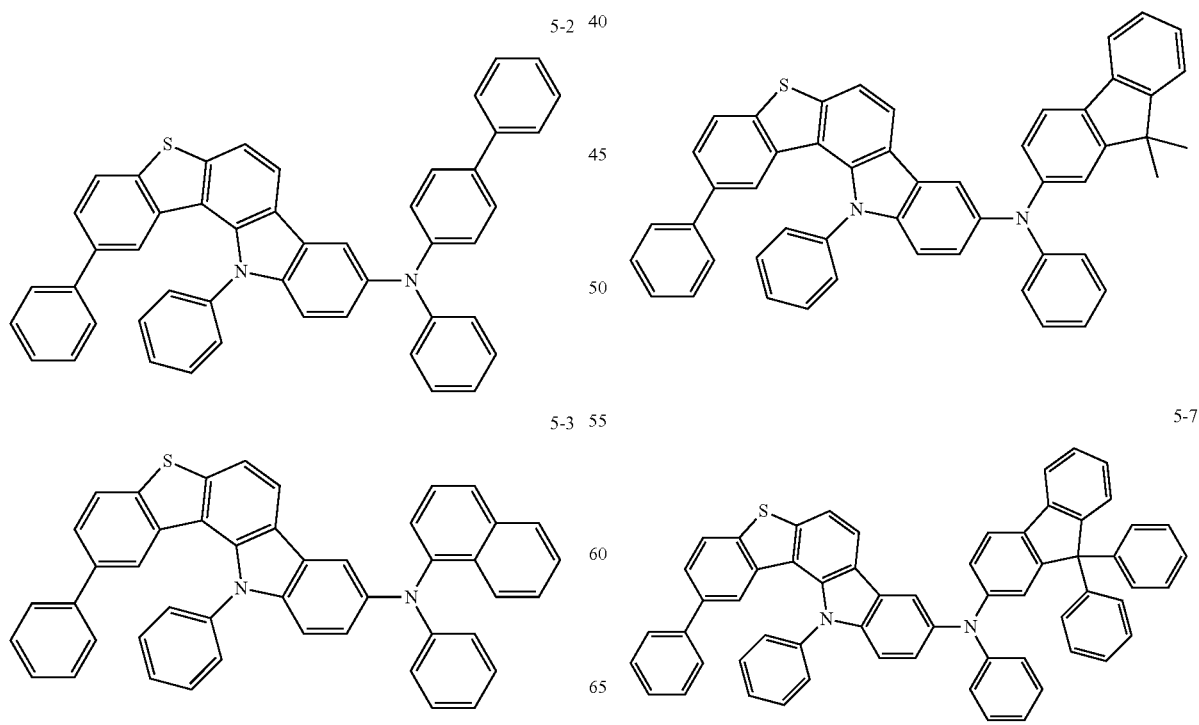

-continued
5-8
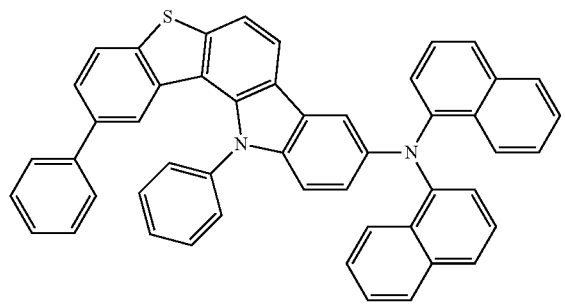
5-9
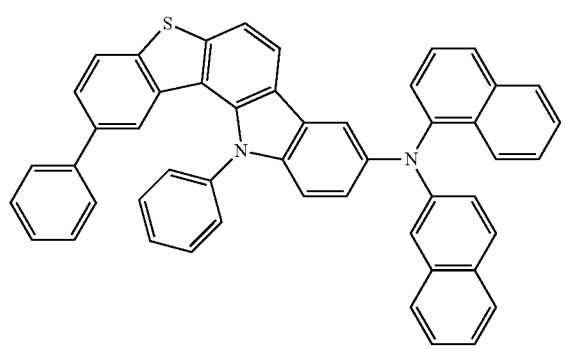
5-10
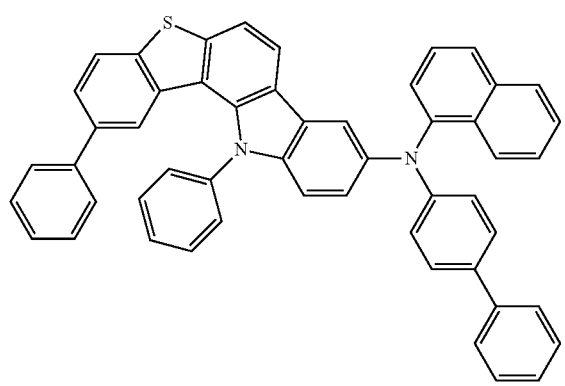
5-11
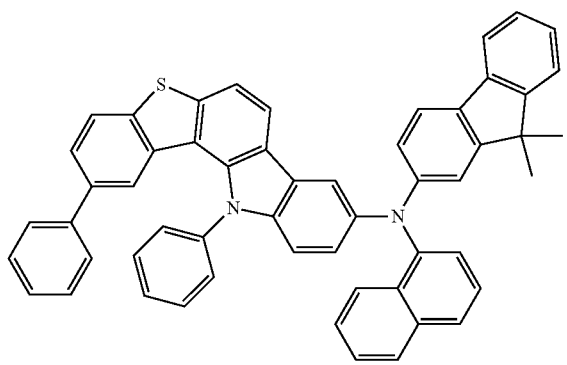
-continued
5-12
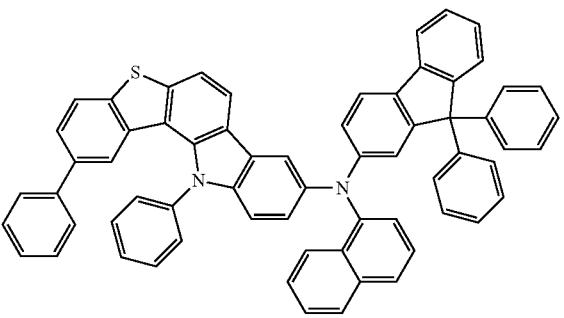
5-13
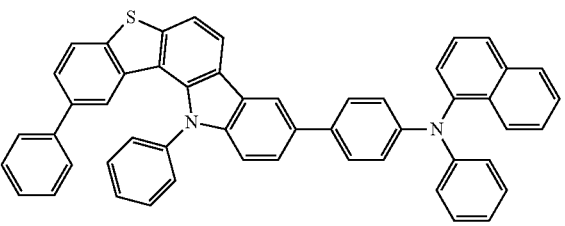
5-14
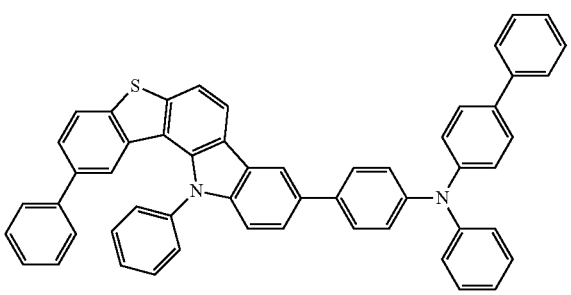
5-15
5-16
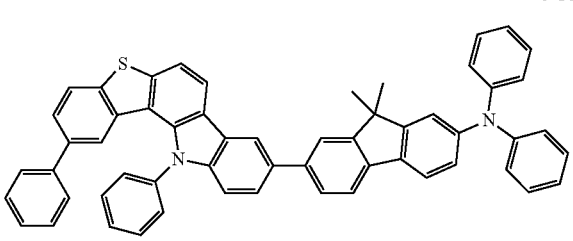

5-17
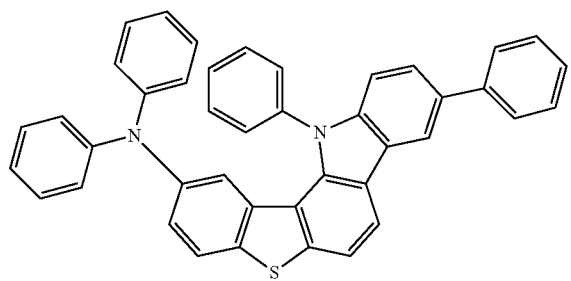
5-18
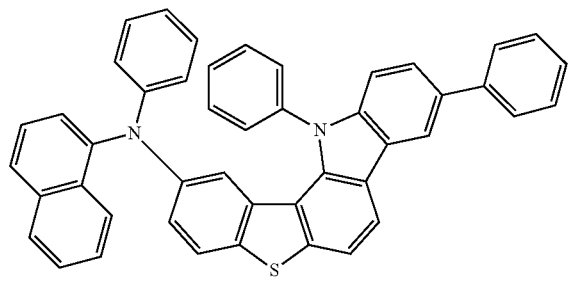
5-19
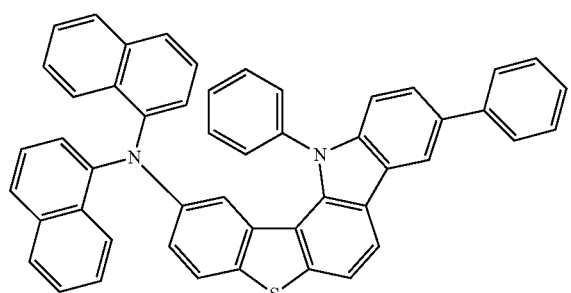
5-20
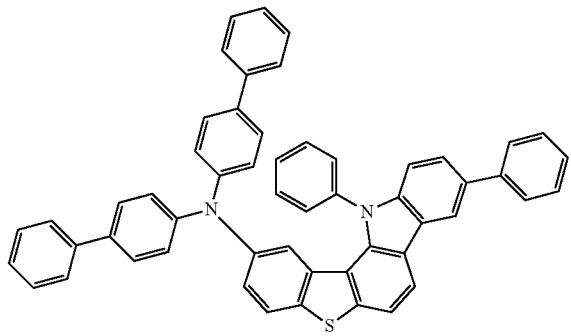
5-21
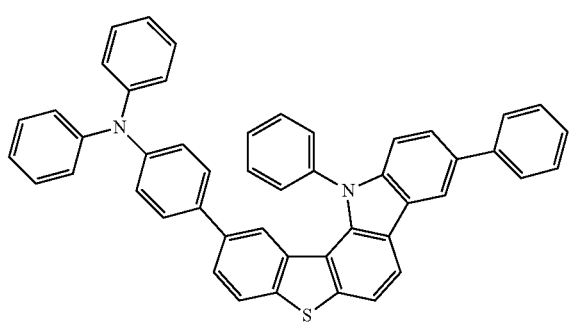
5-22
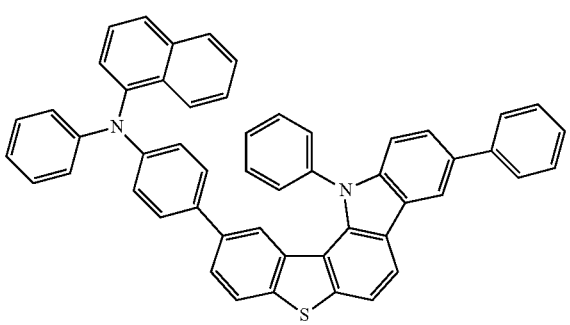
5-23
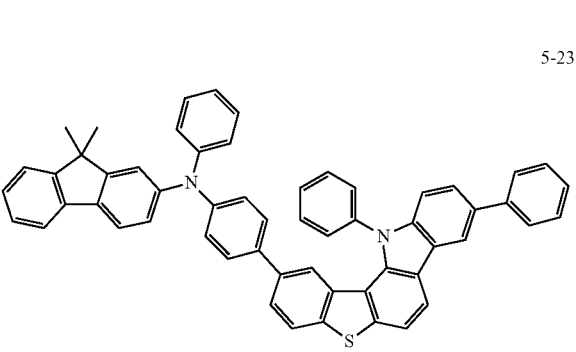
5-24
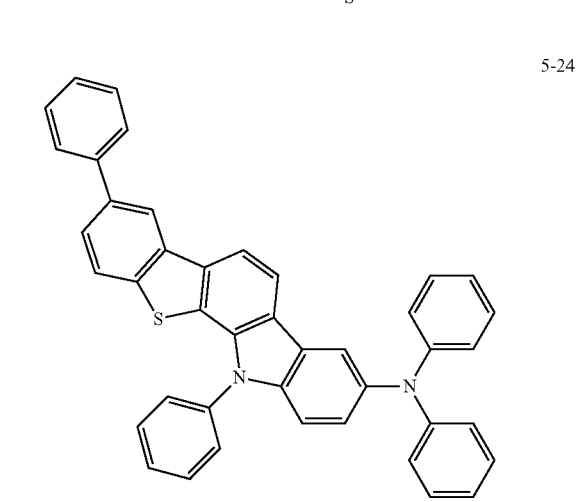
5-25
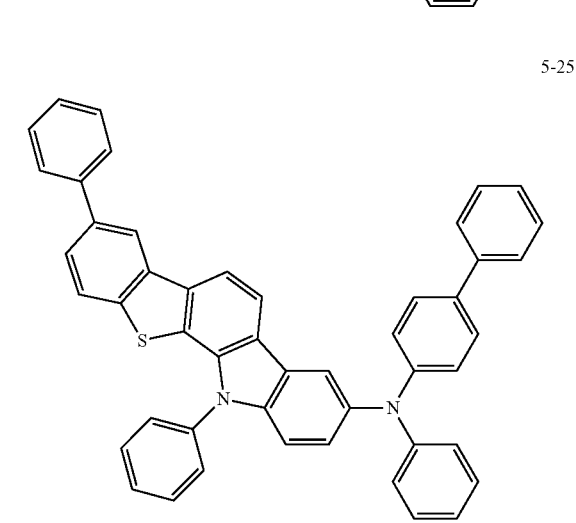

-continued
5-26
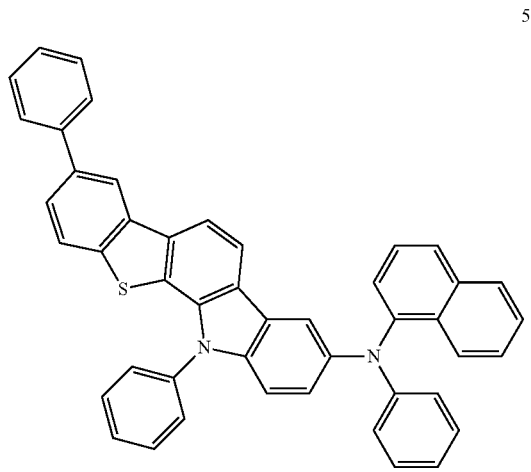
5-29
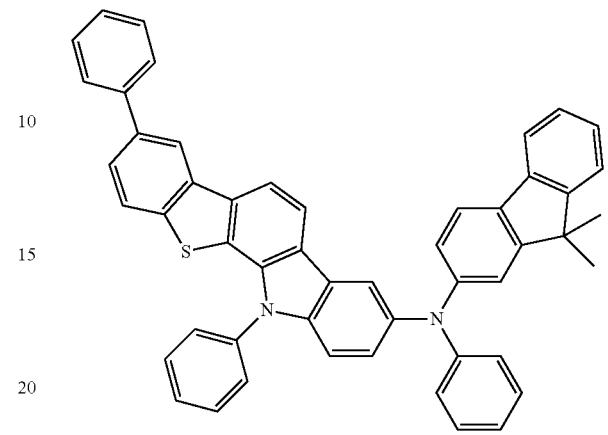
5-27
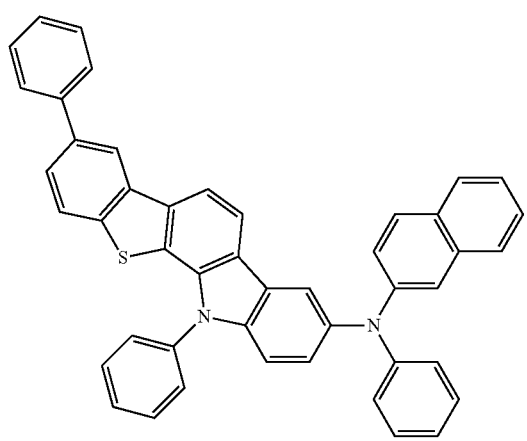
5-30
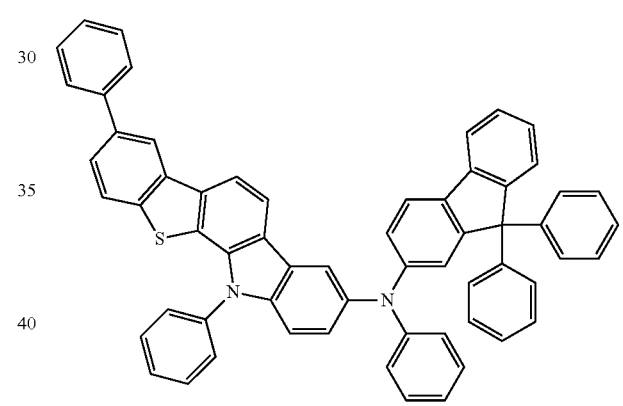
5-28
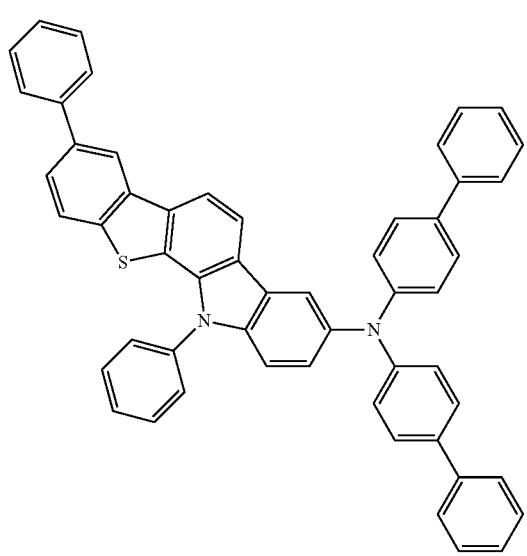
5-31
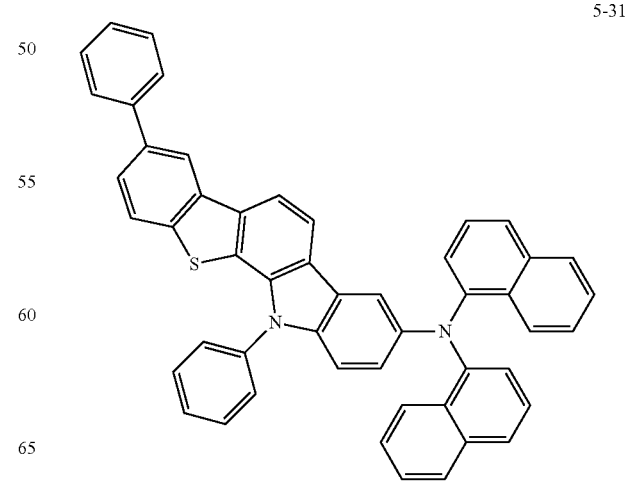

5-32
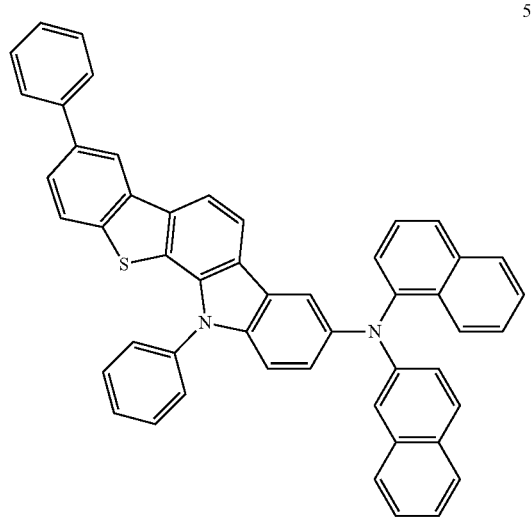
5-33
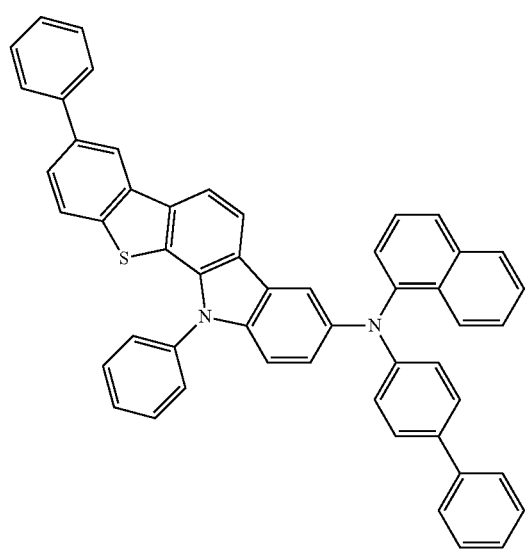
5-34
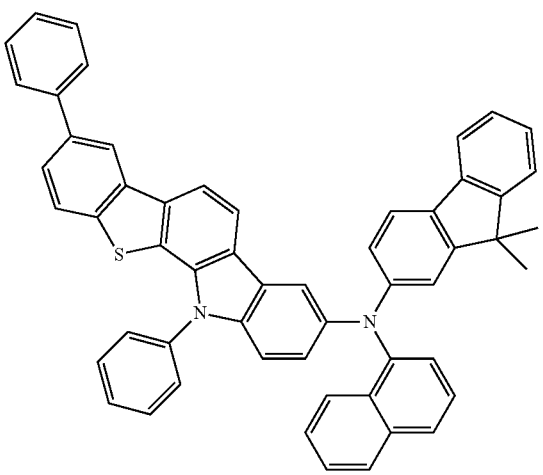
5-35
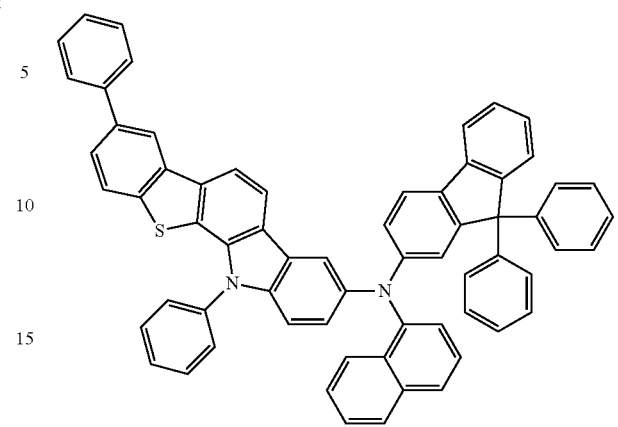
5-36
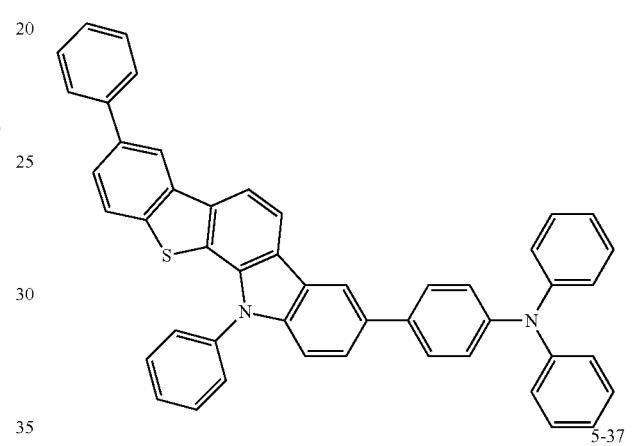
5-37
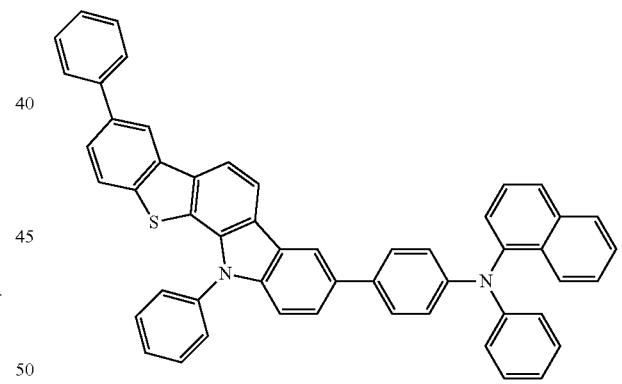
5-38
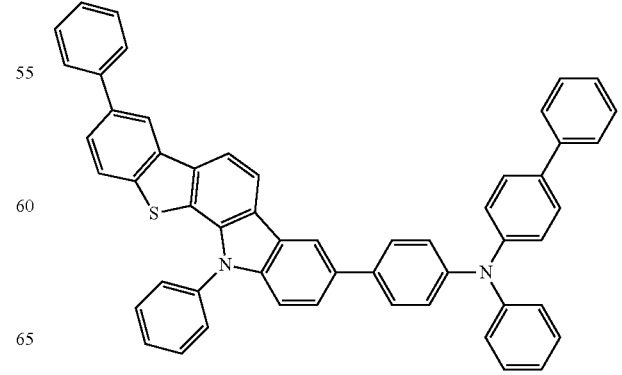

5-39
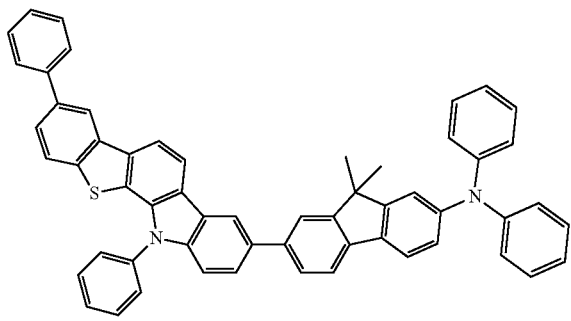
5-40
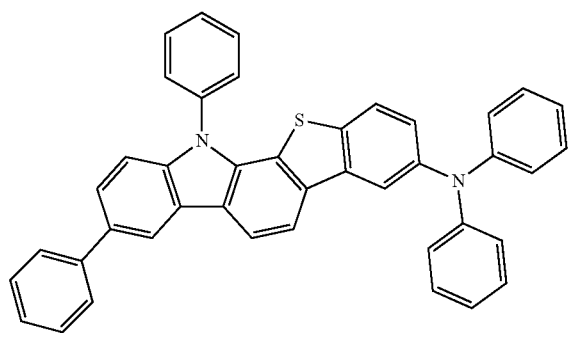
5-41
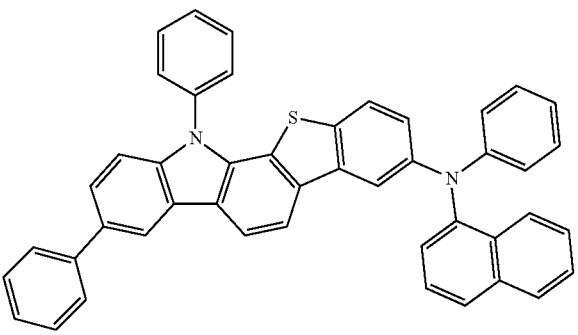
5-42
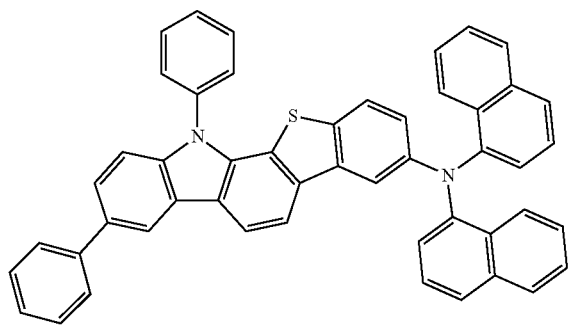
5-43
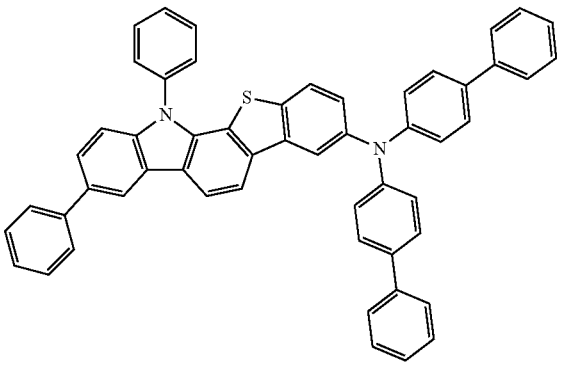
5-44
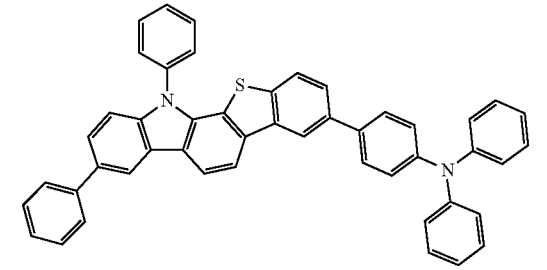
5-45
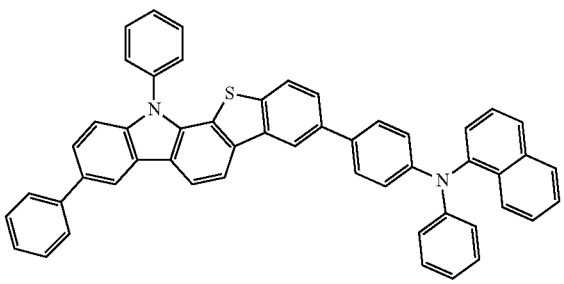
5-46
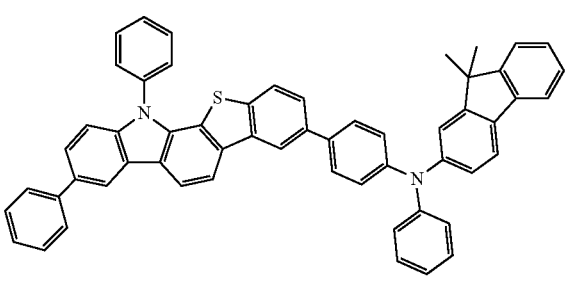

-continued
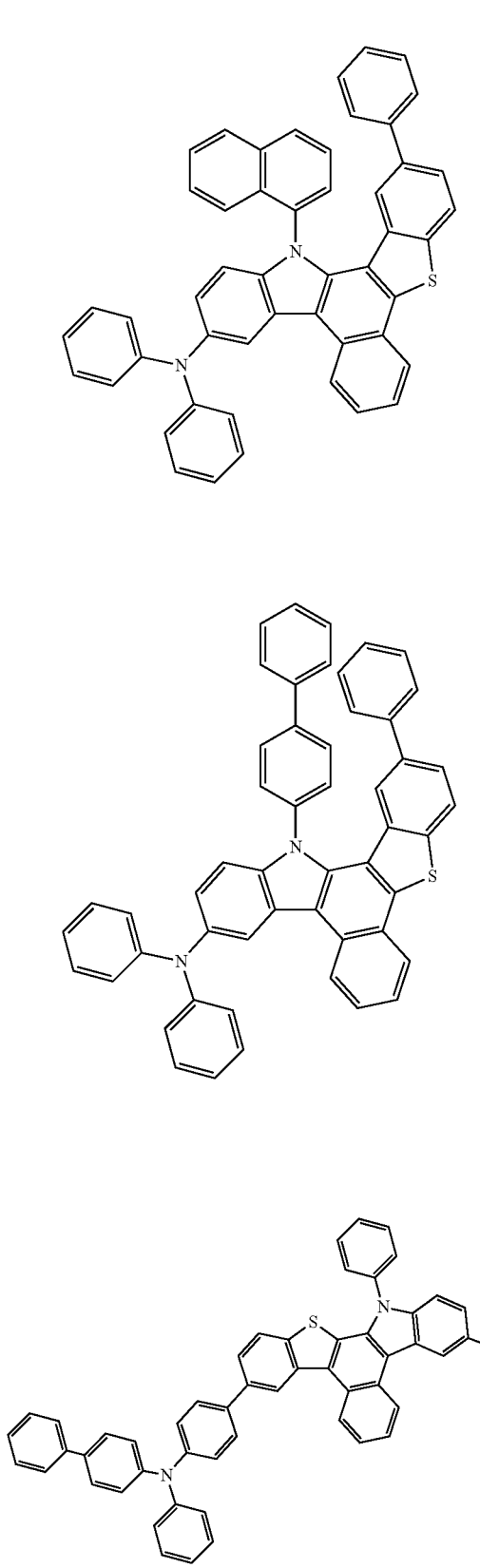
5-47
5-48
5-49
-continued
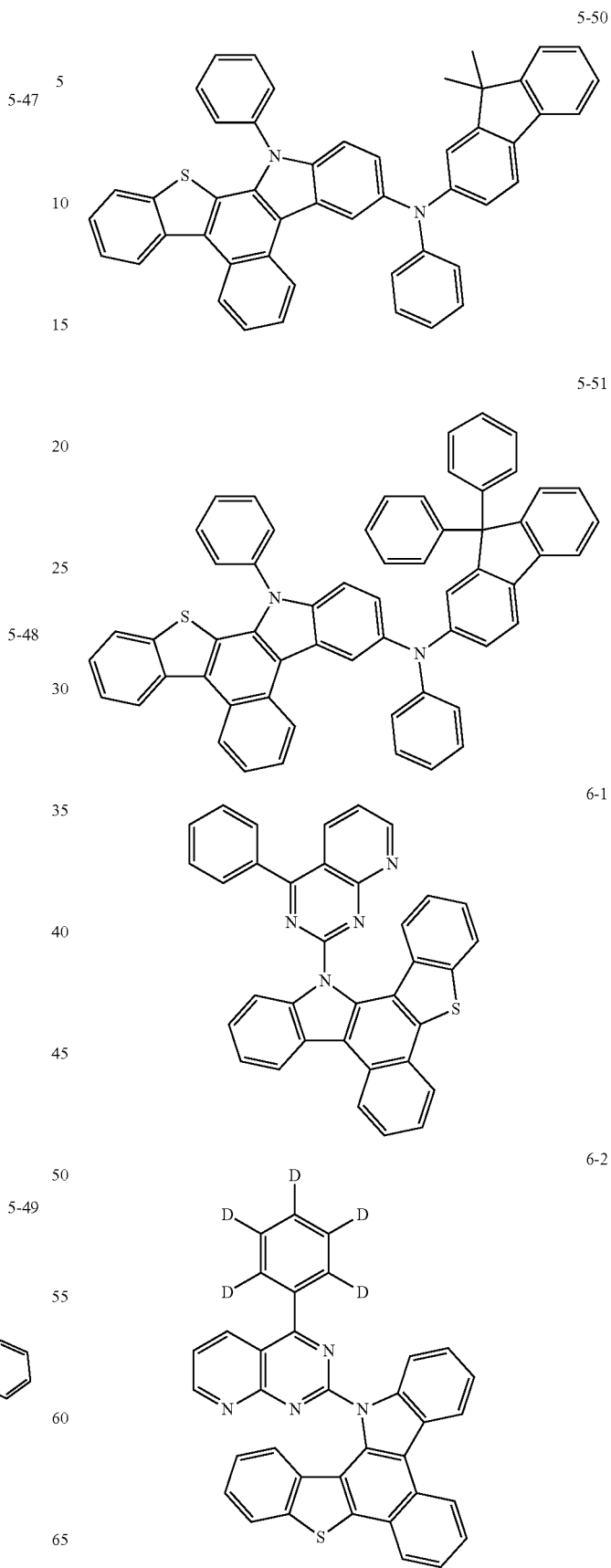
5-50
5-51
6-1
6-2

-continued
6-3
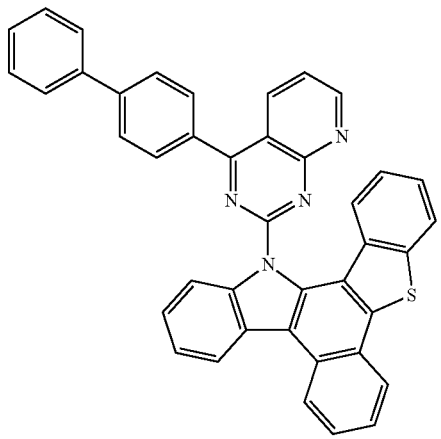
6-4
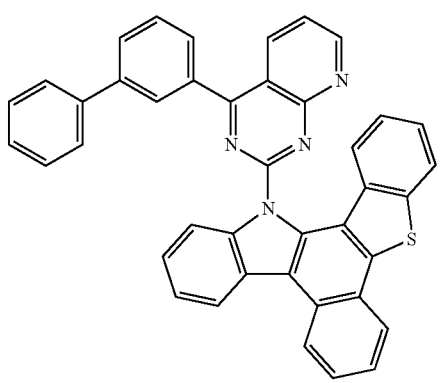
6-5
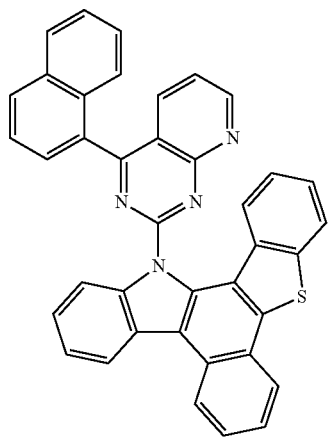
6-6
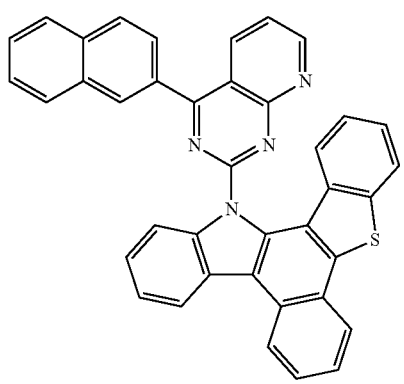
-continued
6-7
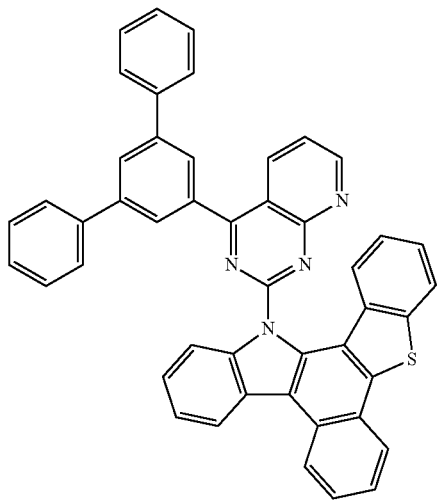
6-8
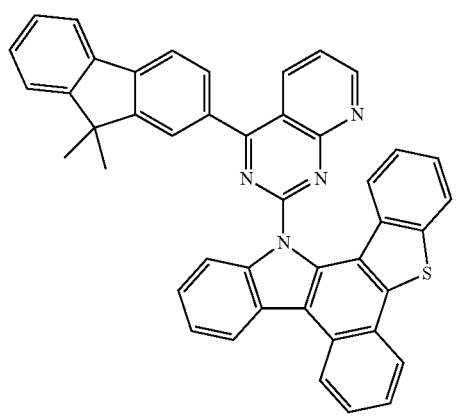
6-9
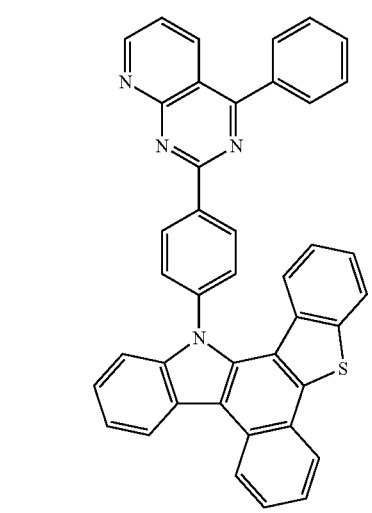

81
-continued
82
-continued
6-10
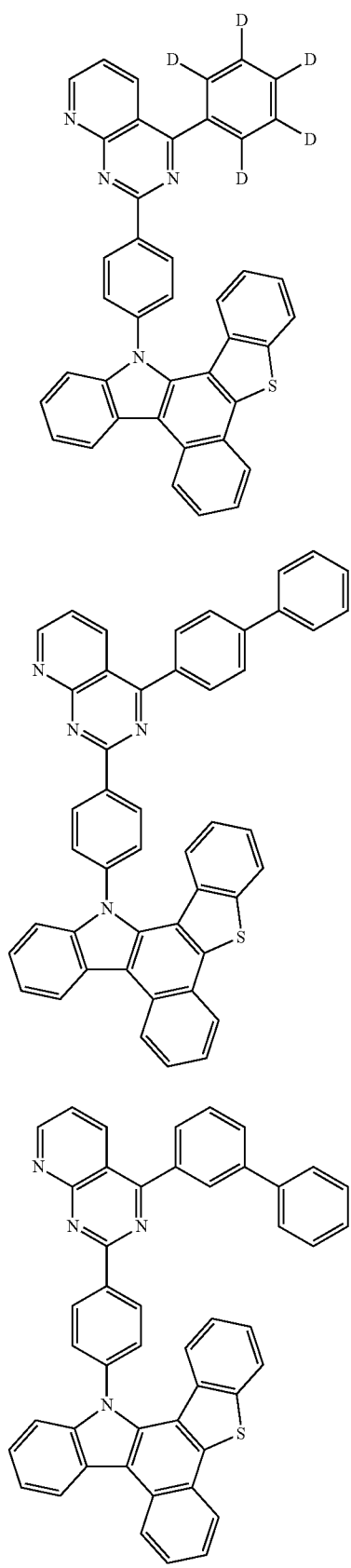
6-11
6-12
6-13
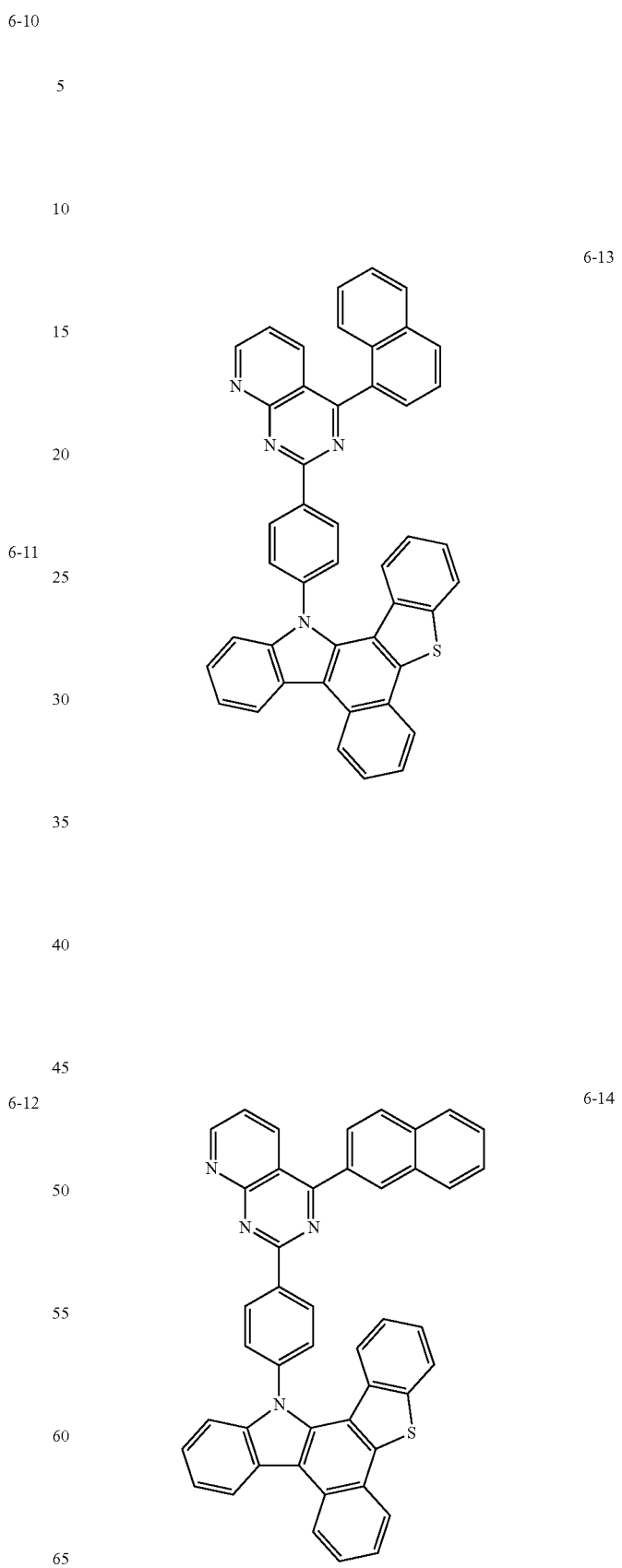
6-14

6-15
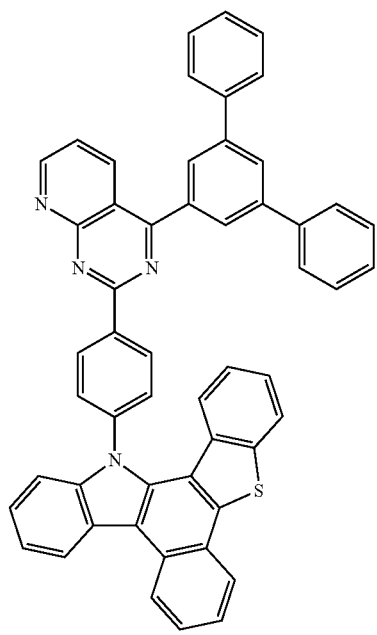
6-16
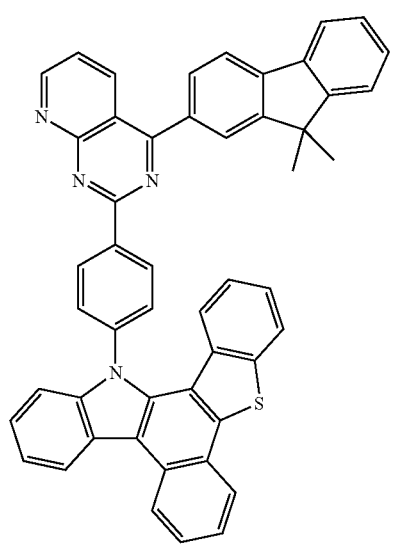
6-17
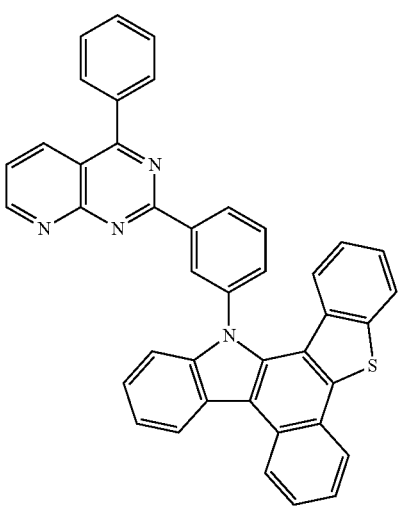
6-18
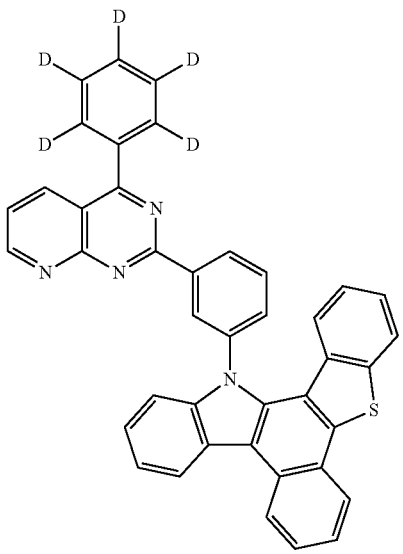
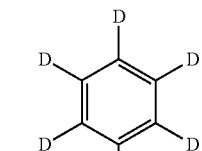
6-19
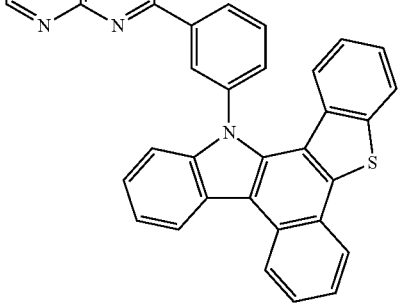

-continued
6-20
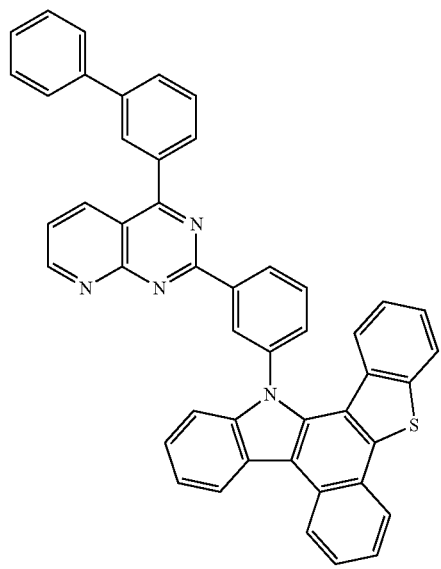
6-21
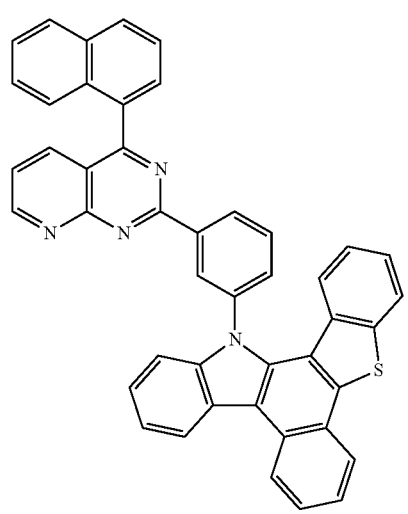
6-22
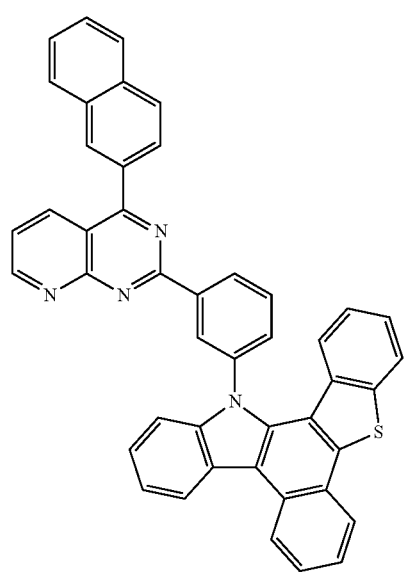
-continued
6-23
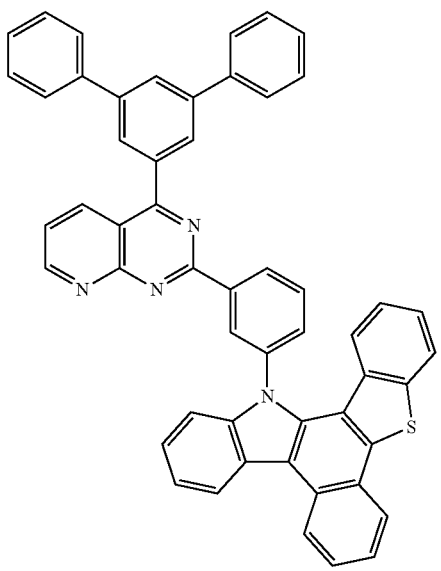
6-24
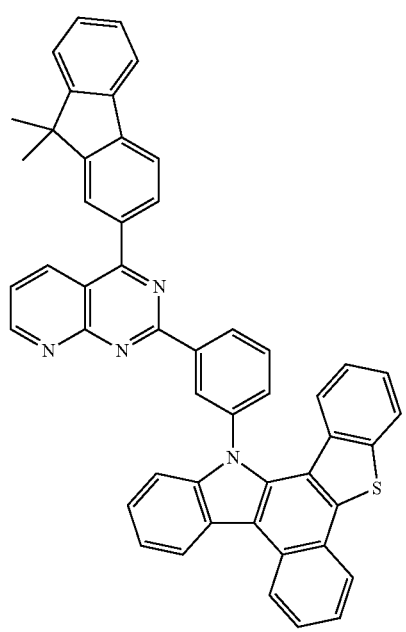
6-25
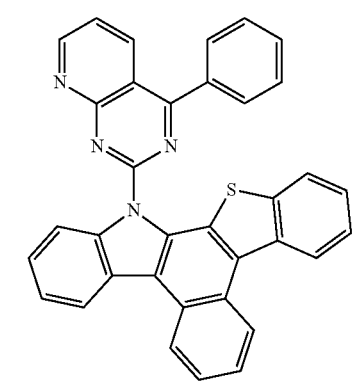

6-26
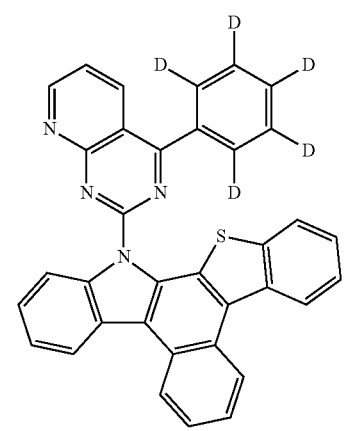
6-27
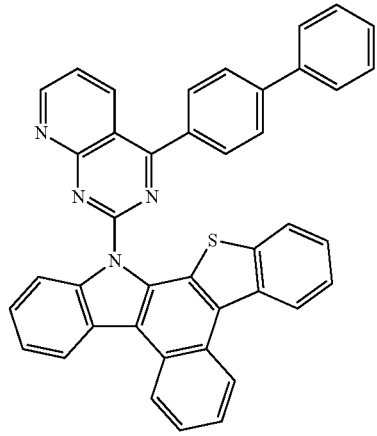
6-28
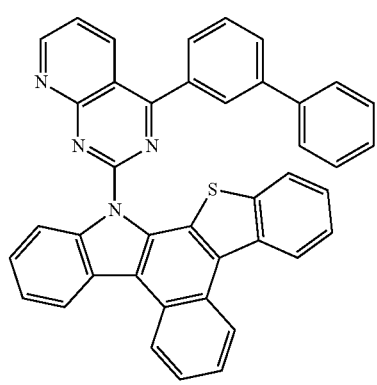
6-29
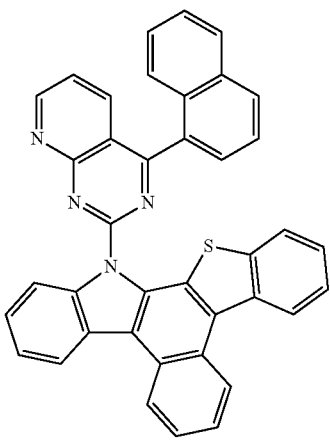
6-30
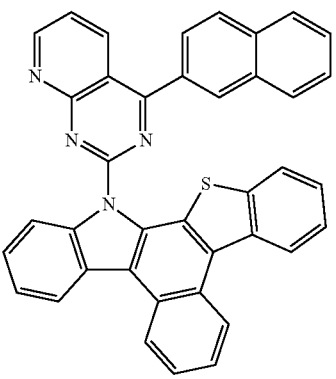
6-31
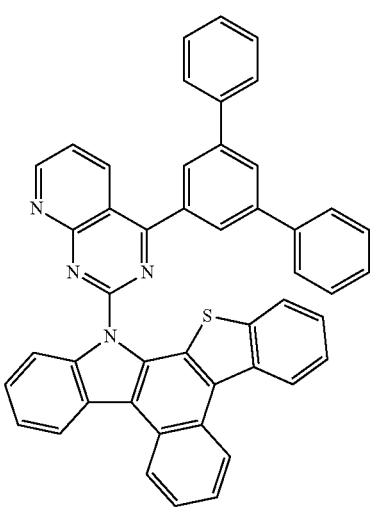

-continued
6-32
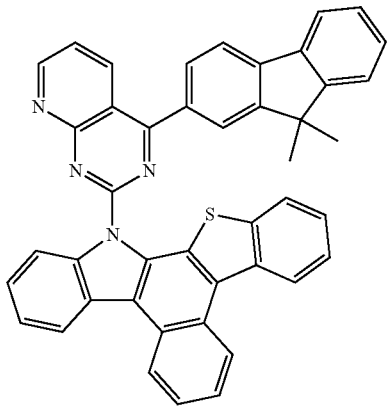
6-33
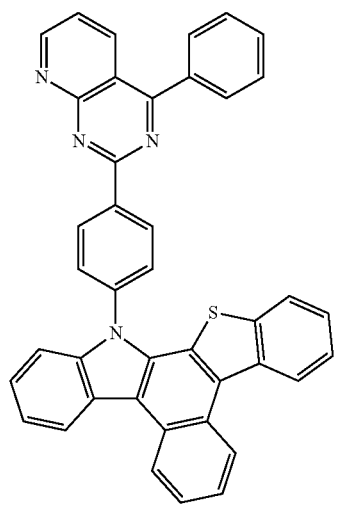
6-34
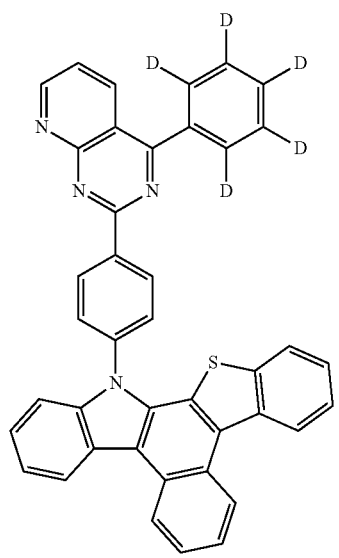
-continued
6-35
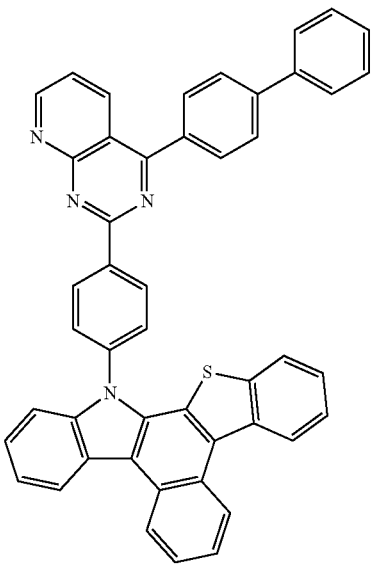
6-36
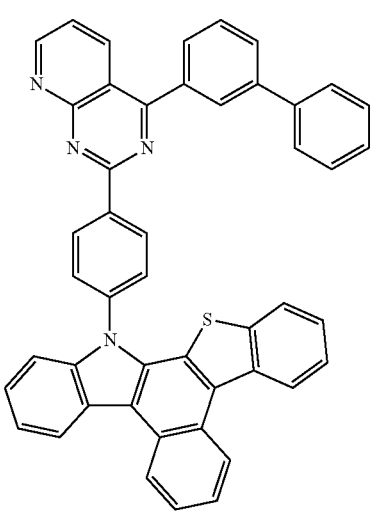
6-37
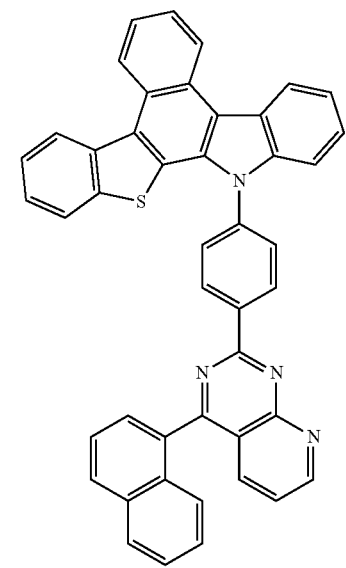

6-38
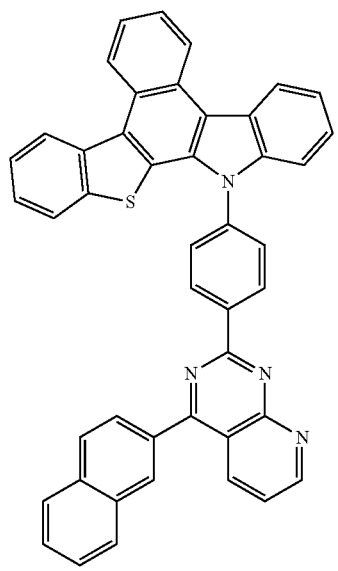
6-39
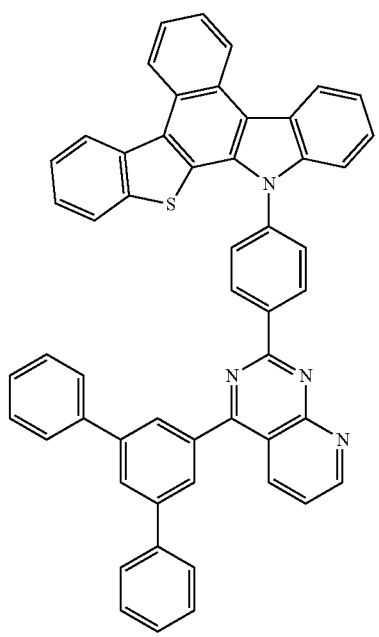
6-40
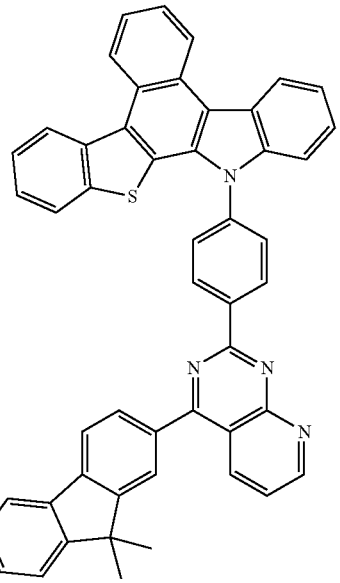
6-41
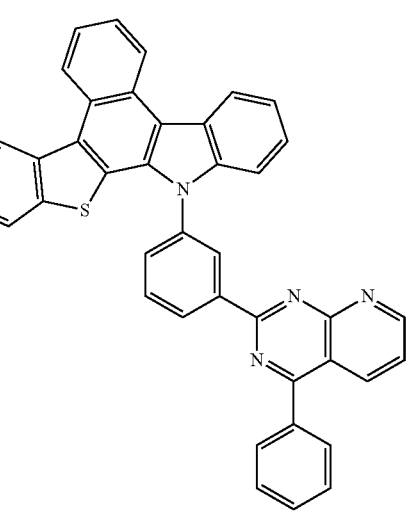
6-42
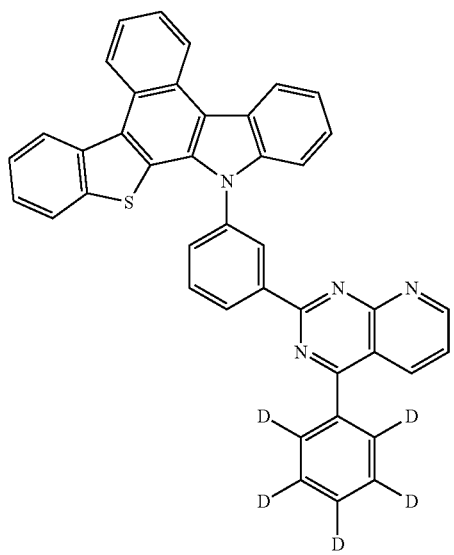

6-43
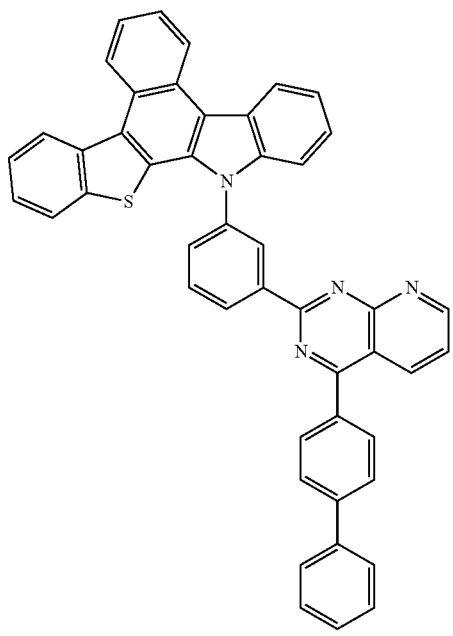
6-44
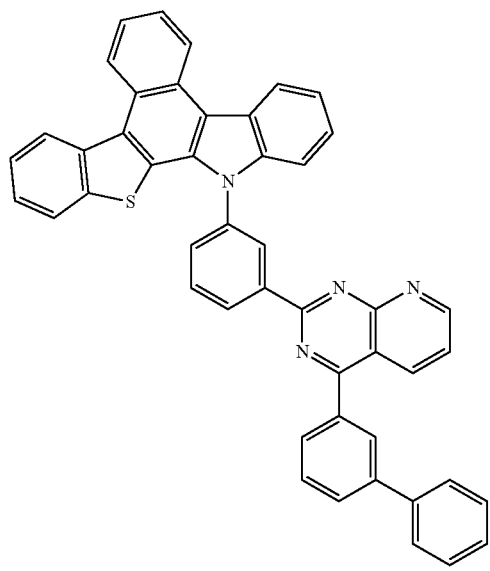
6-45
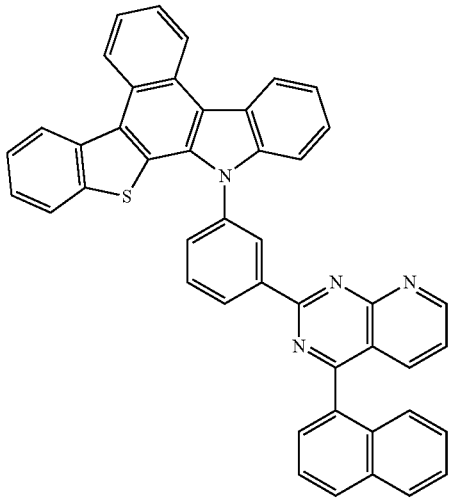
6-46
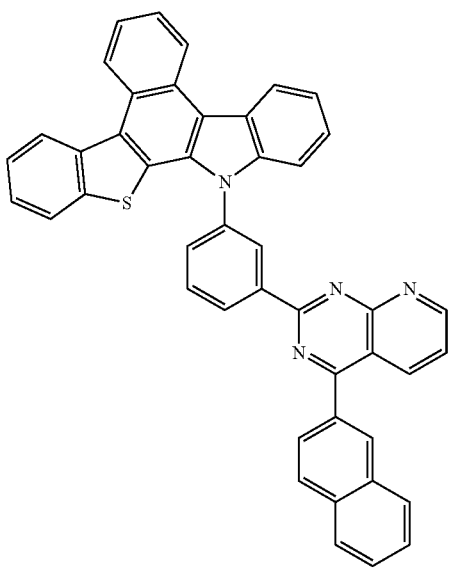
6-47
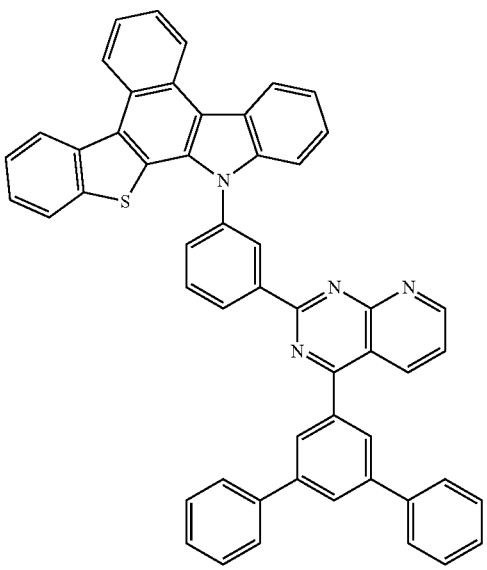

6-48
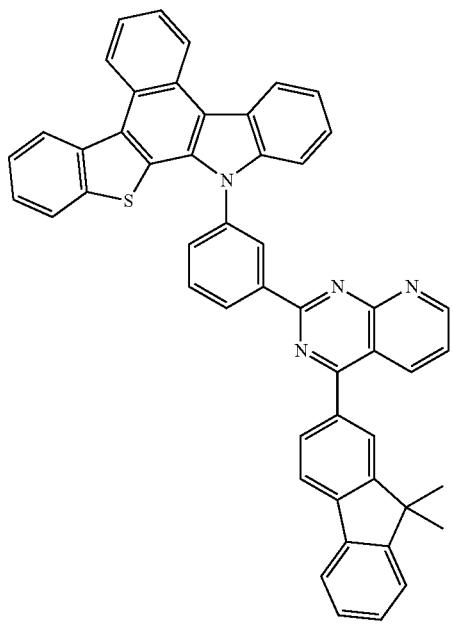
7-1
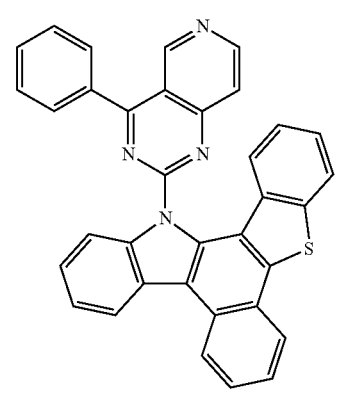
7-2
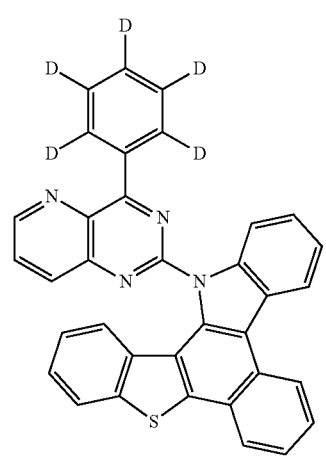
7-3
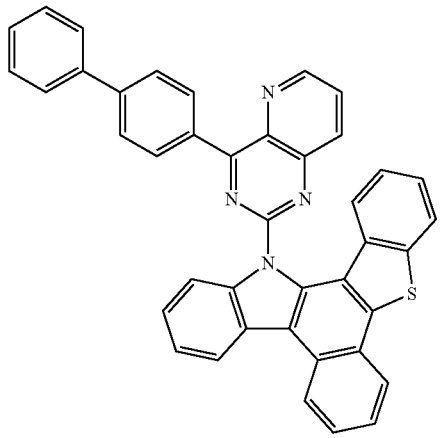
7-4
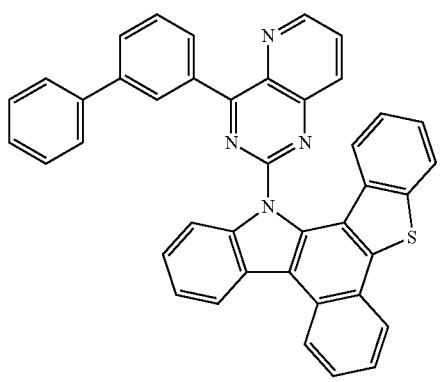
7-5
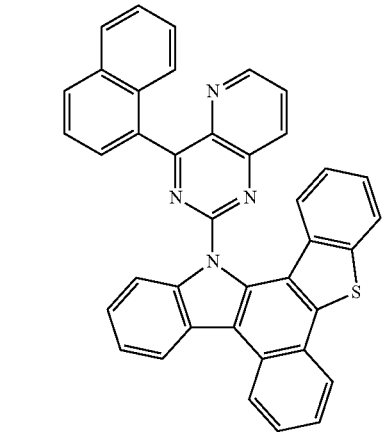
7-6
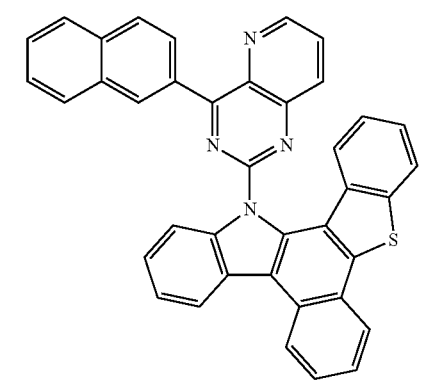

97
-continued
7-7
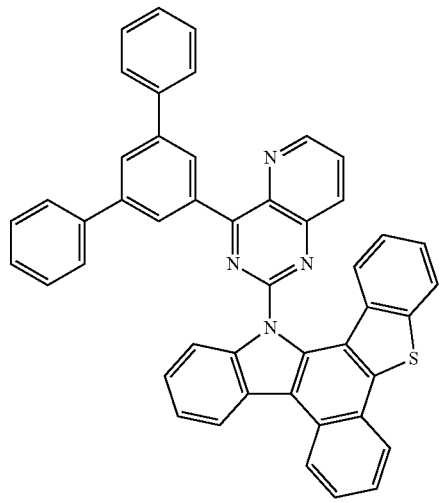
7-8
7-9
98
-continued
7-10
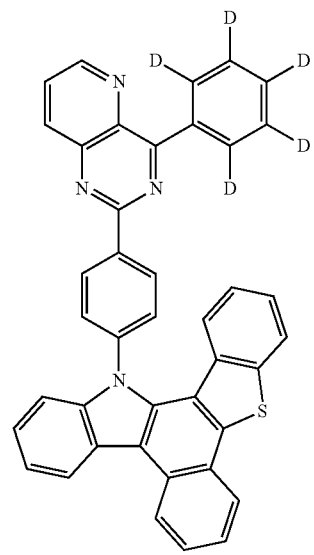
7-11
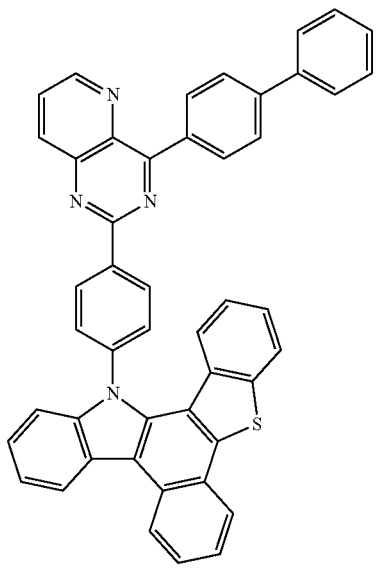
7-12
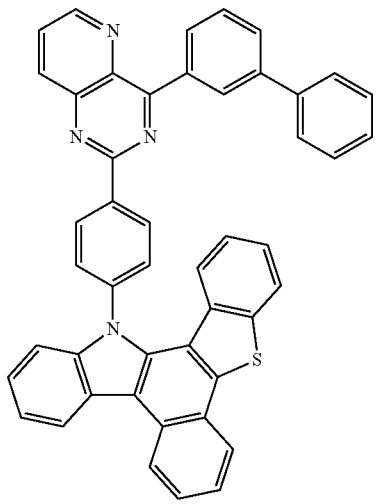

-continued
7-13
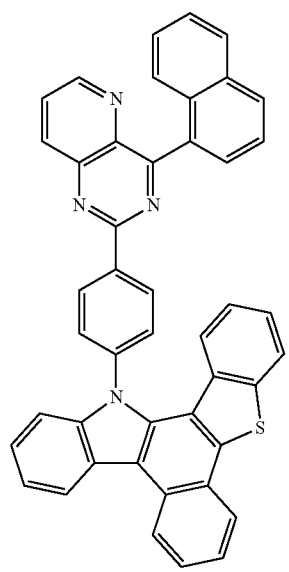
7-14
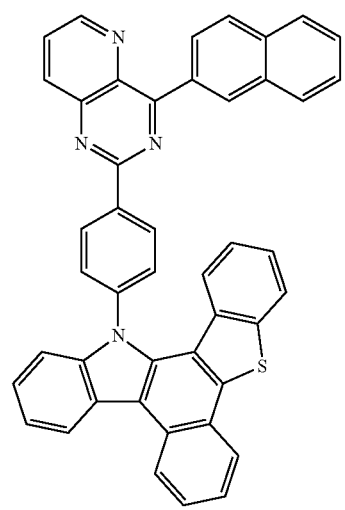
-continued
7-15
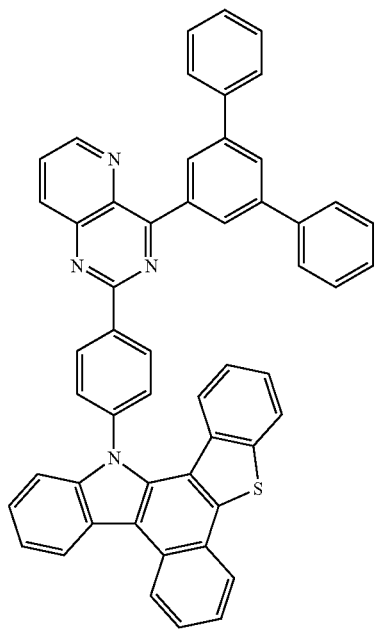
7-16
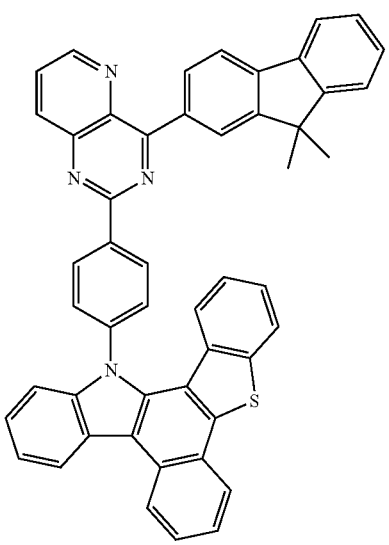
7-17
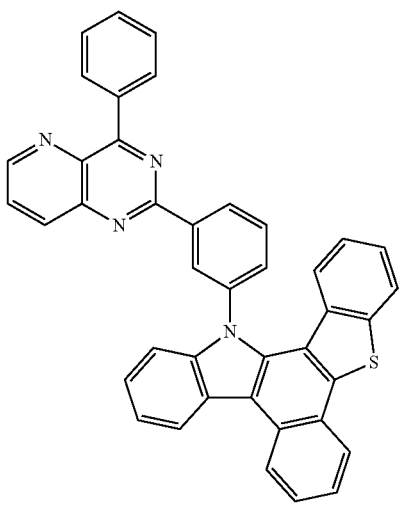

101
-continued
7-18
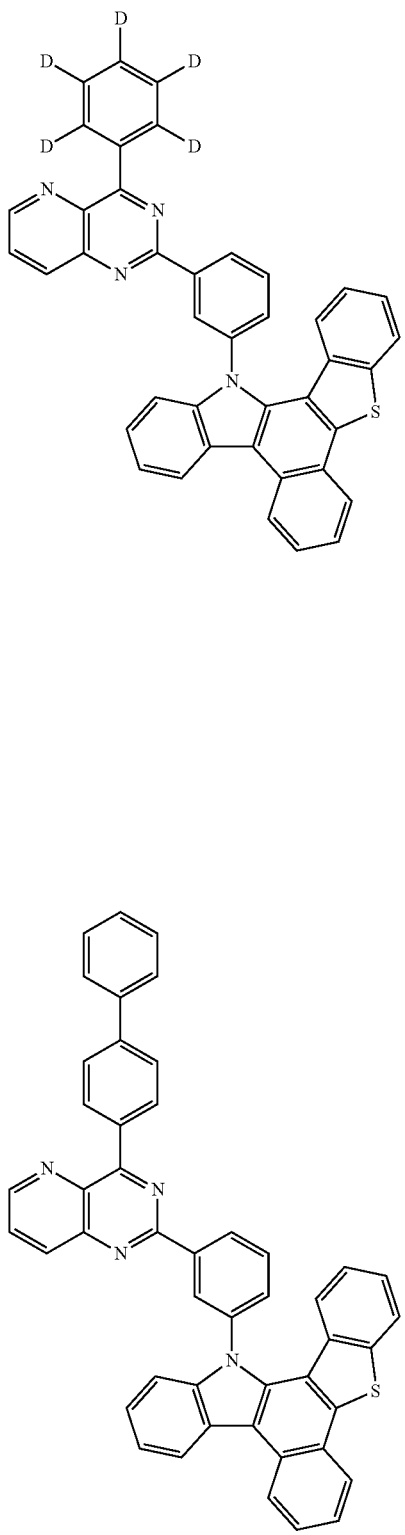
7-19
102
-continued
7-20
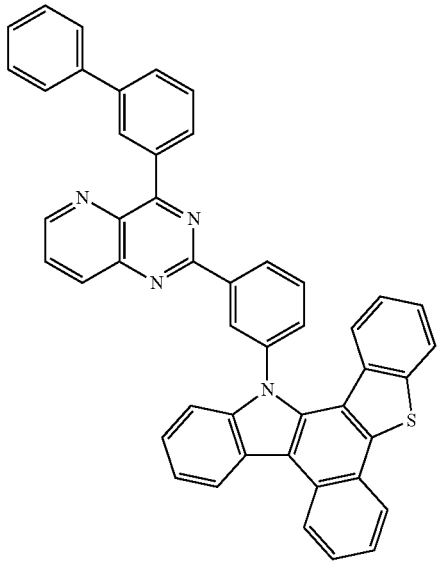
7-21
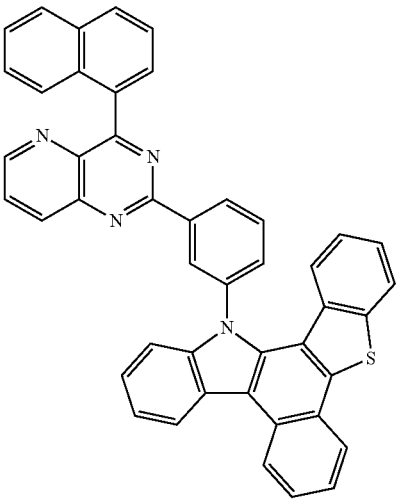
7-22
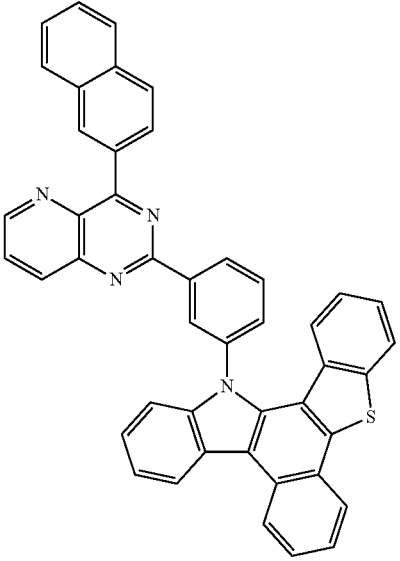

7-23
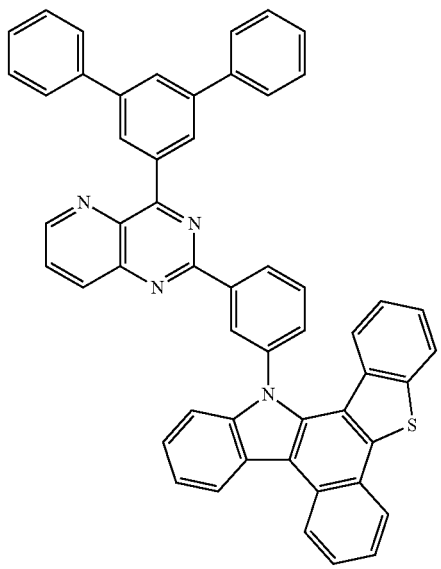
7-24
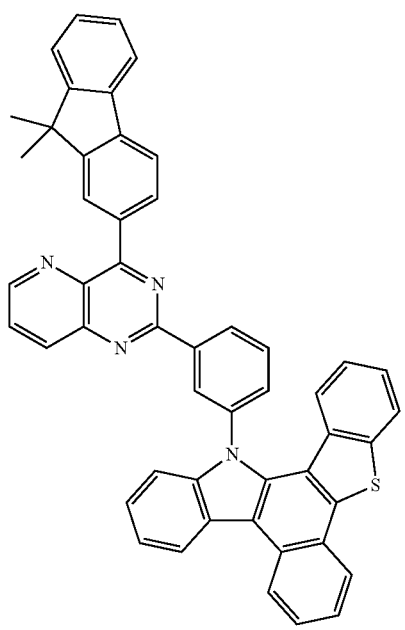
7-25
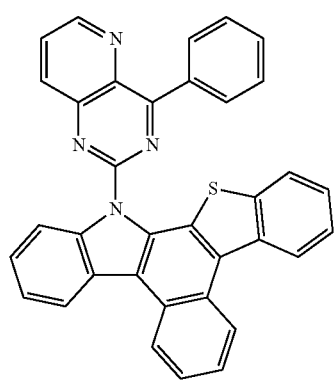
7-26
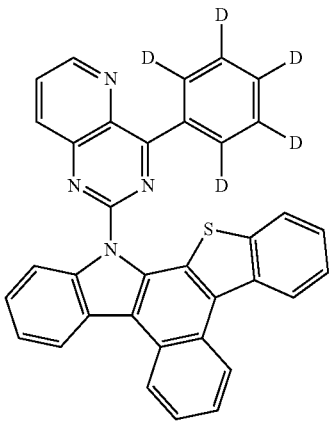
7-27
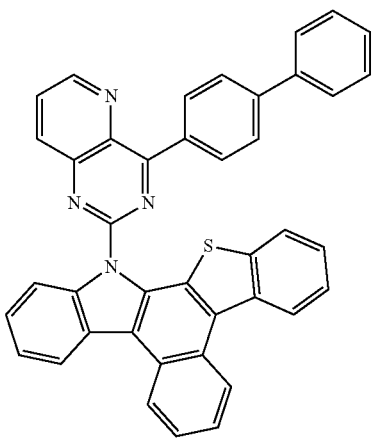
7-28
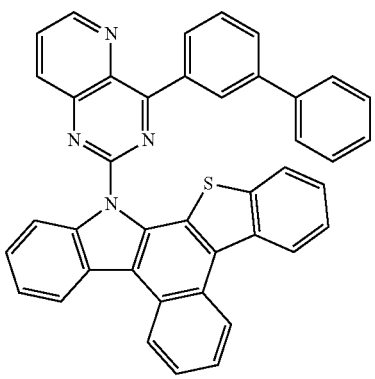

7-29
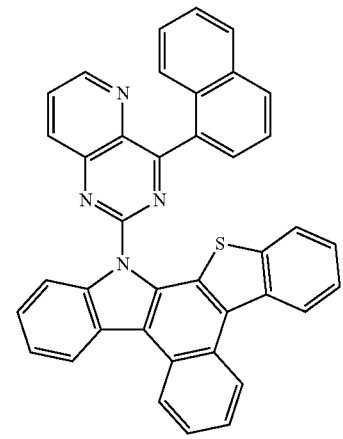
7-30
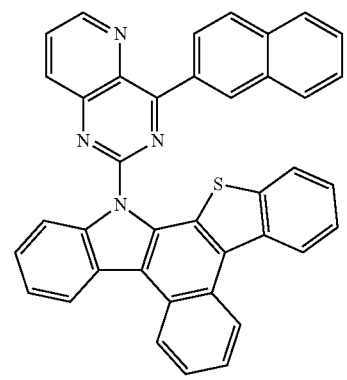
7-31
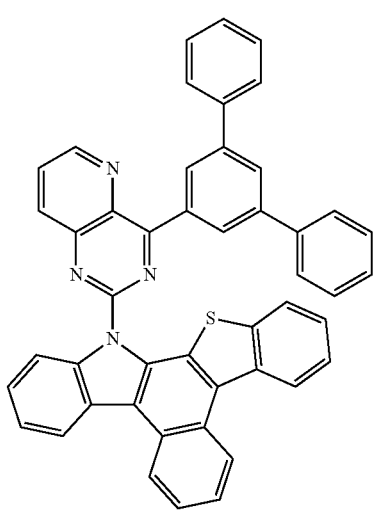
7-32
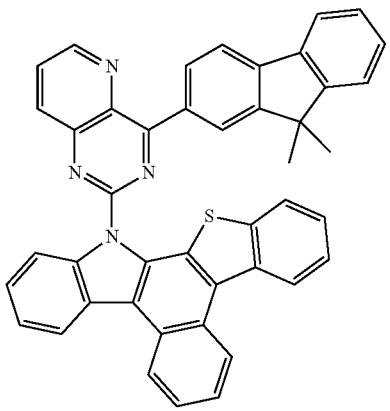
7-33
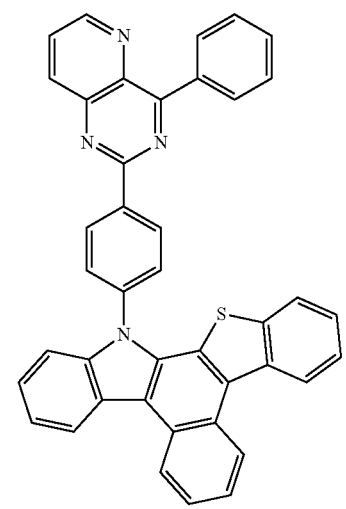
7-34
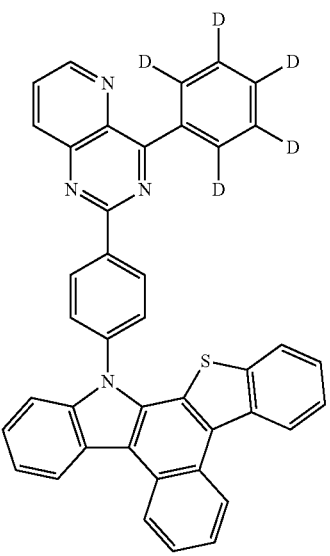

-continued
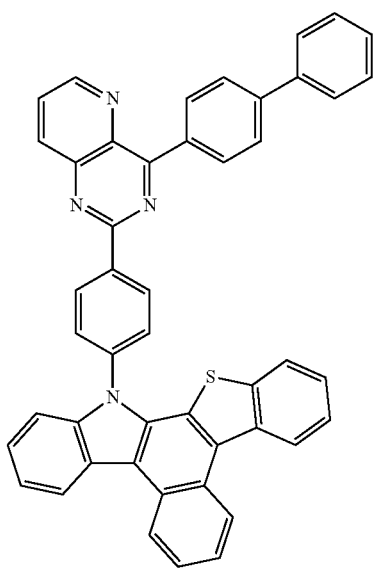
7-35
7-36
7-37
-continued
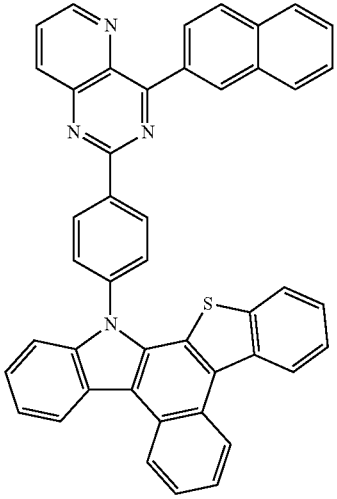
7-38
7-39
7-40

7-41
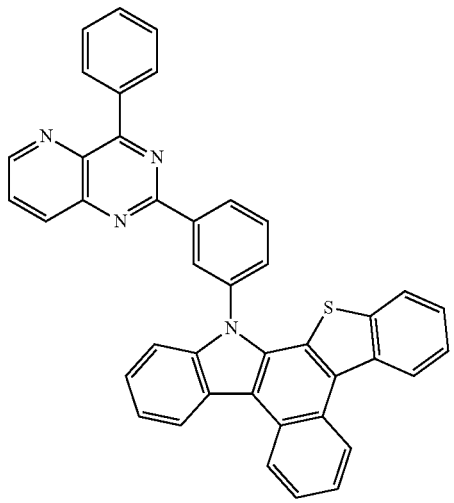
7-42
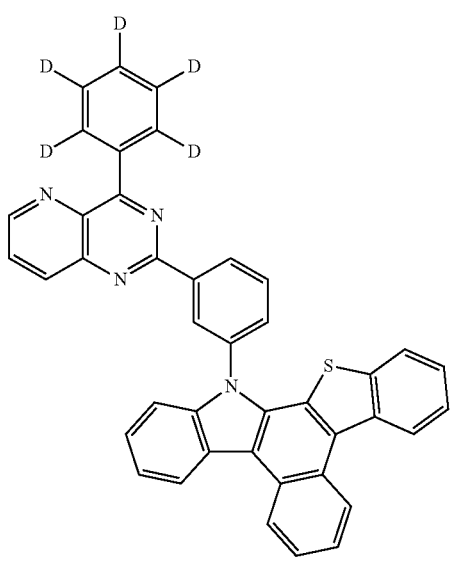
7-43
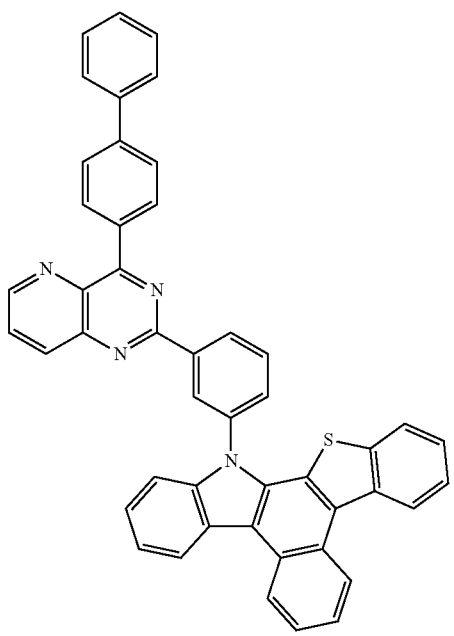
7-44
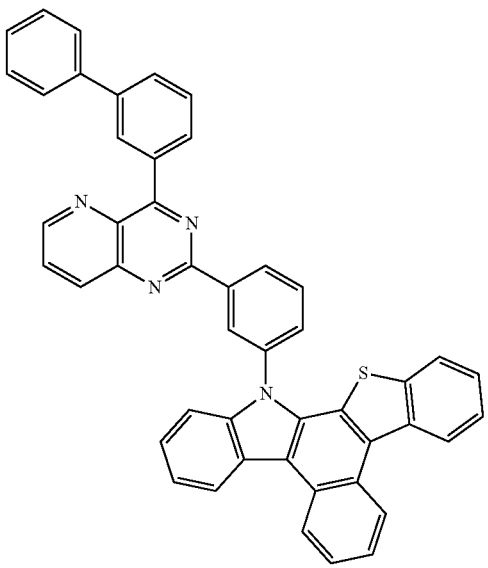
7-45
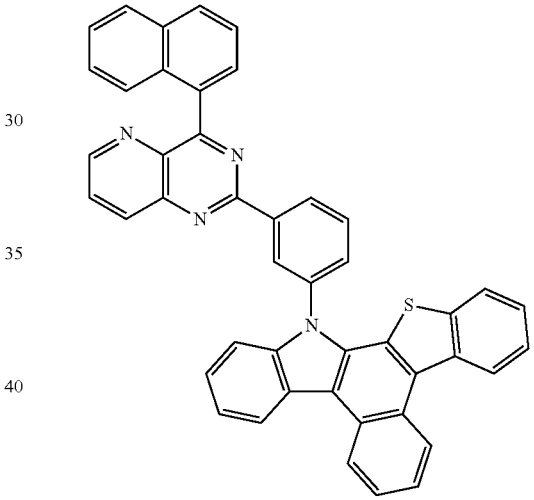
7-46
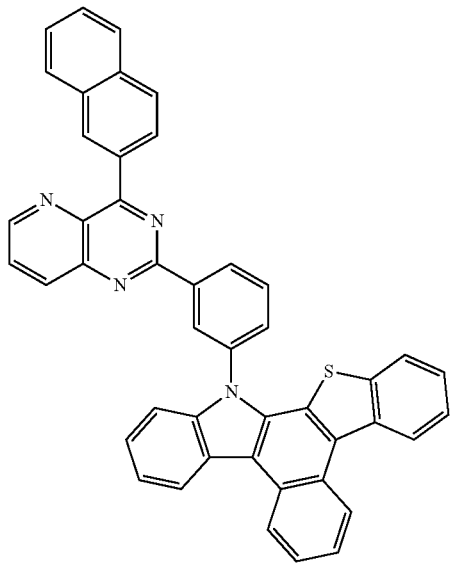

111

-continued 7-47

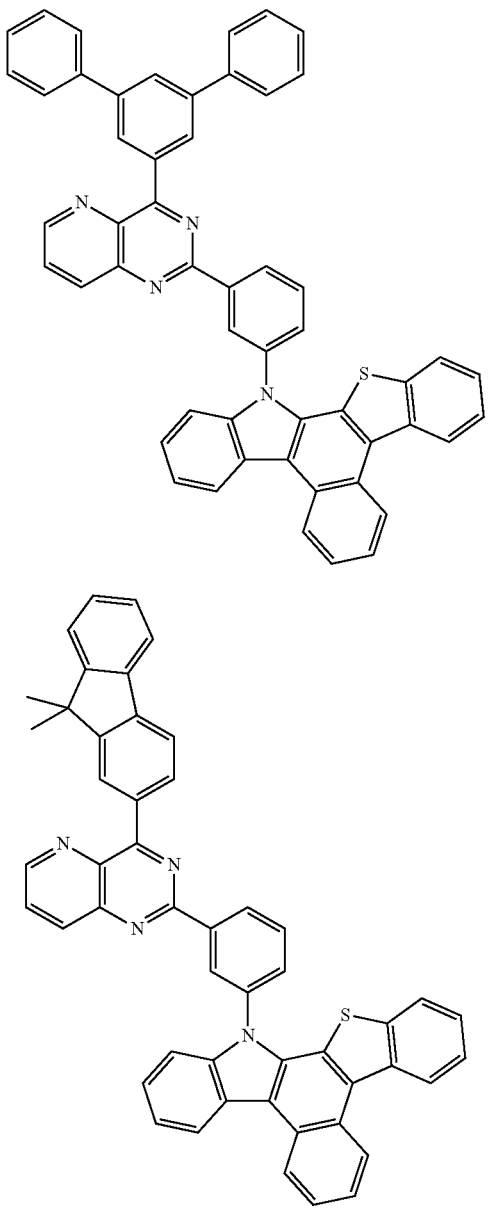

7-48

Hereinafter, Synthesis Examples of the inventive compound represented by Formula 1 above and Preparation Examples of an organic electric element will be described in detail by way of example. However, the following examples are only for illustrative purposes and are not intended to limit the scope of the invention.

Synthesis Example

By way of example, the inventive compound is prepared by reacting one of Sub 1 to Sub 4 with Sub 5, as represented in Reaction Scheme 1 below. Although the following synthesis methods will be described by exemplifying the case where X is S, synthesis is carried out in the same manner as in the following synthesis methods even when X is O or Si, so a separate description thereof will be omitted. In the following Reaction Schemes, $R_1$ corresponds to one of $R_1$ to $R_4$ in Formula 1, $R_2$ corresponds to $R_{21}$ or $R_{22}$ in Formula 1, and $R_3$ corresponds to one of $R_{11}$ to $R_{14}$ in Formula 1.

112

By way of example, the inventive compound may be prepared by Reaction Scheme 1 or Reaction Scheme 2 below.

<Reaction Scheme 1>

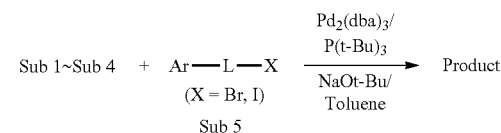

<Reaction Scheme 2>

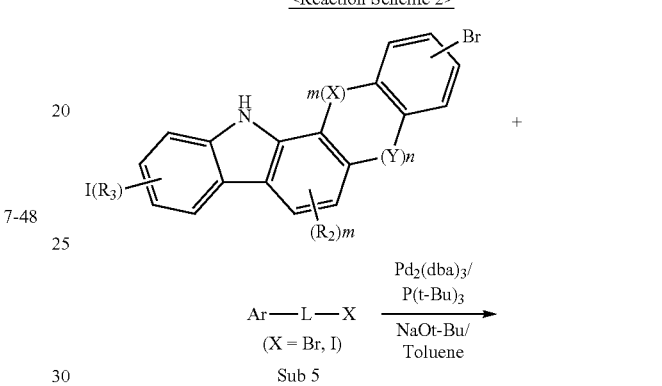

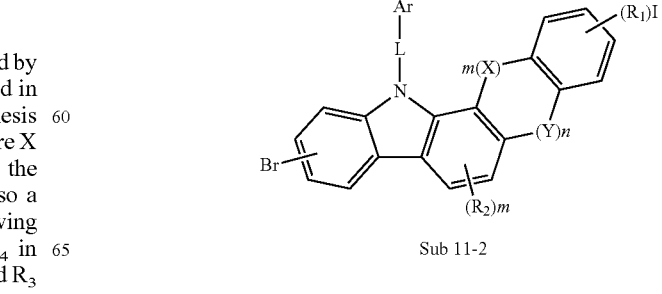

[Method 2-1]

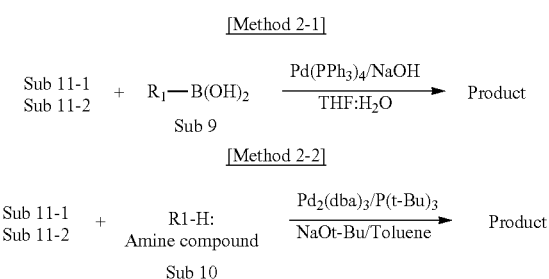

Hereinafter, synthesis methods of Sub 1 to Sub 4 and then preparation methods of the inventive compound according to Reaction Schemes above will be described.

Synthesis Example of Sub 1

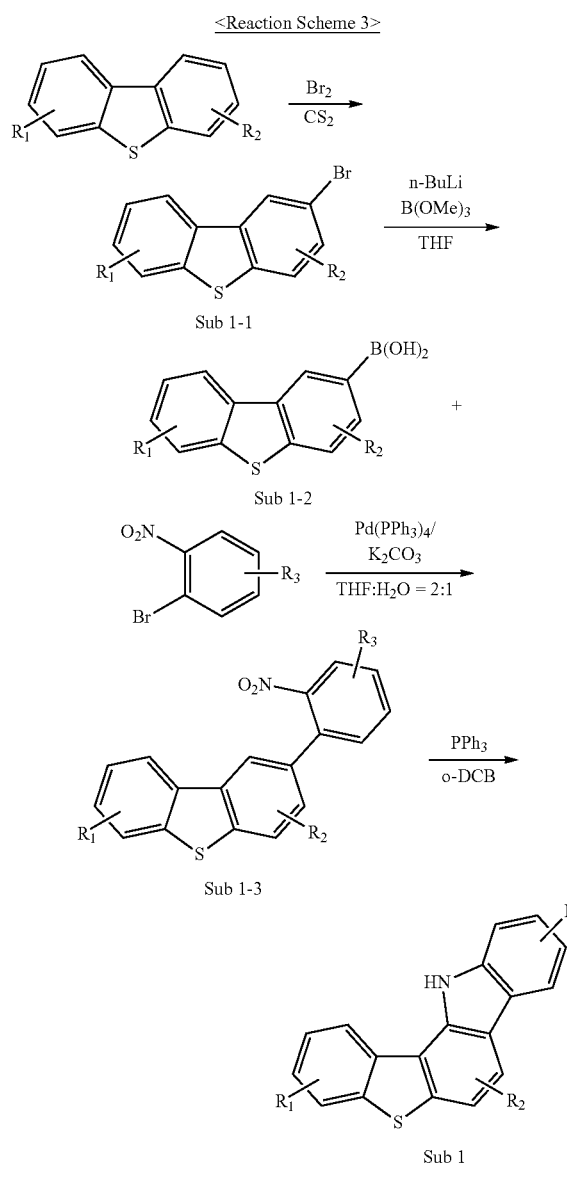

Synthesis Method of Sub 1-1

After a dibenzothiophene derivative substituted by $R_1$, $R_2$ was dissolved in a carbon disulfide solvent under a nitrogen atmosphere, bromine was slowly added dropwise to the reactants, followed by stirring at room temperature for 12 hours. Upon completion of the reaction, the organic solvent was concentrated using a vacuum apparatus, and the resultant product was recrystallized using an ethanol solvent to obtain desired Sub 1-1.

Synthesis Method of Sub 1-2

Sub 1-1 obtained above was dissolved in anhydrous THF, the temperature of the reactants was lowered to −78° C., n-BuLi (2.5M in hexane) was slowly added dropwise to the reactants, and then the reactants were stirred at 0° C. for 1 hour. The temperature of the reactants was lowered to −78° C. again, and trimethyl borate was added dropwise to the reactants, followed by stirring at room temperature for 12 hours. Upon completion of the reaction, the reaction product was added with a 2N—HCl aqueous solution, was stirred for 30 minutes, and then was extracted with ether. The extracted organic layer was dried with $MgSO_4$ and concentrated, and then the produced organic material was separated by a silica gel column and recrystallized to obtain desired Sub 1-2.

Synthesis Method of Sub 1-3

Sub 1-2 obtained above, 1-bromo-2-nitrobenzene substituted by $R_3$, $Pd(PPh_3)_4$, and $K_2CO_3$ were dissolved in anhydrous THF and a small amount of water, followed by reflux for 24 hours. Upon completion of the reaction, the temperature of the reaction product was lowered to room temperature, the reaction product was extracted with $CH_2Cl_2$, and was washed with water. The extracted organic layer was dried with $MgSO_4$ and concentrated, and then the produced organic material was separated by a silica gel column to obtain desired Sub 1-3.

Synthesis Method of Sub 1

Sub 1-3 obtained above and triphenylphosphine were dissolved in o-dichlorobenzene, followed by reflux for 24 hours. Upon completion of the reaction, the solvent was removed using vacuum distillation, and then the concentrated product was separated by a silica gel column and recrystallized to obtain desired Sub 1.

Synthesis Example of Sub 2

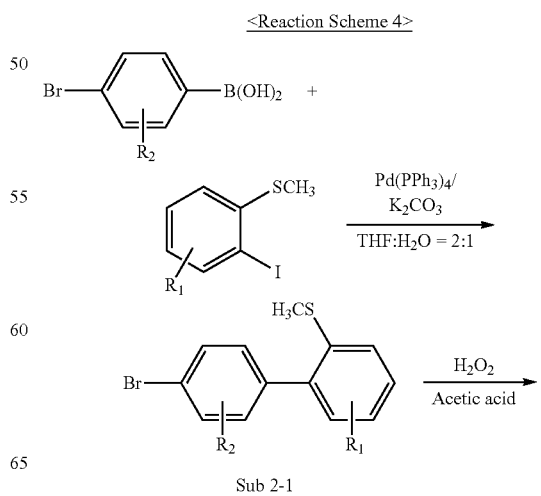

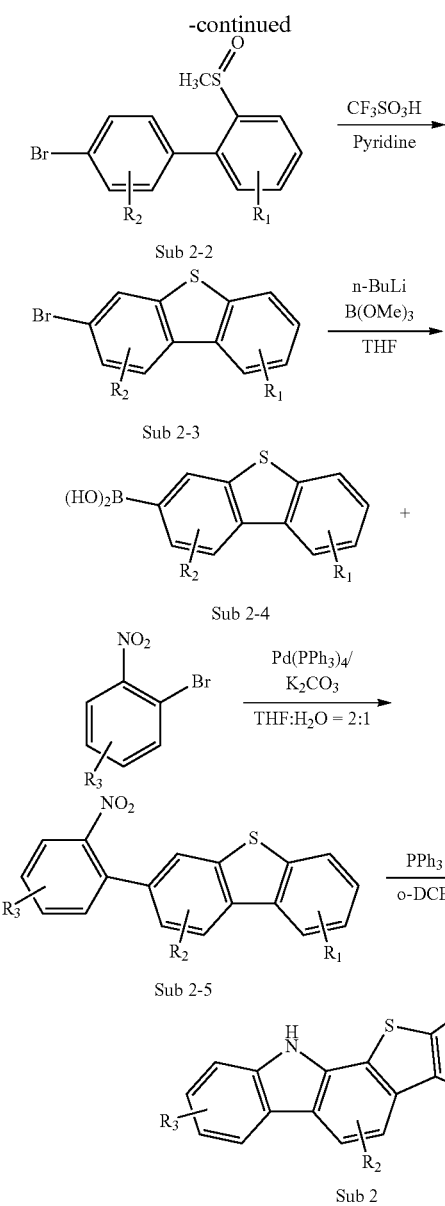

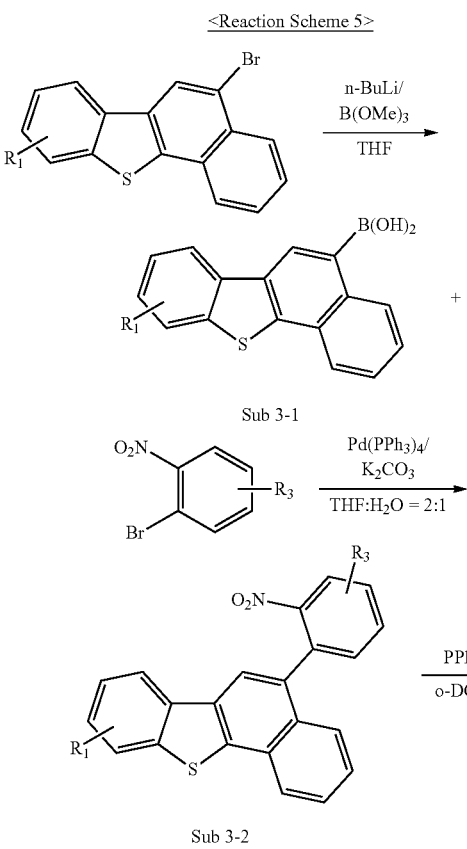

extract was subjected to vacuum-filtration, and then the filtrated organic solvent was concentrated. The resultant product was separated by a silica gel column and recrystallized to obtain desired Sub 2-3.

Synthesis Method of Sub 2-4

Except that Sub 2-3 obtained above was used instead of Sub 1-1, the same procedure as described in Synthesis Method of Sub 1-2 was carried out to obtain desired Sub 2-4.

Synthesis Method of Sub 2-5

Except that Sub 2-4 obtained above, 1-bromo-2-nitrobenzene substituted by $R_3$, $Pd(PPh_3)_4$, $K_2CO_3$, THF, and water were used as reactants, the same procedure as described in Synthesis Method of Sub 1-3 was carried out to obtain desired Sub 2-5.

Synthesis Method of Sub 2

Except that Sub 2-5 obtained above was used instead of Sub 1-3, the same procedure as described in Synthesis Method of Sub 1 was carried out to obtain desired Sub 2.

Synthesis Example of Sub 3

Synthesis Method of Sub 2-1

Except that 4-bromophenylboronic acid substituted by $R_2$, (2-iodophenyl)(methyl)sulfane substituted by $R_1$, $Pd(PPh_3)_4$, $K_2CO_3$, THF, and water were used as reactants, the same procedure as described in Synthesis Method of Sub 1-3 was carried out to obtain desired Sub 2-1.

Synthesis Method of Sub 2-2

Sub 2-1 was dissolved in acetic acid, and hydrogen peroxide dissolved in acetic acid was added dropwise to the reactants, followed by stirring at room temperature for 6 hours. Upon completion of the reaction, acetic acid was removed using a vacuum apparatus, and the resultant product was separated by a silica gel column to obtain desired Sub 2-2.

Synthesis Method of Sub 2-3

Sub 2-3 obtained above and trifluoromethanesulfonic acid were mixed, the mixture was stirred at room temperature for 24 hours, and water and pyridine (8:1) were slowly added to the mixture, followed by reflux for 30 minutes. Upon completion of the reaction, the temperature of the reaction product was lowered, the reaction product was extracted with $CH_2Cl_2$, and was washed with water. A small amount of water was removed from the extract by anhydrous $MgSO_4$, the

117

Synthesis Method of Sub 3-1

Except that 5-bromobenzo[b]naphtha[2,1-d]thiophene was used instead of Sub 1-1, the same procedure as described in Synthesis Method of Sub 1-2 was carried out to obtain desired Sub 3-1.

Synthesis Method of Sub 3-2

Except that Sub 3-1 obtained above, 1-bromo-2-nitrobenzene substituted by $R_3$, Pd(PPh$_3$)$_4$, K$_2$CO$_3$, THF, and water were used as reactants, the same procedure as described in Synthesis Method of Sub 1-3 was carried out to obtain desired Sub 3-2.

Synthesis Method of Sub 3

Except that Sub 3-2 obtained above was used instead of Sub 1-3, the same procedure as described in Synthesis Method of Sub 1 was carried out to obtain desired Sub 3.

Synthesis Example of Sub 4

<Reaction Scheme 6>

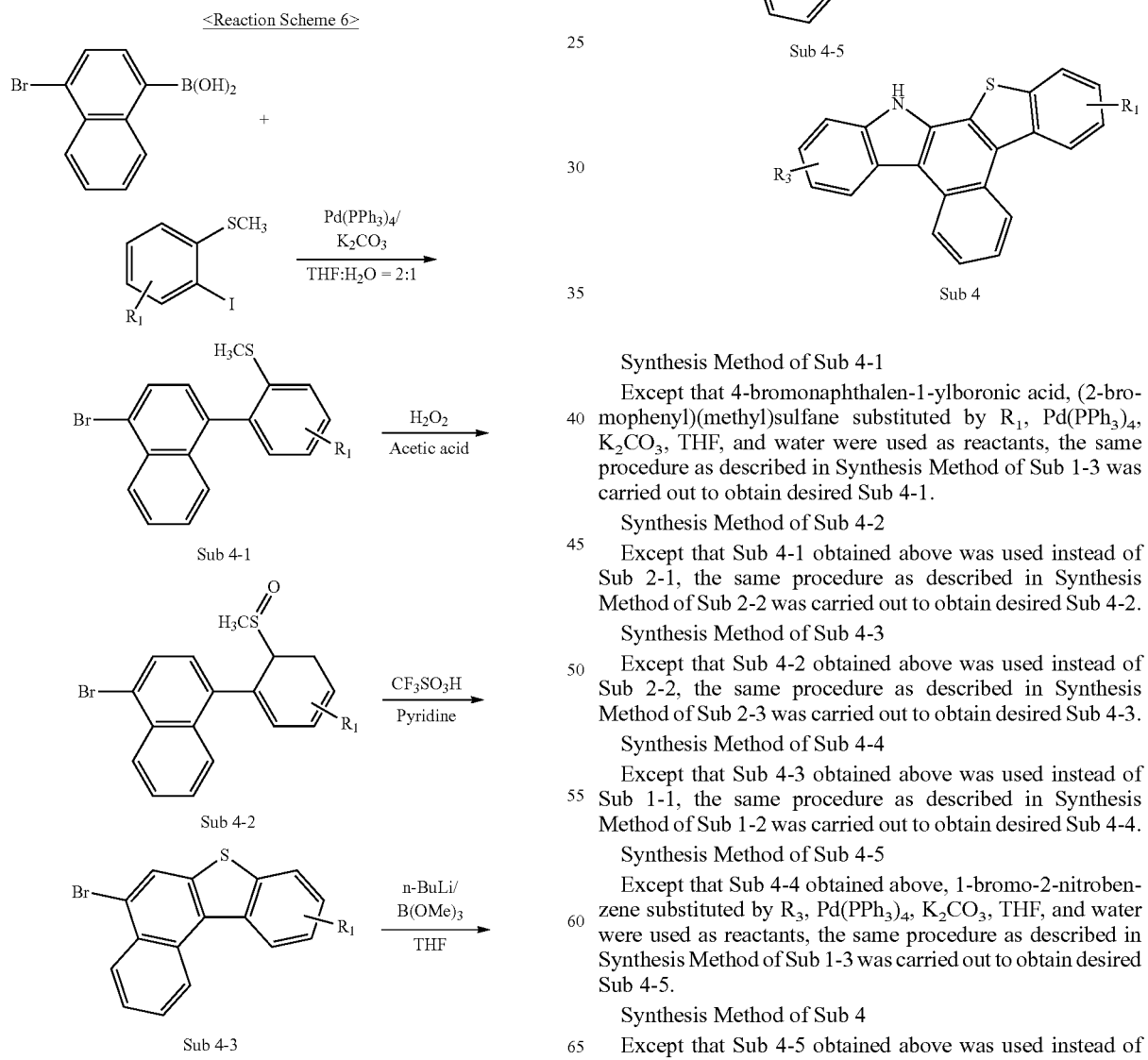

Synthesis Method of Sub 4-1

Except that 4-bromonaphthalen-1-ylboronic acid, (2-bromophenyl)(methyl)sulfane substituted by $R_1$, Pd(PPh$_3$)$_4$, K$_2$CO$_3$, THF, and water were used as reactants, the same procedure as described in Synthesis Method of Sub 1-3 was carried out to obtain desired Sub 4-1.

Synthesis Method of Sub 4-2

Except that Sub 4-1 obtained above was used instead of Sub 2-1, the same procedure as described in Synthesis Method of Sub 2-2 was carried out to obtain desired Sub 4-2.

Synthesis Method of Sub 4-3

Except that Sub 4-2 obtained above was used instead of Sub 2-2, the same procedure as described in Synthesis Method of Sub 2-3 was carried out to obtain desired Sub 4-3.

Synthesis Method of Sub 4-4

Except that Sub 4-3 obtained above was used instead of Sub 1-1, the same procedure as described in Synthesis Method of Sub 1-2 was carried out to obtain desired Sub 4-4.

Synthesis Method of Sub 4-5

Except that Sub 4-4 obtained above, 1-bromo-2-nitrobenzene substituted by $R_3$, Pd(PPh$_3$)$_4$, K$_2$CO$_3$, THF, and water were used as reactants, the same procedure as described in Synthesis Method of Sub 1-3 was carried out to obtain desired Sub 4-5.

Synthesis Method of Sub 4

Except that Sub 4-5 obtained above was used instead of Sub 1-3, the same procedure as described in Synthesis Method of Sub 1 was carried out to obtain desired Sub 4.

Synthesis Example of Product

The compound according to the present invention may be synthesized by Reaction Schemes 1 and 2 above. Examples of synthesizing the inventive compound by these two methods are as follows.

[Method 1] (Reaction Scheme 1)

Sub 1-4 and Sub 5 were mixed with toluene, and $Pd_2(dba)_3$, $P(t-Bu)_3$, and NaOt-Bu were added to the mixture respectively, followed by reflux under stirring at 100° C. for 24 hours. The reaction product was extracted with ether and water, the extracted organic layer was dried with $MgSO_4$ and concentrated, and then the produced organic material was separated by a silica gel column and recrystallized to obtain a final product.

[Method 2-1] (Reaction Scheme 2)

Compound Sub 11-1 or Sub 11-2 (1 equivalent weight) and THF were put into a round bottom flask to dissolve the compound in THF, and compound Sub 9 (1.2 equivalent weight), $Pd(PPh_3)_4$ (0.03 equivalent weight), NaOH (3 equivalent weight), and water were added to the reactants, followed by reflux under stirring. Upon completion of the reaction, the reaction product was extracted with ether and water, the extracted organic layer was dried with $MgSO_4$ and concentrated, and then the produced organic material was separated by a silica gel column and recrystallized to obtain a final product.

[Method 2-2] (Reaction Scheme 2)

Compound Sub 11-1 or Sub 11-2 (1 equivalent weight), compound Sub 10 (1.2 equivalent weight), $Pd_2(dba)_3$ (0.05 equivalent weight), $P(t-Bu)_3$ (0.1 equivalent weight), NaOt-Bu (3 equivalent weight), and toluene (10.5 mL/1 mmol) were put into a round bottom flask, and then the reactants were subjected to the reaction at 100° C. Upon completion of the reaction, the reaction product was extracted with ether and water, the extracted organic layer was dried with $MgSO_4$ and concentrated, and then the produced organic material was separated by a silica gel column and recrystallized to obtain a final product.

Examples of Sub 5, Sub 9, and Sub 10 used in Method 1 and Method 2 include, but not limited to, the following compounds.

Examples of Sub 5

Examples of Sub 5 include, but not limited to, the following materials.

Sub 5-1

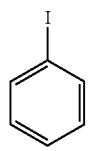

Sub 5-2

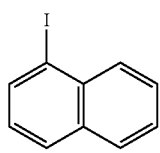

Sub 5-3

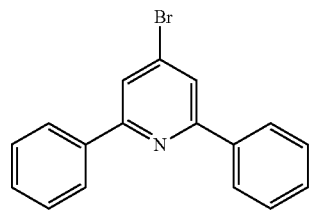

Sub 5-4

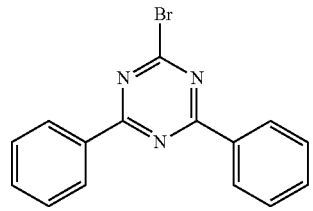

Sub 5-5

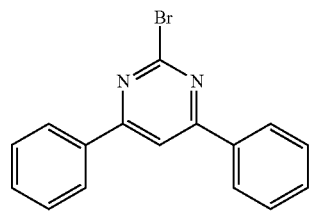

Sub 5-6

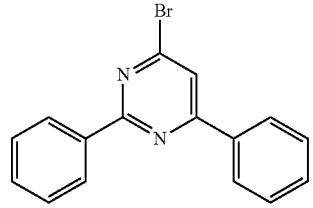

Sub 5-7

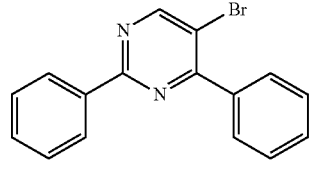

Sub 5-8

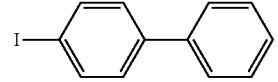

Sub 5-9

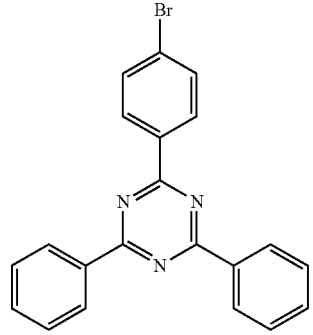

Sub 5-10
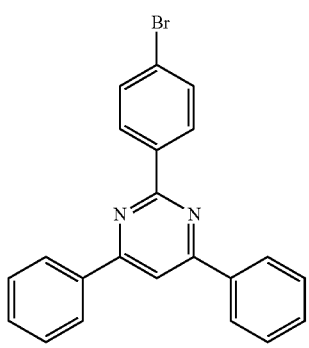
Sub 5-11
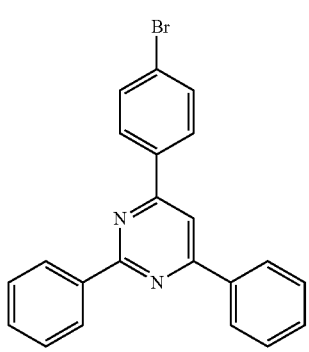
Sub 5-12
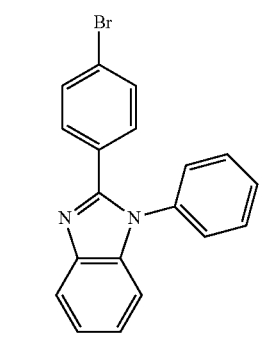
Sub 5-13
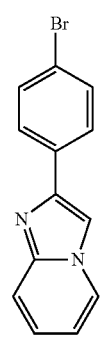
Sub 5-14
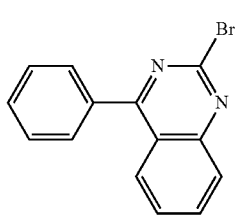
Sub 5-15
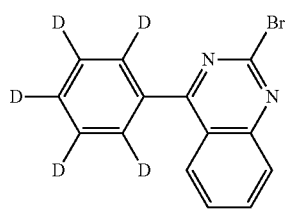
Sub 5-16
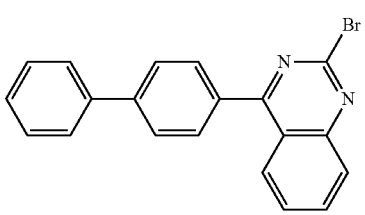
Sub 5-17
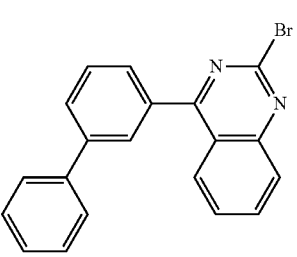
Sub 5-18
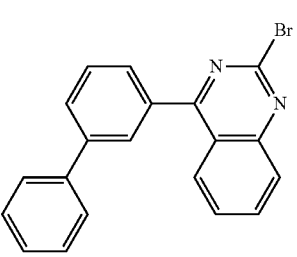
Sub 5-19
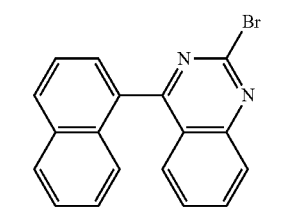
Sub 5-20
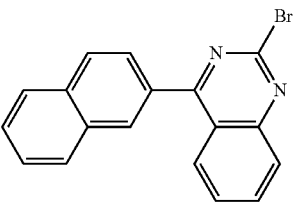
Sub 5-21
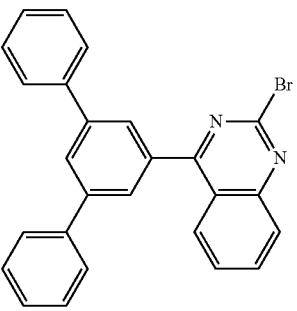

Sub 5-22
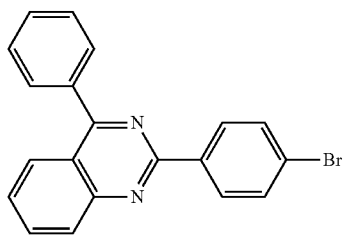
Sub 5-27
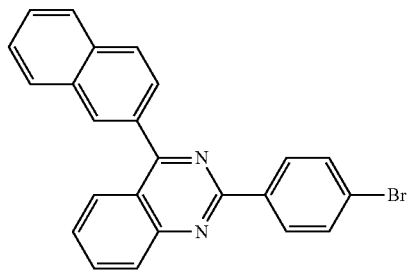
Sub 5-23
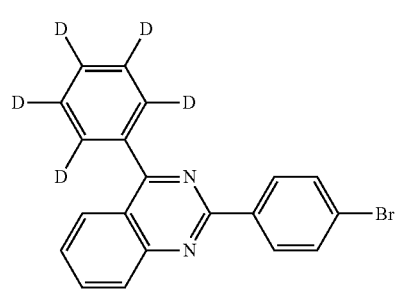
Sub 5-28
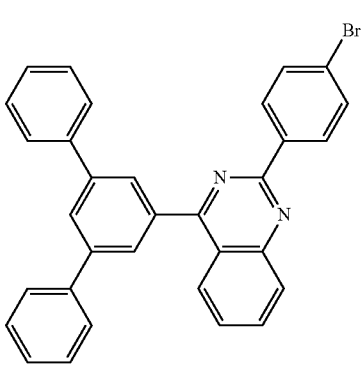
Sub 5-24
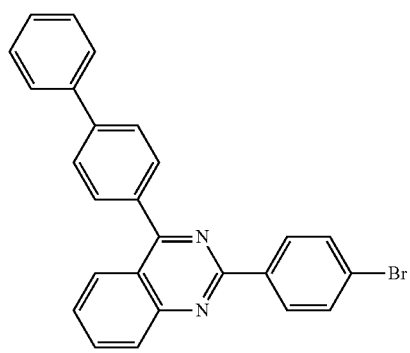
Sub 5-29
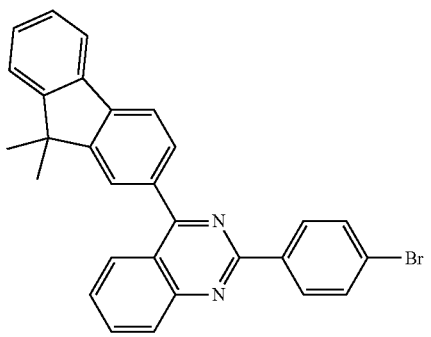
Sub 5-25
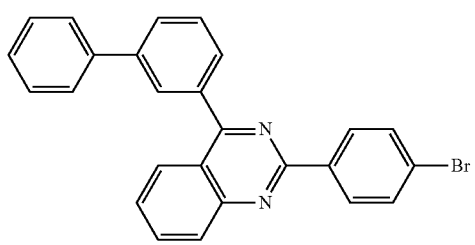
Sub 5-30
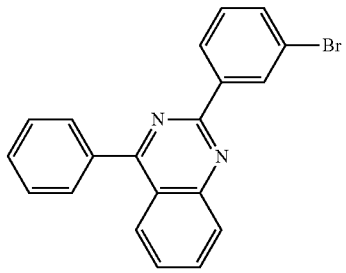
Sub 5-26
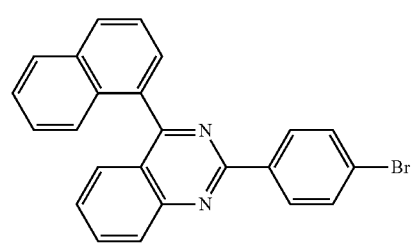
Sub 5-31
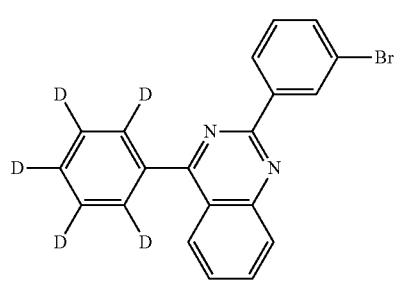

Sub 5-32
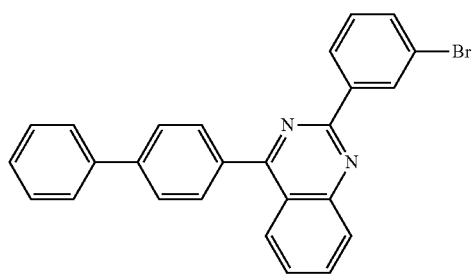
Sub 5-33
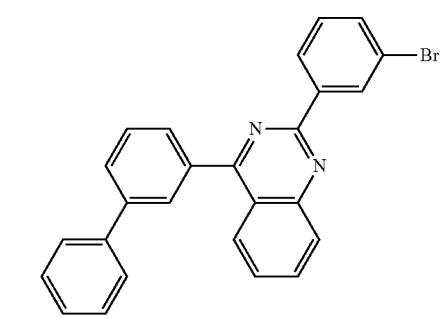
Sub 5-34
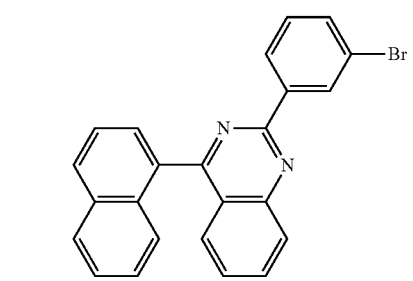
Sub 5-35
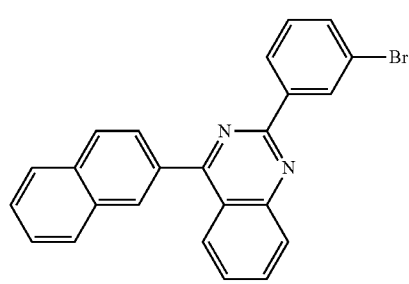
Sub 5-36
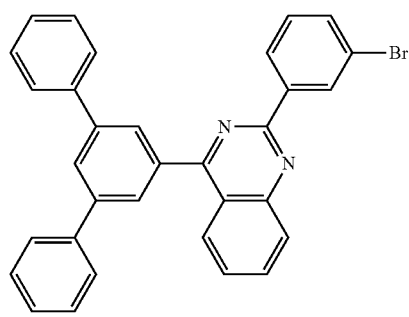
Sub 5-37
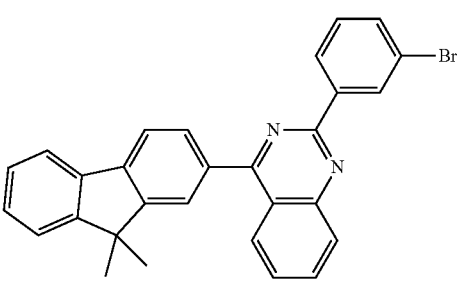
Sub 5-38
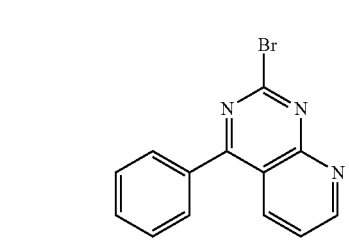
Sub 5-39
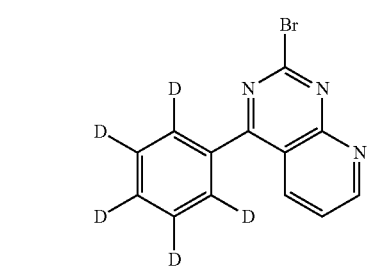
Sub 5-40
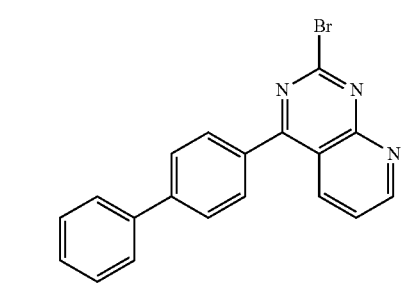
Sub 5-41
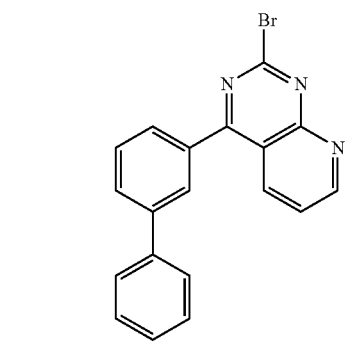

Sub 5-42
Sub 5-43
Sub 5-44
Sub 5-45
Sub 5-46
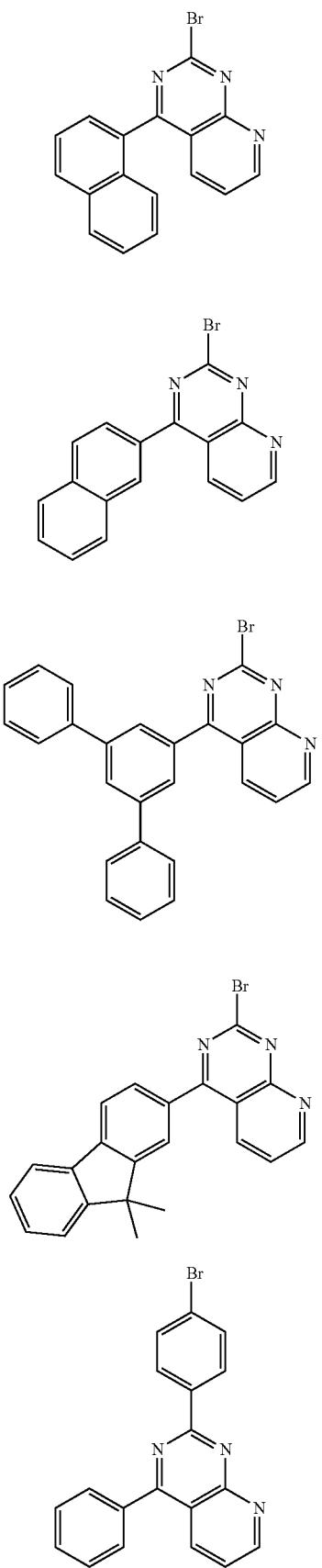
Sub 5-47
Sub 5-48
Sub 5-49
Sub 5-50
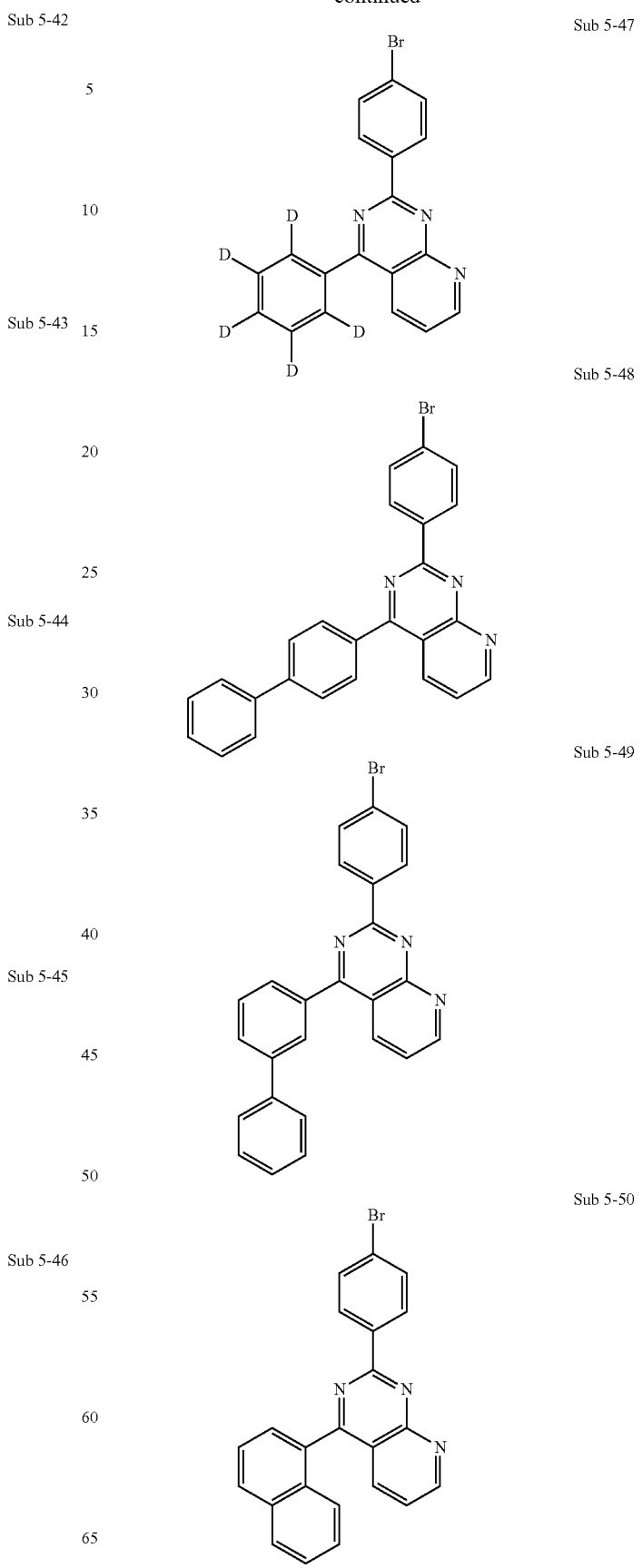

-continued
Sub 5-51
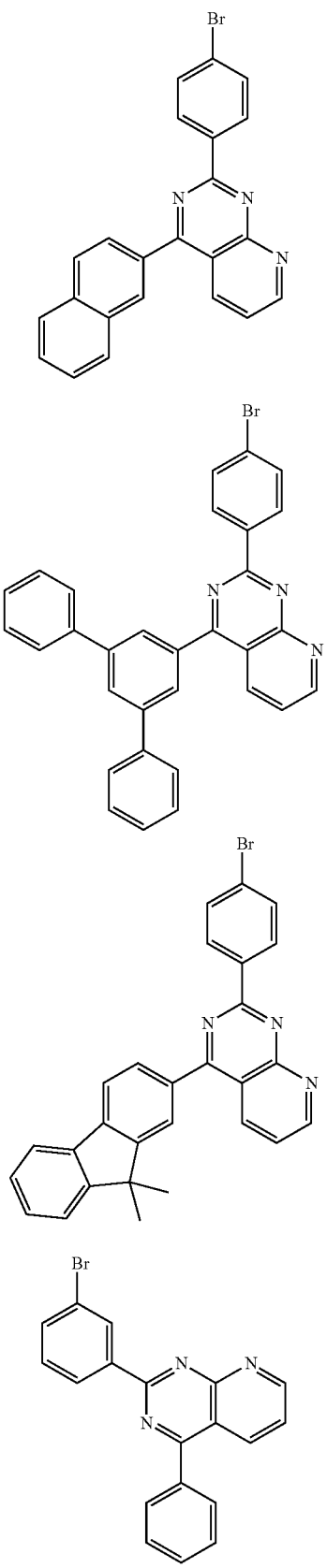
Sub 5-52
Sub 5-53
Sub 5-54
-continued
Sub 5-55
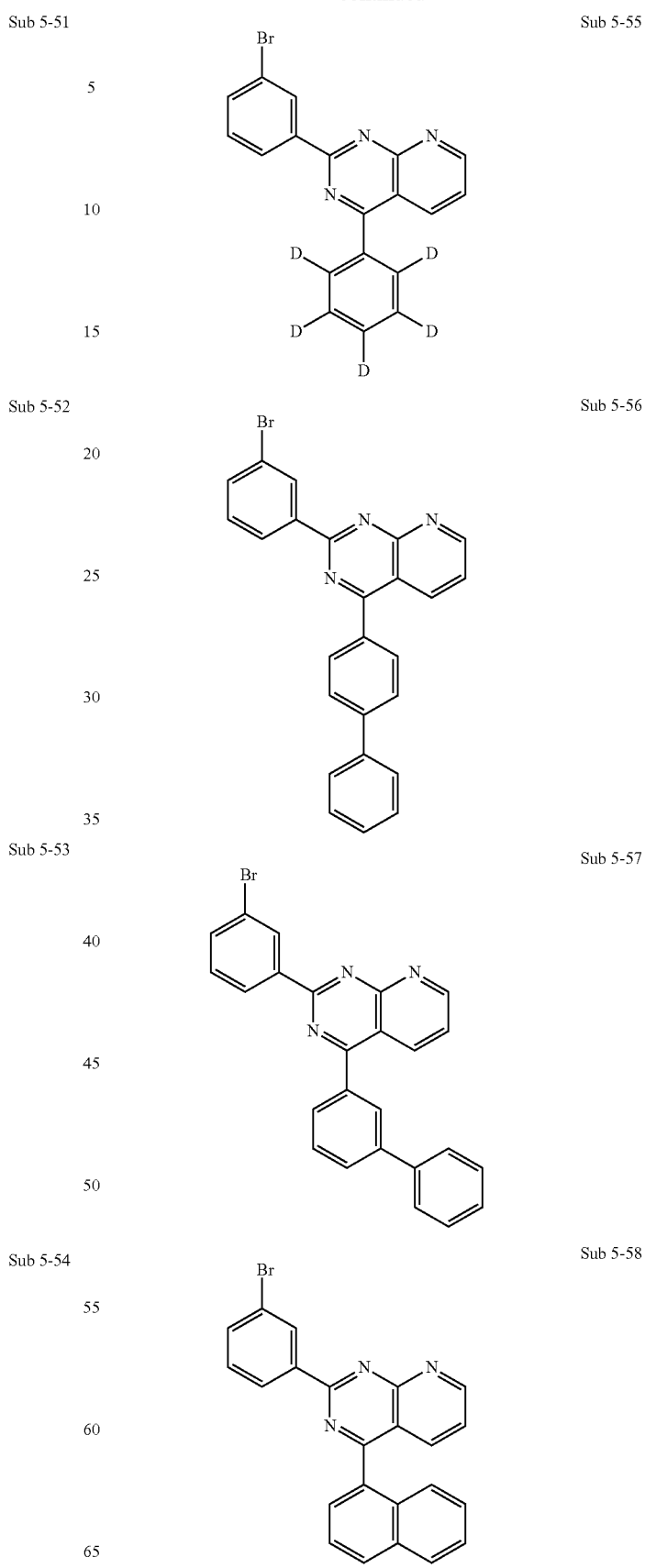
Sub 5-56
Sub 5-57
Sub 5-58

Sub 5-59
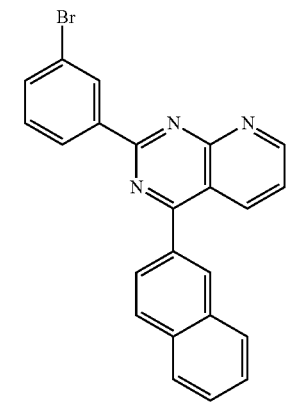
Sub 5-60
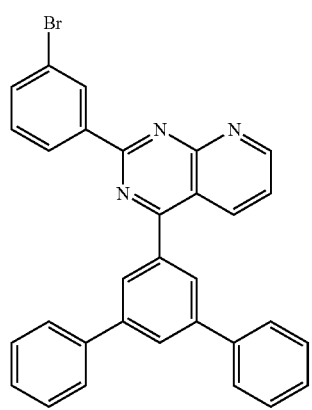
Sub 5-61
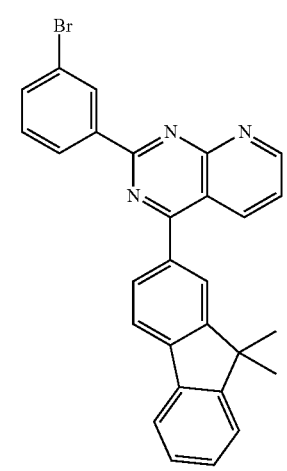
Sub 5-62
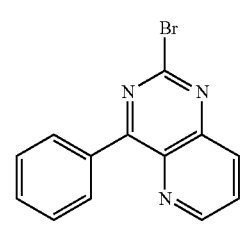
Sub 5-63
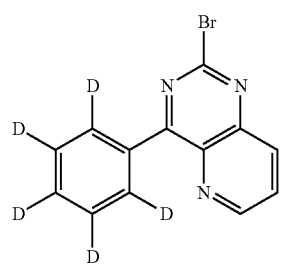
Sub 5-64
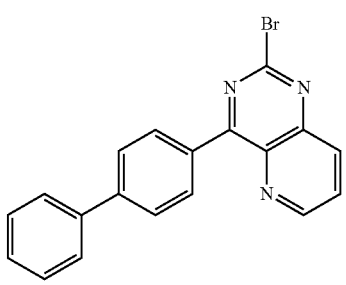
Sub 5-65
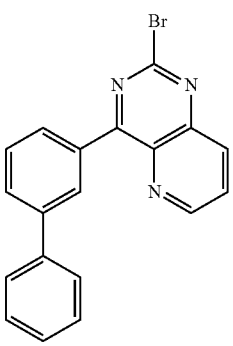
Sub 5-66
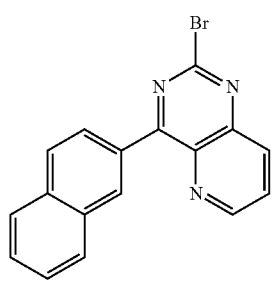
Sub 5-67

Sub 5-68
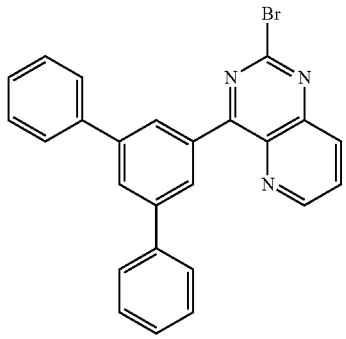
Sub 5-69
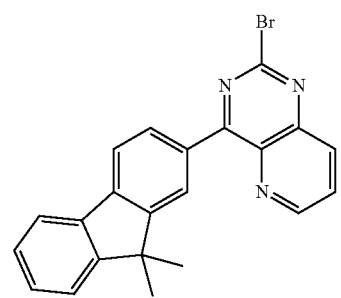
Sub 5-70
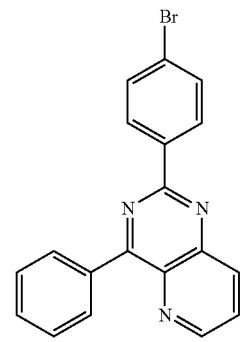
Sub 5-71
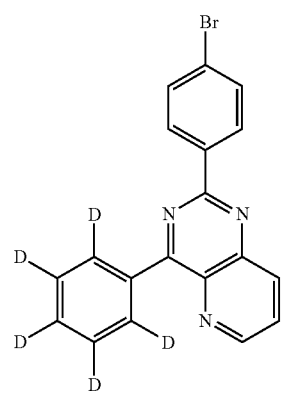
Sub 5-72
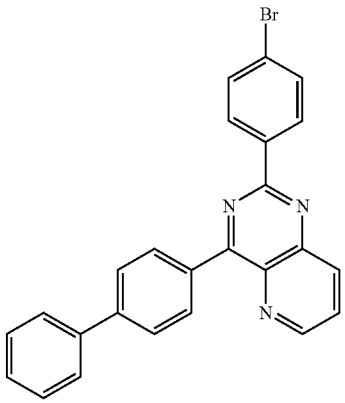
Sub 5-73
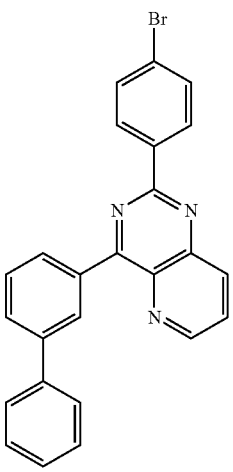
Sub 5-74
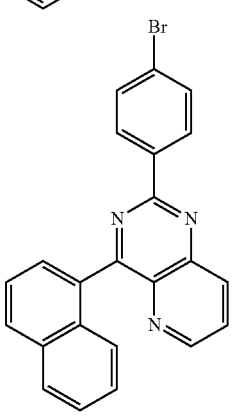
Sub 5-75
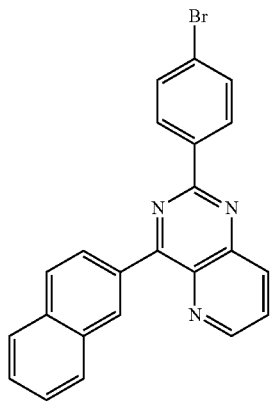

Sub 5-76
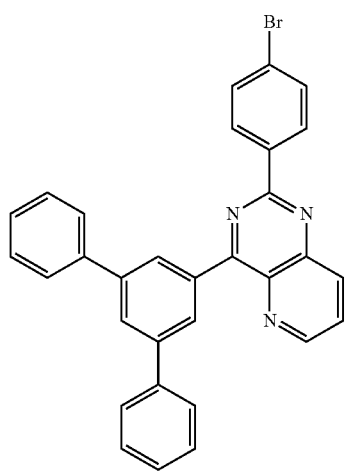
Sub 5-77
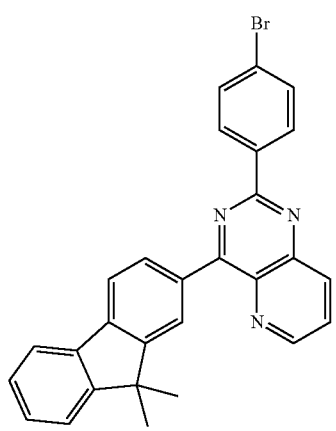
Sub 5-78
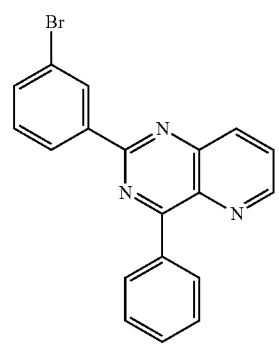
Sub 5-79
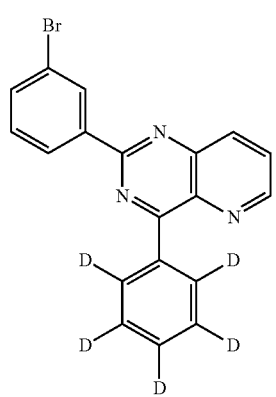
Sub 5-80
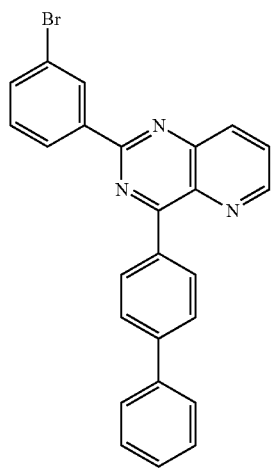
Sub 5-81
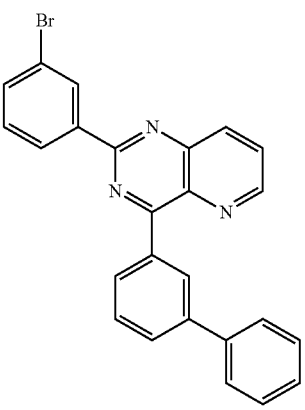
Sub 5-82
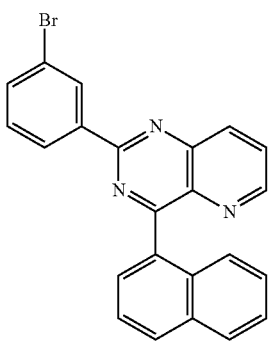
Sub 5-83
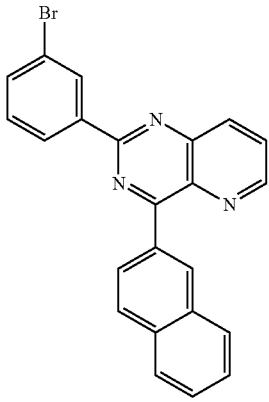

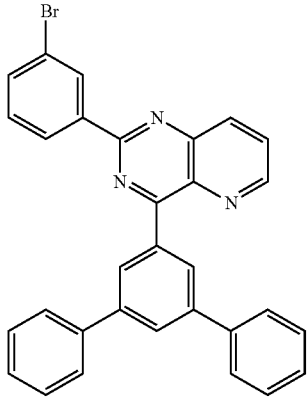

Sub 5-84

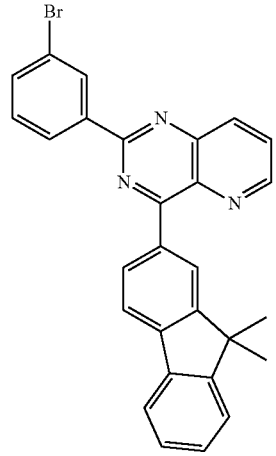

Sub 5-85

Field desorption mass spectrometry (FD-MS) values for the above materials of Sub 5 above are given in Table 1 below.

TABLE 1

| Compound | FD-MS | Compound | FD-MS |
|---|---|---|---|
| Sub 5-1 | m/z = 203.94($C_6H_5I$ = 204.01) | Sub 5-2 | m/z = 253.96($C_{10}H_7I$ = 254.07) |
| Sub 5-3 | m/z = 309.02($C_{17}H_{12}BrN$ = 310.19) | Sub 5-4 | m/z = 311.01($C_{15}H_{10}BrN_3$ = 312.16) |
| Sub 5-5 | m/z = 310.01($C_{16}H_{11}BrN_2$ = 311.18) | Sub 5-6 | m/z = 310.01($C_{16}H_{11}BrN_2$ = 311.18) |
| Sub 5-7 | m/z = 310.01($C_{16}H_{11}BrN_2$ = 311.18) | Sub 5-8 | m/z = 279.97($C_{12}H_9I$ = 280.10) |
| Sub 5-9 | m/z = 387.04($C_{21}H_{14}BrN_3$ = 388.26) | Sub 5-10 | m/z = 386.04($C_{22}H_{15}BrN_2$ = 387.27) |
| Sub 5-11 | m/z = 386.04($C_{22}H_{15}BrN_2$ = 387.27) | Sub 5-12 | m/z = 348.03($C_{19}H_{13}BrN_2$ = 349.22) |
| Sub 5-13 | m/z = 271.99($C_{13}H_9BrN_2$ = 273.13) | Sub 5-14 | m/z = 283.99 ($C_{14}H_9BrN_2$ = 285.14) |
| Sub 5-15 | m/z = 289.03($C_{14}H_4D_5BrN_2$ = 290.17) | Sub 5-16 | m/z = 360.03 ($C_{20}H_{13}BrN_2$ = 361.23) |
| Sub 5-17 | m/z = 360.03 ($C_{20}H_{13}BrN_2$ = 361.23) | Sub 5-18 | m/z = 334.01 ($C_{18}H_{11}BrN_2$ = 335.20) |
| Sub 5-19 | m/z = 334.01 ($C_{18}H_{11}BrN_2$ = 335.20) | Sub 5-20 | m/z = 436.06 ($C_{26}H_{17}BrN_2$ = 437.33) |
| Sub 5-21 | m/z = 400.06 ($C_{23}H_{17}BrN_2$ = 401.30) | Sub 5-22 | m/z = 360.03 ($C_{20}H_{13}BrN_2$ = 361.23) |
| Sub 5-23 | m/z = 365.06 ($C_{20}H_8D_5BrN_2$ = 366.27) | Sub 5-24 | m/z = 436.06 ($C_{26}H_{17}BrN_2$ = 437.33) |
| Sub 5-25 | m/z = 436.06 ($C_{26}H_{17}BrN_2$ = 437.33) | Sub 5-26 | m/z = 410.04 ($C_{24}H_{15}BrN_2$ = 411.29) |
| Sub 5-27 | m/z = 410.04($C_{24}H_{15}BrN_2$ = 411.29) | Sub 5-28 | m/z = 512.09 ($C_{32}H_{21}BrN_2$ = 513.43) |
| Sub 5-29 | m/z = 476.09 ($C_{29}H_{21}BrN_2$ = 477.39) | Sub 5-30 | m/z = 360.03 ($C_{20}H_{13}BrN_2$ = 361.23) |
| Sub 5-31 | m/z = 365.06 ($C_{20}H_8D_5BrN_2$ = 366.27) | Sub 5-32 | m/z = 436.06 ($C_{26}H_{17}BrN_2$ = 437.33) |
| Sub 5-33 | m/z = 436.06 ($C_{26}H_{17}BrN_2$ = 437.33) | Sub 5-34 | m/z = 410.04 ($C_{24}H_{15}BrN_2$ = 411.29) |
| Sub 5-35 | m/z = 410.04 ($C_{24}H_{15}BrN_2$ = 411.29) | Sub 5-36 | m/z = 512.09 ($C_{32}H_{21}BrN_2$ = 513.43) |
| Sub 5-37 | m/z = 476.09 ($C_{29}H_{21}BrN_2$ = 477.39) | Sub 5-38 | m/z = 284.99 ($C_{13}H_8BrN_3$ = 286.13) |
| Sub 5-39 | m/z = 290.02 ($C_{13}H_3D_5BrN_3$ = 291.16) | Sub 5-40 | m/z = 361.02 ($C_{19}H_{12}BrN_3$ = 362.22) |
| Sub 5-41 | m/z = 361.02 ($C_{19}H_{12}BrN_3$ = 362.22) | Sub 5-42 | m/z = 335.01 ($C_{17}H_{10}BrN_3$ = 336.19) |
| Sub 5-43 | m/z = 335.01 ($C_{17}H_{10}BrN_3$ = 336.19) | Sub 5-44 | m/z = 437.05 ($C_{25}H_{16}BrN_3$ = 438.32) |
| Sub 5-45 | m/z = 401.05 ($C_{22}H_{15}BrN_3$ = 402.29) | Sub 5-46 | m/z = 361.02 ($C_{19}H_{12}BrN_3$ = 362.22) |
| Sub 5-47 | m/z = 366.05 ($C_{19}H_7D_5BrN_3$ = 367.25) | Sub 5-48 | m/z = 437.05 ($C_{25}H_{16}BrN_3$ = 438.32) |
| Sub 5-49 | m/z = 437.05 ($C_{25}H_{16}BrN_3$ = 438.32) | Sub 5-50 | m/z = 411.04 ($C_{23}H_{14}BrN_3$ = 412.28) |
| Sub 5-51 | m/z = 411.04 ($C_{23}H_{14}BrN_3$ = 412.28) | Sub 5-52 | m/z = 513.08 ($C_{31}H_{20}BrN_3$ = 514.41) |
| Sub 5-53 | m/z = 477.08 ($C_{28}H_{20}BrN_3$ = 478.38) | Sub 5-54 | m/z = 361.02 ($C_{19}H_{12}BrN_3$ = 362.22) |
| Sub 5-55 | m/z = 366.05 ($C_{19}H_7D_5BrN_3$ = 367.25) | Sub 5-56 | m/z = 437.05 ($C_{25}H_{16}BrN_3$ = 438.32) |
| Sub 5-57 | m/z = 437.05 ($C_{25}H_{16}BrN_3$ = 438.32) | Sub 5-58 | m/z = 411.04 ($C_{23}H_{14}BrN_3$ = 412.28) |
| Sub 5-59 | m/z = 411.04 ($C_{23}H_{14}BrN_3$ = 412.28) | Sub 5-60 | m/z = 513.08 ($C_{31}H_{20}BrN_3$ = 514.41) |
| Sub 5-61 | m/z = 477.08 ($C_{28}H_{20}BrN_3$ = 478.38) | Sub 5-62 | m/z = 284.99 ($C_{13}H_8BrN_3$ = 286.13) |
| Sub 5-63 | m/z = 290.02 ($C_{13}H_3D_5BrN_3$ = 291.16) | Sub 5-64 | m/z = 361.02 ($C_{19}H_{12}BrN_3$ = 362.22) |
| Sub 5-65 | m/z = 361.02 ($C_{19}H_{12}BrN_3$ = 362.22) | Sub 5-66 | m/z = 335.01 ($C_{17}H_{10}BrN_3$ = 336.19) |
| Sub 5-67 | m/z = 335.01 ($C_{17}H_{10}BrN_3$ = 336.19) | Sub 5-68 | m/z = 437.05 ($C_{25}H_{16}BrN_3$ = 438.32) |
| Sub 5-69 | m/z = 401.05 ($C_{22}H_{16}BrN_3$ = 402.29) | Sub 5-70 | m/z = 361.02 ($C_{19}H_{12}BrN_3$ = 362.22) |
| Sub 5-71 | m/z = 366.05 ($C_{19}H_7D_5BrN_3$ = 367.25) | Sub 5-72 | m/z = 437.05 ($C_{25}H_{16}BrN_3$ = 438.32) |
| Sub 5-73 | m/z = 437.05 ($C_{25}H_{16}BrN_3$ = 438.32) | Sub 5-74 | m/z = 411.04 ($C_{23}H_{14}BrN_3$ = 412.28) |
| Sub 5-75 | m/z = 411.04 ($C_{23}H_{14}BrN_3$ = 412.28) | Sub 5-76 | m/z = 513.08 ($C_{31}H_{20}BrN_3$ = 514.41) |
| Sub 5-77 | m/z = 477.08 ($C_{28}H_{20}BrN_3$ = 478.38) | Sub 5-78 | m/z = 361.02 ($C_{19}H_{12}BrN_3$ = 362.22) |
| Sub 5-79 | m/z = 366.05 ($C_{19}H_7D_5BrN_3$ = 367.25) | Sub 5-80 | m/z = 437.05 ($C_{25}H_{16}BrN_3$ = 438.32) |
| Sub 5-81 | m/z = 437.05 ($C_{25}H_{16}BrN_3$ = 438.32) | Sub 5-82 | m/z = 411.04 ($C_{23}H_{14}BrN_3$ = 412.28) |
| Sub 5-83 | m/z = 411.04 ($C_{23}H_{14}BrN_3$ = 412.28) | Sub 5-84 | m/z = 513.08 ($C_{31}H_{20}BrN_3$ = 514.41) |
| Sub 5-85 | m/z = 477.08 ($C_{28}H_{20}BrN_3$ = 478.38) | | |

Examples of Sub 9
Examples of Sub 9 include, but not limited to, the following materials.
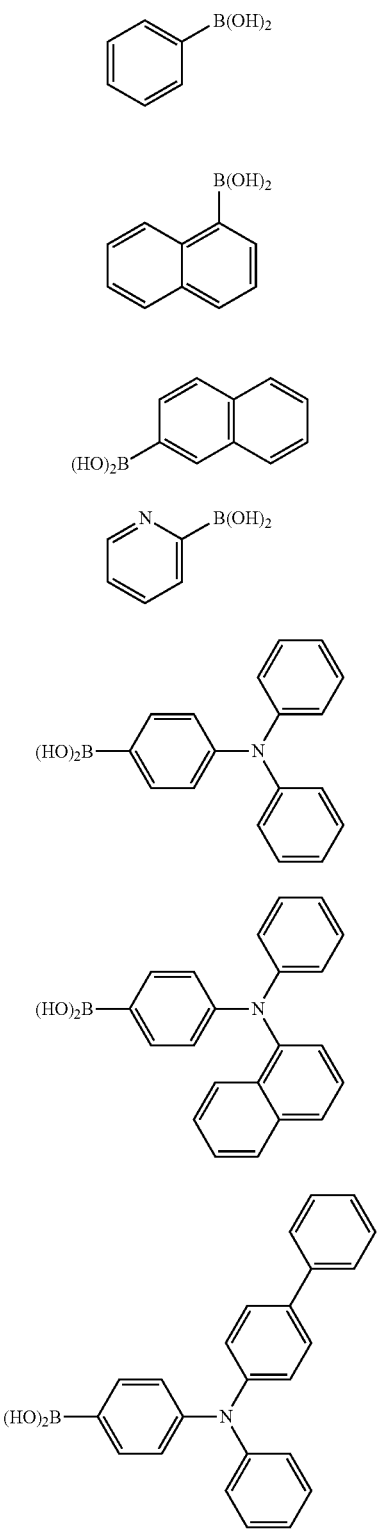
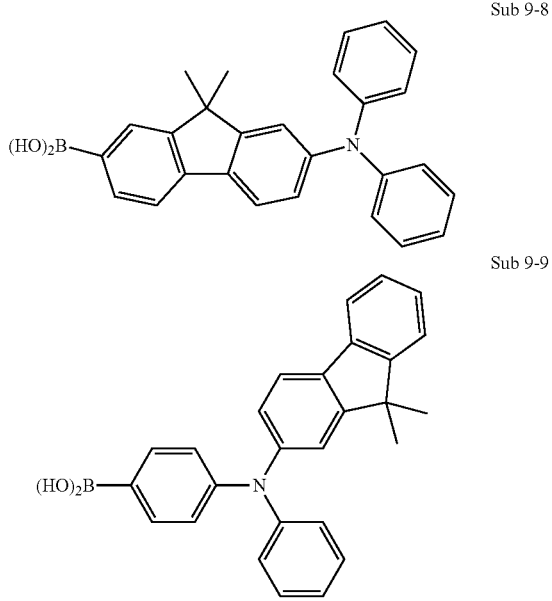
Examples of Sub 10
Examples of Sub 10 include, but not limited to, the following materials.
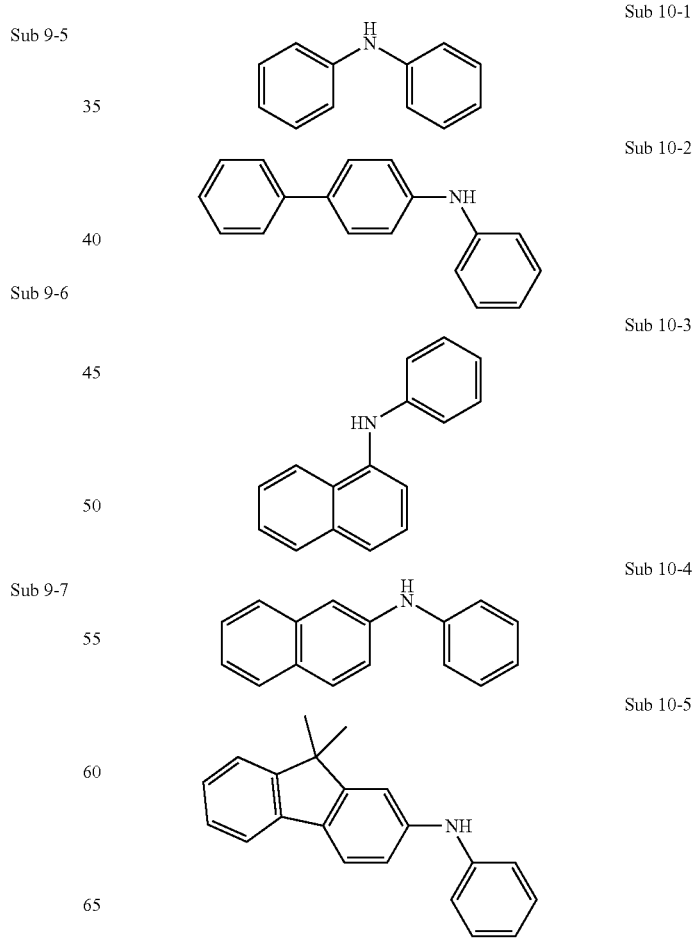

Sub 10-6

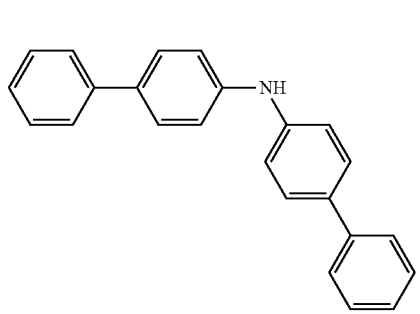

Sub 10-10

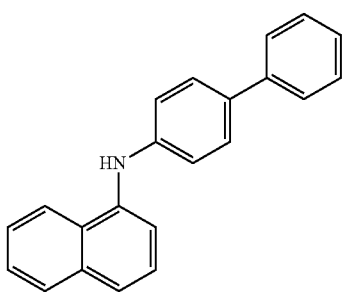

Sub 10-7

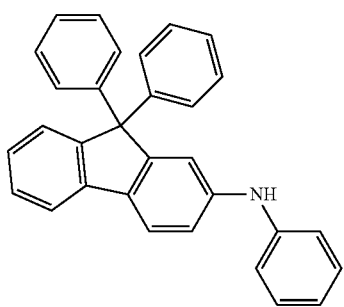

Sub 10-11

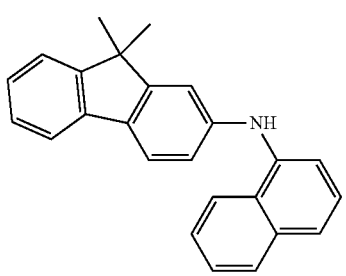

Sub 10-8

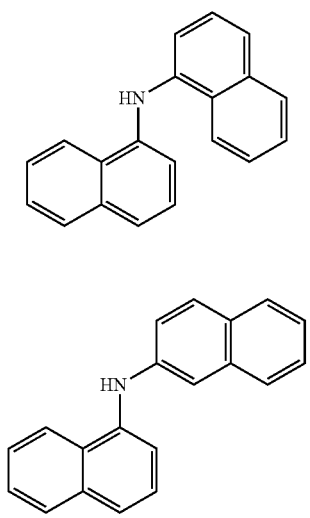

Sub 10-12

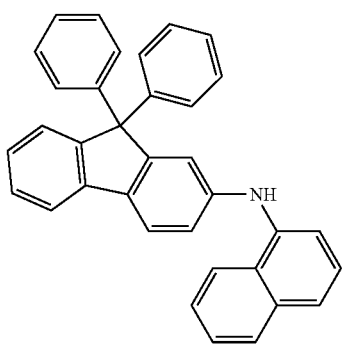

Sub 10-9

FD-MS values for the above materials of Sub 9 and Sub 10 are given in Table 2 below.

TABLE 2

| Compound | FD-MS | Compound | FD-MS |
|---|---|---|---|
| Sub 9-1 | m/z = 122.05 ($C_6H_7BO_2$ = 121.93) | Sub 9-2 | m/z = 172.07 ($C_{10}H_9BO_2$ = 171.99) |
| Sub 9-3 | m/z = 172.07 ($C_{10}H_9BO_2$ = 171.99) | Sub 9-4 | m/z = 123.05 ($C_5H_6BNO_2$ = 122.92) |
| Sub 9-5 | m/z = 289.13 ($C_{18}H_{16}BNO_2$ = 289.14) | Sub 9-6 | m/z = 339.14 ($C_{22}H_{18}BNO_2$ = 339.19) |
| Sub 9-7 | m/z = 365.16 ($C_{24}H_{20}BNO_2$ = 365.23) | Sub 9-8 | m/z = 405.19 ($C_{27}H_{24}BNO_2$ = 405.30) |
| Sub 9-9 | m/z = 405.19 ($C_{27}H_{24}BNO_2$ = 405.30) | | |
| Sub 10-1 | m/z = 169.09 ($C_{12}H_{11}N$ = 169.22) | Sub 10-2 | m/z = 245.12 ($C_{18}H_{15}N$ = 245.32) |
| Sub 10-3 | m/z = 219.10 ($C_{16}H_{13}N$ = 219.28) | Sub 10-4 | m/z = 219.10 ($C_{16}H_{13}N$ = 219.28) |
| Sub 10-5 | m/z = 285.15 ($C_{21}H_{19}N$ = 285.38) | Sub 10-6 | m/z = 321.15 ($C_{24}H_{19}N$ = 321.41) |
| Sub 10-7 | m/z = 409.18 ($C_{31}H_{23}N$ = 409.52) | Sub 10-8 | m/z = 269.12 ($C_{20}H_{15}N$ = 269.34) |
| Sub 10-9 | m/z = 269.12 ($C_{20}H_{15}N$ = 269.34) | Sub 10-10 | m/z = 295.14 ($C_{22}H_{17}N$ = 295.38) |
| Sub 10-11 | m/z = 335.17 ($C_{25}H_{21}N$ = 335.44) | Sub 10-12 | m/z = 459.20 ($C_{35}H_{25}N$ = 459.58) |

Synthesis Example of Product 1-1 [Method 1]

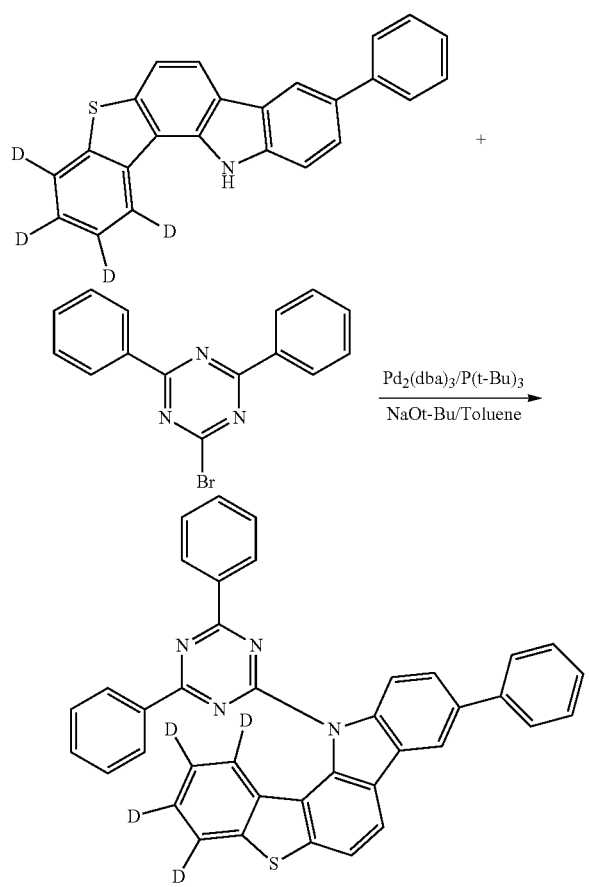

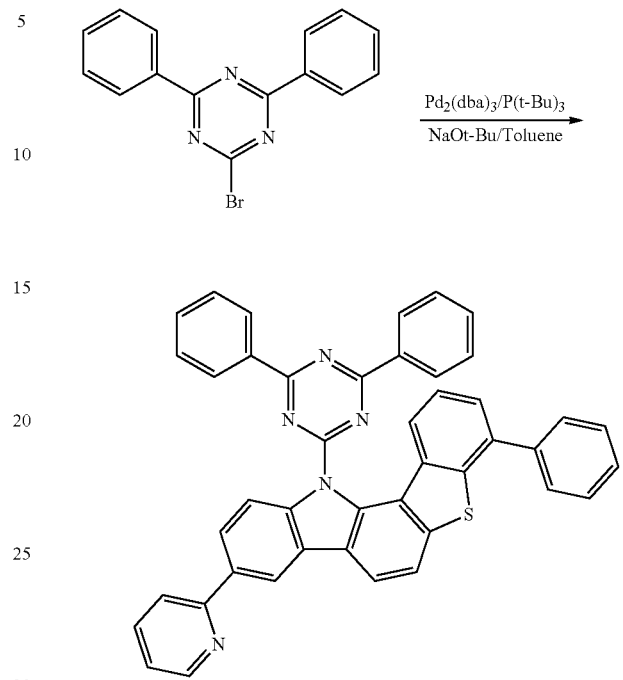

A five-membered heterocyclic compound (7.1 g, 20 mmol) and 2-bromo-4,6-diphenyl-1,3,5-triazine (7.5 g, 24 mmol) were mixed with toluene (210 mL), and Pd$_2$(dba)$_3$ (0.92 g, 1 mmol), P(t-Bu)$_3$ (0.4 g, 2 mmol), and NaOt-Bu (5.8 g, 60 mmol) were added to the mixture respectively, followed by reflux under stirring at 100° C. for 24 hours. The reaction product was extracted with methylene chloride and water, the extracted organic layer was dried with MgSO$_4$ and concentrated, and then the produced organic material was separated by a silica gel column and recrystallized to obtain 8.0 g of product 1-1 (yield 68%).

Synthesis Example of Product 1-13 [Method 1]

Using a five-membered heterocyclic compound (8.5 g, 20 mmol), 2-bromo-4,6-diphenyl-1,3,5-triazine (7.5 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), the same procedure as described in the synthesis method of product 1-1 was carried out to obtain 8.4 g of product 1-13 (yield 64%).

Synthesis Example of Product 2-18 [Method 1]

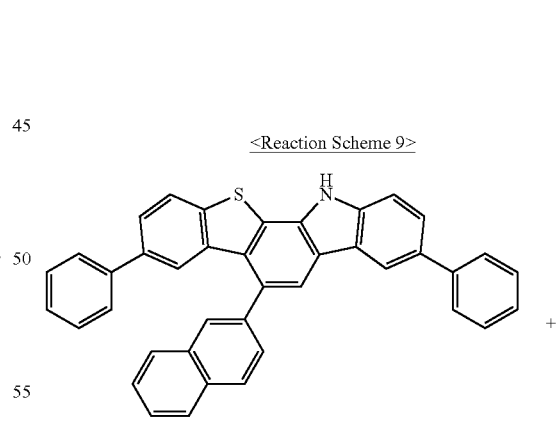

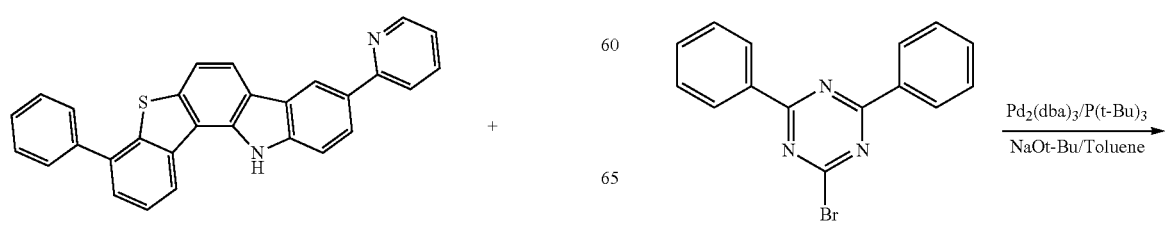

-continued

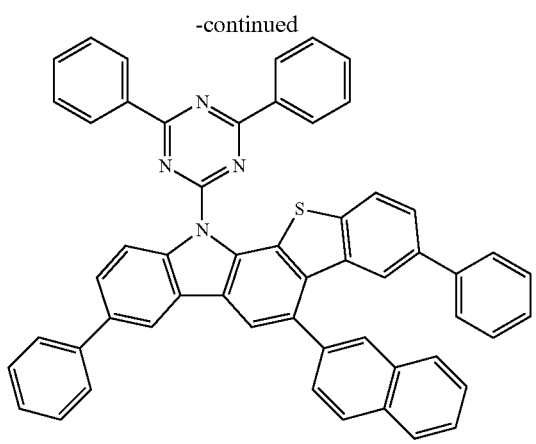

Using a five-membered heterocyclic compound (11 g, 20 mmol), bromobenzene (7.5 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), the same procedure as described in the synthesis method of product 1-1 was carried out to obtain 9.7 g of product 2-18 (yield 62%).

Synthesis Example of Product 2-31 [Method 1]

<Reaction Scheme 10>

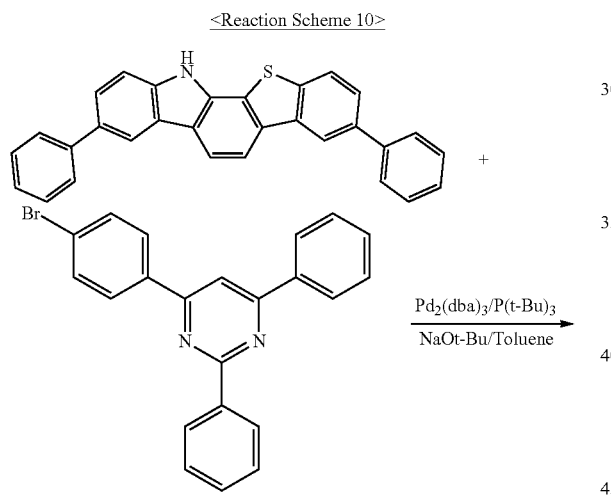

Using a five-membered heterocyclic compound (8.5 g, 20 mmol), 4-(4-bromophenyl)-2,6-diphenylpyrimidine (9.3 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), the same procedure as described in the synthesis method of product 1-1 was carried out to obtain 9.2 g of product 2-31 (yield 63%).

Synthesis Example of Product 3-7 [Method 1]

<Reaction Scheme 11>

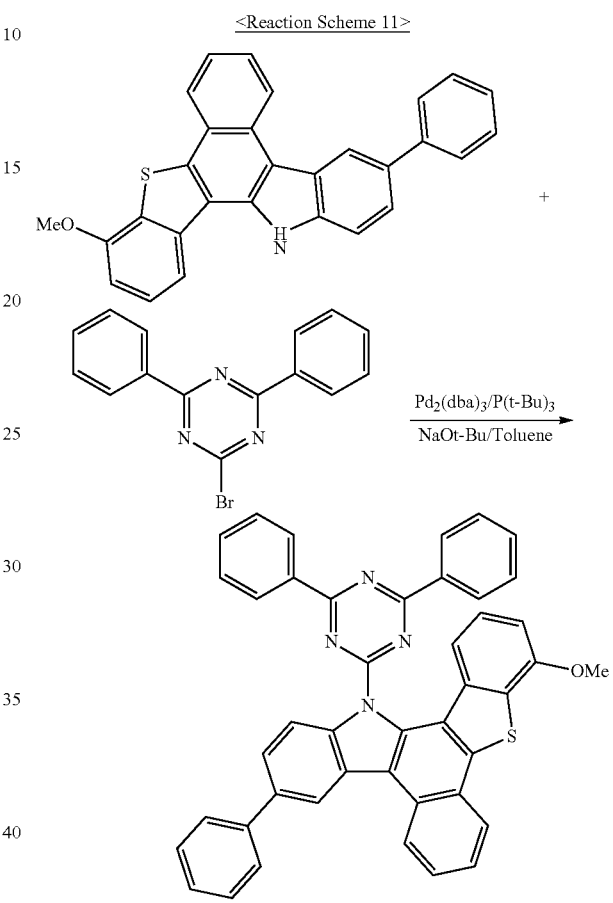

Using a five-membered heterocyclic compound (8.6 g, 20 mmol), 2-bromo-4,6-diphenyl-1,3,5-triazine (7.5 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), the same procedure as described in the synthesis method of product 1-1 was carried out to obtain 8.5 g of product 3-7 (yield 64%).

Synthesis Example of Product 3-12 [Method 1]

<Reaction Scheme 12>

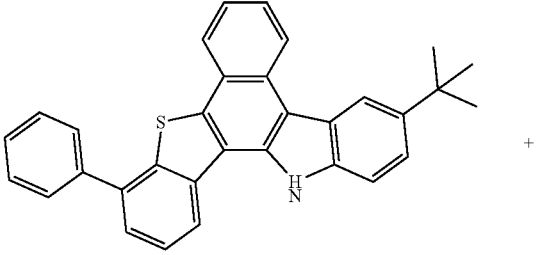

-continued

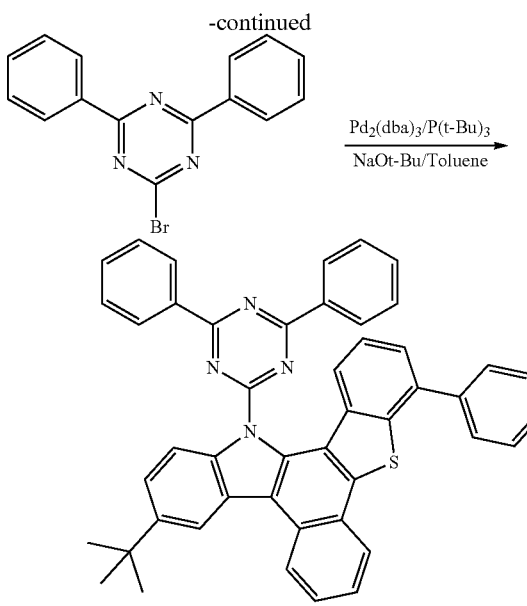

Using a five-membered heterocyclic compound (9.1 g, 20 mmol), 2-bromo-4,6-diphenyl-1,3,5-triazine (7.5 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), the same procedure as described in the synthesis method of product 1-1 was carried out to obtain 8.5 g of product 3-12 (yield 62%).

Synthesis Example of Product 4-19 [Method 1]

<Reaction Scheme 13>

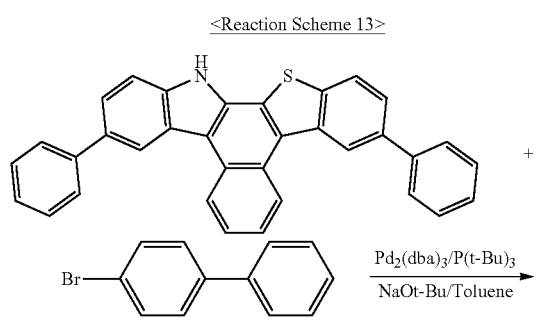

Using a five-membered heterocyclic compound (9.5 g, 20 mmol), 4-bromobiphenyl (5.6 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), the same procedure as described in the synthesis method of product 1-1 was carried out to obtain 8.2 g of product 4-19 (yield 65%).

Synthesis Example of Product 4-27 [Method 1]

<Reaction Scheme 14>

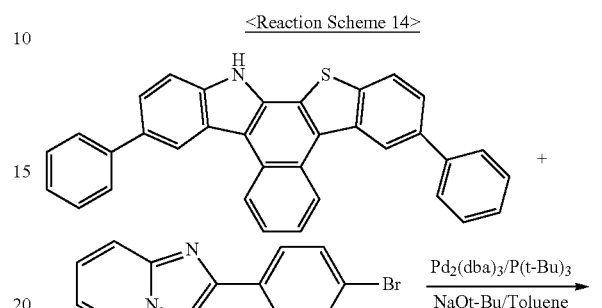

Using a five-membered heterocyclic compound (9.5 g, 20 mmol), 2-(4-bromophenyl)imidazol[1,2-a]pyridine (6.6 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), the same procedure as described in the synthesis method of product 1-1 was carried out to obtain 8.1 g of product 4-27 (yield 61%).

Synthesis Example of Product 3-28 [Method 1]

<Reaction Scheme 15>

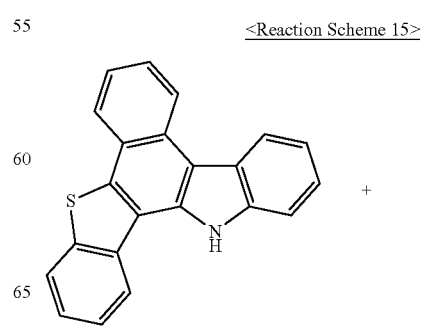

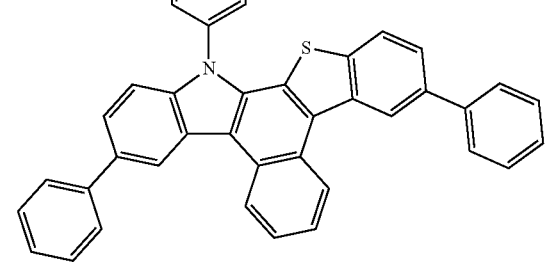

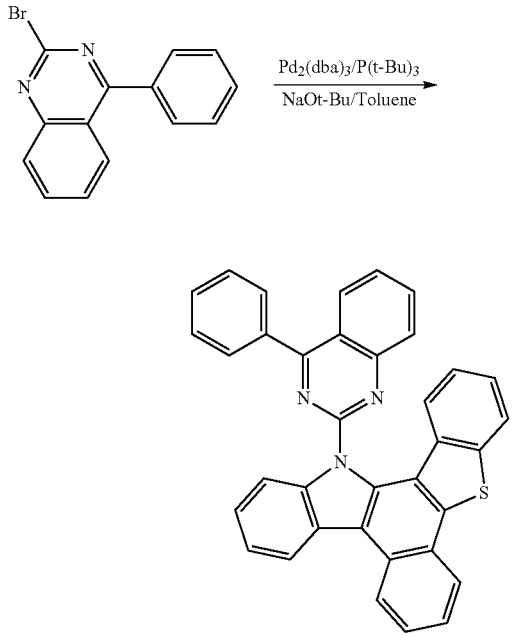

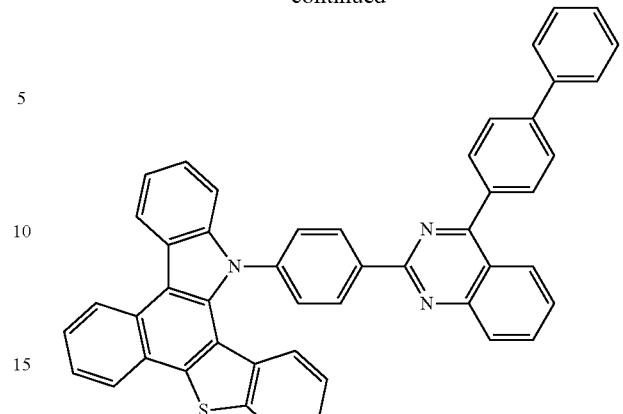

Using a five-membered heterocyclic compound (6.5 g, 20 mmol), 2-bromo-4-phenylquinazoline (6.8 g, 24 mmol), toluene (210 mL), Pd₂(dba)₃ (0.92 g, 1 mmol), P(t-Bu)₃ (0.4 g, 2 mmol), and NaOt-Bu (5.8 g, 60 mmol), the same procedure as described in the synthesis method of product 1-1 was carried out to obtain 7.2 g of product 3-28 (yield 68%).

Synthesis Example of Product 3-38 [Method 1]

<Reaction Scheme 16>

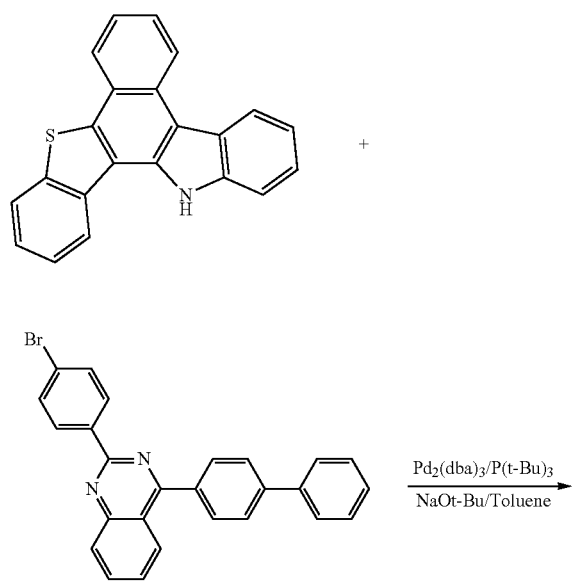

Using a five-membered heterocyclic compound (6.5 g, 20 mmol), 2-bromo-4-phenylquinazoline (10.5 g, 24 mmol), toluene (210 mL), Pd₂(dba)₃ (0.92 g, 1 mmol), P(t-Bu)₃ (0.4 g, 2 mmol), and NaOt-Bu (5.8 g, 60 mmol), the same procedure as described in the synthesis method of product 1-1 was carried out to obtain 8.7 g of product 3-38 (yield 64%).

Synthesis Example of Product 3-44 [Method 1]

<Reaction Scheme 17>

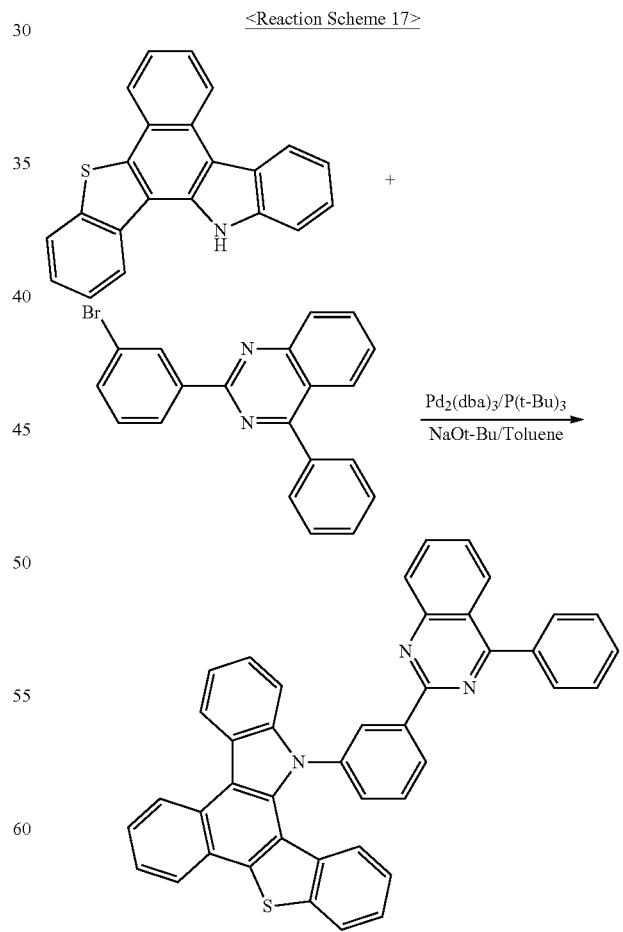

Using a five-membered heterocyclic compound (6.5 g, 20 mmol), 2-(3-bromophenyl)-4-phenylquinazoline (8.7 g, 24 mmol), toluene (210 mL), Pd₂(dba)₃ (0.92 g, 1 mmol), P(t-Bu)₃ (0.4 g, 2 mmol), and NaOt-Bu (5.8 g, 60 mmol), the same procedure as described in the synthesis method of product 1-1 was carried out to obtain 7.4 g of product 3-44 (yield 61%).

Synthesis Example of Product 4-28 [Method 1]

<Reaction Scheme 18>

Using a five-membered heterocyclic compound (6.5 g, 20 mmol), 2-bromo-4-phenylquinazoline (6.8 g, 24 mmol), toluene (210 mL), Pd₂(dba)₃ (0.92 g, 1 mmol), P(t-Bu)₃ (0.4 g, 2 mmol), and NaOt-Bu (5.8 g, 60 mmol), the same procedure as described in the synthesis method of product 1-1 was carried out to obtain 7.1 g of product 4-28 (yield 67%).

Synthesis Example of Product 6-1 [Method 1]

<Reaction Scheme 19>

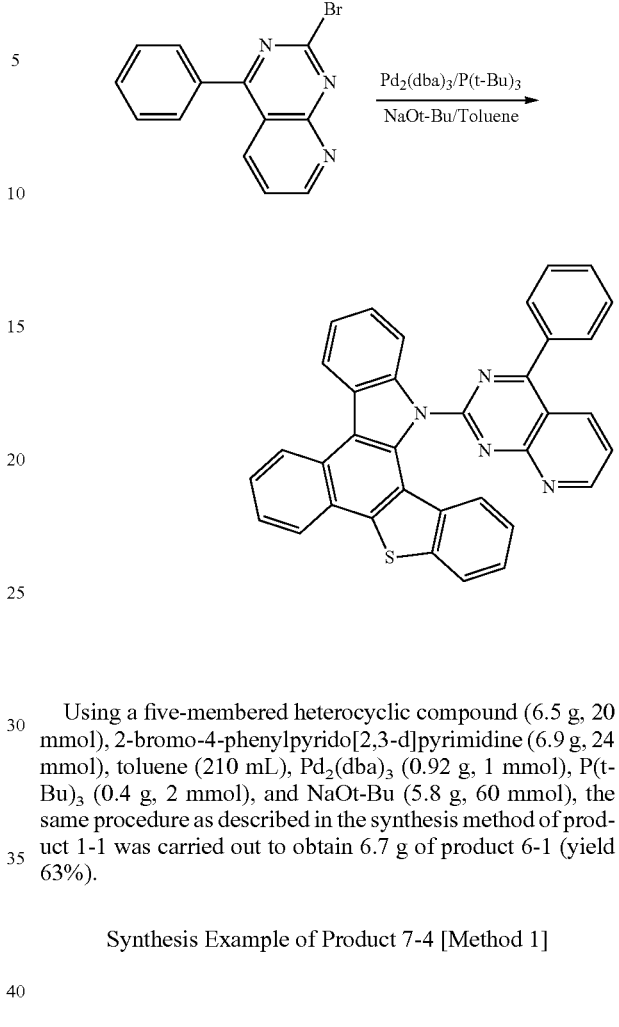

Using a five-membered heterocyclic compound (6.5 g, 20 mmol), 2-bromo-4-phenylpyrido[2,3-d]pyrimidine (6.9 g, 24 mmol), toluene (210 mL), Pd₂(dba)₃ (0.92 g, 1 mmol), P(t-Bu)₃ (0.4 g, 2 mmol), and NaOt-Bu (5.8 g, 60 mmol), the same procedure as described in the synthesis method of product 1-1 was carried out to obtain 6.7 g of product 6-1 (yield 63%).

Synthesis Example of Product 7-4 [Method 1]

<Reaction Scheme 20>

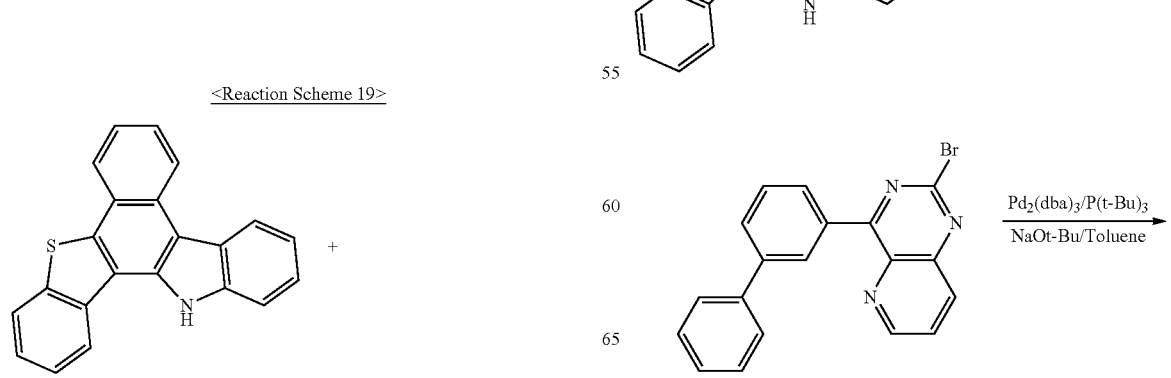

-continued

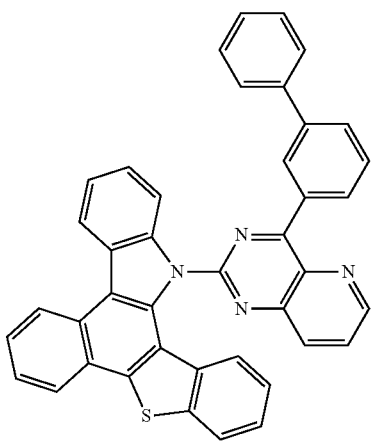

Using a five-membered heterocyclic compound (6.5 g, 20 mmol), 4-([1,1'-biphenyl]-3-yl)-2-bromopyrido[3,2-d]pyrimidine (8.7 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), the same procedure as described in the synthesis method of product 1-1 was carried out to obtain 7.5 g of product 7-4 (yield 62%).

Synthesis Example of Product 5-14 [Method 2-1]

<Reaction Scheme 21>

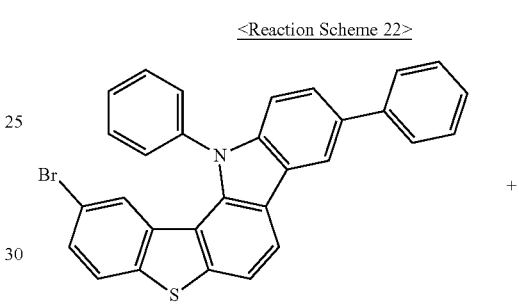

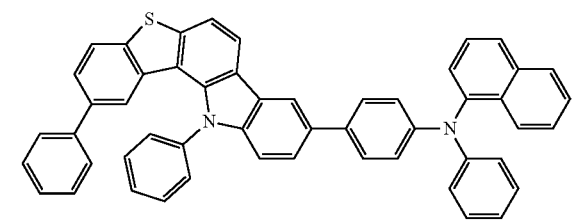

A five-membered heterocyclic compound (10.1 g, 20 mmol) and (4-(naphthalene-1-yl(phenyl)amino)phenyl)boronic acid (8.14 g, 24 mmol) were dissolved in THF, and Pd(PPh$_3$)$_4$ (0.7 g, 0.6 mmol), NaOH (2.4 g, 60 mmol), and water were added to the reactants, followed by reflux under stirring. Upon completion of the reaction, the reaction product was extracted with ether and water, the extracted organic layer was dried with MgSO$_4$ and concentrated, and then the produced organic material was separated by a silica gel column and recrystallized to obtain 8.9 g of product 5-14 (yield 62%).

Synthesis Example of Product 5-23 [Method 2-1]

<Reaction Scheme 22>

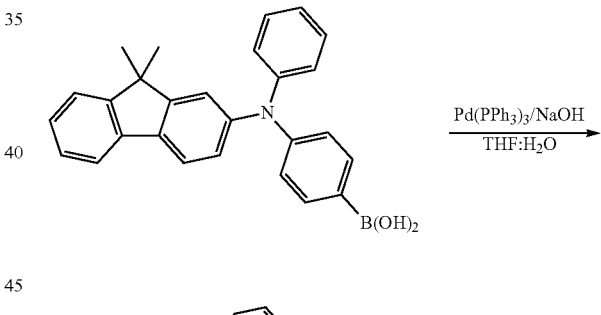

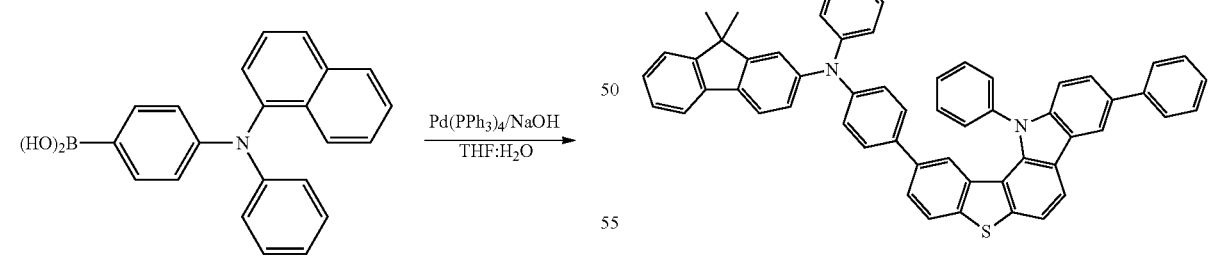

Using a five-membered heterocyclic compound (10.1 g, 20 mmol), (4-((9,9-dimethyl-9H-fluoren-2-yl)(phenyl)amino)phenyl)boronic acid (9.73 g, 24 mmol), Pd(PPh$_3$)$_4$ (0.7 g, 0.6 mmol), and NaOH (2.4 g, 60 mmol), the same procedure as described in the synthesis method of product 5-14 was carried out to obtain 9.4 g of product 5-23 (yield 60%).

Synthesis Example of Product 5-49 [Method 2-1]

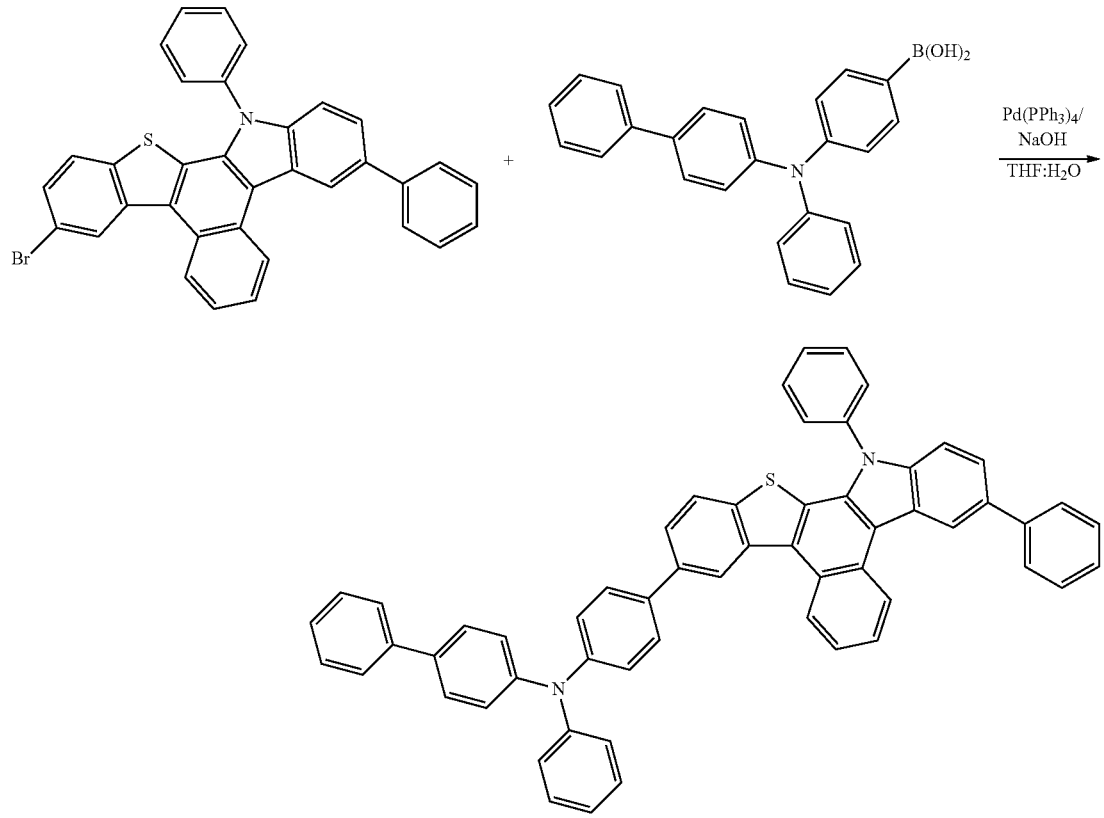

<Reaction Scheme 23>

Using a five-membered heterocyclic compound (11.1 g, 20 mmol), (4-([1,1'-biphenyl]-4-yl(phenyl)amino)phenyl)boronic acid (8.77 g, 24 mmol), Pd(PPh$_3$)$_4$ (0.7 g, 0.6 mmol), and NaOH (2.4 g, 60 mmol), the same procedure as described in the synthesis method of product 5-14 was carried out to obtain 10 g of product 5-49 (yield 63%).

Synthesis Example of Product 5-5 [Method 2-2]

<Reaction Scheme 24>

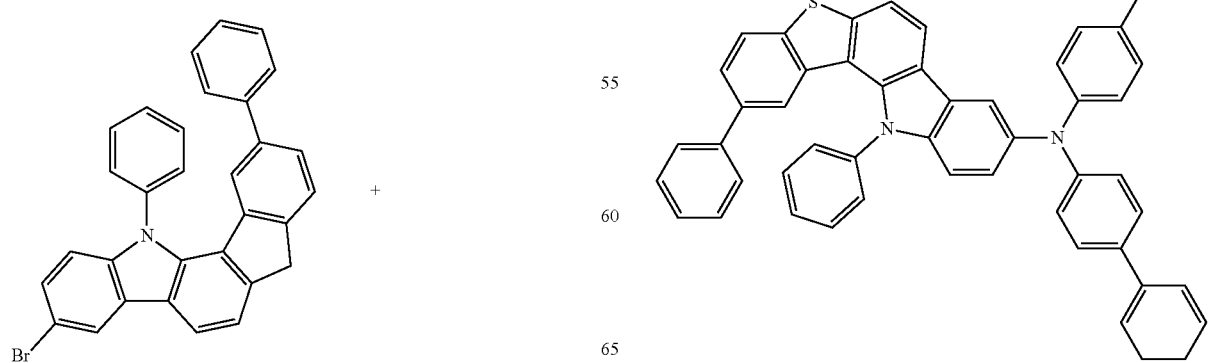

Using Di([1,1'-biphenyl]-4-yl)amine (6.4 g, 20 mmol), a five-membered heterocyclic compound (12.1 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), the same procedure as described in the synthesis method of product 1-1 was carried out to obtain 9.39 g of product 5-5 (yield 63%).

Synthesis Example of Product 5-6 [Method 2-2]

same procedure as described in the synthesis method of product 1-1 was carried out to obtain 8.8 g of product 5-6 (yield 62%).

Synthesis Example of Product 5-19 [Method 2-2]

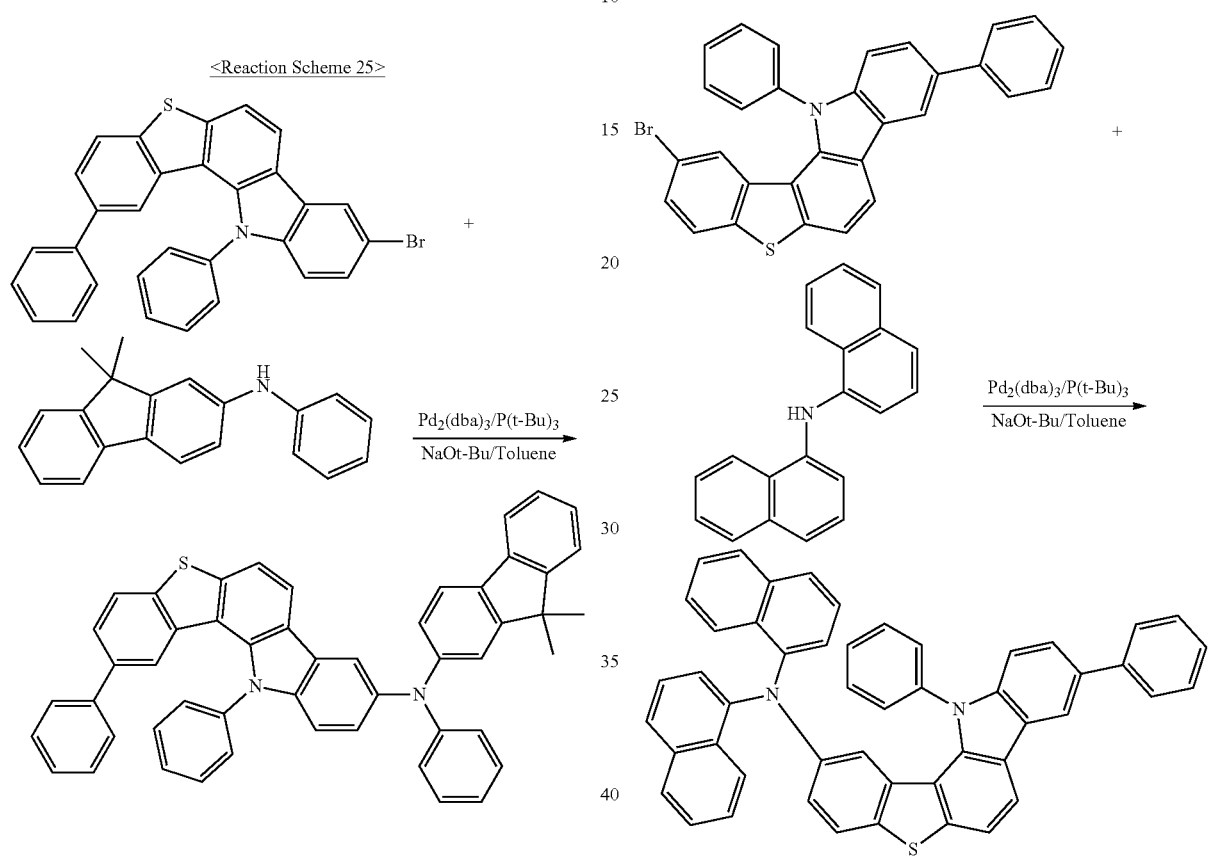

<Reaction Scheme 25>

<Reaction Scheme 26>

Using 9,9-dimethyl-N-phenyl-9H-fluoren-2-amine (5.7 g, 20 mmol), a five-membered heterocyclic compound (12.1 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), the FD-MS values for compounds 5-1 to 7-48 are given in Table 3 below.

TABLE 3

| Compound | FD-MS | Compound | FD-MS |
|---|---|---|---|
| 5-1 | m/z = 592.20 (C$_{42}$H$_{28}$N$_2$S = 592.75) | 5-2 | m/z = 668.23 (C$_{48}$H$_{32}$N$_2$S = 668.85) |
| 5-3 | m/z = 642.21 (C$_{46}$H$_{30}$N$_2$S = 642.81) | 5-4 | m/z = 642.21 (C$_{46}$H$_{30}$N$_2$S = 642.81) |
| 5-5 | m/z = 744.26 (C$_{54}$H$_{36}$N$_2$S = 744.94) | 5-6 | m/z = 708.26 (C$_{51}$H$_{36}$N$_2$S = 708.91) |
| 5-7 | m/z = 832.29 (C$_{61}$H$_{40}$N$_2$S = 833.05) | 5-8 | m/z = 692.23 (C$_{50}$H$_{32}$N$_2$S = 692.87) |
| 5-9 | m/z = 692.23 (C$_{50}$H$_{32}$N$_2$S = 692.87) | 5-10 | m/z = 718.24 (C$_{52}$H$_{34}$N$_2$S = 718.90) |
| 5-11 | m/z = 758.28 (C$_{55}$H$_{38}$N$_2$S = 758.97) | 5-12 | m/z = 882.31 (C$_{65}$H$_{42}$N$_2$S = 883.11) |
| 5-13 | m/z = 668.23 (C$_{48}$H$_{32}$N$_2$S = 668.85) | 5-14 | m/z = 718.24 (C$_{52}$H$_{34}$N$_2$S = 718.90) |
| 5-15 | m/z = 744.26 (C$_{54}$H$_{36}$N$_2$S = 744.94) | 5-16 | m/z = 784.29 (C$_{57}$H$_{40}$N$_2$S = 785.01) |
| 5-17 | m/z = 592.20 (C$_{42}$H$_{28}$N$_2$S = 592.75) | 5-18 | m/z = 642.21 (C$_{46}$H$_{30}$N$_2$S = 642.81) |
| 5-19 | m/z = 692.23 (C$_{50}$H$_{32}$N$_2$S = 692.87) | 5-20 | m/z = 744.26 (C$_{54}$H$_{36}$N$_2$S = 744.94) |
| 5-21 | m/z = 668.23 (C$_{48}$H$_{32}$N$_2$S = 668.85) | 5-22 | m/z = 718.24 (C$_{52}$H$_{34}$N$_2$S = 718.90) |
| 5-23 | m/z = 784.29 (C$_{57}$H$_{40}$N$_2$S = 785.01) | 5-24 | m/z = 592.20 (C$_{42}$H$_{28}$N$_2$S = 592.75) |
| 5-25 | m/z = 668.23 (C$_{48}$H$_{32}$N$_2$S = 668.85) | 5-26 | m/z = 642.21 (C$_{46}$H$_{30}$N$_2$S = 642.81) |
| 5-27 | m/z = 642.21 (C$_{46}$H$_{30}$N$_2$S = 642.81) | 5-28 | m/z = 744.26 (C$_{54}$H$_{36}$N$_2$S = 744.94) |
| 5-29 | m/z = 708.26 (C$_{51}$H$_{36}$N$_2$S = 708.91) | 5-30 | m/z = 832.29 (C$_{61}$H$_{40}$N$_2$S = 833.05) |
| 5-31 | m/z = 692.23 (C$_{50}$H$_{32}$N$_2$S = 692.87) | 5-32 | m/z = 692.23 (C$_{50}$H$_{32}$N$_2$S = 692.87) |
| 5-33 | m/z = 718.24 (C$_{52}$H$_{34}$N$_2$S = 718.90) | 5-34 | m/z = 758.28 (C$_{55}$H$_{38}$N$_2$S = 758.97) |
| 5-35 | m/z = 882.31 (C$_{65}$H$_{42}$N$_2$S = 883.11) | 5-36 | m/z = 668.23 (C$_{48}$H$_{32}$N$_2$S = 668.85) |
| 5-37 | m/z = 718.24 (C$_{52}$H$_{34}$N$_2$S = 718.90) | 5-38 | m/z = 744.26 (C$_{54}$H$_{36}$N$_2$S = 744.94) |
| 5-39 | m/z = 784.29 (C$_{57}$H$_{40}$N$_2$S = 785.01) | 5-40 | m/z = 592.20 (C$_{42}$H$_{28}$N$_2$S = 592.75) |

TABLE 3-continued

| Compound | FD-MS | Compound | FD-MS |
|---|---|---|---|
| 5-41 | m/z = 642.21 ($C_{46}H_{30}N_2S$ = 642.81) | 5-42 | m/z = 692.23 ($C_{50}H_{32}N_2S$ = 692.87) |
| 5-43 | m/z = 744.26 ($C_{54}H_{36}N_2S$ = 744.94) | 5-44 | m/z = 668.23 ($C_{48}H_{32}N_2S$ = 668.85) |
| 5-45 | m/z = 718.24 ($C_{52}H_{34}N_2S$ = 718.90) | 5-46 | m/z = 784.29 ($C_{57}H_{40}N_2S$ = 785.01) |
| 5-47 | m/z = 692.23 ($C_{50}H_{32}N_2S$ = 692.87) | 5-48 | m/z = 718.24 ($C_{52}H_{34}N_2S$ = 718.90) |
| 5-49 | m/z = 794.28 ($C_{58}H_{38}N_2S$ = 795.00) | 5-50 | m/z = 682.24 ($C_{49}H_{34}N_2S$ = 682.87) |
| 5-51 | m/z = 806.28 ($C_{59}H_{38}N_2S$ = 807.01) | 6-1 | m/z = 528.14 ($C_{35}H_{20}N_4S$ = 528.63) |
| 6-2 | m/z = 533.17 ($C_{35}H_{15}D_5N_4S$ = 533.66) | 6-3 | m/z = 604.17 ($C_{41}H_{24}N_4S$ = 604.72) |
| 6-4 | m/z = 604.17 ($C_{41}H_{24}N_4S$ = 604.72) | 6-5 | m/z = 578.16 ($C_{39}H_{22}N_4S$ = 578.68) |
| 6-6 | m/z = 578.16 ($C_{39}H_{22}N_4S$ = 578.68) | 6-7 | m/z = 680.20 ($C_{47}H_{28}N_4S$ = 680.82) |
| 6-8 | m/z = 644.20 ($C_{44}H_{28}N_4S$ = 644.78) | 6-9 | m/z = 604.17 ($C_{41}H_{24}N_4S$ = 604.72) |
| 6-10 | m/z = 609.20 ($C_{41}H_{19}D_5N_4S$ = 609.75) | 6-11 | m/z = 680.20 ($C_{47}H_{28}N_4S$ = 680.82) |
| 6-12 | m/z = 680.20 ($C_{47}H_{28}N_4S$ = 680.82) | 6-13 | m/z = 654.19 ($C_{45}H_{26}N_4S$ = 654.78) |
| 6-14 | m/z = 654.19 ($C_{45}H_{26}N_4S$ = 654.78) | 6-15 | m/z = 756.23 ($C_{53}H_{32}N_4S$ = 756.91) |
| 6-16 | m/z = 720.23 ($C_{50}H_{32}N_4S$ = 720.88) | 6-17 | m/z = 604.17 ($C_{41}H_{24}N_4S$ = 604.72) |
| 6-18 | m/z = 609.20 ($C_{41}H_{19}D_5N_4S$ = 609.75) | 6-19 | m/z = 680.20 ($C_{47}H_{28}N_4S$ = 680.82) |
| 6-20 | m/z = 680.20 ($C_{47}H_{28}N_4S$ = 680.82) | 6-21 | m/z = 654.19 ($C_{45}H_{26}N_4S$ = 654.78) |
| 6-22 | m/z = 654.19 ($C_{45}H_{26}N_4S$ = 654.78) | 6-23 | m/z = 756.23 ($C_{53}H_{32}N_4S$ = 756.91) |
| 6-24 | m/z = 720.23 ($C_{50}H_{32}N_4S$ = 720.88) | 6-25 | m/z = 528.14 ($C_{35}H_{20}N_4S$ = 528.63) |
| 6-26 | m/z = 533.17 ($C_{35}H_{15}D_5N_4S$ = 533.66) | 6-27 | m/z = 604.17 ($C_{41}H_{24}N_4S$ = 604.72) |
| 6-28 | m/z = 604.17 ($C_{41}H_{24}N_4S$ = 604.72) | 6-29 | m/z = 578.16 ($C_{39}H_{22}N_4S$ = 578.68) |
| 6-30 | m/z = 578.16 ($C_{39}H_{22}N_4S$ = 578.68) | 6-31 | m/z = 680.20 ($C_{47}H_{28}N_4S$ = 680.82) |
| 6-32 | m/z = 644.20 ($C_{44}H_{28}N_4S$ = 644.78) | 6-33 | m/z = 604.17 ($C_{41}H_{24}N_4S$ = 604.72) |
| 6-34 | m/z = 609.20 ($C_{41}H_{19}D_5N_4S$ = 609.75) | 6-35 | m/z = 680.20 ($C_{47}H_{28}N_4S$ = 680.82) |
| 6-36 | m/z = 680.20 ($C_{47}H_{28}N_4S$ = 680.82) | 6-37 | m/z = 654.19 ($C_{45}H_{26}N_4S$ = 654.78) |
| 6-38 | m/z = 654.19 ($C_{45}H_{26}N_4S$ = 654.78) | 6-39 | m/z = 756.23 ($C_{53}H_{32}N_4S$ = 756.91) |
| 6-40 | m/z = 720.23 ($C_{50}H_{32}N_4S$ = 720.88) | 6-41 | m/z = 604.17 ($C_{41}H_{24}N_4S$ = 604.72) |
| 6-42 | m/z = 609.20 ($C_{41}H_{19}D_5N_4S$ = 609.75) | 6-43 | m/z = 680.20 ($C_{47}H_{28}N_4S$ = 680.82) |
| 6-44 | m/z = 680.20 ($C_{47}H_{28}N_4S$ = 680.82) | 6-45 | m/z = 654.19 ($C_{45}H_{26}N_4S$ = 654.78) |
| 6-46 | m/z = 654.19 ($C_{45}H_{26}N_4S$ = 654.78) | 6-47 | m/z = 756.23 ($C_{53}H_{32}N_4S$ = 756.91) |
| 6-48 | m/z = 720.23 ($C_{50}H_{32}N_4S$ = 720.88) | 7-1 | m/z = 528.14 ($C_{35}H_{20}N_4S$ = 528.63) |
| 7-2 | m/z = 533.17 ($C_{35}H_{15}D_5N_4S$ = 533.66) | 7-3 | m/z = 604.17 ($C_{41}H_{24}N_4S$ = 604.72) |
| 7-4 | m/z = 604.17 ($C_{41}H_{24}N_4S$ = 604.72) | 7-5 | m/z = 578.16 ($C_{39}H_{22}N_4S$ = 578.68) |
| 7-6 | m/z = 578.16 ($C_{39}H_{22}N_4S$ = 578.68) | 7-7 | m/z = 680.20 ($C_{47}H_{28}N_4S$ = 680.82) |
| 7-8 | m/z = 644.20 ($C_{44}H_{28}N_4S$ = 644.78) | 7-9 | m/z = 604.17 ($C_{41}H_{24}N_4S$ = 604.72) |
| 7-10 | m/z = 609.20 ($C_{41}H_{19}D_5N_4S$ = 609.75) | 7-11 | m/z = 680.20 ($C_{47}H_{28}N_4S$ = 680.82) |
| 7-12 | m/z = 680.20 ($C_{47}H_{28}N_4S$ = 680.82) | 7-13 | m/z = 654.19 ($C_{45}H_{26}N_4S$ = 654.78) |
| 7-14 | m/z = 654.19 ($C_{45}H_{26}N_4S$ = 654.78) | 7-15 | m/z = 756.23 ($C_{53}H_{32}N_4S$ = 756.91) |
| 7-16 | m/z = 720.23 ($C_{50}H_{32}N_4S$ = 720.88) | 7-17 | m/z = 604.17 ($C_{41}H_{24}N_4S$ = 604.72) |
| 7-18 | m/z = 609.20 ($C_{41}H_{19}D_5N_4S$ = 609.75) | 7-19 | m/z = 680.20 ($C_{47}H_{28}N_4S$ = 680.82) |
| 7-20 | m/z = 680.20 ($C_{47}H_{28}N_4S$ = 680.82) | 7-21 | m/z = 654.19 ($C_{45}H_{26}N_4S$ = 654.78) |
| 7-22 | m/z = 654.19 ($C_{45}H_{26}N_4S$ = 654.78) | 7-23 | m/z = 756.23 ($C_{53}H_{32}N_4S$ = 756.91) |
| 7-24 | m/z = 720.23 ($C_{50}H_{32}N_4S$ = 720.88) | 7-25 | m/z = 528.14 ($C_{35}H_{20}N_4S$ = 528.63) |
| 7-26 | m/z = 533.17 ($C_{35}H_{15}D_5N_4S$ = 533.66) | 7-27 | m/z = 604.17 ($C_{41}H_{24}N_4S$ = 604.72) |
| 7-28 | m/z = 604.17 ($C_{41}H_{24}N_4S$ = 604.72) | 7-29 | m/z = 578.16 ($C_{39}H_{22}N_4S$ = 578.68) |
| 7-30 | m/z = 578.16 ($C_{39}H_{22}N_4S$ = 578.68) | 7-31 | m/z = 680.20 ($C_{47}H_{28}N_4S$ = 680.82) |
| 7-32 | m/z = 644.20 ($C_{44}H_{28}N_4S$ = 644.78) | 7-33 | m/z = 604.17 ($C_{41}H_{24}N_4S$ = 604.72) |
| 7-34 | m/z = 609.20 ($C_{41}H_{19}D_5N_4S$ = 609.75) | 7-35 | m/z = 680.20 ($C_{47}H_{28}N_4S$ = 680.82) |
| 7-36 | m/z = 680.20 ($C_{47}H_{28}N_4S$ = 680.82) | 7-37 | m/z = 654.19 ($C_{45}H_{26}N_4S$ = 654.78) |
| 7-38 | m/z = 654.19 ($C_{45}H_{26}N_4S$ = 654.78) | 7-39 | m/z = 756.23 ($C_{53}H_{32}N_4S$ = 756.91) |
| 7-40 | m/z = 720.23 ($C_{50}H_{32}N_4S$ = 720.88) | 7-41 | m/z = 604.17 ($C_{41}H_{24}N_4S$ = 604.72) |
| 7-42 | m/z = 609.20 ($C_{41}H_{19}D_5N_4S$ = 609.75) | 7-43 | m/z = 680.20 ($C_{47}H_{28}N_4S$ = 680.82) |
| 7-44 | m/z = 680.20 ($C_{47}H_{28}N_4S$ = 680.82) | 7-45 | m/z = 654.19 ($C_{45}H_{26}N_4S$ = 654.78) |
| 7-46 | m/z = 654.19 ($C_{45}H_{26}N_4S$ = 654.78) | 7-47 | m/z = 756.23 ($C_{53}H_{32}N_4S$ = 756.91) |
| 7-48 | m/z = 720.23 ($C_{50}H_{32}N_4S$ = 720.88) | | |

Fabrication and Evaluation of Organic Electric Element

Test Example 1

Phosphorescent Green Host

Organic light emitting diodes (OLEDs) were fabricated according to a conventional method by using the synthesized inventive compounds as a light emitting host material of a light emitting layer. Each OLED was fabricated as follows. First, an ITO layer (anode) was formed on a glass substrate, and a film of $N^1$-(naphthalen-2-yl)-$N^4$,$N^4$-bis(4-(naphthalen-2-yl(phenyl)amino)phenyl)-$N^1$-phenylbenzene-1,4-diamine (hereinafter abbreviated as "2-TNATA") was vacuum-deposited on the ITO layer to form a hole injection layer with a thickness of 60 nm. Subsequently, a film of 4,4-bis[N-(1-naphthyl)-N-phenylamino]biphenyl (hereinafter abbreviated as "NPD") was vacuum-deposited with a thickness of 20 nm on the hole injection layer to form a hole transport layer. Also, a light emitting layer with a thickness of 30 nm was deposited on the hole transport layer by doping the hole transport layer with the inventive compound (1-1-1-32, 2-1-2-32, 3-1-1-3-27, 4-1-4-27) as a host material and Ir(ppy)$_3$[tris(2-phenylpyridine)-iridium] as a dopant material in a weight ratio of 95:5. Next, a film of (1,1'-bisphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, and then a film of tris(8-quinolinolato)aluminum (hereinafter abbreviated as "Alq$_3$") was formed with a thickness of 40 nm on the hole blocking layer to form an electron injection layer. Next, LiF as halogenated alkali metal was deposited with a thickness of 0.2 nm on the electron injection layer, and then Al was deposited with a thickness of 150 nm thereon to form an Al/LiF cathode. In this way, an OLED was completed.

Comparative Example 1

An OLED was manufactured in the same manner as described in Test Example 1, except that Comparative Compound 1 (4,4'-di(9H-carbazol-9-yl)-1,1'-biphenyl) represented below was used as the host material of the light emitting layer, instead of the inventive compound.

<Comparative Compound 1>

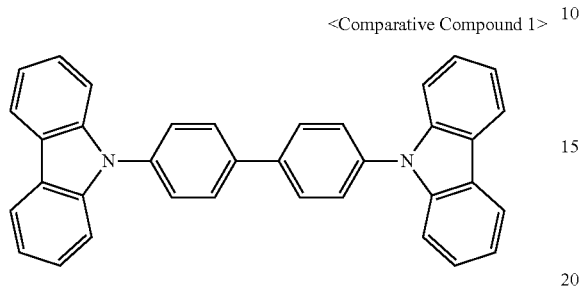

Comparative Example 2

An OLED was manufactured in the same manner as described in Test Example 1, except that Comparative Compound 2 (9-(9-(4,6-diphenylpyrimidin-2-yl)-9H-carbazol-3-yl)-12-phenyl-12H-benzo[4,5]thieno[3,2-a]carbazole) represented below was used as the host material of the light emitting layer, instead of the inventive compound.

<Comparative Compound 2>

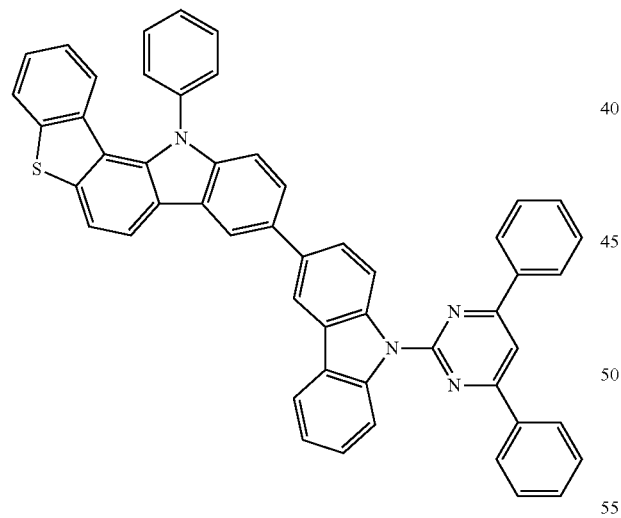

Comparative Example 3

An OLED was manufactured in the same manner as described in Test Example 1, except that Comparative Compound 3 (3-(9-(4,6-diphenyl-1,3,5-triazin-2-yl)-9H-carbazol-3-yl)-12-phenyl-12H-benzo[4,5]thieno[2,3-a]carbazole) represented below was used as the host material of the light emitting layer, instead of the inventive compound.

<Comparative Compound 3>

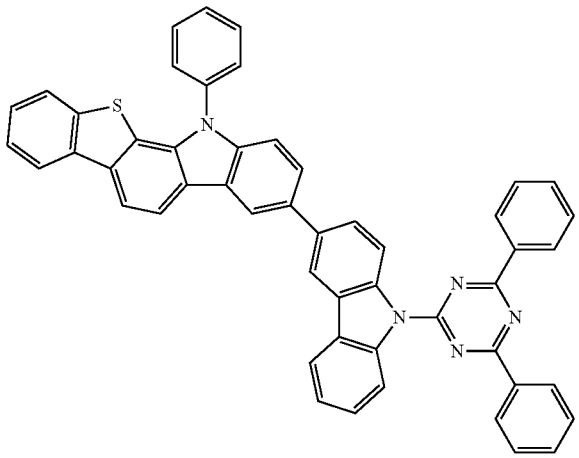

Comparative Example 4

An OLED was manufactured in the same manner as described in Test Example 1, except that Comparative Compound 4 (12-(5-phenylpyrimidin-2-yl)-12H-benzo[4,5]thieno[3,2-a]carbazole) represented below was used as the host material of the light emitting layer, instead of the inventive compound.

<Comparative Compound 4>

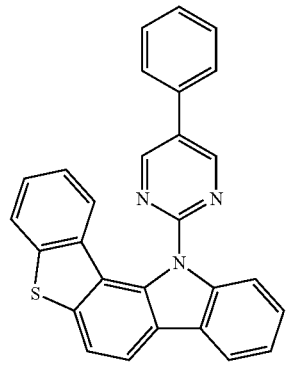

Comparative Example 5

An OLED was manufactured in the same manner as described in Test Example 1, except that Comparative Compound 5 (12-(4-(4,6-diphenylpyrimidin-2-yl)phenyl)-12H-benzo[4,5]thieno[2,3-a]carbazole) represented below was used as the host material of the light emitting layer, instead of the inventive compound.

<Comparative Compound 5>

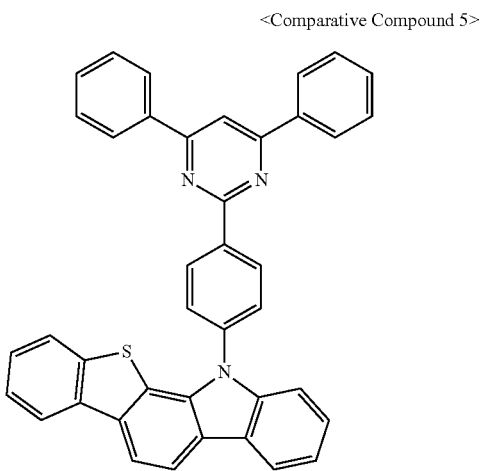 [SMILES: c1ccc(-c2cc(-c3ccccc3)nc(-c3ccc(-n4c5ccccc5c5ccc6c7ccccc7sc6c54)cc3)n2)cc1]

A forward bias DC voltage was applied to each of the OLEDs manufactured in Test Example 1 and Comparative Examples 1 to 5, and electro-luminescence (EL) characteristics of the OLED were measured by PR-650 (Photoresearch). Also, T95 life span was measured by life span measuring equipment (Mcscience) at a reference brightness of 300 cd/m$^2$. Table 4 below shows the measurement results. In Table 4, Examples 1 to 103 represent the inventive OLEDs manufactured according to Test Example 1.

TABLE 4

|  | Compond | Driving Voltage | Current Density (mA/cm2) | Brightness (cd/m2) | Efficiency (cd/A) | T(95) | CIE (x, y) |
| --- | --- | --- | --- | --- | --- | --- | --- |
| Comp. Ex. (1) | Comp. Com. (1) | 6.3 | 7.0 | 300 | 4.3 | 51.8 | (0.33, 0.61) |
| Comp. Ex. (2) | Comp. Com. (2) | 5.8 | 5.9 | 300 | 5.1 | 70.6 | (0.33, 0.61) |
| Comp. Ex. (3) | Comp. Com. (3) | 5.7 | 6.0 | 300 | 5 | 65.6 | (0.33, 0.61) |
| Comp. Ex. (4) | Comp. Com. (4) | 5.6 | 5.8 | 300 | 5.2 | 82.5 | (0.33, 0.61) |
| Comp. Ex. (5) | Comp. Com. (5) | 5.6 | 5.9 | 300 | 5.1 | 86.7 | (0.33, 0.61) |
| Ex. (1) | Com. (1-1) | 5.3 | 4.6 | 300 | 6.6 | 110.6 | (0.32, 0.61) |
| Ex. (2) | Com. (1-2) | 5.1 | 4.7 | 300 | 6.4 | 113.9 | (0.33, 0.60) |
| Ex. (3) | Com. (1-3) | 5.1 | 4.9 | 300 | 6.2 | 109.0 | (0.30, 0.61) |
| Ex. (4) | Com. (1-4) | 5.4 | 5.0 | 300 | 6.0 | 107.5 | (0.30 0.61) |
| Ex. (5) | Com. (1-5) | 5.4 | 4.6 | 300 | 6.6 | 108.9 | (0.31, 0.60) |
| Ex. (6) | Com. (1-6) | 5.6 | 5.8 | 300 | 5.2 | 82.7 | (0.33, 0.61) |
| Ex. (7) | Com. (1-7) | 5.0 | 5.0 | 300 | 6.0 | 115.7 | (0.32, 0.60) |
| Ex. (8) | Com. (1-8) | 4.9 | 4.3 | 300 | 7.0 | 136.2 | (0.32, 0.61) |
| Ex. (9) | Com. (1-9) | 5.0 | 4.2 | 300 | 7.2 | 145.9 | (0.33, 0.60) |
| Ex. (10) | Com. (1-10) | 5.3 | 4.7 | 300 | 6.3 | 137.4 | (0.30, 0.60) |
| Ex. (11) | Com. (1-11) | 5.2 | 4.3 | 300 | 7.0 | 145.2 | (0.30, 0.61) |
| Ex. (12) | Com. (1-12) | 4.9 | 4.7 | 300 | 6.4 | 134.8 | (0.31, 0.61) |
| Ex. (13) | Com. (1-13) | 5.5 | 5.7 | 300 | 5.3 | 93.5 | (0.31, 0.61) |
| Ex. (14) | Com. (1-14) | 4.9 | 5.1 | 300 | 5.9 | 130.8 | (0.31, 0.60) |
| Ex. (15) | Com. (1-15) | 5.2 | 4.5 | 300 | 6.7 | 132.9 | (0.31, 0.60) |
| Ex. (16) | Com. (1-16) | 5.1 | 5.2 | 300 | 5.8 | 114.5 | (0.32, 0.61) |
| Ex. (17) | Com. (1-17) | 5.0 | 4.0 | 300 | 7.5 | 147.7 | (0.31, 0.61) |
| Ex. (18) | Com. (1-18) | 5.0 | 4.2 | 300 | 7.2 | 137.7 | (0.33, 0.60) |
| Ex. (19) | Com. (1-19) | 5.0 | 4.4 | 300 | 6.9 | 123.8 | (0.31, 0.60) |
| Ex. (20) | Com. (1-20) | 5.0 | 4.0 | 300 | 7.4 | 138.6 | (0.32, 0.61) |
| Ex. (21) | Com. (1-21) | 5.4 | 4.8 | 300 | 6.3 | 129.8 | (0.32, 0.61) |
| Ex. (22) | Com. (1-22) | 4.9 | 4.6 | 300 | 6.5 | 132.2 | (0.33, 0.60) |
| Ex. (23) | Com. (1-23) | 5.0 | 4.9 | 300 | 6.2 | 115.0 | (0.30, 0.61) |
| Ex. (24) | Com. (1-24) | 5.1 | 4.1 | 300 | 7.3 | 112.9 | (0.31, 0.61) |
| Ex. (25) | Com. (1-25) | 5.3 | 4.2 | 300 | 7.2 | 120.7 | (0.30, 0.60) |
| Ex. (26) | Com. (1-26) | 4.9 | 5.2 | 300 | 5.8 | 120.6 | (0.33, 0.61) |
| Ex. (27) | Com. (1-27) | 5.3 | 4.4 | 300 | 6.9 | 140.7 | (0.32, 0.61) |
| Ex. (28) | Com. (1-28) | 5.0 | 4.2 | 300 | 7.2 | 137.7 | (0.33, 0.60) |
| Ex. (29) | Com. (1-29) | 5.3 | 5.1 | 300 | 5.9 | 106.8 | (0.30, 0.61) |
| Ex. (30) | Com. (1-30) | 5.1 | 4.6 | 300 | 6.6 | 139.2 | (0.31, 0.61) |
| Ex. (31) | Com. (1-31) | 5.0 | 4.8 | 300 | 6.3 | 143.0 | (0.31, 0.60) |
| Ex. (32) | Com. (1-32) | 5.2 | 4.2 | 300 | 7.2 | 123.3 | (0.33, 0.61) |
| Ex. (33) | Com. (2-1) | 4.9 | 5.2 | 300 | 5.8 | 149.0 | (0.32, 0.60) |
| Ex. (34) | Com. (2-2) | 5.4 | 5.3 | 300 | 5.6 | 123.5 | (0.32, 0.61) |
| Ex. (35) | Com. (2-3) | 5.2 | 4.7 | 300 | 6.3 | 129.4 | (0.33, 0.61) |
| Ex. (36) | Com. (2-4) | 5.0 | 5.2 | 300 | 5.8 | 105.8 | (0.30, 0.60) |
| Ex. (37) | Com. (2-5) | 5.0 | 4.9 | 300 | 6.1 | 132.9 | (0.30, 0.61) |
| Ex. (38) | Com. (2-6) | 5.6 | 6.1 | 300 | 4.9 | 80.2 | (0.32, 0.61) |
| Ex. (39) | Com. (2-7) | 5.1 | 4.5 | 300 | 6.7 | 131.2 | (0.30, 0.61) |
| Ex. (40) | Com. (2-8) | 5.1 | 4.8 | 300 | 6.3 | 117.8 | (0.31, 0.60) |
| Ex. (41) | Com. (2-9) | 5.3 | 5.1 | 300 | 5.9 | 102.8 | (0.31, 0.60) |
| Ex. (42) | Com. (2-10) | 5.0 | 4.2 | 300 | 7.2 | 108.6 | (0.32, 0.61) |
| Ex. (43) | Com. (2-11) | 5.1 | 4.7 | 300 | 6.3 | 114.6 | (0.31, 0.61) |
| Ex. (44) | Com. (2-12) | 5.0 | 5.2 | 300 | 5.8 | 114.4 | (0.33, 0.60) |
| Ex. (45) | Com. (2-13) | 5.7 | 5.8 | 300 | 5.2 | 81.9 | (0.31, 0.60) |

TABLE 4-continued

|  | Compond | Driving Voltage | Current Density (mA/cm2) | Brightness (cd/m2) | Efficiency (cd/A) | T(95) | CIE (x, y) |
|---|---|---|---|---|---|---|---|
| Ex. (46) | Com. (2-14) | 4.9 | 5.1 | 300 | 5.8 | 131.1 | (0.32, 0.60) |
| Ex. (47) | Com. (2-15) | 4.8 | 4.9 | 300 | 6.1 | 119.0 | (0.32, 0.61) |
| Ex. (48) | Com. (2-16) | 4.9 | 4.6 | 300 | 6.6 | 139.4 | (0.33, 0.60) |
| Ex. (49) | Com. (2-17) | 4.9 | 5.3 | 300 | 5.6 | 131.2 | (0.30, 0.61) |
| Ex. (50) | Com. (2-18) | 5.3 | 4.7 | 300 | 6.4 | 136.8 | (0.31, 0.61) |
| Ex. (51) | Com. (2-19) | 5.0 | 4.4 | 300 | 6.8 | 127.5 | (0.31, 0.60) |
| Ex. (52) | Com. (2-20) | 5.0 | 4.3 | 300 | 7.0 | 145.6 | (0.33, 0.61) |
| Ex. (53) | Com. (2-21) | 5.1 | 5.0 | 300 | 6.0 | 132.6 | (0.32, 0.61) |
| Ex. (54) | Com. (2-22) | 4.9 | 5.1 | 300 | 5.9 | 106.9 | (0.33, 0.60) |
| Ex. (55) | Com. (2-23) | 5.3 | 4.5 | 300 | 6.7 | 127.7 | (0.30, 0.61) |
| Ex. (56) | Com. (2-24) | 4.9 | 4.5 | 300 | 6.7 | 110.6 | (0.31, 0.61) |
| Ex. (57) | Com. (2-25) | 5.3 | 4.4 | 300 | 6.8 | 116.4 | (0.31, 0.60) |
| Ex. (58) | Com. (2-26) | 5.0 | 4.5 | 300 | 6.7 | 102.7 | (0.33, 0.60) |
| Ex. (59) | Com. (2-27) | 5.3 | 4.2 | 300 | 7.1 | 105.1 | (0.32, 0.60) |
| Ex. (60) | Com. (2-28) | 4.9 | 4.0 | 300 | 7.5 | 100.7 | (0.32, 0.60) |
| Ex. (61) | Com. (2-29) | 5.3 | 5.3 | 300 | 5.6 | 137.9 | (0.33, 0.60) |
| Ex. (62) | Com. (2-30) | 5.1 | 4.1 | 300 | 7.2 | 123.7 | (0.30, 0.60) |
| Ex. (63) | Com. (2-31) | 5.3 | 4.8 | 300 | 6.2 | 123.7 | (0.30, 0.61) |
| Ex. (64) | Com. (2-32) | 5.0 | 4.4 | 300 | 6.9 | 112.8 | (0.32, 0.60) |
| Ex. (65) | Com. (3-1) | 5.2 | 4.2 | 300 | 7.1 | 103.2 | (0.31, 0.61) |
| Ex. (66) | Com. (3-2) | 5.2 | 4.7 | 300 | 6.4 | 135.2 | (0.31, 0.60) |
| Ex. (67) | Com. (3-3) | 4.8 | 4.5 | 300 | 6.6 | 140.5 | (0.31, 0.60) |
| Ex. (68) | Com. (3-4) | 5.0 | 4.2 | 300 | 7.1 | 141.5 | (0.32, 0.61) |
| Ex. (69) | Com. (3-5) | 4.8 | 4.7 | 300 | 6.3 | 133.8 | (0.31, 0.61) |
| Ex. (70) | Com. (3-6) | 5.6 | 5.8 | 300 | 5.2 | 93.1 | (0.33, 0.60) |
| Ex. (71) | Com. (3-7) | 5.0 | 4.0 | 300 | 7.5 | 112.9 | (0.31, 0.60) |
| Ex. (72) | Com. (3-8) | 5.3 | 4.9 | 300 | 6.1 | 130.1 | (0.32, 0.61) |
| Ex. (73) | Com. (3-9) | 5.1 | 4.2 | 300 | 7.2 | 123.3 | (0.32, 0.61) |
| Ex. (74) | Com. (3-10) | 4.8 | 4.5 | 300 | 6.6 | 149.0 | (0.33, 0.60) |
| Ex. (75) | Com. (3-11) | 5.1 | 4.6 | 300 | 6.5 | 106.1 | (0.30, 0.61) |
| Ex. (76) | Com. (3-12) | 5.0 | 4.3 | 300 | 7.0 | 127.6 | (0.31, 0.60) |
| Ex. (77) | Com. (3-13) | 5.5 | 5.8 | 300 | 5.2 | 85.6 | (0.31, 0.60) |
| Ex. (78) | Com. (3-14) | 5.1 | 4.9 | 300 | 6.2 | 134.0 | (0.33, 0.61) |
| Ex. (79) | Com. (3-15) | 5.2 | 4.5 | 300 | 6.7 | 132.2 | (0.32, 0.61) |
| Ex. (80) | Com. (3-16) | 5.3 | 4.7 | 300 | 6.4 | 124.4 | (0.33, 0.60) |
| Ex. (81) | Com. (3-17) | 5.1 | 4.3 | 300 | 7.0 | 113.8 | (0.32, 0.61) |
| Ex. (82) | Com. (3-18) | 5.0 | 4.1 | 300 | 7.3 | 147.6 | (0.33, 0.60) |
| Ex. (83) | Com. (3-19) | 5.1 | 4.2 | 300 | 7.1 | 100.6 | (0.30, 0.61) |
| Ex. (84) | Com. (3-20) | 4.9 | 5.0 | 300 | 6.0 | 106.7 | (0.30, 0.61) |
| Ex. (85) | Com. (3-21) | 5.0 | 5.1 | 300 | 5.9 | 140.2 | (0.31, 0.60) |
| Ex. (86) | Com. (3-22) | 5.1 | 4.8 | 300 | 6.2 | 118.8 | (0.33, 0.61) |
| Ex. (87) | Com. (3-23) | 54 | 4.1 | 300 | 7.3 | 100.0 | (0.32, 0.60) |
| Ex. (88) | Com. (3-24) | 5.2 | 5.0 | 300 | 6.0 | 121.2 | (0.32, 0.61) |
| Ex. (89) | Com. (3-25) | 5.1 | 4.7 | 300 | 6.3 | 145.9 | (0.33, 0.60) |
| Ex. (90) | Com. (3-26) | 5.0 | 4.2 | 300 | 7.1 | 136.9 | (0.30, 0.60) |
| Ex. (91) | Com. (3-27) | 5.1 | 4.1 | 300 | 7.3 | 132.8 | (0.30, 0.61) |
| Ex. (92) | Com. (4-1) | 4.8 | 4.7 | 300 | 6.4 | 106.2 | (0.31, 0.61) |
| Ex. (93) | Com. (4-2) | 5.3 | 5.1 | 300 | 5.9 | 106.6 | (0.31, 0.61) |
| Ex. (94) | Com. (4-3) | 4.9 | 4.3 | 300 | 7.0 | 146.7 | (0.31, 0.60) |
| Ex. (95) | Com. (4-4) | 5.1 | 4.1 | 300 | 7.4 | 146.4 | (0.31, 0.61) |
| Ex. (96) | Com. (4-5) | 4.9 | 4.9 | 300 | 6.1 | 135.8 | (0.32, 0.61) |
| Ex. (97) | Com. (4-6) | 5.7 | 6.0 | 300 | 5.0 | 80.3 | (0.31, 0.61) |
| Ex. (98) | Com. (4-7) | 4.8 | 4.4 | 300 | 6.8 | 127.4 | (0.33, 0.60) |
| Ex. (99) | Com. (4-8) | 5.3 | 4.9 | 300 | 6.1 | 131.6 | (0.31, 0.61) |
| Ex. (100) | Com. (4-9) | 4.9 | 5.1 | 300 | 5.8 | 100.8 | (0.32, 0.61) |
| Ex. (101) | Com. (4-10) | 4.9 | 5.0 | 300 | 6.1 | 107.3 | (0.32, 0.61) |
| Ex. (102) | Com. (4-11) | 5.2 | 4.6 | 300 | 6.5 | 119.6 | (0.33, 0.60) |
| Ex. (103) | Com. (4-12) | 4.9 | 4.2 | 300 | 7.2 | 127.7 | (0.30, 0.60) |
| Ex. (104) | Com. (4-13) | 5.6 | 5.8 | 300 | 5.2 | 84.7 | (0.31, 0.61) |
| Ex. (105) | Com. (4-14) | 5.0 | 4.7 | 300 | 6.4 | 135.5 | (0.30, 0.60) |
| Ex. (106) | Com. (4-15) | 5.4 | 4.4 | 300 | 6.8 | 112.7 | (0.33, 0.61) |
| Ex. (107) | Com. (4-16) | 5.1 | 4.0 | 300 | 7.4 | 107.2 | (0.32, 0.61) |
| Ex. (108) | Com. (4-17) | 5.1 | 4.4 | 300 | 6.7 | 139.7 | (0.33, 0.60) |
| Ex. (109) | Com. (4-18) | 5.2 | 5.1 | 300 | 5.9 | 104.8 | (0.30, 0.61) |
| Ex. (110) | Com. (4-19) | 5.1 | 4.6 | 300 | 6.5 | 109.3 | (0.31, 0.61) |
| Ex. (111) | Com. (4-20) | 4.9 | 4.6 | 300 | 6.5 | 115.0 | (0.31, 0.60) |
| Ex. (112) | Com. (4-21) | 5.3 | 5.2 | 300 | 5.8 | 139.2 | (0.33, 0.61) |
| Ex. (113) | Com. (4-22) | 5.2 | 5.0 | 300 | 5.9 | 133.3 | (0.32, 0.60) |
| Ex. (114) | Com. (4-23) | 4.9 | 4.1 | 300 | 7.2 | 141.0 | (0.32, 0.61) |
| Ex. (115) | Com. (4-24) | 5.3 | 5.3 | 300 | 5.7 | 137.9 | (0.33, 0.60) |
| Ex. (116) | Com. (4-25) | 5.3 | 4.3 | 300 | 7.0 | 120.8 | (0.30, 0.60) |
| Ex. (117) | Com. (4-26) | 5.2 | 5.1 | 300 | 5.9 | 124.0 | (0.30, 0.61) |
| Ex. (118) | Com. (4-27) | 4.9 | 4.4 | 300 | 6.8 | 107.0 | (0.32, 0.61) |

It can be seen from the results given in Table 4 above that most of the OLEDs manufactured using the inventive compounds showed low driving voltage, high efficiency, and long life span, as compared to Comparative Examples 1 to 5. Also, the inventive compounds, each containing heterocyclic groups at positions $R_1$ to $R_4$ and $R_{11}$ to $R_{14}$ of the core, showed relatively high driving voltage, low efficiency, and short life span as in the case of Comparative Examples 2 and 3. This is believed because when heterocyclic groups are linked to positions $R_1$ to $R_4$ and $R_{11}$ to $R_{14}$, the band gap is relatively low, HOMO is increased, hole mobility is reduced, and driving voltage is increased, resulting in low efficiency and short lifespan. It can also be noted that Comparative Examples 4 and 5, which are compounds substituted by hydrogen at positions $R_1$ to $R_4$ and $R_{11}$ to $R_{14}$, showed shorter life span than the inventive compounds.

Test Example 2

Phosphorescent Red Host

First, an ITO layer (anode) was formed on a glass substrate, and 2-TNATA was vacuum-deposited on the ITO layer to form a hole injection layer with a thickness of 60 nm. Subsequently, NPD was vacuum-deposited with a thickness of 20 nm on the hole injection layer to form a hole transport layer. Next, a light emitting layer with a thickness of 30 nm was deposited on the hole transport layer by doping the hole transport layer with the inventive compound (3-28-3-51, 4-28-4-51, 6-1-6-48, 7-1-7-48) as a host material and (piq)$_2$Ir(acac)[bis-(1-phenylisoquinolyl)iridium(III)acetylacetonate] as a dopant material in a weight ratio of 95:5. Also, BAlq was vacuum-deposited with a thickness of 10 nm on the light emitting layer to form a hole blocking layer, and a film of Alq$_3$ was formed with a thickness of 40 nm on the hole blocking layer to form an electron injection layer. Next, LiF as halogenated alkali metal was deposited with a thickness of 0.2 nm on the electron injection layer, and then Al was deposited with a thickness of 150 nm thereon to form an Al/LiF cathode. In this way, an OLED was completed.

Comparative Example 6

An OLED was manufactured in the same manner as described in Test Example 2, except that Comparative Compound 1 (4,4'-di(9H-carbazol-9-yl)-1,1'-biphenyl) was used as the host material of the light emitting layer, instead of the inventive compound.

Comparative Example 7

An OLED was manufactured in the same manner as described in Test Example 2, except that Comparative Compound 2 (9-(9-(4,6-diphenylpyrimidin-2-yl)-9H-carbazol-3-yl)-12-phenyl-12H-benzo[4,5]thieno[3,2-a]carbazole) was used as the host material of the light emitting layer, instead of the inventive compound.

Comparative Example 8

An OLED was manufactured in the same manner as described in Test Example 2, except that Comparative Compound 3 (3-(9-(4,6-diphenyl-1,3,5-triazin-2-yl)-9H-carbazol-3-yl)-12-phenyl-12H-benzo[4,5]thieno[2,3-a]carbazole) was used as the host material of the light emitting layer, instead of the inventive compound.

Comparative Example 9

An OLED was manufactured in the same manner as described in Test Example 2, except that Comparative Compound 4 (12-(5-phenylpyrimidin-2-yl)-12H-benzo[4,5]thieno[3,2-a]carbazole) was used as the host material of the light emitting layer, instead of the inventive compound.

Comparative Example 10

An OLED was manufactured in the same manner as described in Test Example 2, except that Comparative Compound 5 (12-(4-(4,6-diphenylpyrimidin-2-yl)phenyl)-12H-benzo[4,5]thieno[2,3-a]carbazole) was used as the host material of the light emitting layer, instead of the inventive compound.

A forward bias DC voltage was applied to each of the OLEDs manufactured in Test Example 2 and Comparative Examples 6 to 10, and EL characteristics of the OLED were measured by PR-650 (Photoresearch). Also, T95 life span was measured by life span measuring equipment (Mcscience) at a reference brightness of 300 cd/m$^2$. Table 5 below shows the measurement results. In Table 5, Examples 119 to 262 represent the inventive OLEDs manufactured according to Test Example 2.

TABLE 5

| | Compond | Driving Voltage | Current Density (mA/cm2) | Brightness (cd/m2) | Efficiency (cd/A) | T(95) | CIE (x, y) |
|---|---|---|---|---|---|---|---|
| Comp. Ex. (6) | Comp. Com. (1) | 6.0 | 7.5 | 300 | 4.0 | 55.6 | (0.62, 0.37) |
| Comp. Ex. (7) | Comp. Com. (2) | 5.4 | 5.6 | 300 | 5.4 | 76.4 | (0.62, 0.37) |
| Comp. Ex. (8) | Comp. Com. (3) | 5.6 | 5.2 | 300 | 5.8 | 86.8 | (0.62, 0.37) |
| Comp. Ex. (9) | Comp. Com. (4) | 5.5 | 5.8 | 300 | 5.2 | 72.9 | (0.62, 0.37) |
| Comp. Ex. (10) | Comp. Com. (5) | 5.7 | 6.3 | 300 | 4.8 | 71.7 | (0.62, 0.37) |
| Ex. (119) | Com. (3-28) | 5.2 | 4.9 | 300 | 6.2 | 131.0 | (0.66, 0.32) |
| Ex. (120) | Com. (3-29) | 5.3 | 4.8 | 300 | 6.2 | 129.0 | (0.67, 0.33) |
| Ex. (121) | Com. (3-30) | 5.2 | 4.8 | 300 | 6.2 | 97.4 | (0.67, 0.33) |
| Ex. (122) | Com. (3-31) | 4.9 | 4.6 | 300 | 6.5 | 122.2 | (0.65, 0.33) |
| Ex. (123) | Com. (3-32) | 5.0 | 4.2 | 300 | 7.2 | 138.5 | (0.67, 0.32) |
| Ex. (124) | Com. (3-33) | 5.1 | 4.8 | 300 | 6.2 | 115.4 | (0.66, 0.32) |
| Ex. (125) | Com. (3-34) | 5.3 | 4.0 | 300 | 7.5 | 129.3 | (0.66, 0.33) |
| Ex. (126) | Com. (3-35) | 4.8 | 4.1 | 300 | 7.4 | 136.9 | (0.66, 0.32) |
| Ex. (127) | Com. (3-36) | 5.3 | 4.4 | 300 | 6.9 | 125.7 | (0.66, 0.32) |
| Ex. (128) | Com. (3-37) | 5.3 | 4.8 | 300 | 6.2 | 110.5 | (0.66, 0.32) |
| Ex. (129) | Com. (3-38) | 5.1 | 4.2 | 300 | 7.1 | 126.3 | (0.66, 0.32) |
| Ex. (130) | Com. (3-39) | 4.8 | 5.1 | 300 | 5.9 | 96.0 | (0.66, 0.33) |
| Ex. (131) | Com. (3-40) | 5.0 | 4.6 | 300 | 6.5 | 121.8 | (0.67, 0.32) |

TABLE 5-continued

|  | Compond | Driving Voltage | Current Density (mA/cm2) | Brightness (cd/m2) | Efficiency (cd/A) | T(95) | CIE (x, y) |
|---|---|---|---|---|---|---|---|
| Ex. (132) | Com. (3-41) | 5.3 | 4.6 | 300 | 6.5 | 122.6 | (0.66, 0.33) |
| Ex. (133) | Com. (3-42) | 4.9 | 4.4 | 300 | 6.9 | 130.4 | (0.65, 0.32) |
| Ex. (134) | Com. (3-43) | 4.9 | 4.7 | 300 | 6.3 | 135.9 | (0.66, 0.32) |
| Ex. (135) | Com. (3-44) | 5.2 | 4.2 | 300 | 7.2 | 132.7 | (0.66, 0.32) |
| Ex. (136) | Com. (3-45) | 4.8 | 4.3 | 300 | 6.9 | 95.1 | (0.66, 0.32) |
| Ex. (137) | Com. (3-46) | 5.3 | 4.9 | 300 | 6.1 | 125.3 | (0.65, 0.33) |
| Ex. (138) | Com. (3-47) | 5.2 | 4.5 | 300 | 6.6 | 101.7 | (0.65, 0.32) |
| Ex. (139) | Com. (3-48) | 5.0 | 4.7 | 300 | 6.4 | 119.8 | (0.67, 0.33) |
| Ex. (140) | Com. (3-49) | 5.3 | 4.2 | 300 | 7.1 | 122.2 | (0.66, 0.32) |
| Ex. (141) | Com. (3-50) | 4.9 | 4.9 | 300 | 6.1 | 139.7 | (0.67, 0.33) |
| Ex. (142) | Com. (3-51) | 5.1 | 4.6 | 300 | 6.5 | 105.8 | (0.66, 0.33) |
| Ex. (143) | Com. (4-28) | 5.3 | 4.3 | 300 | 6.9 | 122.1 | (0.65, 0.32) |
| Ex. (144) | Com. (4-29) | 5.3 | 4.3 | 300 | 7.0 | 111.7 | (0.66, 0.32) |
| Ex. (145) | Com. (4-30) | 4.9 | 4.0 | 300 | 7.4 | 114.3 | (0.67, 0.32) |
| Ex. (146) | Com. (4-31) | 5.2 | 4.6 | 300 | 6.5 | 136.9 | (0.65, 0.32) |
| Ex. (147) | Com. (4-32) | 5.3 | 4.1 | 300 | 7.2 | 131.4 | (0.65, 0.33) |
| Ex. (148) | Com. (4-33) | 4.9 | 4.3 | 300 | 7.0 | 137.5 | (0.66, 0.32) |
| Ex. (149) | Com. (4-34) | 5.3 | 4.4 | 300 | 6.8 | 138.4 | (0.67, 0.33) |
| Ex. (150) | Com. (4-35) | 5.4 | 4.7 | 300 | 6.4 | 98.9 | (0.66, 0.33) |
| Ex. (151) | Com. (4-36) | 4.9 | 5.0 | 300 | 6.0 | 103.6 | (0.66, 0.32) |
| Ex. (152) | Com. (4-37) | 5.2 | 4.5 | 300 | 6.7 | 131.1 | (0.66, 0.32) |
| Ex. (153) | Com. (4-38) | 5.1 | 4.8 | 300 | 6.3 | 127.2 | (0.66, 0.32) |
| Ex. (154) | Com. (4-39) | 5.2 | 4.4 | 300 | 6.8 | 117.6 | (0.65, 0.32) |
| Ex. (155) | Com. (4-40) | 5.2 | 5.0 | 300 | 6.0 | 123.5 | (0.65, 0.33) |
| Ex. (156) | Com. (4-41) | 5.3 | 4.1 | 300 | 7.3 | 109.0 | (0.66, 0.33) |
| Ex. (157) | Com. (4-42) | 5.2 | 4.0 | 300 | 7.5 | 106.0 | (0.66, 0.33) |
| Ex. (158) | Com. (4-43) | 5.0 | 4.5 | 300 | 6.6 | 119.5 | (0.65, 0.32) |
| Ex. (159) | Com. (4-44) | 5.1 | 5.1 | 300 | 5.9 | 138.1 | (0.66, 0.32) |
| Ex. (160) | Com. (4-45) | 5.3 | 4.3 | 300 | 6.9 | 101.8 | (0.66, 0.32) |
| Ex. (161) | Com. (4-46) | 5.3 | 4.2 | 300 | 7.2 | 117.2 | (0.67, 0.32) |
| Ex. (162) | Com. (4-47) | 5.3 | 4.7 | 300 | 6.4 | 100.5 | (0.67, 0.33) |
| Ex. (163) | Com. (4-48) | 5.2 | 4.4 | 300 | 6.8 | 105.5 | (0.66, 0.32) |
| Ex. (164) | Com. (4-49) | 5.2 | 4.8 | 300 | 6.3 | 114.5 | (0.65, 0.32) |
| Ex. (165) | Com. (4-50) | 5.0 | 5.1 | 300 | 5.9 | 115.5 | (0.67, 0.32) |
| Ex. (166) | Com. (4-51) | 4.9 | 4.8 | 300 | 6.3 | 117.3 | (0.66, 0.32) |
| Ex. (167) | Com. (6-1) | 5.1 | 4.7 | 300.0 | 6.4 | 131.4 | (0.66, 0.32) |
| Ex. (168) | Com. (6-2) | 5.1 | 4.1 | 300.0 | 7.4 | 128.3 | (0.65, 0.33) |
| Ex. (169) | Com. (6-3) | 5.2 | 4.0 | 300.0 | 7.5 | 110.2 | (0.65, 0.32) |
| Ex. (170) | Com. (6-4) | 4.9 | 4.3 | 300.0 | 7.0 | 116.3 | (0.67, 0.33) |
| Ex. (171) | Com. (6-5) | 4.9 | 4.3 | 300.0 | 7.0 | 97.3 | (0.66, 0.32) |
| Ex. (172) | Com. (6-6) | 5.2 | 4.2 | 300.0 | 7.1 | 105.6 | (0.67, 0.33) |
| Ex. (173) | Com. (6-7) | 4.9 | 4.2 | 300.0 | 7.2 | 126.2 | (0.66, 0.32) |
| Ex. (174) | Com. (6-8) | 5.1 | 4.1 | 300.0 | 7.3 | 118.4 | (0.65, 0.32) |
| Ex. (175) | Com. (6-9) | 5.3 | 4.8 | 300.0 | 6.3 | 108.1 | (0.66, 0.32) |
| Ex. (176) | Com. (6-10) | 5.2 | 4.3 | 300.0 | 7.0 | 127.3 | (0.67, 0.32) |
| Ex. (177) | Com. (6-11) | 4.8 | 4.3 | 300.0 | 7.0 | 134.8 | (0.65, 0.32) |
| Ex. (178) | Com. (6-12) | 4.9 | 4.5 | 300.0 | 6.7 | 139.0 | (0.65, 0.33) |
| Ex. (179) | Com. (6-13) | 5.0 | 4.3 | 300.0 | 7.0 | 102.4 | (0.66, 0.32) |
| Ex. (180) | Com. (6-14) | 5.0 | 4.7 | 300.0 | 6.4 | 132.9 | (0.67, 0.33) |
| Ex. (181) | Com. (6-15) | 5.0 | 4.2 | 300.0 | 7.2 | 104.3 | (0.66, 0.32) |
| Ex. (182) | Com. (6-16) | 5.0 | 4.4 | 300.0 | 6.8 | 126.0 | (0.66, 0.32) |
| Ex. (183) | Com. (6-17) | 4.8 | 4.4 | 300.0 | 6.8 | 133.7 | (0.66, 0.33) |
| Ex. (184) | Com. (6-18) | 5.1 | 4.7 | 300.0 | 6.4 | 121.3 | (0.66, 0.32) |
| Ex. (185) | Com. (6-19) | 4.9 | 4.0 | 300.0 | 7.4 | 102.1 | (0.65, 0.32) |
| Ex. (186) | Com. (6-20) | 4.9 | 4.0 | 300.0 | 7.5 | 96.8 | (0.65, 0.33) |
| Ex. (187) | Com. (6-21) | 5.2 | 4.1 | 300.0 | 7.4 | 117.6 | (0.66, 0.32) |
| Ex. (188) | Com. (6-22) | 5.1 | 4.1 | 300.0 | 7.3 | 96.9 | (0.65, 0.33) |
| Ex. (189) | Com. (6-23) | 4.9 | 4.5 | 300.0 | 6.7 | 106.8 | (0.65, 0.32) |
| Ex. (190) | Com. (6-24) | 5.1 | 4.1 | 300.0 | 7.3 | 136.7 | (0.67, 0.33) |
| Ex. (191) | Com. (6-25) | 4.9 | 4.1 | 300.0 | 7.3 | 97.2 | (0.66, 0.32) |
| Ex. (192) | Com. (6-26) | 5.2 | 4.1 | 300.0 | 7.4 | 112.6 | (0.67, 0.33) |
| Ex. (193) | Com. (6-27) | 4.9 | 4.6 | 300.0 | 6.5 | 124.0 | (0.66, 0.32) |
| Ex. (194) | Com. (6-28) | 5.1 | 4.2 | 300.0 | 7.1 | 127.3 | (0.65, 0.32) |
| Ex. (195) | Com. (6-29) | 4.9 | 4.6 | 300.0 | 6.5 | 102.5 | (0.66, 0.32) |
| Ex. (196) | Com. (6-30) | 5.0 | 4.6 | 300.0 | 6.5 | 115.8 | (0.67, 0.32) |
| Ex. (197) | Com. (6-31) | 4.9 | 4.2 | 300.0 | 7.2 | 138.2 | (0.65, 0.32) |
| Ex. (198) | Com. (6-32) | 4.9 | 4.4 | 300.0 | 6.8 | 134.9 | (0.65, 0.32) |
| Ex. (199) | Com. (6-33) | 4.9 | 4.5 | 300.0 | 6.7 | 115.9 | (0.66, 0.32) |
| Ex. (200) | Com. (6-34) | 5.1 | 4.3 | 300.0 | 7.0 | 128.8 | (0.67, 0.32) |
| Ex. (201) | Com. (6-35) | 5.0 | 4.4 | 300.0 | 6.8 | 117.4 | (0.66, 0.32) |
| Ex. (202) | Com. (6-36) | 5.1 | 4.7 | 300.0 | 6.4 | 135.0 | (0.66, 0.32) |
| Ex. (203) | Com. (6-37) | 5.1 | 4.1 | 300.0 | 7.2 | 124.0 | (0.66, 0.32) |
| Ex. (204) | Com. (6-38) | 5.1 | 4.7 | 300.0 | 6.4 | 105.6 | (0.66, 0.32) |
| Ex. (205) | Com. (6-39) | 5.0 | 4.8 | 300.0 | 6.3 | 133.9 | (0.65, 0.32) |
| Ex. (206) | Com. (6-40) | 5.3 | 4.4 | 300.0 | 6.8 | 109.1 | (0.65, 0.33) |
| Ex. (207) | Com. (6-41) | 4.9 | 4.2 | 300.0 | 7.2 | 95.5 | (0.66, 0.32) |

TABLE 5-continued

| | Compond | Driving Voltage | Current Density (mA/cm2) | Brightness (cd/m2) | Efficiency (cd/A) | T(95) | CIE (x, y) |
|---|---|---|---|---|---|---|---|
| Ex. (208) | Com. (6-42) | 5.3 | 4.7 | 300.0 | 6.4 | 109.6 | (0.65, 0.33) |
| Ex. (209) | Com. (6-43) | 5.1 | 4.7 | 300.0 | 6.3 | 109.7 | (0.65, 0.32) |
| Ex. (210) | Com. (6-44) | 5.0 | 4.3 | 300.0 | 7.0 | 135.5 | (0.67, 0.33) |
| Ex. (211) | Com. (6-45) | 5.2 | 4.8 | 300.0 | 6.3 | 131.0 | (0.66, 0.32) |
| Ex. (212) | Com. (6-46) | 4.9 | 4.2 | 300.0 | 7.2 | 109.1 | (0.67, 0.33) |
| Ex. (213) | Com. (6-47) | 4.8 | 4.1 | 300.0 | 7.2 | 108.6 | (0.66, 0.33) |
| Ex. (214) | Com. (6-48) | 5.0 | 4.5 | 300.0 | 6.7 | 116.7 | (0.65, 0.32) |
| Ex. (215) | Com. (7-1) | 5.2 | 4.6 | 300.0 | 6.5 | 130.8 | (0.66, 0.32) |
| Ex. (216) | Com. (7-2) | 5.1 | 4.5 | 300.0 | 6.7 | 137.3 | (0.67, 0.32) |
| Ex. (217) | Com. (7-3) | 5.1 | 4.5 | 300.0 | 6.6 | 123.2 | (0.65, 0.32) |
| Ex. (218) | Com. (7-4) | 5.2 | 4.6 | 300.0 | 6.5 | 101.9 | (0.65, 0.33) |
| Ex. (219) | Com. (7-5) | 5.1 | 4.4 | 300.0 | 6.8 | 119.1 | (0.66, 0.32) |
| Ex. (220) | Com. (7-6) | 5.0 | 4.5 | 300.0 | 6.7 | 107.7 | (0.67, 0.33) |
| Ex. (221) | Com. (7-7) | 4.8 | 4.7 | 300.0 | 6.4 | 128.5 | (0.66, 0.33) |
| Ex. (222) | Com. (7-8) | 4.9 | 4.2 | 300.0 | 7.1 | 101.7 | (0.66, 0.32) |
| Ex. (223) | Com. (7-9) | 5.0 | 4.5 | 300.0 | 6.7 | 102.9 | (0.66, 0.33) |
| Ex. (224) | Com. (7-10) | 5.1 | 4.3 | 300.0 | 7.0 | 110.8 | (0.66, 0.32) |
| Ex. (225) | Com. (7-11) | 5.1 | 4.7 | 300.0 | 6.4 | 114.7 | (0.65, 0.32) |
| Ex. (226) | Com. (7-12) | 5.0 | 4.3 | 300.0 | 7.0 | 121.7 | (0.65, 0.32) |
| Ex. (227) | Com. (7-13) | 5.1 | 4.4 | 300.0 | 6.8 | 121.2 | (0.66, 0.32) |
| Ex. (228) | Com. (7-14) | 5.0 | 4.4 | 300.0 | 6.9 | 128.8 | (0.65, 0.32) |
| Ex. (229) | Com. (7-15) | 5.0 | 4.8 | 300.0 | 6.3 | 122.2 | (0.65, 0.32) |
| Ex. (230) | Com. (7-16) | 4.9 | 4.7 | 300.0 | 6.3 | 132.4 | (0.67, 0.33) |
| Ex. (231) | Com. (7-17) | 4.9 | 4.2 | 300.0 | 7.1 | 114.6 | (0.66, 0.32) |
| Ex. (232) | Com. (7-18) | 4.8 | 4.2 | 300.0 | 7.1 | 102.1 | (0.67, 0.33) |
| Ex. (233) | Com. (7-19) | 4.9 | 4.8 | 300.0 | 6.3 | 135.9 | (0.66, 0.32) |
| Ex. (234) | Com. (7-20) | 5.1 | 4.2 | 300.0 | 7.1 | 113.2 | (0.65, 0.32) |
| Ex. (235) | Com. (7-21) | 5.1 | 4.8 | 300.0 | 6.2 | 136.6 | (0.66, 0.32) |
| Ex. (236) | Com. (7-22) | 4.8 | 4.8 | 300.0 | 6.3 | 136.0 | (0.67, 0.32) |
| Ex. (237) | Com. (7-23) | 4.8 | 4.0 | 300.0 | 7.5 | 117.6 | (0.65, 0.32) |
| Ex. (238) | Com. (7-24) | 5.3 | 4.5 | 300.0 | 6.6 | 118.2 | (0.65, 0.33) |
| Ex. (239) | Com. (7-25) | 5.2 | 4.1 | 300.0 | 7.4 | 96.5 | (0.66, 0.32) |
| Ex. (240) | Com. (7-26) | 5.0 | 4.6 | 300.0 | 6.5 | 122.8 | (0.67, 0.33) |
| Ex. (241) | Com. (7-27) | 4.8 | 4.6 | 300.0 | 6.6 | 138.3 | (0.66, 0.33) |
| Ex. (242) | Com. (7-28) | 4.9 | 4.7 | 300.0 | 6.3 | 127.8 | (0.66, 0.33) |
| Ex. (243) | Com. (7-29) | 5.3 | 4.2 | 300.0 | 7.2 | 116.1 | (0.66, 0.33) |
| Ex. (244) | Com. (7-30) | 4.9 | 4.1 | 300.0 | 7.3 | 117.2 | (0.66, 0.33) |
| Ex. (245) | Com. (7-31) | 4.9 | 4.3 | 300.0 | 6.9 | 121.4 | (0.65, 0.32) |
| Ex. (246) | Com. (7-32) | 4.9 | 4.5 | 300.0 | 6.7 | 108.3 | (0.65, 0.32) |
| Ex. (247) | Com. (7-33) | 5.1 | 4.4 | 300.0 | 6.9 | 123.9 | (0.66, 0.33) |
| Ex. (248) | Com. (7-34) | 5.1 | 4.2 | 300.0 | 7.1 | 102.7 | (0.67, 0.32) |
| Ex. (249) | Com. (7-35) | 5.0 | 4.8 | 300.0 | 6.2 | 114.8 | (0.65, 0.32) |
| Ex. (250) | Com. (7-36) | 5.1 | 4.1 | 300.0 | 7.3 | 120.6 | (0.65, 0.33) |
| Ex. (251) | Com. (7-37) | 5.1 | 4.6 | 300.0 | 6.5 | 100.0 | (0.66, 0.32) |
| Ex. (252) | Com. (7-38) | 5.2 | 4.7 | 300.0 | 6.4 | 132.4 | (0.67, 0.33) |
| Ex. (253) | Com. (7-39) | 5.0 | 4.1 | 300.0 | 7.4 | 119.4 | (0.66, 0.32) |
| Ex. (254) | Com. (7-40) | 4.9 | 4.3 | 300.0 | 6.9 | 124.4 | (0.66, 0.32) |
| Ex. (255) | Com. (7-41) | 5.3 | 4.5 | 300.0 | 6.7 | 108.5 | (0.66, 0.32) |
| Ex. (256) | Com. (7-42) | 5.2 | 4.2 | 300.0 | 7.2 | 100.9 | (0.66, 0.32) |
| Ex. (257) | Com. (7-43) | 5.2 | 4.3 | 300.0 | 7.0 | 117.7 | (0.65, 0.32) |
| Ex. (258) | Com. (7-44) | 4.9 | 4.6 | 300.0 | 6.6 | 110.5 | (0.66, 0.32) |
| Ex. (259) | Com. (7-45) | 5.2 | 4.3 | 300.0 | 7.0 | 116.3 | (0.66, 0.32) |
| Ex. (260) | Com. (7-46) | 4.8 | 4.0 | 300.0 | 7.4 | 120.5 | (0.66, 0.33) |
| Ex. (261) | Com. (7-47) | 4.9 | 4.7 | 300.0 | 6.4 | 132.9 | (0.66, 0.32) |
| Ex. (262) | Com. (7-48) | 5.0 | 4.1 | 300.0 | 7.3 | 135.4 | (0.65, 0.32) |

It can be seen from the results given in Table 5 above that Examples using the inventive compounds as the phosphorescent red host showed lower driving voltage, higher efficiency, and longer life span than Comparative Examples 6 to 10. Especially, it can be noted from Table 5 above that Comparative Compounds 4 and 5 showed longer life span than Comparative Compounds 2 and 3 when being used as the phosphorescent green host, but showed lower efficiency and shorter life span than Comparative Compounds 2 and 3 when being used as the phosphorescent red host.

Test Example 3

Hole Transport Layer

First, an ITO layer (anode) was formed on a glass substrate, and 2-TNATA was vacuum-deposited on the ITO layer to form a hole injection layer with a thickness of 60 nm. Subsequently, the inventive compound (5-1-5-7, 5-11-5-14, 5-17-5-31, 5-33-5-35) was vacuum-deposited with a thickness of 20 nm on the hole injection layer to form a hole transport layer. Thereafter, a light emitting layer with a thickness of 30 nm was deposited on the hole transport layer by doping the hole transport layer with CBP[4,4'-N,N'-dicarbazole-bisphenyl] as a host material and Ir(ppy)$_3$[tris(2-phenylpyridine)-iridium] as a dopant material in a weight ratio of 90:10. Next, BAlq was vacuum-deposited with a thickness of 10 nm on the light emitting layer to form a hole blocking layer, and then a film of Alq$_3$ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form an Al/LiF cathode. In this way, an OLED was completed.

Comparative Example 11

An OLED was manufactured in the same manner as described in Test Example 3, except that Comparative Compound 6 (N4,N4'-di(naphthalene-1-yl)-N4,N4'-diphenyl-[1,1'-biphenyl]-4,4'-diamine) was used as the hole transport layer material, instead of the inventive compound.

<Comparative Compound 6>

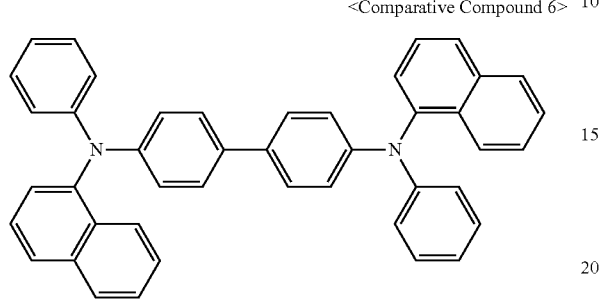

Comparative Example 12

An OLED was manufactured in the same manner as described in Test Example 3, except that the hole transport layer was formed using Comparative Compound 7 (N,N,12-triphenyl-12H-benzo[4,5]thieno[3,2-a]carbazol-9-amine), instead of the inventive compound.

<Comparative Compound 7>

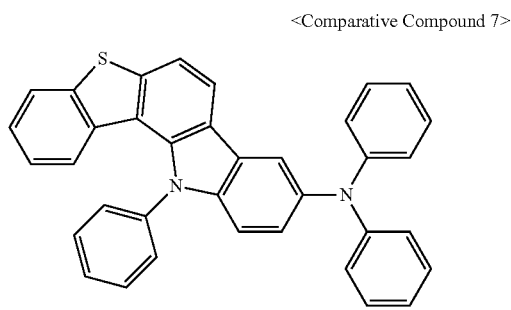 [SMILES: c1ccc(N(c2ccccc2)c2ccc3c(c2)c2ccc4sc5ccccc5c4c2n3-c2ccccc2)cc1]

Comparative Example 13

An OLED was manufactured in the same manner as described in Test Example 3, except that the hole transport layer was formed using Comparative Compound 8 (N-(9,9-dimethyl-9H-fluoren-2-yl)-N,12-diphenyl-12H-benzo[4,5]thieno[3,2-a]carbazol-9-amine), instead of the inventive compound.

<Comparative Compound 8>

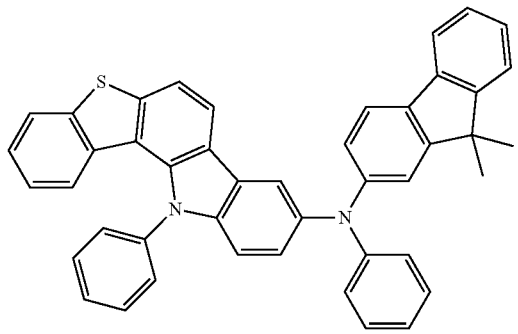

Comparative Example 14

An OLED was manufactured in the same manner as described in Test Example 3, except that the hole transport layer was formed using Comparative Compound 9 (N,N-di([1,1'-biphenyl]-4-yl)-12-phenyl-12H-benzo[4,5]thieno[2,3-a]carbazol-8-amine), instead of the inventive compound.

<Comparative Compound 9>

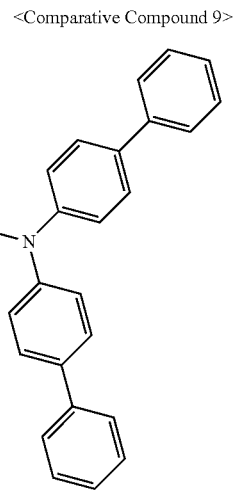

A forward bias DC voltage was applied to each of the OLEDs manufactured in Test Example 3 and Comparative Examples 11 to 14, and EL characteristics of the OLED were measured by PR-650 (Photoresearch). Also, T95 life span was measured by life span measuring equipment (Mcscience) at a reference brightness of 300 cd/m$^2$. Table 6 below shows the measurement results. In Table 5, Examples 262 to 290 represent the inventive OLEDs manufactured according to Test Example 3.

TABLE 6

|  | Compound | Driving Voltage | Current Density (mA/cm2) | Brightness (cd/m2) | Efficiency (cd/A) | T(95) |
|---|---|---|---|---|---|---|
| Comp. Ex. (11) | Comp. Com. (6) | 6.2 | 7.5 | 300.0 | 4.0 | 74.0 |
| Comp. Ex. (12) | Comp. Com. (7) | 5.5 | 5.3 | 300.0 | 5.7 | 94.9 |
| Comp. Ex. (13) | Comp. Com. (8) | 5.1 | 5.8 | 300.0 | 4.8 | 93.1 |
| Comp. Ex. (14) | Comp. Com. (9) | 5.4 | 5.2 | 300.0 | 5.8 | 60.5 |
| Ex. (262) | Com. (5-1) | 5.1 | 4.8 | 300.0 | 6.2 | 124.5 |
| Ex. (263) | Com. (5-2) | 5.1 | 4.8 | 300.0 | 6.2 | 106.7 |
| Ex. (264) | Com. (5-3) | 4.8 | 4.4 | 300.0 | 6.8 | 120.0 |

TABLE 6-continued

|  | Compound | Driving Voltage | Current Density (mA/cm2) | Brightness (cd/m2) | Efficiency (cd/A) | T(95) |
|---|---|---|---|---|---|---|
| Ex. (265) | Com. (5-4) | 5.0 | 4.4 | 300.0 | 6.8 | 127.0 |
| Ex. (266) | Com. (5-5) | 5.1 | 4.8 | 300.0 | 6.3 | 105.6 |
| Ex. (267) | Com. (5-6) | 5.0 | 4.7 | 300.0 | 6.3 | 120.0 |
| Ex. (268) | Com. (5-10) | 4.8 | 4.6 | 300.0 | 6.5 | 108.1 |
| Ex. (269) | Com. (5-11) | 5.1 | 4.5 | 300.0 | 6.7 | 121.3 |
| Ex. (270) | Com. (5-12) | 5.0 | 4.7 | 300.0 | 6.4 | 107.4 |
| Ex. (271) | Com. (5-13) | 4.9 | 4.5 | 300.0 | 6.6 | 97.7 |
| Ex. (272) | Com. (5-14) | 4.8 | 4.8 | 300.0 | 6.3 | 115.3 |
| Ex. (273) | Com. (5-17) | 4.9 | 4.6 | 300.0 | 6.5 | 121.9 |
| Ex. (274) | Com. (5-18) | 4.8 | 4.9 | 300.0 | 6.2 | 108.2 |
| Ex. (275) | Com. (5-19) | 4.9 | 4.6 | 300.0 | 6.5 | 119.7 |
| Ex. (276) | Com. (5-20) | 5.0 | 4.8 | 300.0 | 6.2 | 113.9 |
| Ex. (277) | Com. (5-21) | 4.8 | 4.9 | 300.0 | 6.2 | 112.5 |
| Ex. (278) | Com. (5-22) | 5.1 | 4.4 | 300.0 | 6.8 | 110.2 |
| Ex. (279) | Com. (5-23) | 4.8 | 4.5 | 300.0 | 6.7 | 127.2 |
| Ex. (280) | Com. (5-24) | 4.6 | 4.2 | 300.0 | 7.1 | 112.9 |
| Ex. (281) | Com. (5-25) | 4.7 | 4.6 | 300.0 | 6.5 | 108.3 |
| Ex. (282) | Com. (5-26) | 4.9 | 4.1 | 300.0 | 7.3 | 102.1 |
| Ex. (283) | Com. (5-27) | 4.8 | 4.1 | 300.0 | 7.3 | 141.7 |
| Ex. (284) | Com. (5-28) | 4.7 | 4.5 | 300.0 | 6.7 | 128.9 |
| Ex. (285) | Com. (5-29) | 4.8 | 4.4 | 300.0 | 6.8 | 122.6 |
| Ex. (286) | Com. (5-30) | 4.5 | 4.3 | 300.0 | 6.9 | 122.0 |
| Ex. (287) | Com. (5-31) | 4.5 | 4.5 | 300.0 | 6.6 | 114.4 |
| Ex. (288) | Com. (5-33) | 4.8 | 4.1 | 300.0 | 7.3 | 126.6 |
| Ex. (289) | Com. (5-34) | 4.8 | 4.1 | 300.0 | 7.3 | 105.9 |
| Ex. (290) | Com. (5-35) | 4.5 | 4.2 | 300.0 | 7.2 | 148.4 |

It can be seen from the results given in Table 6 above that Examples using the inventive compounds as the hole transport layer showed lower driving voltage, higher efficiency, and longer life span than Comparative Examples 11 to 14. This is believed because compounds substituted by an aryl group at one of positions $R_1$ to $R_4$ and $R_{11}$ to $R_{14}$ of the core and containing an aryl amine group at another position more easily transport holes into the light emitting layer due to a decreased HOMO level, and thus show low driving voltage, resulting in long life span.

Test Example 4

Emission-Auxiliary Layer

First, an ITO layer (anode) was formed on a glass substrate, and 2-TNATA was vacuum-deposited on the ITO layer to form a hole injection layer with a thickness of 60 nm. Subsequently, 4,4-bis[N-(1-naphthyl)-N-phenylamino]biphenyl (Comparative Compound 6) was vacuum-deposited with a thickness of 20 nm on the hole injection layer to form a hole transport layer. Next, the inventive compound (5-1-5-7, 5-11-5-14, 5-17-5-31, 5-33-5-35, 5-47-5-51) was vacuum-deposited with a thickness of 20 nm on the hole transport layer to form an emission-auxiliary layer. Thereafter, a light emitting layer with a thickness of 30 nm was deposited on the emission-auxiliary layer by doping the emission-auxiliary layer with CBP[4,4'-N,N'-dicarbazole-bisphenyl] as a host material and Ir(ppy)$_3$[tris(2-phenylpyridine)-iridium] as a dopant material in a weight ratio of 95:5. Also, BAlq was vacuum-deposited with a thickness of 10 nm on the light emitting layer to form a hole blocking layer, and then a film of Alq$_3$ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form an Al/LiF cathode. In this way, an OLED was completed.

Comparative Example 15

An OLED was manufactured in the same manner as described in Test Example 4, except that Comparative Compound 6 (N4,N4'-di(naphthalene-1-yl)-N4,N4'-diphenyl-[1,1'-biphenyl]-4,4'-diamine) was used as the emission-auxiliary layer material, instead of the inventive compound.

Comparative Example 16

An OLED was manufactured in the same manner as described in Test Example 4, except that the emission-auxiliary layer was formed using Comparative Compound 7 (N,N,12-triphenyl-12H-benzo[4,5]thieno[3,2-a]carbazol-9-amine), instead of the inventive compound.

Comparative Example 17

An OLED was manufactured in the same manner as described in Test Example 4, except that the emission-auxiliary layer was formed using Comparative Compound 8 (N-(9,9-dimethyl-9H-fluoren-2-yl)-N,12-diphenyl-12H-benzo[4,5]thieno[3,2-a]carbazol-9-amine), instead of the inventive compound.

Comparative Example 18

An OLED was manufactured in the same manner as described in Test Example 4, except that the emission-auxiliary layer was formed using Comparative Compound 9 (N,N-di([1,1'-biphenyl]-4-yl)-12-phenyl-12H-benzo[4,5]thieno[2,3-a]carbazol-8-amine), instead of the inventive compound.

A forward bias DC voltage was applied to each of the OLEDs manufactured in Test Example 4 and Comparative Examples 15 to 18, and EL characteristics of the OLED were measured by PR-650 (Photoresearch). Also, T95 life span was measured by life span measuring equipment (Mcscience) at a reference brightness of 300 cd/m$^2$. Table 7 below shows the measurement results. In Table 7, Examples 291 to 324 represent the inventive OLEDs manufactured according to Test Example 4.

TABLE 7

|  | Compound | Driving Voltage | Current Density (mA/cm2) | Brightness (cd/m2) | Efficiency (cd/A) | T(95) |
| --- | --- | --- | --- | --- | --- | --- |
| Comp. Ex. (15) | Comp. Com. (6) | 5.9 | 6.3 | 300.0 | 4.8 | 86.3 |
| Comp. Ex. (16) | Comp. Com. (7) | 5.1 | 5.8 | 300.0 | 5.2 | 91.3 |
| Comp. Ex. (17) | Comp. Com. (8) | 5.7 | 5.8 | 300.0 | 5.2 | 92.7 |
| Comp. Ex. (18) | Comp. Com. (9) | 5.7 | 5.8 | 300.0 | 5.2 | 89.1 |
| Ex. (291) | Com. (5-1) | 5.0 | 4.0 | 300.0 | 7.4 | 109.4 |
| Ex. (292) | Com. (5-2) | 5.2 | 3.8 | 300.0 | 7.8 | 112.5 |
| Ex. (293) | Com. (5-3) | 5.2 | 3.9 | 300.0 | 7.6 | 97.9 |
| Ex. (294) | Com. (5-4) | 5.2 | 3.9 | 300.0 | 7.6 | 104.9 |
| Ex. (295) | Com. (5-5) | 5.0 | 4.1 | 300.0 | 7.4 | 129.8 |
| Ex. (296) | Com. (5-6) | 4.9 | 3.7 | 300.0 | 8.0 | 111.8 |
| Ex. (297) | Com. (5-7) | 5.2 | 4.0 | 300.0 | 7.4 | 101.1 |
| Ex. (298) | Com. (5-11) | 5.0 | 3.9 | 300.0 | 7.7 | 97.9 |
| Ex. (299) | Com. (5-12) | 5.2 | 3.8 | 300.0 | 8.0 | 121.1 |
| Ex. (300) | Com. (5-13) | 5.1 | 4.0 | 300.0 | 7.5 | 126.1 |
| Ex. (301) | Com. (5-14) | 5.0 | 4.0 | 300.0 | 7.6 | 118.2 |
| Ex. (302) | Com. (5-17) | 5.1 | 4.1 | 300.0 | 7.3 | 97.0 |
| Ex. (303) | Com. (5-18) | 5.0 | 4.1 | 300.0 | 7.2 | 104.0 |
| Ex. (304) | Com. (5-19) | 5.1 | 3.9 | 300.0 | 7.8 | 103.0 |
| Ex. (305) | Com. (5-20) | 4.9 | 3.6 | 300.0 | 8.4 | 109.0 |
| Ex. (306) | Com. (5-21) | 5.1 | 3.7 | 300.0 | 8.1 | 107.8 |
| Ex. (307) | Com. (5-22) | 5.1 | 3.5 | 300.0 | 8.5 | 113.2 |
| Ex. (308) | Com. (5-23) | 5.2 | 3.7 | 300.0 | 8.1 | 116.2 |
| Ex. (309) | Com. (5-24) | 5.0 | 3.9 | 300.0 | 7.8 | 142.7 |
| Ex. (310) | Com. (5-25) | 5.1 | 3.6 | 300.0 | 8.3 | 100.0 |
| Ex. (311) | Com. (5-26) | 5.1 | 3.9 | 300.0 | 7.7 | 120.4 |
| Ex. (312) | Com. (5-27) | 5.1 | 4.0 | 300.0 | 7.4 | 134.9 |
| Ex. (313) | Com. (5-28) | 5.0 | 3.7 | 300.0 | 8.2 | 146.0 |
| Ex. (314) | Com. (5-29) | 5.2 | 4.0 | 300.0 | 7.5 | 142.3 |
| Ex. (315) | Com. (5-30) | 5.0 | 3.9 | 300.0 | 7.7 | 114.9 |
| Ex. (316) | Com. (5-31) | 5.0 | 3.7 | 300.0 | 8.2 | 123.9 |
| Ex. (317) | Com. (5-33) | 5.0 | 4.0 | 300.0 | 7.4 | 136.8 |
| Ex. (318) | Com. (5-34) | 4.8 | 3.7 | 300.0 | 8.1 | 130.5 |
| Ex. (319) | Com. (5-35) | 4.9 | 4.0 | 300.0 | 7.6 | 130.9 |
| Ex. (320) | Com. (5-47) | 4.6 | 3.3 | 300.0 | 9.0 | 125.3 |
| Ex. (321) | Com. (5-48) | 4.5 | 3.7 | 300.0 | 8.1 | 136.8 |
| Ex. (322) | Com. (5-49) | 4.4 | 3.5 | 300.0 | 8.7 | 123.2 |
| Ex. (323) | Com. (5-50) | 4.7 | 3.4 | 300.0 | 8.9 | 140.8 |
| Ex. (324) | Com. (5-51) | 4.5 | 4.0 | 300.0 | 7.5 | 129.5 |

It can be seen from the results given in Table 6 that when the inventive compounds were used as the emission-auxiliary layer between the hole transport layer and the light emitting layer in order to increase efficiency and life span, luminous efficiency and life span were improved as compared to when the comparative compounds were used as the emission-auxiliary layer. This is believed because use of the emission-auxiliary layer with a HMO level that lies between the HOMO level of Comparative Compound 6 used as the hole transport layer and the HOMO level of the light emitting layer leads to high efficiency and long life span.

It is obvious that even when the inventive compounds are used in other organic material layers of an OLED, for example, an electron injection layer, an electron transport layer, and a hole injection layer, the same effects can be obtained.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:
1. A compound of Formula 9,

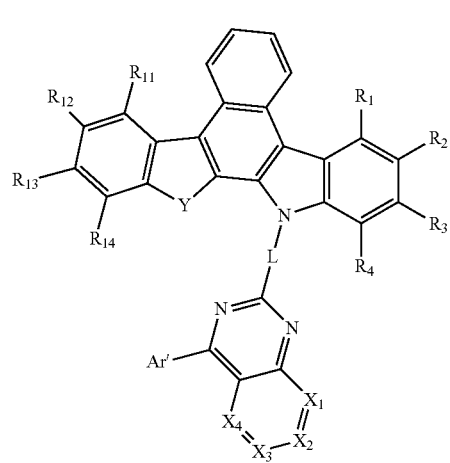

[Formula 9]

wherein Y is S,
R₁ to R₄ and R₁₁ to R₁₄ are hydrogen;
L is a single bond or a C₆-C₆₀ arylene group;
Ar' is a substituted or unsubstituted C₆-C₆₀ aryl group, or a substituted or unsubstituted fluorenyl group, wherein the aryl group is optionally substituted by a deuterium or C₆-C₂₀ aryl group, and the fluorenyl group is optionally substituted by a C₁-C₂₀ alkyl group; and
X₁ to X₄ are each independently CR₄₁ or N, wherein R₄₁ is hydrogen.

2. The compound of claim 1, wherein Ar' is an unsubstituted C₆-C₂₀ aryl group or a C₆-C₂₀ aryl group substituted with a deuterium.

3. The compound of claim 1, wherein X₁ to X₄ are CH.

4. The compound of claim 1, wherein Ar' is an unsubstituted C₆-C₂₀ aryl group and X₁ to X₄ are CH.

5. The compound of claim 4, wherein Ar' is phenyl.

6. The compound of claim 1 represented by one of the following compounds:

4-28

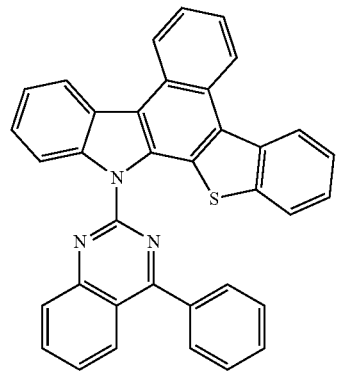

4-29

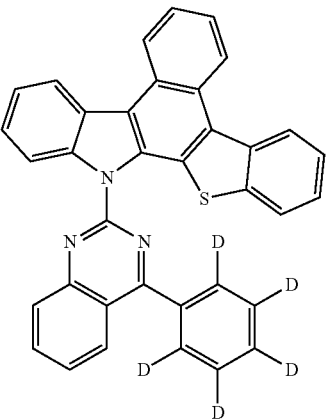

4-30

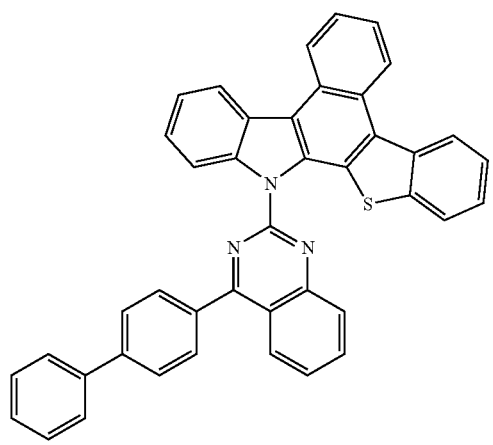

4-31

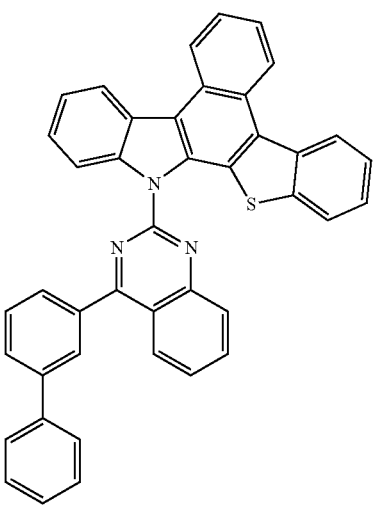

4-32

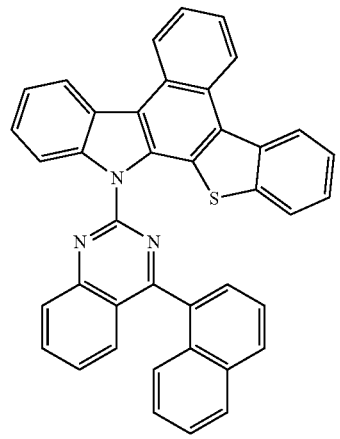

4-33

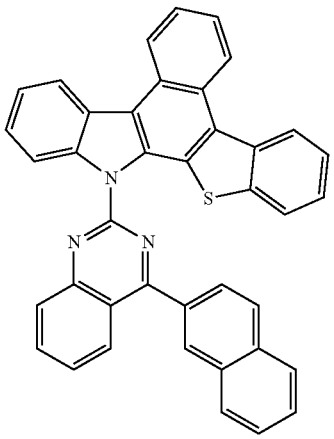

-continued
4-34
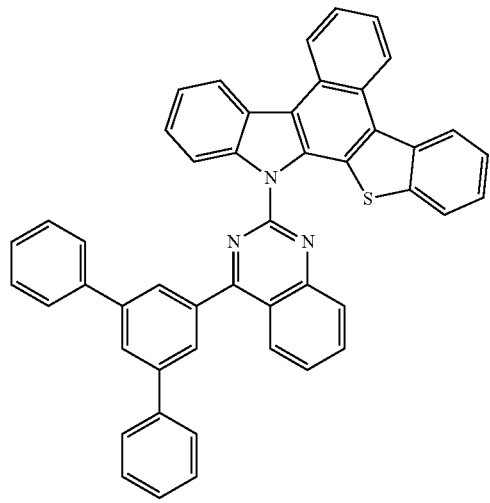
4-35
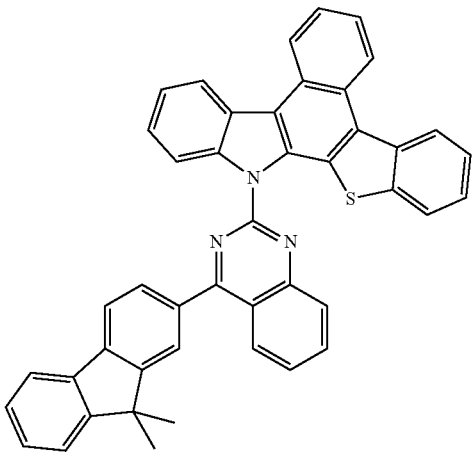
4-36
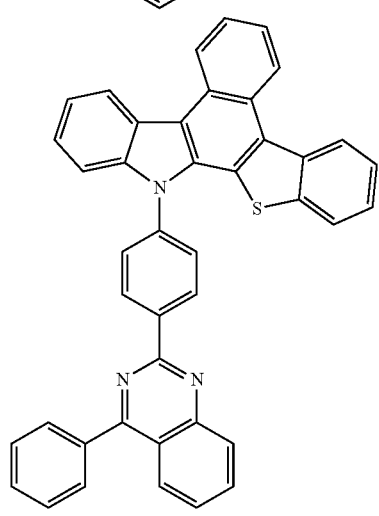
4-37
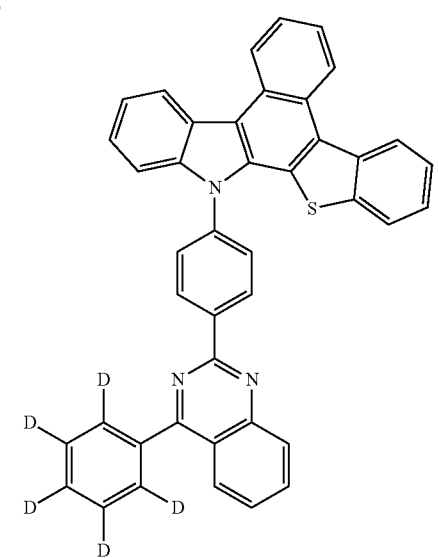
4-38
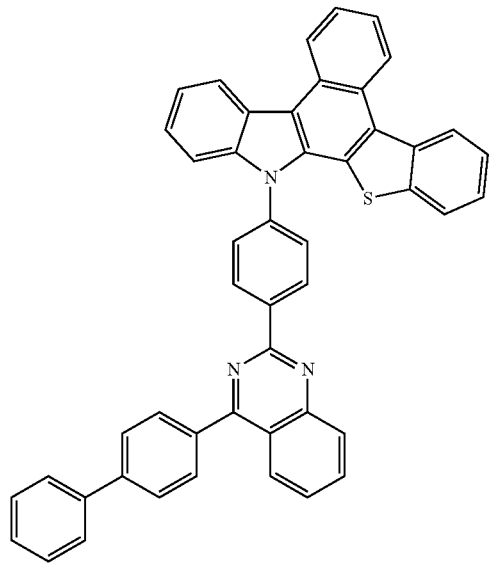
4-39
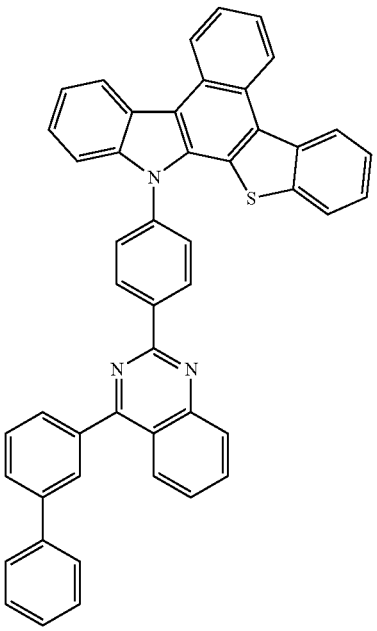

-continued
4-40
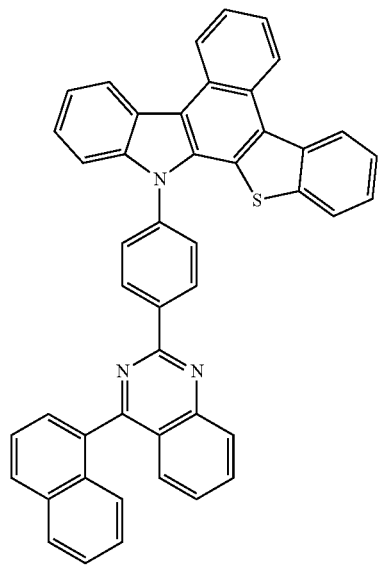
4-41
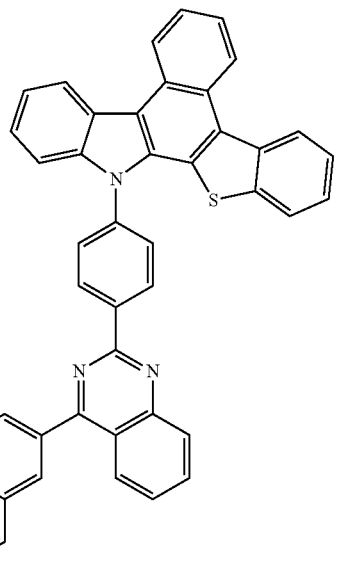
4-42
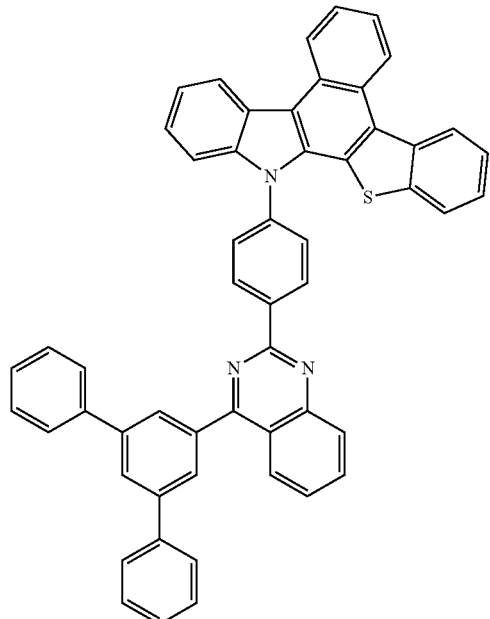
4-43
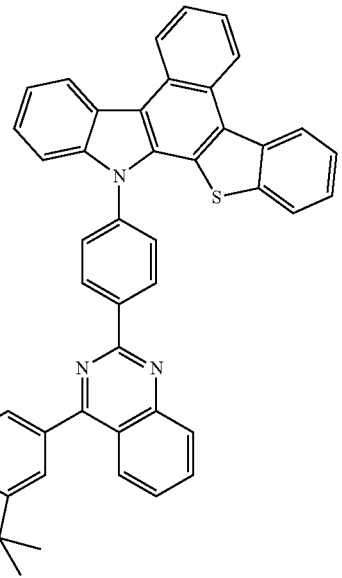
4-44
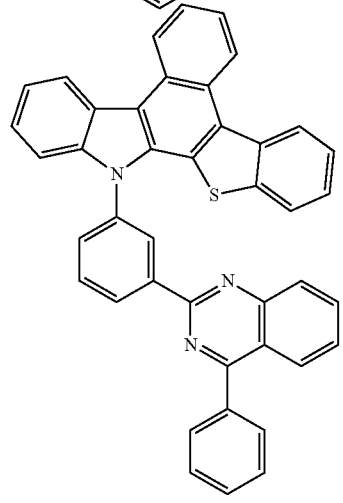
4-45
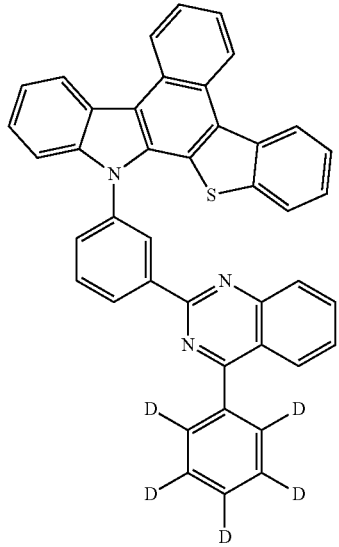

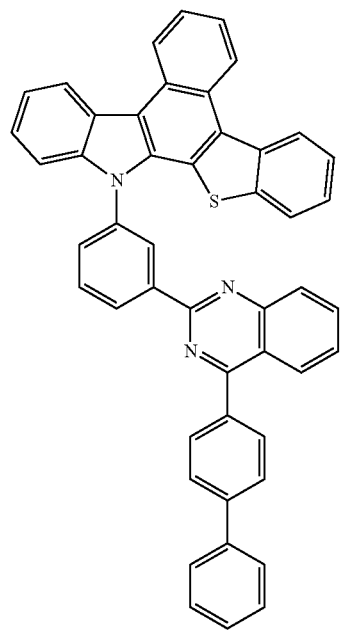
4-46
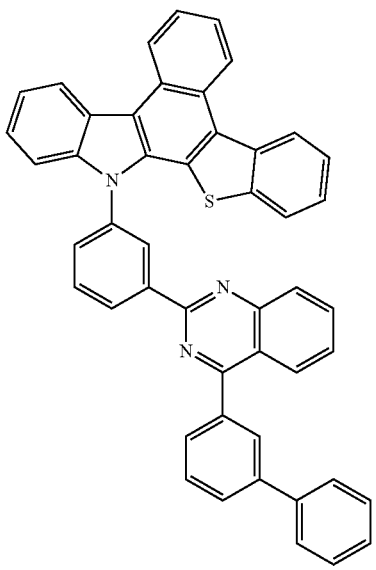
4-47
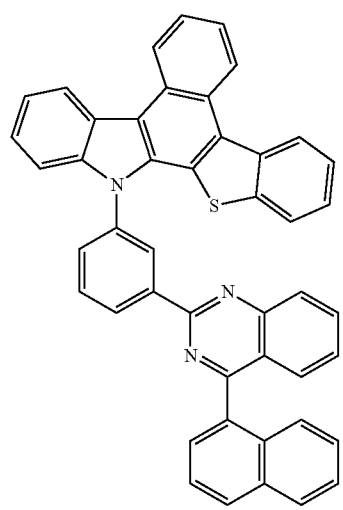
4-48
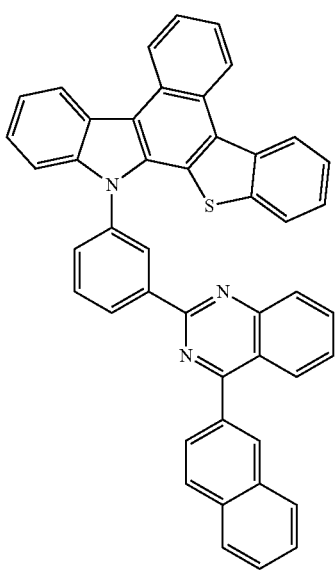
4-49

-continued
4-50
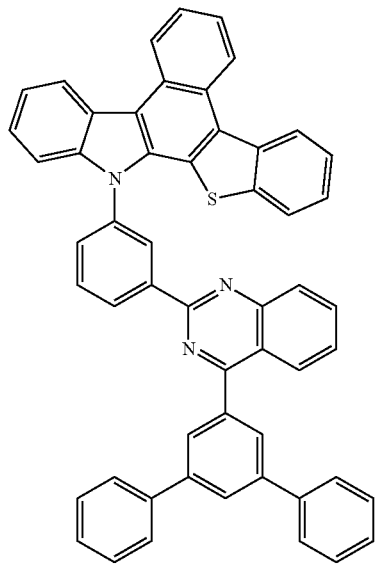
4-51
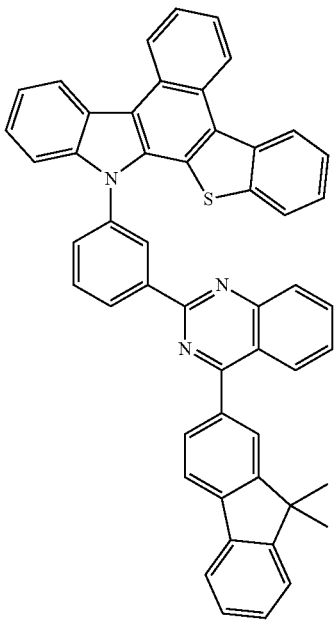
6-25
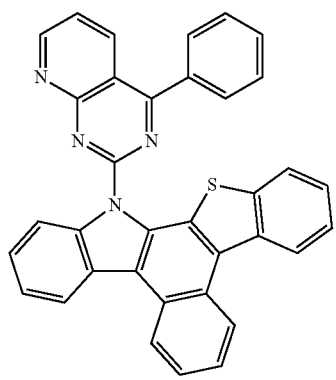
6-26
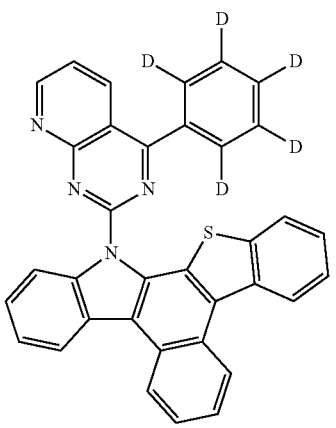
6-27
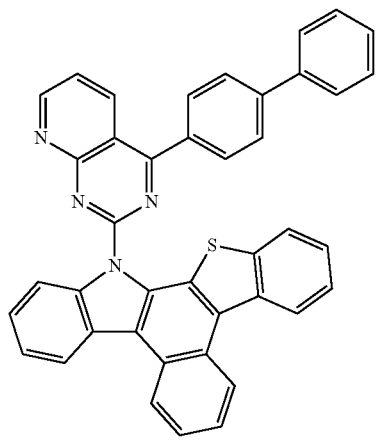
6-28
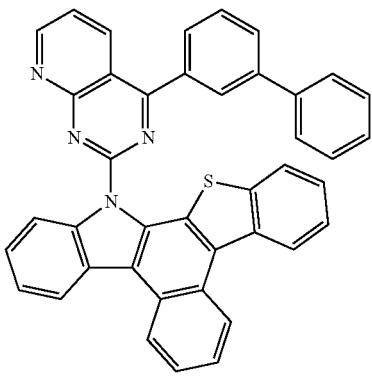

-continued
6-29
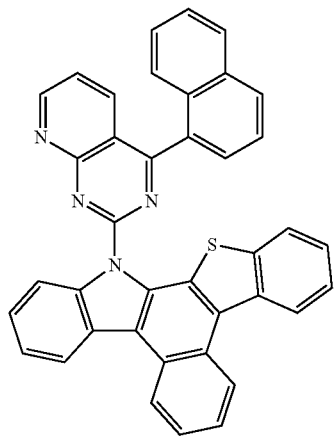
6-30
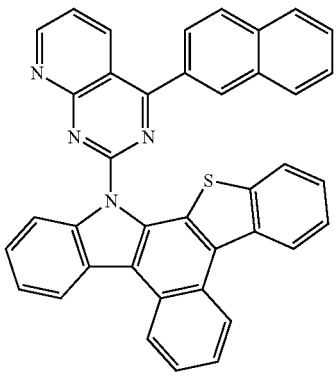
6-31
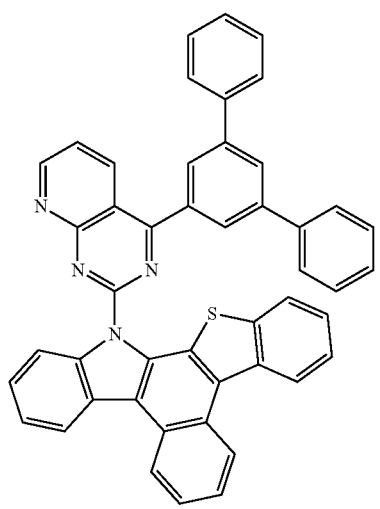
6-32
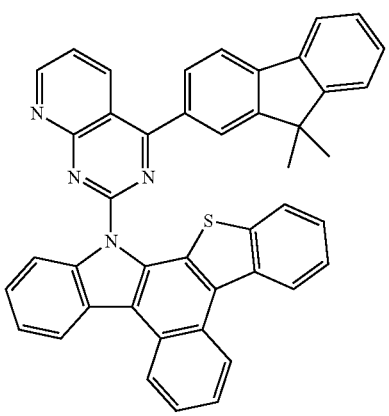
6-33
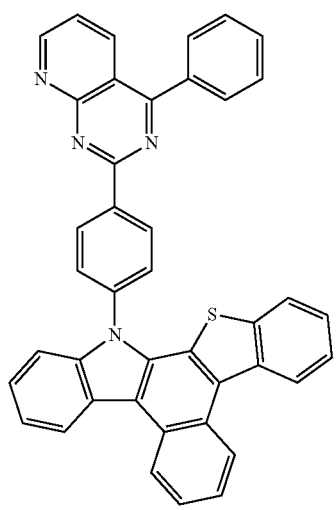
6-34
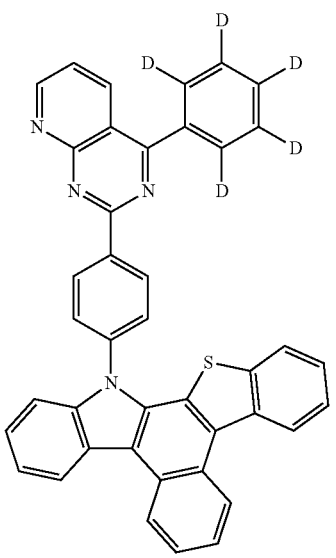

6-35
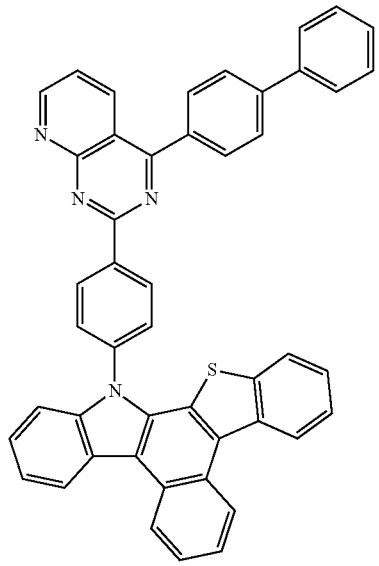
6-36
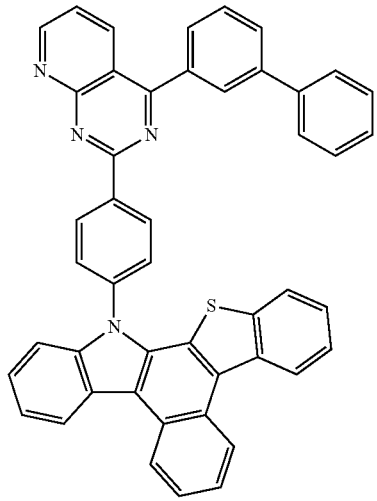
6-37
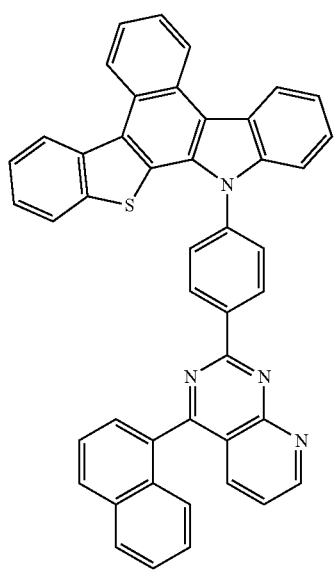
6-38
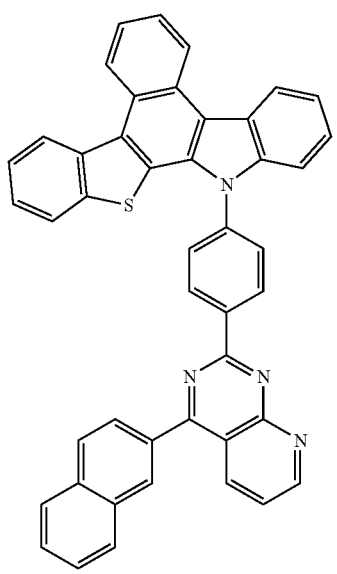

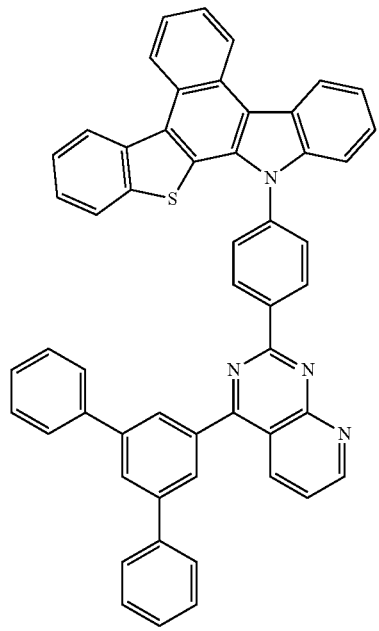
6-39
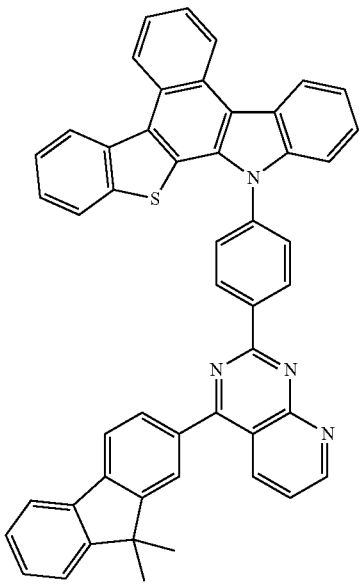
6-40
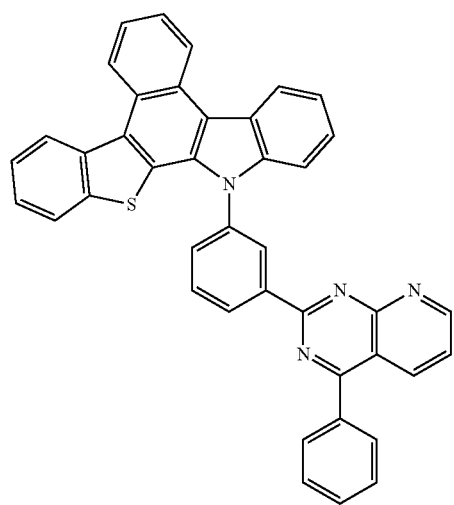
6-41
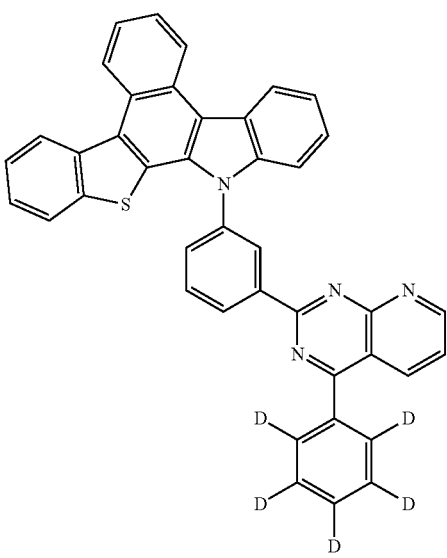
6-42

197 198
-continued
6-43
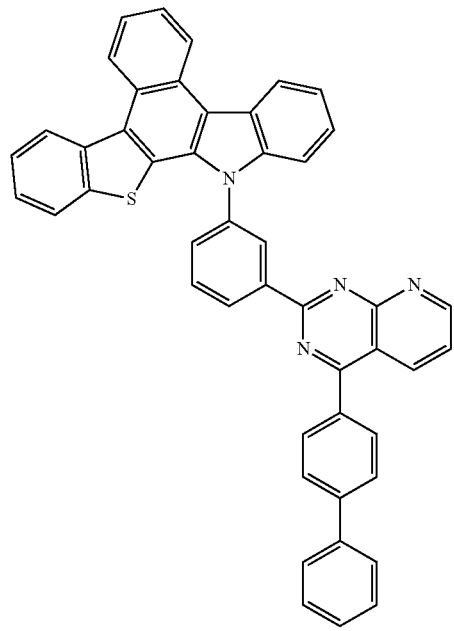
6-44
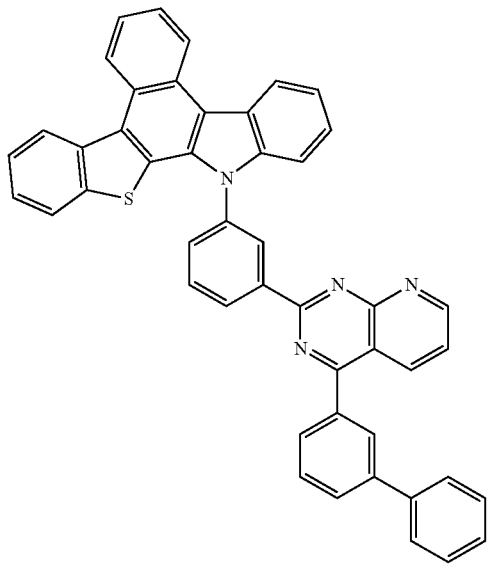
6-45
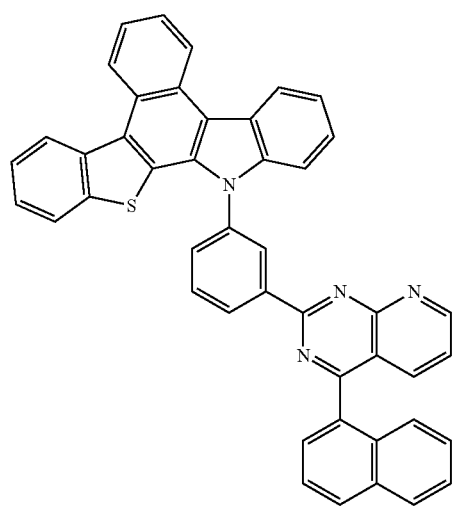
6-46
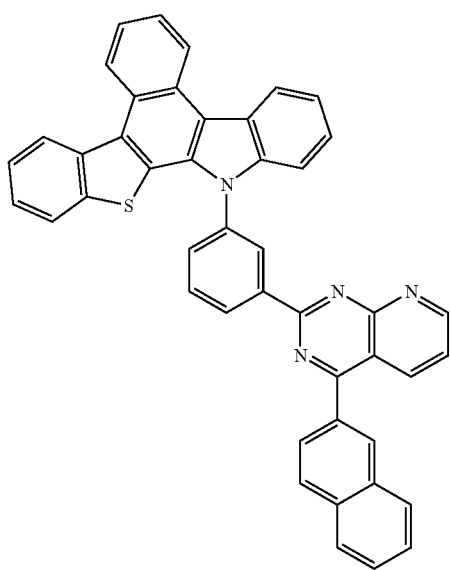

-continued
6-47
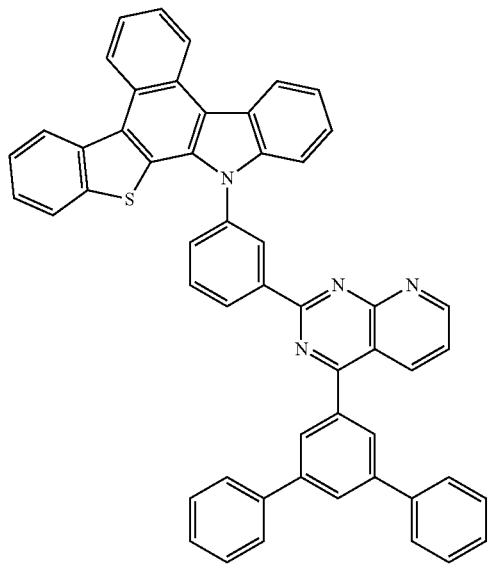
6-48
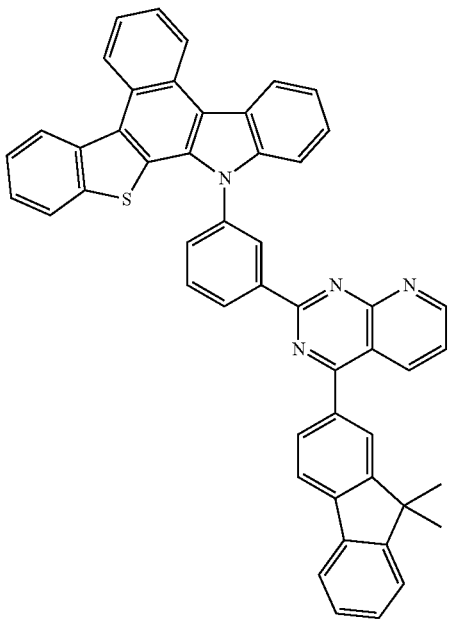
7-25
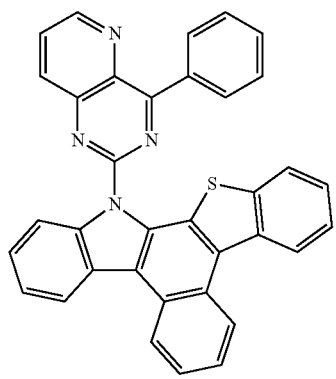
7-26
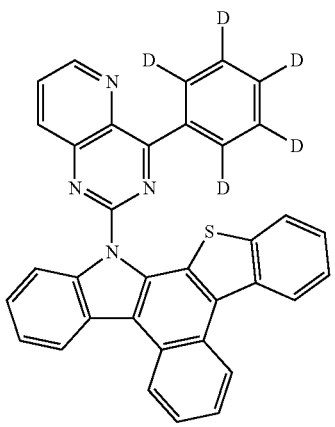
7-27
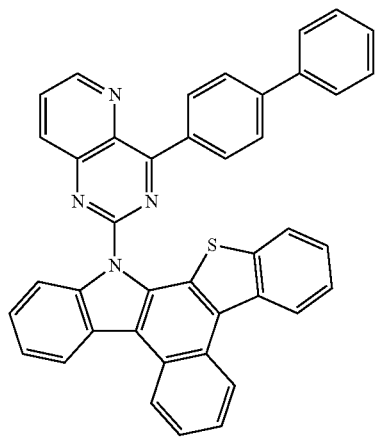
7-28
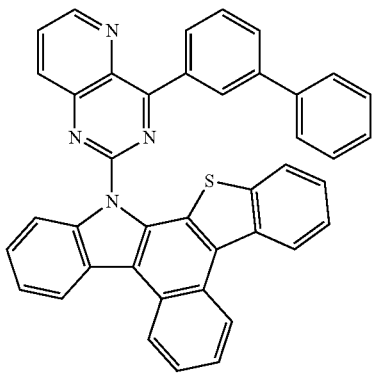

-continued
7-29
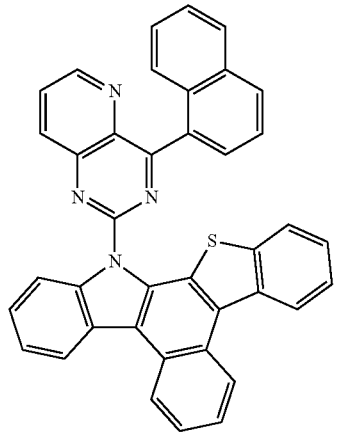
7-30
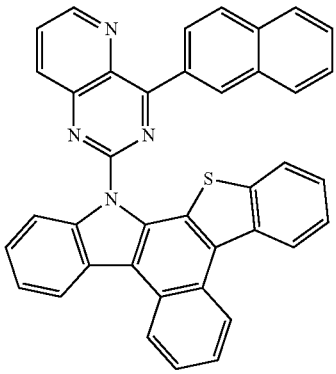
7-31
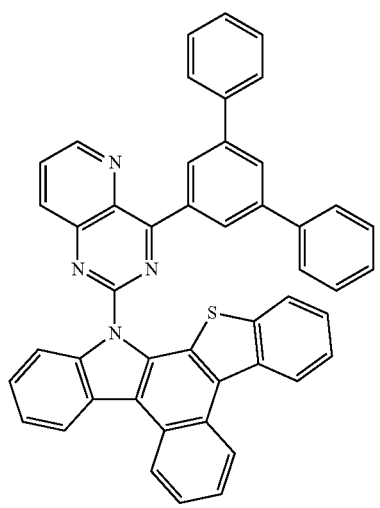
7-32
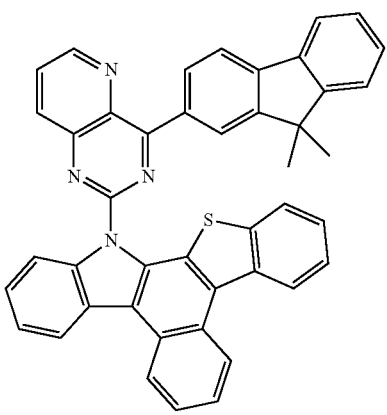
7-33
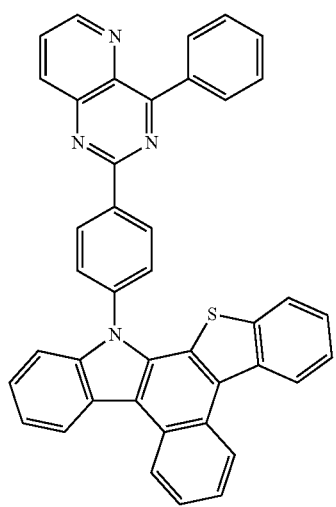
7-34
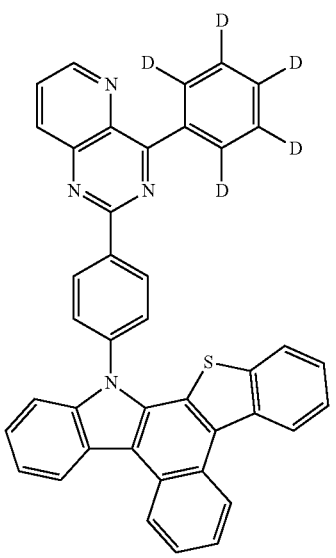

7-35
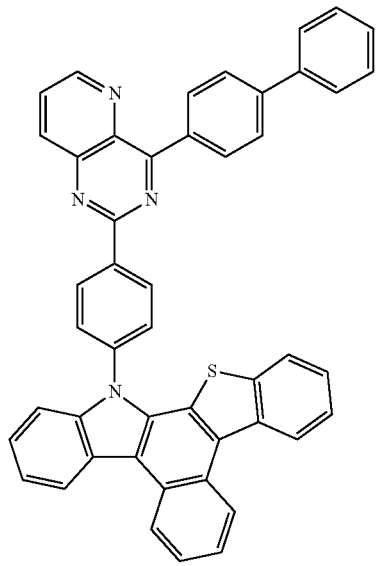
7-36
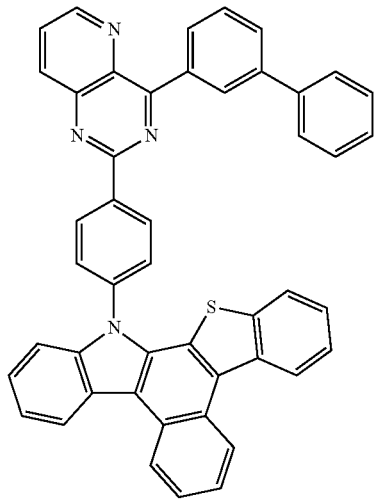
7-37
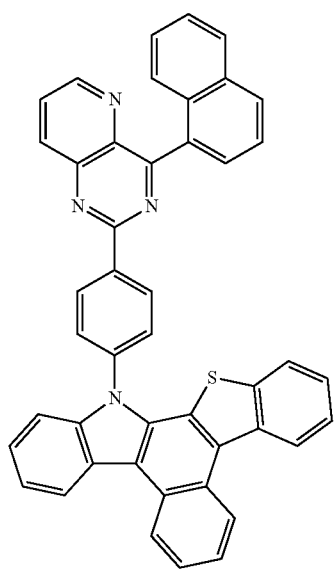
7-38
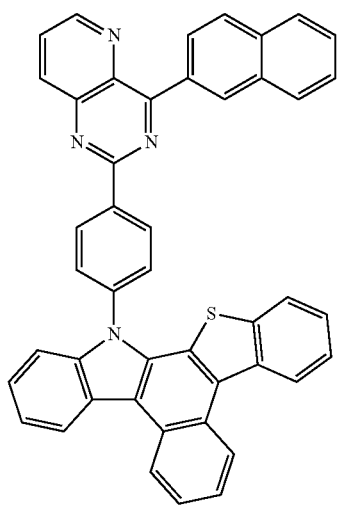

7-39 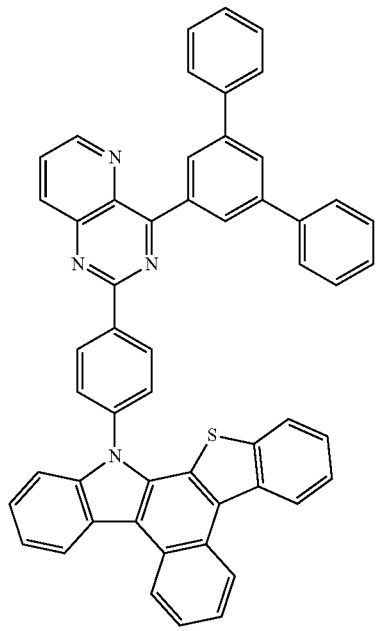
7-40 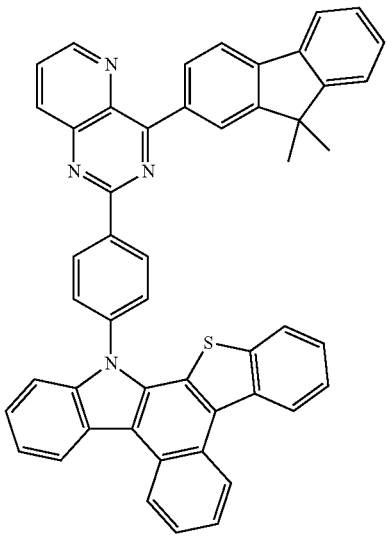
7-41 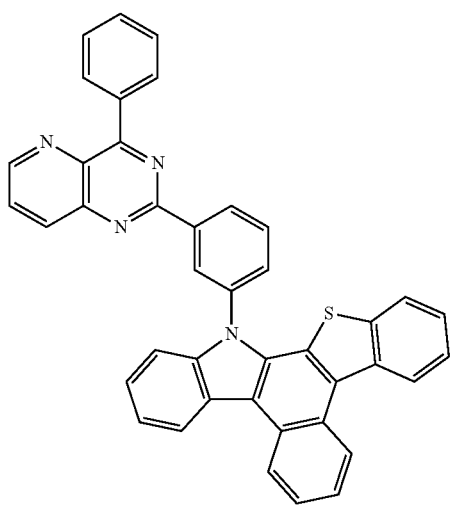
7-42 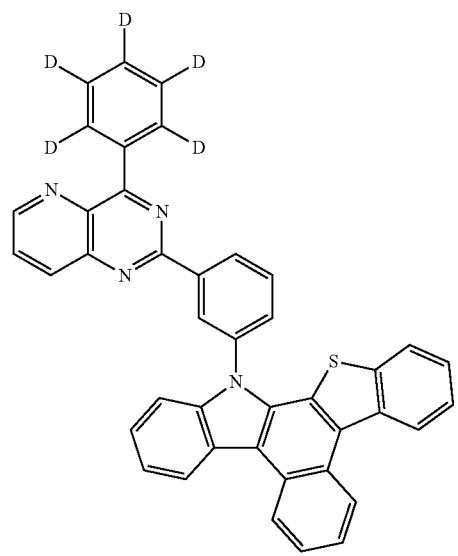

7-43
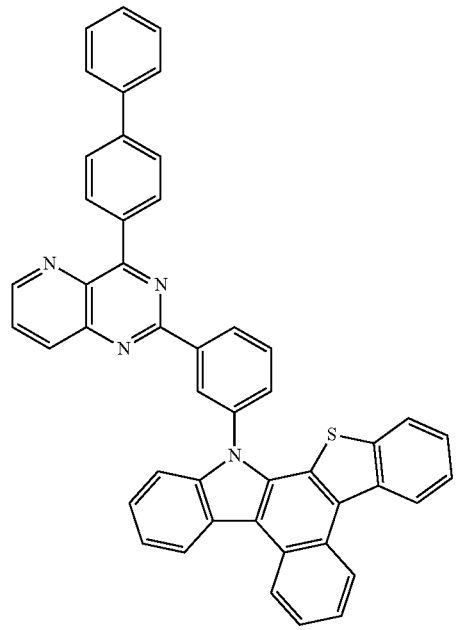
7-44
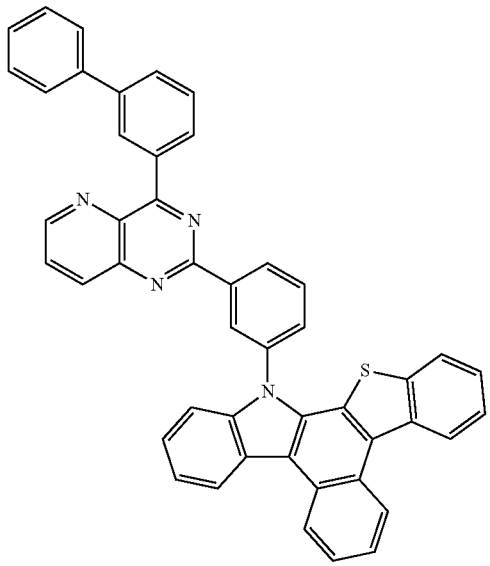
7-45
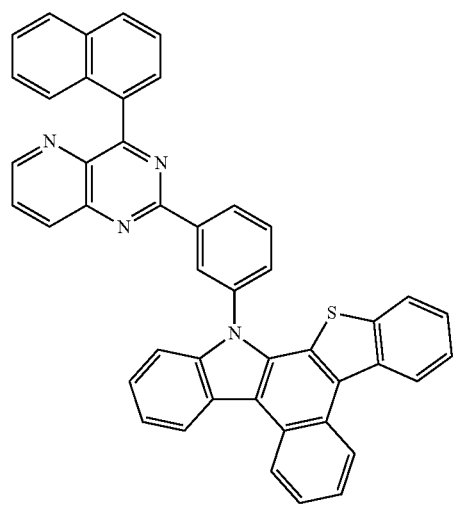
7-46
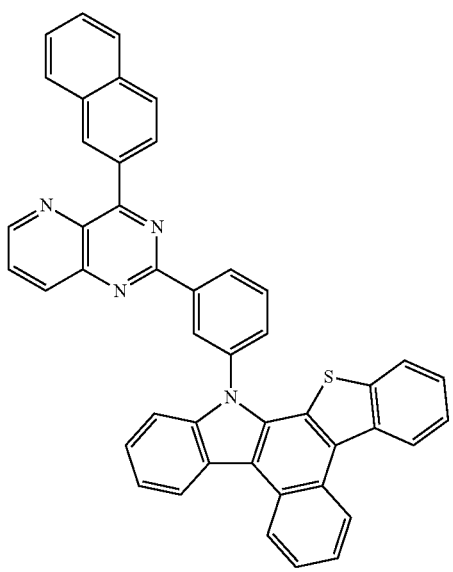

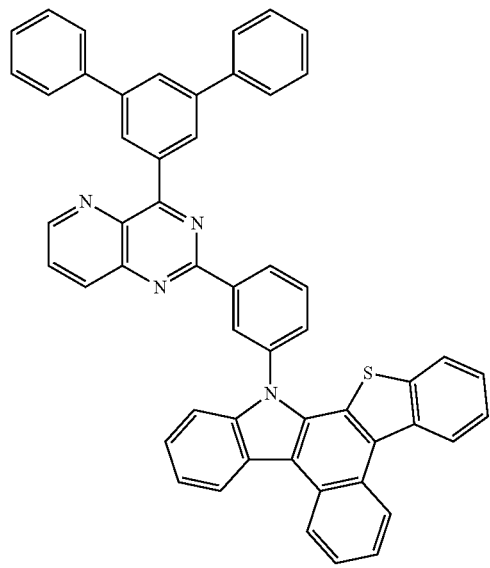

7-47

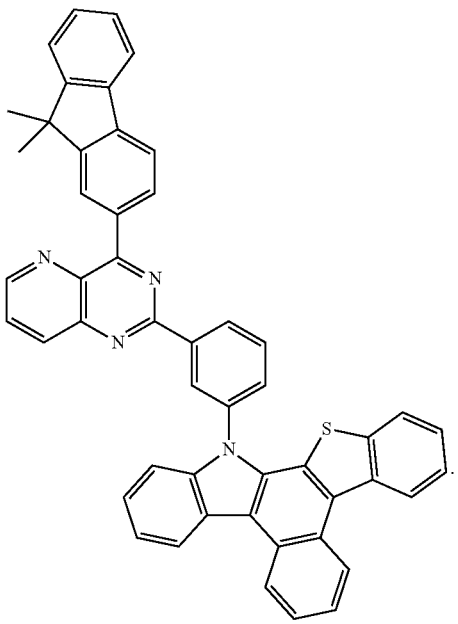

7-48

7. An organic electric element comprising a first electrode, a second electrode and an organic material layer disposed between the first electrode and the second electrode, wherein the organic material layer comprises the compound of claim 1.

8. An organic electric element comprising a first electrode, a second electrode and an organic material layer disposed between the first electrode and the second electrode, wherein the organic material layer comprises the compound of claim 3.

9. An organic electric element comprising a first electrode, a second electrode and an organic material layer disposed between the first electrode and the second electrode, wherein the organic material layer comprises the compound of claim 5.

10. An organic electric element comprising a first electrode, a second electrode and an organic material layer disposed between the first electrode and the second electrode, wherein the organic material layer is formed with the compound of claim 1 by a soluble process.

11. An organic electric element comprising a first electrode, a second electrode and an organic material layer disposed between the first electrode and the second electrode, wherein the organic material layer comprises a light emitting layer comprising the compound of claim 1.

12. An organic electric element comprising a first electrode, a second electrode and an organic material layer disposed between the first electrode and the second electrode, wherein the organic material layer comprises a light emitting layer comprising the compound of claim 1 as phosphorescent red host material.

13. An electronic device comprising a display device, the display device comprising the organic electric element of claim 4 and a control unit for driving the display device.

14. The electronic device of claim 13, wherein the organic electric element comprises at least one of an organic light emitting diode (OLED), an organic solar cell, an organic photo conductor (OPC), an organic transistor (organic TFT), and an element for monochromatic or white illumination.

* * * * *